US007358273B2

(12) United States Patent
Wannamaker et al.

(10) Patent No.: US 7,358,273 B2
(45) Date of Patent: *Apr. 15, 2008

(54) INHIBITORS OF CASPASES

(75) Inventors: Marion W Wannamaker, Stow, MA (US); Guy W Bemis, Arlington, MA (US); Paul S Charifson, Framingham, MA (US); David J Lauffer, Stow, MA (US); Michael D Mullican, Needham, MA (US); Mark A Murcko, Holliston, MA (US); Keith P Wilson, Hopkinton, MA (US); James W Janetka, Waltham, MA (US); Robert J Davies, Cambridge, MA (US); Anne-Laure Grillot, Cambridge, MA (US); Zhan Shi, Shrewsbury, MA (US); Cornelia J Forster, Pelham, NH (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/314,103

(22) Filed: Dec. 6, 2002

(65) Prior Publication Data

US 2003/0232986 A1  Dec. 18, 2003

Related U.S. Application Data

(60) Division of application No. 09/665,503, filed on Sep. 19, 2000, now Pat. No. 6,531,474, which is a continuation of application No. PCT/US99/05919, filed on Mar. 19, 1999.

(60) Provisional application No. 60/078,770, filed on Mar. 19, 1998.

(51) Int. Cl.
  *C07D 207/08* (2006.01)
  *A61K 31/401* (2006.01)

(52) U.S. Cl. .................................... 514/422; 548/517
(58) Field of Classification Search ................ 548/517; 514/422
See application file for complete search history.

(56) References Cited

U.S. PATENT DOCUMENTS

| | | | |
|---|---|---|---|
| 4,465,679 A | 8/1984 | Huang et al. ............... 424/244 |
| 5,008,245 A | 4/1991 | Digenis et al. ............... 514/18 |
| 5,055,451 A | 10/1991 | Krantz et al. ................. 514/19 |
| 5,158,936 A | 10/1992 | Krantz et al. ................. 514/19 |
| 5,411,985 A | 5/1995 | Bills et al. .................. 514/460 |
| 5,416,013 A | 5/1995 | Black et al. ................. 435/226 |
| 5,430,128 A | 7/1995 | Chapman et al. ............ 530/330 |
| 5,434,248 A | 7/1995 | Chapman et al. ............ 530/330 |
| 5,462,939 A | 10/1995 | Dolle et al. ................ 514/231.5 |
| 5,463,124 A | 10/1995 | Jacobi et al. ................ 564/155 |
| 5,486,623 A | 1/1996 | Zimmerman et al. ........ 549/417 |
| 5,498,616 A | 3/1996 | Mallamo et al. ............. 514/300 |
| 5,498,695 A | 3/1996 | Daumy et al. ............... 530/331 |
| 5,519,113 A | 5/1996 | Jendralla et al. ............ 530/322 |
| 5,552,400 A | 9/1996 | Dolle et al. ................. 514/221 |
| 5,565,430 A | 10/1996 | Dolle et al. .................. 514/19 |
| 5,585,357 A | 12/1996 | Dolle et al. .................. 514/18 |
| 5,585,486 A | 12/1996 | Dolle et al. ................. 544/182 |
| 5,639,745 A | 6/1997 | Dolle et al. ................. 514/183 |
| 5,656,627 A | 8/1997 | Bemis et al. ................ 514/221 |
| 5,670,494 A | 9/1997 | Dolle et al. ................... 514/86 |
| 5,710,153 A | 1/1998 | Ohmoto et al. ............. 514/236.2 |
| 5,716,929 A | 2/1998 | Bemis et al. .................. 514/18 |
| 5,756,466 A | 5/1998 | Bemis et al. .................. 514/18 |
| 5,847,135 A | 12/1998 | Bemis et al. ................ 544/264 |
| 5,874,424 A | 2/1999 | Batchelor et al. ........... 514/221 |
| 5,973,111 A | 10/1999 | Bemis et al. ................ 530/330 |
| 6,531,474 B1 * | 3/2003 | Wannamaker et al. ...... 514/248 |
| 2002/0013278 A1 * | 1/2002 | Wannamaker et al. ........ 514/19 |

FOREIGN PATENT DOCUMENTS

AU  A-64514/94  12/1994

(Continued)

OTHER PUBLICATIONS

M. Ator, "Peptide and Non-peptide Inhibitors of Interleukin-1β Converting Enzyme", *Cambridge Healthtech Institute (Inflammatory Cytokine Antagonists Targets, Strategies, and Indication)*, pp. 1-15 (1994).

M.A. Ator and R. E. Dolle, "Interleukin-1β Converting Enzyme: Biology and the Chemistry of Inhibitors", *Curr. Pharm. Design*, 1, pp. 191-210 (1995).

K. Chapman, "Synthesis of a Potent, Reversible Inhibitor of Interleukin-1β Converting Enzyme", *Bioorg. Med. Chem. Lett.*, 2, pp. 613-618 (1992).

(Continued)

*Primary Examiner*—Deepak Rao
(74) *Attorney, Agent, or Firm*—Ropes & Gray LLP; James F. Haley, Jr.; Nina R. Horan

(57) ABSTRACT

The present invention relates to novel classes of compounds which are caspase inhibitors, in particular interleukin-1β converting enzyme ("ICE") inhibitors. This invention also relates to pharmaceutical compositions comprising these compounds. The compounds and pharmaceutical compositions of this invention are particularly well suited for inhibiting caspase activity and consequently, may be advantageously used as agents against interleukin-1-("IL-1"), apoptosis-, interferon-γ inducing factor-(IGIF), or interferon-γ-("IFN-γ") mediated diseases, including inflammatory diseases, autoimmune diseases, destructive bone disorders, proliferative disorders, infectious diseases, and degenerative diseases. This invention also relates to methods for inhibiting caspase activity and decreasing IGIF production and IFN-γ production and methods for treating interleukin-1, apoptosis-, and interferon-γ-mediated diseases using the compounds and compositions of this invention. This invention also relates to methods of preparing the compounds of this invention.

15 Claims, No Drawings

FOREIGN PATENT DOCUMENTS

| | | |
|---|---|---|
| EP | A-0 135 349 | 3/1985 |
| EP | A-0 410 411 | 1/1991 |
| EP | A-0 417 721 | 3/1991 |
| EP | A-0 519 748 | 12/1992 |
| EP | A-0 525 420 | 2/1993 |
| EP | A-0 528 487 | 2/1993 |
| EP | A-0 529 713 | 3/1993 |
| EP | A-0 533 226 | 3/1993 |
| EP | A-0 533 350 | 3/1993 |
| EP | A-0 547 699 | 6/1993 |
| EP | A-0 618 223 | 10/1994 |
| EP | A-0 623 592 | 11/1994 |
| EP | A-0 623 606 | 11/1994 |
| EP | A-0 644 197 | 3/1995 |
| EP | A-0 644 198 | 3/1995 |
| WO | WO 91/15577 | 10/1991 |
| WO | WO 93/05071 | 3/1993 |
| WO | WO 93/09135 | 5/1993 |
| WO | WO 93/12076 | 6/1993 |
| WO | WO 93/14777 | 8/1993 |
| WO | WO 93/16710 | 9/1993 |
| WO | WO 94/00154 | 1/1994 |
| WO | WO 94/03480 | 2/1994 |
| WO | WO 95/00160 | 1/1995 |
| WO | WO 95/05192 | 2/1995 |
| WO | WO 95/26958 | 10/1995 |
| WO | WO 95/29672 | 11/1995 |
| WO | WO 95/31535 | 11/1995 |
| WO | WO 95/35308 | 12/1995 |
| WO | WO 95/35367 | 12/1995 |
| WO | WO 96/03982 | 2/1996 |
| WO | WO 96/25408 | 8/1996 |
| WO | WO 96/30395 | 10/1996 |
| WO | WO 96/33209 | 10/1996 |
| WO | WO 96/40647 | 12/1996 |
| WO | WO 97/07805 | 3/1997 |
| WO | WO 97/08174 | 3/1997 |
| WO | WO 97/22619 | 6/1997 |
| WO | WO 97/24339 | 7/1997 |
| WO | WO 98/01133 | 1/1998 |
| WO | WO 98/04539 | 2/1998 |
| WO | WO 98/10778 | 3/1998 |
| WO | WO 98/11109 | 3/1998 |
| WO | WO 98/11129 | 3/1998 |
| WO | WO 01/90063 | 11/2001 |

OTHER PUBLICATIONS

R. Dolle et al., "Aspartyl α-((Diphenylphosphinyl)oxy)methyl Ketones as Novel Inhibitors of Interleukin-1β Converting Enzyme. Utility of the Diphenylphosphinic Acid Leaving Group for the Inhibition of Cysteine Proteases", *J. Med. Chem.*, 38, pp. 220-222 (1995).

R. Dolle et al., "Aspartyl α-((1-Phenyl-3-(trifluoromethyl)-pyrazol-5-yl)oxy)methyl Ketones as Interleukin-1β Converting Enzyme Inhibitors. Significance of the $P_1$ and $P_3$ Amido Nitrogens for Enzyme-Peptide Inhibitor Binding", *J. Med. Chem.*, 37, pp. 3863-3865 (1994).

R. Dolle et al., "$P_1$ Aspartate-Based Peptide α-((2,6-Dichlorobenzoyl)oxy)methyl Ketones as Potent Time-Dependent Inhibitors of Interleukin-1β-Converting Enzyme", *J. Med. Chem.*, 37, pp. 563-564 (1994).

P. Edwards et al., "Design, Synthesis, and Kinetic Evaluation of a Unique Class of Elastase Inhibitors, the Peptidyl α-Ketobenzoxazoles, and the X-ray Crystal Structure of the Covalent Complex between Porcine Pancreatic Elastase and Ac-Ala-Pro-Val-2-Benzoxazole", *J. Am. Chem. Soc.*, 114, pp. 1854-1863 (1992).

P.R. Elford et al., "Reduction of Inflammation and Pyrexia in the Rat by Oral Administration of SDZ 224-015, an Inhibitor of the Interleukin-1β Converting Enzyme", *Br. J. Pharmacology*, 115, pp. 601-606 (1995).

T.P.D. Fan et al., "Stimulation of Angiogenesis by Substance P and Interleukin-1 in the Rat and Its Inhibition by $NK_1$ or Interleukin-1 Receptor Antagonists", *Br. J. Pharmacol.*, 110, 43-49 (1993).

I. Fauszt et al., "Inhibition of Interleukin-1β Converting Enzyme by Peptide Derivatives", *Proc. of the 13th Am. Peptide Symp.*, Jun. 20-25, 1993; Hodges, R.S. and Smith, J.A., Eds., *Peptides*, pp. 589-591 (1994).

D. Fletcher et al., "A Synthetic Inhibitor of Interleukin-1β Converting Enzyme Prevents Endotoxin-Induced Interleukin-1β Production In Vitro and In Vivo", *J. Interfer. Cytokine Res.*, 15, pp. 243-248 (1995).

T. Graybill et al., "The Preparation and Evaluation of Peptidic Aspartyl Hemiacetals as Reversible Inhibitors of ICE", *Am. Chem. Soc. Abs. (206th Natl. Mtg.)*, MEDI 235 (1993).

T. Graybill, et al., "Preparation and Evaluation of Peptidic Aspartyl Hemiacetals as Reversible Inhibitors of Interleukin-1β Converting Enzyme (ICE)", Int. J. Peptide Protein Res., 44, pp. 173-182 (1994).

S. Hanessian et al., "Design and Synthesis of a Prototype Model Antagonist of Tachykinin NK-2 Receptor", *Bioorg. Med. Chem. Lett.*, 11, 1397-1400 (1994).

D. Karanewsky et al., "Conformationally Constrained Inhibitors of Caspase-1 (Interleukin-1β Converting Enzyme) and of the Human CED-3 Homologue Caspase-3) (CPP32, Apopain)", *Bioorg. Med. Chem. Lett.*, pp. 2757-2762 (1998).

R. B. Layzer, "Degenerative Diseases of the Nervous System", *Cecil Textbook of Medicine, 20th Edition*, vol. 2, pp. 2050-2057 (1996).

A. MacKenzie et al., "An Inhibitor of the Interleukin-1β-Processing Enzyme Blocks IL-1 Release and Reduces Pyrexia and Acute Inflammation", *Inflammation Research Association (7th Internat. Conf.)*, W42 (1994).

B. Miller et al., "Inhibition of Mature IL-1β Production in Murine Macrophages and a Murine Model of Inflammation by WIN 67694, an Inhibitor of IL-1β Converting Enzyme", *J. Immunol.*, 154, pp. 1331-1338 (1995).

A.M.M. Mjalli et al., "Activated Ketones as Potent Reversible Inhibitors of Interleukin-1β Converting Enzyme", *Bioorg. Med. Chem. Lett.*, 4, pp. 1965-1968 (1994).

A.M.M. Mjalli et al., "Phenylalkyl Ketones as Potent Reversible Inhibitors of Interleukin-1β Converting Enzyme", *Bioorg. Med. Chem. Lett.*, 3, pp. 2689-2692 (1993).

M.D. Mullican et al., "The Synthesis and Evaluation of Peptidyl Aspartyl Aldehydes as Inhibitors of ICE", *Bioorg. Med. Chem. Lett.*, 4, 2359-2364 (1994).

Y. Okamoto et al., "Peptide Based Interleukin-1b Converting Enzyme (ICE) Inhibitors: Synthesis, Structure Activity Relationships and Crystallographic Study of the ICE-inhibitor Complex", *Chem. Pharm. Bull.*, 47(1), pp. 11-21 (1999).

M. Pennington & N. Thornberry, "Synthesis of a Fluorogenic Interleukin-1β Converting Enzyme Substrate Based on Resonance Energy Transfer", *Pept. Res.*, 7, pp. 72-76 (1994).

C. Prasad et al., "$P_1$ Aspartate-Based Peptide α-Arylacyloxy- and α-Aryloxymethyl Ketones as Potent Time-Dependent Inhibitors of Interleukin 1β Converting Enzyme", *Am. Chem. Soc. Abs. (24th Med. Chem. Symp.)*, 66 (1994).

C. Ray et al., "Viral Inhibition of Inflammation: Cowpox Virus Encodes an Inhibitor of the Interleukin-1β Converting Enzyme", *Cell*, 69, pp. 597-604 (1992).

L. Reiter, "Peptidic p-Nitroanilide Substrates of Interleukin-1β-Converting Enzyme", *Int. J. Pept. Protein Res.*, 43, pp. 87-96 (1994).

L. Revesz et al., "Synthesis of P1 Aspartate-Based Peptide Acyloxymethyl and Fluoromethyl Ketones as Inhibitors of Interleukin-1β-Converting Enzyme", *Tetrahedron Lett.*, 35, pp. 9693-9696 (1994).

R.P. Robinson and K.M. Donahue, "Synthesis of a Peptidyl Difluoro Ketone Bearing the Aspartic Acid Side Chain: An Inhibitor of Interleukin-1β Converting Enzyme", *J. Org. Chem.*, 57, 7309-7314 (1992).

S. Schmidt et al., "Synthesis and Evaluation of Aspartyl α-Chloro-, α-Aryloxy-, and α-Arylacyloxymethyl Ketones as Inhibitors of Interleukin-1β Converting Enzyme", *Am. Chem. Soc. Abs. (208th Natl. Mtg.)*, MEDI 4, (1994).

J.V. Simone, "Oncology: Introduction", *Cecil Textbook of Medicine*, 20th Edition, vol. 1, pp. 1004-1010 (1996).

P. Sleath et al., "Substrate Specificity of the Protease that Processes Human Interleukin-1β", *J. Biol. Chem.*, 265, pp. 14526-14528 (1990).

A.F. Spatola, in "Chemistry and Biochemistry of Amino Acids, Peptides, and Proteins", 7, ch. 5, pp. 267-281, Weinstein, B., ed., Marcel Dekker, Inc., New York (1983).

N. Thornberry et al., "Inactivation of Interleukin-1β Converting Enzyme by Peptide (Acyloxy)methyl Ketones", *Biochemistry*, 33, pp. 3934-3940 (1994).

M.J. Tocci, PubMed Abstract, "Structure and function of interleukin-1 beta converting enzyme", *Vitam. Horm.*, 53, pp. 27-63 (1997).

J. Uhl et al., "Secretion of Human Monocyte Mature IL-1β: Optimization of Culture Conditions and Inhibition by ICE Inhibitors", *Inflammation Res.*, 44, pp. S211-S212 (1995).

P. Villa et al., "Caspases and Caspase Inhibitors", *Trends in Biochemical Sciences*, 22, pp. 388-393 (1997).

E. Frèrot et al., "PyBOP®[1] and PyBroP: Two Reagents For the Difficult Coupling of the α, α-Dialkyl Amino Acid, Aib." *Tetrahedron* vol. 47, No. 2, pp. 259-270, (1991).

J.T. Gerig et al., "Attemped Synthesis of 2-Methylalanyl-L-prolyl-Ltryptophan An Unexpected Result." *J. Org. Chem*, vol. 41, No. 9, pp. 1653-1655, (1976).

R. Nagaraj et al., "Racemization At Proline Residues During Peptide Bond Formation: A Study of Diastereomeric Mixtures of Synthetic Alamethicin Fragments By 270 MHz $^1$H NMR." *Tetrahedron* vol. 37, pp. 2001-2005, (1981).

R. Nagaraj et al., "Solution Phase Synthesis of Alamethicin I." *Tetrahedron* vol. 37, pp. 1263-1270, (1981).

Chris A. Veale et al., "Orally Active Trifluoromethyl Ketone Inhibitors of Human Leukocyte Elastase", *J. Med. Chem.* vol. 40, pp. 3173-3181, (1997).

Office Action of Jan. 6, 2006 in U.S. Appl. No. 09/860,750.
Office Action of Apr. 26, 2005 in U.S. Appl. No. 09/860,750.
Office Action of Aug. 10, 2004 in U.S. Appl. No. 09/860,750.
Office Action of Dec. 15, 2003 in U.S. Appl. No. 09/860,750.

* cited by examiner

INHIBITORS OF CASPASES

CROSS REFERENCE TO RELATED APPLICATIONS

This application is a divisional application of U.S. application Ser. No. 09/665,503, filed Sep. 19, 2000 now U.S. Pat. No. 6,531,474; which is a continuation of International patent application PCT/US99/05919, filed Mar. 19, 1999, which designated United States; which claims priority from the U.S. Provisional Application 60/078,770, filed Mar. 19, 1998.

TECHNICAL FIELD OF THE INVENTION

The present invention relates to novel classes of compounds which are caspase inhibitors, in particular interleukin-1β converting enzyme ("ICE") inhibitors. This invention also relates to pharmaceutical compositions comprising these compounds. The compounds and pharmaceutical compositions of this invention are particularly well suited for inhibiting caspase activity and consequently, may be advantageously used as agents against interleukin-1-("IL-1"), apoptosis-, interferon-γ inducing factor-(IGIF), or interferon-γ-("IFN-γ") mediated diseases, including inflammatory diseases, autoimmune diseases, destructive bone disorders, proliferative disorders, infectious diseases, and degenerative diseases. This invention also relates to methods for inhibiting caspase activity and decreasing IGIF production and IFN-γ production and methods for treating interleukin-1, apoptosis-, and interferon-γ-mediated diseases using the compounds and compositions of this invention. This invention also relates to methods of preparing the compounds of this invention.

BACKGROUND OF THE INVENTION

Interleukin 1 ("IL-1") is a major pro-inflammatory and immunoregulatory protein that stimulates fibroblast differentiation and proliferation the production of prostaglandins, collagenase and phospholipase by synovial cells and chondrocytes, basophil and eosinophil degranulation and neutrophil activation. Oppenheim, J. H. et al, *Immunology Today*, 7, pp. 45-56 (1986). As such, it is involved in the pathogenesis of chronic and acute inflammatory and autoimmune diseases. For example, in rheumatoid arthritis, IL-1 is both a mediator of inflammatory symptoms and of the destruction of the cartilage proteoglycan in afflicted joints. Wood, D. D. et al., *Arthritis Rheum.* 26, 975, (1983); Pettipher, E. J. et al., *Proc. Natl. Acad. Sci. USA* 71, 295 (1986); Arend, W. P. and Dayer, J. M., *Arthritis Rheum.* 38, 151 (1995). IL-1 is also a highly potent bone resorption agent. Jandiski, J. J., *J. Oral Path* 17, 145 (1988); Dewhirst, F. E. et al., *J. Immunol.* 8, 2562 1985). It is alternately referred to as "osteoclast activating factor" in destructive bone diseases such as osteoarthritis and multiple myeloma. Bataille, R. et al., *Int. J. Clin. Lab. Res.* 21(4), 283 (1992). In certain proliferative disorders, such as acute myelogenous leukemia and multiple myeloma, IL-1 can promote tumor cell growth and adhesion. Bani, M. R., *J. Natl. Cancer Inst.* 83, 123 (1991); Vidal-Vanaclocha, F., *Cancer Res.* 54, 2667 (1994). In these disorders, IL-1 also stimulates production of other cytokines such as IL-6, which can modulate tumor development (Tartour et al., *Cancer Res.* 54, p. 6243 (1994). IL-1 is predominantly produced by peripheral blood monocytes as part of the inflammatory response and exists in two distinct agonist forms, IL-1α and IL-1β. Mosely, B. S. et al., *Proc. Nat. Acad. Sci.*, 84, pp. 4572-4576 (1987); Lonnemann, G. et al., *Eur. J. Immunol.*, 19, pp. 1531-1536 (1989).

IL-1β is synthesized as a biologically inactive precursor, pIL-1β. pIL-1β lacks a conventional leader sequence and is not processed by a signal peptidase. March, C. J., *Nature*, 315, pp.641-647 (1985). Instead, pIL-1β is cleaved by interleukin-1β converting enzyme ("ICE") between Asp-116 and Ala-117 to produce the biologically active C-terminal fragment found in human serum and synovial fluid. Sleath, P. R., et al., *J. Biol. Chem.*, 265, pp.14526-14528 (1992); A. D. Howard et al., *J. Immunol.*, 147, pp.2964-2969 (1991). ICE is a cysteine protease localized primarily in monocytes. It converts precursor IL-1β to the mature form. Black, R. A. et al., *FEBS Lett.*, 247, pp. 386-390 (1989); Kostura, M. J. et al., *Proc. Natl. Acad. Sci. U.S.A.*, 86, pp.5227-5231 (1989). Processing by ICE is also necessary for the transport of mature IL-1β through the cell membrane.

ICE (or caspase-1) is a member of a family of homologous enzymes called caspases. These homologs have sequence similarities in the active site regions of the enzymes. Such homologs (caspases) include TX (or $ICE_{rel-II}$ or ICH-2) (caspase-4) (Faucheu, et al., *EMBO J.*, 14, p. 1914 (1995); Kamens J., et al., *J. Biol. Chem.*, 270, p. 15250 (1995); Nicholson et al., *J. Biol. Chem.*, 270 15870 (1995)), TY (or $ICE_{rel-III}$) (caspase-5) (Nicholson et al., *J. Biol. Chem.*, 270, p. 15870 (1995); ICH-1 (or Nedd-2) (caspase-2) (Wang, L. et al., *Cell*, 78, p. 739 (1994)), MCH-2 (caspase-6), (Fernandes-Alnemri, T. et al., *Cancer Res.*, 55, p. 2737 (1995), CPP32 (or YAMA or apopain) (caspase-3) (Fernandes-Alnemri, T. et al., *J. Biol. Chem.*, 269, p. 30761 (1994); Nicholson, D. W. et al., Nature, 376, p. 37 (1995)), CMH-1 (or MCH-3) (caspase-7) (Lippke, et al., *J. Biol. Chem.*, 271(4), p1825-1828 (1996)); Fernandes-Alnemri, T. et al., *Cancer Res.*, (1995)), Mch5 (caspase-8) (Muzio, M. et al., *Cell* 85(6), 817-827, (1996)), MCH-6 (caspase-9) (Duan, H. et. al., *J. Biol. Chem.*, 271(34), p. 16720-16724 (1996)), Mch4 (caspase-10) (Vincenz, C. et. al., *J. Biol. Chem.*, 272, p. 6578-6583 (1997); Fernandes-Alnemri, T. et. al., *Proc. Natl. Acad. Sci.* 93, p. 7464-7469 (1996)), Ich-3 (caspase-11) (Wang, S. et. al., *J. Biol. Chem.*, 271, p. 20580-20587 (1996)), mCASP-12 (caspase-12), (Van de Craen, M. et. al., *FEBS Lett.* 403, p. 61-69 (1997); Yuan, Y. and Miura, M. PCT Publication WO95/00160 (1995)), ERICE (caspase-13), (Humke, E. W., et. al., *J. Biol. Chem.*, 273(25) p. 15702-15707 (1998)), and MICE (caspase-14) (Hu, S. et. al., *J. Biol. Chem.*, 273(45) p. 29-648-29653 (1998)).

Each of these ICE homologs, as well as ICE itself, is capable of inducing apoptosis when overexpressed in transfected cell lines. Inhibition of one or more of these homologs with the peptidyl ICE inhibitor Tyr-Val-Ala-Asp-chloromethylketone results in inhibition of apoptosis in primary cells or cell lines. Lazebnik et al., *Nature*, 371, p. 346 (1994).

Caspases also appear to be involved in the regulation of programmed cell death or apoptosis. Yuan, J. et al., *Cell*, 75, pp.641-652 (1993); Miura, M. et al., *Cell*, 75, pp. 653-660 (1993); Nett-Fiordalisi, M. A. et al., *J. Cell Biochem.*, 17B, p. 117 (1993). In particular, ICE or ICE homologs are thought to be associated with the regulation of apoptosis in neurodegenerative diseases, such as Alzheimer's and Parkinson's disease. Marx, J. and M. Baringa, *Science*, 259, pp. 760-762 (1993); Gagliardini, V. et al., *Science*, 263, pp. 826-828 (1994). Therapeutic applications for inhibition of apoptosis may include treatment of Alzheimer's disease, Parkinson's disease, stroke, myocardial infarction, spinal atrophy, and aging.

ICE has been demonstrated to mediate apoptosis (programmed cell death) in certain tissue types. Steller, H.,

*Science,* 267, p. 1445 (1995); Whyte, M. and Evan, G., *Nature,* 376, p. 17 (1995); Martin, S. J. and Green, D. R., *Cell,* 82, p. 349 (1995); Alnemri, E. S., et al., *J. Biol. Chem.,* 270, p. 4312 (1995); Yuan, J. *Curr. Opin. Cell Biol.,* 7, p. 211 (1995). A transgenic mouse with a disruption of the ICE gene is deficient in Fas-mediated apoptosis (Kuida, K. et al., *Science* 267, 2000 (1995)). This activity of ICE is distinct from its role as the processing enzyme for pro-IL-1β. It is conceivable that in certain tissue types, inhibition of ICE may not affect secretion of mature IL-1β, but may inhibit apoptosis.

Enzymatically active ICE has been previously described as a heterodimer composed of two subunits, p20 and p10 (20 kDa and 10 kDa molecular weight, respectively). These subunits are derived from a 45 kDa proenzyme (p45) by way of a p30 form, through an activation mechanism that is autocatalytic. Thornberry, N. A. et al., *Nature,* 356, pp.768-774 (1992). The ICE proenzyme has been divided into several functional domains: a prodomain (p14), a p22/20 subunit, a polypeptide linker and a p10 subunit. Thornberry *et al., supra*; Casano et al., *Genomics,* 20, pp. 474-481 (1994).

Full length p45 has been characterized by its cDNA and amino acid sequences. PCT patent applications WO 91/15577 and WO 94/00154. The p20 and p10 cDNA and amino acid sequences are also known. Thornberry *et al, supra*. Murine and rat ICE have also been sequenced and cloned. They have high amino acid and nucleic acid sequence homology to human ICE. Miller, D. K. et al., *Ann. N.Y. Acad. Sci.,* 696, pp. 133-148 (1993); Molineaux, S. M. et al., *Proc. Nat. Acad. Sci.,* 90, pp. 1809-1813 (1993). The three-dimensional structure of ICE has been determined at atomic resolution by X-ray crystallography. Wilson, K. P., et al., *Nature,* 370, pp. 270-275 (1994). The active enzyme exists as a tetramer of two p20 and two p10 subunits.

Recently, ICE and other members of the ICE/CED-3 family have been linked to the conversion of pro-IGIF to IGIF or to the production of IFN-γ in vivo (PCT application PCT/US96/20843, publication no. WO 97/22619, which is incorporated herein by reference) IGIF is synthesized in vivo as the precursor protein "pro-IGIF".

Interferon-gamma inducing factor (IGIF) is an approximately 18-kDa polypeptide that stimulates T-cell production of interferon-gamma (IFN-γ). IGIF is produced by activated Kupffer cells and macrophages in vivo and is exported out of such cells upon endotoxin stimulation. Thus, a compound that decreases IGIF production would be useful as an inhibitor of such T-cell stimulation which in turn would reduce the levels of IFN-γ production by those cells.

IFN-γ is a cytokine with immunomodulatory effects on a variety of immune cells. In particular, IFN-γ is involved in macrophage activation and Th1 cell selection (F. Belardelli, *APMIS,* 103, p. 161 (1995)). IFN-γ exerts its effects in part by modulating the expression of genes through the STAT and IRF pathways (C. Schindler and J. E. Darnell, *Ann. Rev. Biochem.,* 64, p. 621 (1995); T. Taniguchi, *J. Cancer Res. Clin. Oncol.,* 121, p. 516 (1995)).

Mice lacking IFN-γ or its receptor have multiple defects in immune cell function and are resistant to endotoxic shock (S. Huang et al., *Science,* 259, p.1742 (1993); D. Dalton et al., Science, 259, p. 1739 (1993); B. D. Car et al., *J. Exp. Med.,* 179, p.1437 (1994)). Along with IL-12, IGIF appears to be a potent inducer of IFN-γ production by T cells (H. Okamura et al., *Infection and Immunity,* 63, p.3966 (1995); H. Okamura et al., *Nature,* 378, p.88 (1995); S. Ushio et al., *J. Immunol.,* 156, p.4274 (1996)).

IFN-γ has been shown to contribute to the pathology associated with a variety of inflammatory, infectious and autoimmune disorders and diseases. Thus, compounds capable of decreasing IFN-γ production would be useful to ameliorate the effects of IFN-γ related pathologies.

Accordingly, compositions and methods capable of regulating the conversion of pro-IGIF to IGIF would be useful for decreasing IGIF and IFN-γ production in vivo, and thus for ameliorating the detrimental effects of these proteins which contribute to human disorders and diseases.

Caspase inhibitors represent a class of compounds useful for the control of inflammation or apoptosis or both. Peptide and peptidyl inhibitors of ICE have been described (PCT patent applications WO 91/15577, WO 93/05071, WO 93/09135, WO 93/12076, WO 93/14777, WO 93/16710, WO 95/35308, WO 96/30395, WO 96/33209 and WO 98/01133; European patent applications 503 561, 547 699, 618 223, 623 592, and 623 606; and U.S. Pat. Nos. 5,434, 248, 5,710,153, 5,716,929, and 5,744,451). Such peptidyl inhibitors of ICE have been observed to block the production of mature IL-1β in a mouse model of inflammation (vide infra) and to suppress growth of leukemia cells in vitro (Estrov et al., *Blood,* 84, 380a (1994)). However, due to their peptidic nature, such inhibitors are typically characterized by undesirable pharmacologic properties, such as poor cellular penetration and cellular activity, poor oral absorption, instability and rapid metabolism. Plattner, J. J. and D. W. Norbeck, in *Drug Discovery Technologies*, C. R. Clark and W. H. Moos, Eds. (Ellis Horwood, Chichester, England, 1990), pp.92-126. These properties has hampered their development into effective drugs.

Non-peptidyl compounds have also been reported to inhibit ICE in vitro. PCT patent application WO 95/26958; U.S. Pat. No. 5,552,400; Dolle et al., *J. Med. Chem.,* 39, pp. 2438-2440 (1996).

It is not clear however whether these compounds have the appropriate pharmacological profiles to be therapeutically useful.

Accordingly, the need exists for compounds that can effectively inhibit caspases, and that have favorable in vivo activity, for use as agents for preventing and treating chronic and acute forms of IL-1-, apoptosis-, IGIF-, or IFN-γ-mediated diseases, as well as inflammatory, autoimmune, destructive bone, proliferative, infectious, or degenerative diseases.

SUMMARY OF THE INVENTION

The present invention provides novel classes of compounds, and pharmaceutically acceptable derivatives thereof, that are useful as caspase inhibitors, in particular, as ICE inhibitors. These compounds can be used alone or in combination with other therapeutic or prophylactic agents, such as antibiotics, immunomodulators or other anti-inflammatory agents, for the treatment or prophylaxis of diseases mediated by IL-1, apoptosis, IGIF, or IFN-γ. According to a preferred embodiment, the compounds of this invention are capable of binding to the active site of a caspase and inhibiting the activity of that enzyme.

It is a principal object of this invention to provide novel classes of compounds represented by formula I, which have favorable in vivo profiles:

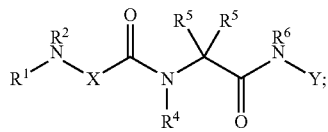

wherein the various substituents are described herein.

It is a further objective of this invention to provide pharmaceutical compositions, including multi-component compositions. This invention also provides methods for using and preparing the compounds of this invention and related compounds.

DETAILED DESCRIPTION OF THE INVENTION

In order that the invention described herein may be more fully understood, the following detailed description is set forth.

The following abbreviations and definitions are used throughout the application.

| Abbreviations | |
|---|---|
| Ac$_2$O | acetic anhydride |
| MeCN | acetonitrile |
| AMC | aminomethyl coumarin |
| n-Bu | normal-butyl |
| DMF | dimethylformamide |
| DIEA | N,N-diisopropylethylamine |
| DMA | N,N-dimethylacetamide |
| EDC | 1-(3-Dimethylaminopropyl)-3-ethylcarbodiimide hydrochloride |
| Et$_2$O | diethyl ether |
| EtOAc | ethyl acetate |
| Fmoc | 9-fluorenylmethyoxycarbonyl |
| HBTU | O-benzotriazol-1-yl-N,N,N',N'-tetramethyluronium hexafluorophosphate |
| HOBT | 1-hydroxybenzotriazole hydrate |
| MeOH | methanol |
| NMP | N-methylpyrrolidinone |
| TFA | trifluoroacetic acid |
| pNA | p-nitroaniline |

The term "caspase" refers to an enzyme that is a member of the family of enzymes that includes ICE (see H. Hara, Natl. Acad. Sci., 94, pp. 2007-2012 (1997)).

The terms "HBV", "HCV" and "HGV" refer to hepatitis-B virus, hepatitis-C virus and hepatitis-G virus, respectively.

The term "$K_i$" refers to a numerical measure of the effectiveness of a compound in inhibiting the activity of a target enzyme such as ICE. Lower values of $K_i$ reflect higher effectiveness. The $K_i$ value is a derived by fitting experimentally determined rate data to standard enzyme kinetic equations (see I. H. Segel, *Enzyme Kinetics*, Wiley-Interscience, 1975).

The term "interferon gamma inducing factor" or "IGIF" refers to a factor which is capable of stimulating the endogenous production of IFN-γ.

The term "caspase inhibitor" refer to a compound which is capable of demonstrating detectable inhibition of one or more caspases. The term "ICE inhibitor" refers to a compound which is capable of demonstrating detectable inhibition of ICE and optionally one or more additional caspases.

Inhibition of these enzymes may be determined using the methods described and incorporated by reference herein.

The skilled practitioner realizes that an in vivo enzyme inhibitor is not necessarily an in vitro enzyme inhibitor. For example, a prodrug form of a compound typically demonstrates little or no activity in in vitro assays. Such prodrug forms may be altered by metabolic or other biochemical processes in the patient to provide an in vivo ICE inhibitor.

The term "cytokine" refers to a molecule which mediates interactions between cells.

The term "condition" refers to any disease, disorder or effect that produces deleterious biological consequences in a subject.

The term "subject" refers to an animal, or to one or more cells derived from an animal. Preferably, the animal is a mammal, most preferably a human. Cells may be in any form, including but not limited to cells. retained in tissue, cell clusters, immortalized cells, transfected or transformed cells, and cells derived from an animal that have been physically or phenotypically altered.

The term "patient" as used in this application refers to any mammal, preferably humans.

The term "alkyl" refers to a straight-chained or branched, saturated aliphatic hydrocarbon containing 1 to 6 carbon atoms.

The term "alkenyl" refers to a straight-chained or branched unsaturated hydrocarbon containing 2 to 6 carbon atoms and at least one double bond.

The term "alkynyl" refers to a straight-chained or branched unsaturated hydrocarbon containing 2 to 6 carbon atoms and at least one triple bond.

The term "cycloalkyl" refers to a mono- or polycyclic, non-aromatic, hydrocarbon ring system which may optionally contain unsaturated bonds in the ring system. Examples include cyclohexyl, adamantyl. norbornyl, and spirocyclopentyl.

The term "aryl" refers to a mono- or polycyclic ring system which contains 6, 10, 12 or 14 carbons in which at least one ring of the ring system is aromatic. The aryl groups of this invention are optionally singly or multiply substituted with $R^{11}$. Examples of aryl ring systems include, phenyl, naphthyl, and tetrahydronaphthyl.

The term "heteroaryl" refers to a mono- or polycyclic ring system which contains 1 to 15 carbon atoms and 1 to 4 heteroatoms, and in which at least one ring of the-ring system is aromatic. Heteroatoms are sulfur, nitrogen or oxygen. The heteroaryl groups of this invention are optionally singly or multiply substituted with $R^{11}$.

The term "heterocyclic" refers to a mono- or polycyclic ring system which contains 1 to 15 carbon atoms and 1 to 4 heteroatoms, in which the mono- or polycyclic ring system may optionally contain unsaturated bonds but is not aromatic. Heteroatoms are independently sulfur, nitrogen, or oxygen.

The term "alkylaryl" refers to an alkyl group, wherein a hydrogen atom of the alkyl group is replaced by an aryl radical.

The term "alkylheteroaryl" refers to an alkyl group, wherein a hydrogen atom of the alkyl group is replaced by a heteroaryl radical.

The term "amino acid side chain" refers to any group attached to the α carbon of a naturally or non-naturally occuring amino acid.

The term "substitute" refers to the replacement of a hydrogen atom in a compound with a substituent group.

The term "straight chain" refers to a contiguous unbranching string of covalently bound atoms. The straight chain may be substituted, but these substituents are not a part of the straight chain.

In chemical formulas, parenthesis are used herein to denote connectivity in molecules or groups. In particular, parentheses are used to indicate: 1) that more than one atom or group is bonded to a particular atom; or 2) a branching point (i.e., the atom immediately before the open parenthesis is bonded both to the atom or group in the parentheses and the atom or group immediately after the closed parenthesis). An example of the first use is "—N(alkyl)$_2$", indicating two alkyl groups bond to an N atom. An example of the second use is "—C(O)NH$_2$", indicating a carbonyl group and an amino ("NH$_2$") group. both bonded to the indicated carbon atom. A "—C(O)NH$_2$" group may be represented in other ways, including the following structure:

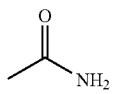

Substituents may be represented in various forms. These various forms are known to the skilled practitioner and may be used interchangeably. For example, a methyl substituent on a phenyl ring may be represented in any of the following forms:

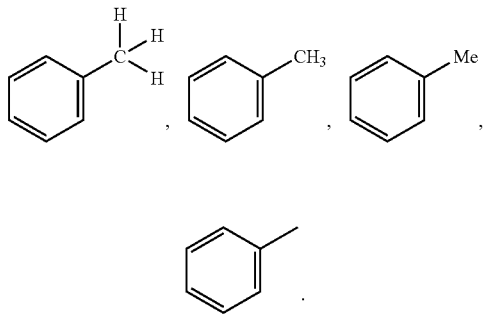

Various forms of substituents such as methyl are used herein interchangeably.

Other definitions are set forth in the specification where necessary.

Compounds of this Invention

The compounds of one embodiment A of this invention are those of formula I:

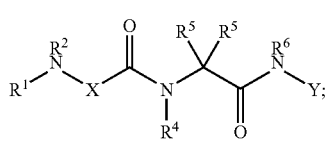

wherein: Y is:

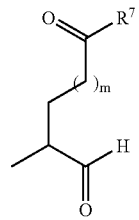

(a)

provided that when $R^7$ is —OH then Y can also be:

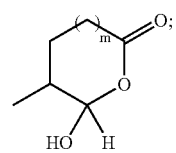

(b)

X is —C($R^3$)$_2$— or —N($R^3$)—;

m is 0 or 1;

$R^1$ is H, —C(O)$R^8$, —C(O)C(O)$R^8$, —S(O)$_2$$R^8$, —S(O)$R^8$, —C(O)O$R^8$, —C(O)N(H)$R^8$, —S(O)$_2$N(H)—$R^8$, —S(O)N(H)—$R^8$, —C(O)C(O)N(H)$R^8$, —C(O)CH=CH$R^8$, —C(O)CH$_2$O$R^8$, —C(O)CH$_2$N(H)$R^8$, —C(O)N($R^8$)$_2$, —S(O)$_2$N($R^8$)$_2$, —S(O)N($R^8$)$_2$, —C(O)C(O)N($R^8$)$_2$, —C(O)CH$_2$N($R^8$)$_2$, —CH$_2$$R^8$, —CH$_2$-alkenyl-$R^8$, or —CH$_2$-alkynyl-$R^8$;

$R^2$ is —H and each $R^3$ is independently —H, an amino acid side chain, —$R^8$, alkenyl-$R^9$, or alkynyl-$R^9$, or $R^2$ and one $R^3$ together with the atoms to which they are bound, form a 3 to 7 membered cyclic or heterocyclic ring system, wherein a hydrogen atom bound to any -alkyl or -cycloalkyl carbon atom is optionally replaced by —$R^{10}$, a hydrogen atom bound to any -aryl or -heteroaryl carbon atom is optionally replaced by —$R^{11}$, a hydrogen atom bound to any nitrogen atom of the ring system is optionally replaced by —$R^1$;

$R^4$ is —H and each $R^5$ is independently —H, an amino acid side chain, —$R^8$, -alkenyl-$R^9$, or -alkynyl-$R^9$, or $R^4$ and one $R^5$ together with the atoms to which they are bound form a 3 to 7 membered cyclic or heterocyclic ring system, wherein a hydrogen atom bound to any -alkyl or -cycloalkyl carbon atom is optionally replaced by $R^{10}$, a hydrogen atom bound to any -aryl or -heteroaryl carbon atom is optionally replaced by $R^{11}$, and a hydrogen atom bound to any nitrogen atom of the ring system is optionally replaced with $R^1$;

$R^6$ is —H;

$R^7$ is —OH, —O$R^8$, or —N(H)OH;

each $R^8$ is independently -alkyl, -cycloalkyl, -aryl, -heteroaryl, -heterocyclyl, -alkylcycloalkyl -alkylaryl, -alkylheteroaryl, or -alkylheterocyclyl, wherein a hydrogen atom bound to any -alkyl or -cycloalkyl carbon atom is optionally replaced by $R^{10}$, a hydrogen atom bound to any -aryl or -heteroaryl carbon atom is optionally replaced by $R^{11}$, and a hydrogen atom bound to any nitrogen atom is optionally replaced by $R^1$;

each $R^9$ is independently -aryl, -heteroaryl, cycloalkyl, or -heterocyclyl, wherein a hydrogen atom bound to any -alkyl or -cycloalkyl carbon atom is optionally replaced by $R^{10}$, a hydrogen atom bound to any -aryl or -heteroaryl carbon atom is optionally replaced by $R^{11}$, and a hydrogen atom bound to any nitrogen atom is optionally replaced by $R^1$;

each $R^{10}$ is independently —OH, —SH, —F, —Cl, —Br, —I, —NO$_2$, —CN, —NH$_2$, —CO$_2$H, —C(O)NH$_2$, —N(H)C(O)H, —N(H)C(O)NH$_2$, -perfluoroalkyl, —O-alkyl, —O-aryl, —O-alkylaryl, —N(H)alkyl, —N(H)aryl, —N(H)-alkylaryl, —N(alkyl)$_2$, —C(O)N(H)alkyl, —C(O)N(alkyl)$_2$, —N(H)C(O)alkyl, —N(H)C(O)N(H)alkyl, —N(H)C(O)N(alkyl)$_2$, —S-alkyl, —S-aryl, —S-alkylaryl, —S(O)$_2$alkyl, —S(O)alkyl, —C(O)alkyl, —CH$_2$NH$_2$, —CH$_2$N(H)alkyl, or —CH$_2$N(alkyl)$_2$, -alkyl, -cycloalkyl, -aryl, -heteroaryl, -heterocyclyl, -alkylcycloalkyl -alkylaryl, -alkylheteroaryl, or -alkylheterocyclyl, wherein a hydrogen atom bound to any -aryl or -heteroaryl carbon atomis optionally replaced by $R^{11}$ and a hydrogen atom bound to any nitrogen atom is optionally replaced by $R^1$; and each $R^{11}$ is independently —OH, —SH, —F, —Cl, —Br, —I, —NO$_2$, —CN, —NH$_2$, —CO$_2$H, —C(O)NH$_2$, —N(H)C(O)H, —N(H)C(O)NH$_2$, -alkyl, -cycloalkyl, -perfluoroalkyl, —O-alkyl, —O-aryl, —O-alkylaryl, —N(H)alkyl, —N(H)aryl, —N(H)-alkylaryl, —N(alkyl)$_2$, —C(O)N(H)alkyl, —C(O)N(alkyl)$_2$, —N(H)C(O)alkyl, —N(H)C(O)N(H)alkyl, —N(H)C(O)N(alkyl)$_2$, —S-alkyl, —S-aryl, —S-alkylaryl, —S(O)$_2$alkyl, —S(O)alkyl, —C(O)alkyl, —CH$_2$NH$_2$, —CH$_2$N(H)alkyl, or —CH$_2$N(alkyl)$_2$.

In an alternative form of embodiment A:

$R^1$ is H, —$R^8$, —C(O)$R^8$, —C(O)C(O)$R^8$, —S(O)$_2R^8$, —S(O)$R^8$, —C(O)O$R^8$, —C(O)N(H)$R^8$, —S(O)$_2$N(H)—$R^8$, —S(O)N(H)—$R^8$, —C(O)C(O)N(H)$R^8$, —C(O)CH=CH$R^8$, —C(O)CH$_2$O$R^8$, —C(O)CH$_2$N(H)$R^8$, —C(O)N($R^8$)$_2$, —S(O)$_2$N($R^8$)$_2$, —S(O)N($R^8$)$_2$, —C(O)C(O)N($R^8$)$_2$, —C(O)CH$_2$N($R^8$)$_2$, —CH$_2R^8$, —CH$_2$-alkenyl-$R^8$, or —CH$_2$-alkynyl-$R^8$;

$R^2$ is —H and each $R^3$ is independently —H, an amino acid side chain, —$R^8$, alkenyl-$R^9$, or alkynyl-$R^9$, or each $R^3$, together with the atom to which they are bound, form a 3 to 7 membered cyclic or heterocyclic cyclic ring system, or $R^2$ and one $R^3$ together with the atoms to which they are bound, form a 3 to 7 membered cyclic or heterocyclic ring system, wherein a hydrogen atom bound to any -alkyl or -cycloalkyl carbon atom is optionally replaced by —$R^{10}$, a hydrogen atom bound to any--aryl or -heteroaryl carbon atom is optionally replaced by —$R^{11}$, a hydrogen atom bound to any nitrogen atom of the ring system is optionally replaced by —$R^1$;

each $R^{10}$ is independently —OH, —SH, —F, —Cl, —Br, —I, —NO$_2$, —CN, —NH$_2$, —CO$_2$H, —C(O)NH$_2$, —N(H)C(O)H, —N(H)C(O)NH$_2$, -perfluoroalkyl, —O-alkyl, —O-aryl, —O-alkylaryl, —N(H)alkyl, —N(H)aryl, —N(H)-alkylaryl, —N(alkyl)$_2$, —C(O)N(H)alkyl, —C(O)N(alkyl)$_2$, —N(H)C(O)alkyl, —N(H)C(O)Oalkyl, —N(H)C(O)Oaryl, —N(H)C(O)Oalkylaryl, —N(H)C(O)Oheteroaryl, —N(H)C(O)Oalkylheteroaryl, —N(H)C(O)Ocycloalkyl, —N(H)C(O)N(H)alkyl, —N(H)C(O)N(alkyl)$_2$, —N(H)C(O)N(H)aryl, —N(H)C(O)N(H)alkylaryl, —N(H)C(O)N(H)heteroaryl, —N(H)C(O)N(H)alkylheteroaryl, —N(H)C(O)N(H)cycloalkyl, —S-alkyl, —S-aryl, —S-alkylaryl, —S(O)$_2$alkyl, —S(O)alkyl, —C(O)alkyl, —CH$_2$NH$_2$, —CH$_2$N(H)alkyl, or —CH$_2$N(alkyl)$_2$, -alkyl, -cycloalkyl, -aryl, -heteroaryl, -heterocyclyl, -alkylcycloalkyl -alkylaryl, -alkylheteroaryl, or -alkylheterocyclyl, wherein a hydrogen atom bound to any -aryl or -heteroaryl carbon atom is optionally replaced by $R^{11}$ and a hydrogen atom bound to any nitrogen atom is optionally replaced by $R^1$; and the other substituents are as defined above.

Preferably, in any of the above embodiments:
m is 0;
$R^2$ is —H;
one $R^3$ is —H and the other $R^3$ is —$R^8$, -alkenyl-$R^9$, or -alkynyl-$R^9$; or $R^4$ and one $R^5$ together with the atoms to which they are bound form a 3 to 7 membered cyclic or heterocyclic ring system, wherein a hydrogen atom bound to any -alkyl or -cycloalkyl carbon atom is optionally replaced by $R^{10}$, a hydrogen atom bound to any -aryl or -heteroaryl carbon atom is optionally replaced by $R^{11}$, and a hydrogen atom bound to any nitrogen atom of the ring system is optionally replaced with $R^1$, wherein the ring system is:

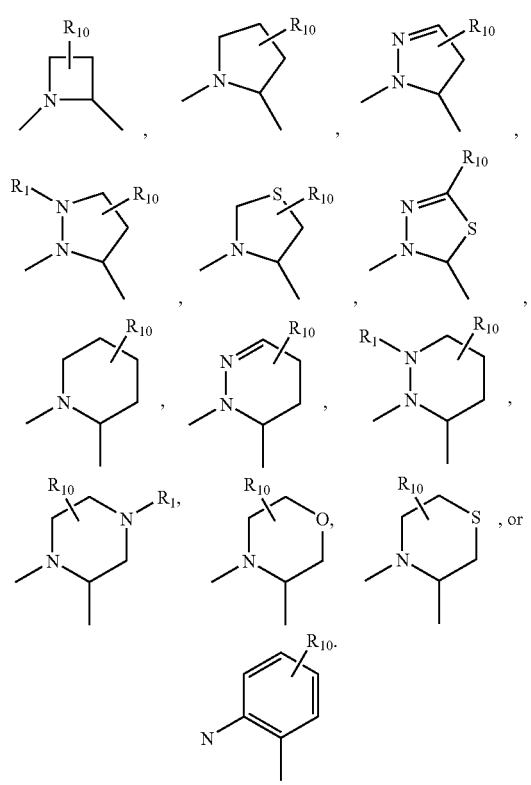

In an alternative preferred embodiment, X is C($R^3$)$_2$ or one $R^3$ is an amino acid side chain, —$R^8$, alkenyl-$R^9$, or alkynyl-$R^9$.

More preferably, one $R^3$ is —H and the other $R^3$ is -alkyl; or $R^4$ and one $R^5$ together with the atoms to which they are bound form a 3 to 7 membered cyclic or heterocyclic ring system, wherein any hydrogen atom bound to a carbon atom of the ring system is optionally replaced by $R^{10}$ and any hydrogen atom bound to a nitrogen atom of the ring system is optionally replaced by $R^1$, selected from:

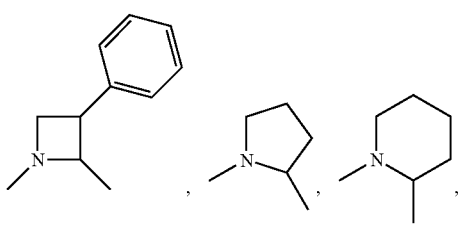

-continued

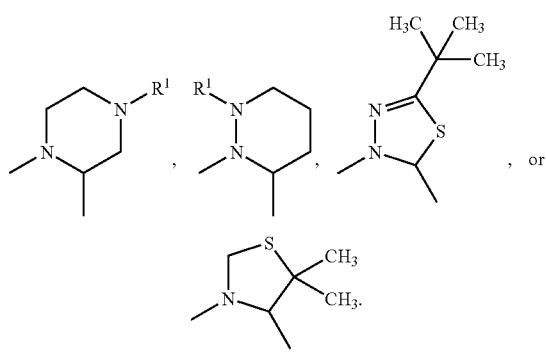

Most preferably, one $R^3$ is —H and the other $R^3$ is —C(H)(CH$_3$)$_2$ or —C(CH$_3$)$_3$; and $R^4$ and one $R^5$ together with the atoms to which they are bound form a 3 to 7 membered cyclic or heterocyclic ring system, wherein any hydrogen atom bound to a carbon atom of the ring system is optionally replaced by $R^{10}$ and any hydrogen atom bound to a nitrogen atom of the ring system is optionally replaced by $R^1$, selected from:

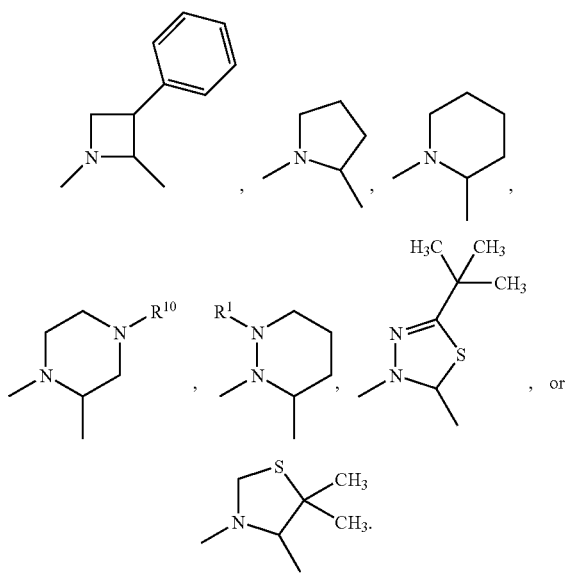

In an alternative most preferred embodiment, one $R^3$ is —H and the other $R^3$ is —CH$_3$, —C(H) (CH$_3$)$_2$ or —C(CH$_3$)$_3$ and $R^4$ and $R^5$ are as defined directly above.

According to another embodiment B, the present invention provides a compound of formula I, wherein Y is:

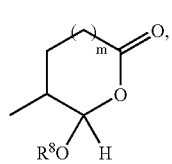

-continued

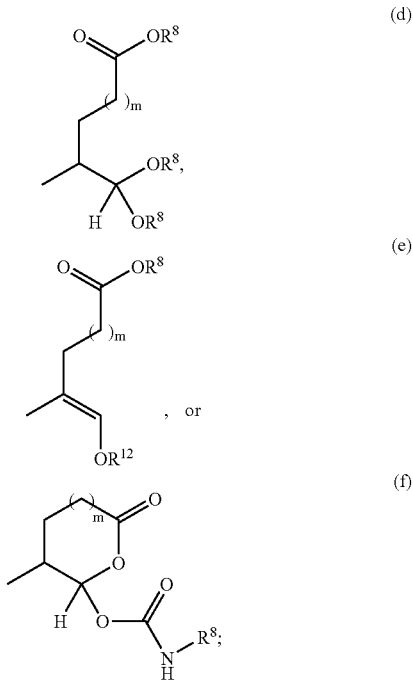

provided that when $R^6$ is not hydrogen, $R^6$ and Y, together with the nitrogen to which they are bound, form a ring (g):

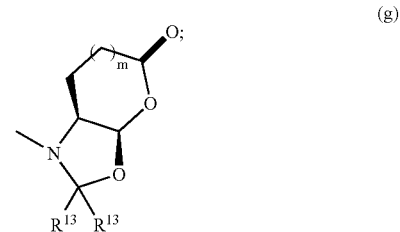

$R^{12}$ is —C(O)alkyl, —C(O)cycloalkyl, —C(O)alkenyl, —C(O)alkynyl, —C(O)alkylaryl, —C(O)alkylheteroaryl, —C(O)heterocyclyl, or —C(O)alkylheterocyclyl;

$R^{13}$ is —H, -alkyl, -aryl, -alkylaryl or -alkylheteroaryl; and the other substituents are as described above.

Preferably, in (c), (d), (e), or (f), $R^8$ is methyl, ethyl, n-propyl, isopropyl, cyclopentyl, phenethyl, or benzyl.

Preferred definitions for the other individual components of embodiment B are the same as those set forth above for embodiment A.

A preferred embodiment C of this invention provides compounds of formula I:

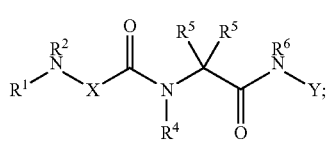

wherein:

Y is:

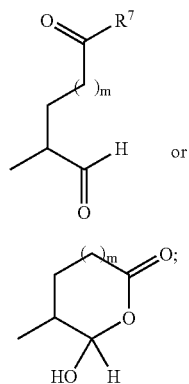

m is 0 or 1;

X is —C(R$^3$)$_2$—

R$^1$ is H, —R$^8$, —C(O)R$^8$, —C(O)C(O)R$^8$, —S(O)$_2$R$^8$, —S(O)R$^8$, —C(O)OR$^8$, —C(O)N(H)R$^8$, —S(O)$_2$N(H)—R$^8$, —S(O)N(H)—R$^8$, —C(O)C(O)N(H)R$^8$, —C(O)CH=CHR$^8$, —C(O)CH$_2$OR$^8$, —C(O)CH$_2$N(H)R$^8$, —C(O)N(R$^8$)$_2$, —S(O)$_2$N(R$^8$)$_2$, —S(O)N(R$^8$)$_2$, —C(O)C(O)N(R$^8$)$_2$, —C(O)CH$_2$N(R$^8$)$_2$, —CH$_2$R$^8$, —CH$_2$-alkenyl-R$^8$, or —CH$_2$-alkynyl-R$^8$;

R$^2$ is —H and each R$^3$ is independently —H, an amino acid side chain, —R$^8$, alkenyl-R$^9$, or alkynyl-R$^9$, or each —R$^3$ together with the atom to which they are bound, form a 3 to 7 membered cyclic or heterocyclic ring system, wherein a hydrogen atom bound to any -alkyl or -cycloalkyl carbon atom is optionally replaced by —R$^{10}$, a hydrogen atom bound to any -aryl or -heteroaryl carbon atom is optionally replaced by —R$^{11}$, a hydrogen atom bound to any nitrogen atom of the ring system is optionally replaced by —R$^1$;

R$^4$ is —H and each R$^5$ is independently —H, an amino acid side chain, —R$^8$, -alkenyl-R$^9$, or -alkynyl-R$^9$, or R$^4$ and one R$^5$ together with the atoms to which they are bound form a 3 to 7 membered cyclic or heterocyclic ring system, wherein a hydrogen atom bound to any -alkyl or -cycloalkyl carbon atom is optionally replaced by R$^{10}$, a hydrogen atom bound to any -aryl or -heteroaryl carbon atom is optionally replaced by R$^{11}$, and a hydrogen atom bound to any nitrogen atom of the ring system is optionally replaced with R$^1$;

R$^6$ is —H;

R$^7$ is —OH, —OR$^8$, —N(H)OH, or —N(H)S(O)$_2$R$^8$;

each R$^8$ is independently -alkyl, -cycloalkyl, -aryl, -heteroaryl, -heterocyclyl, -alkylcycloalkyl -alkylaryl, -alkylheteroaryl, or -alkylheterocyclyl, wherein a hydrogen atom bound to any -alkyl or -cycloalkyl carbon atom is optionally replaced by R$^{10}$, a hydrogen atom bound to any -aryl or -heteroaryl carbon atom is optionally replaced by R$^{11}$, and a hydrogen atom bound to any nitrogen atom is optionally replaced by R$^1$;

each R$^9$ is independently -aryl, -heteroaryl, cycloalkyl, or -heterocyclyl, wherein a hydrogen atom bound to any -alkyl or -cycloalkyl carbon atom is optionally replaced by R$^{10}$, a hydrogen atom bound to any -aryl or -heteroaryl carbon atom is optionally replaced by R$^{11}$, and a hydrogen atom bound to any nitrogen atom is optionally replaced by R$^1$;

each R$^{10}$ is independently —OH, —SH, —F, —Cl, —Br, —I, —NO$_2$, —CN, —NH$_2$, —CO$_2$H, —C(O)NH$_2$, —N(H)C(O)H, —N(H)C(O)NH$_2$, -perfluoroalkyl, —O-alkyl, —O-aryl, —O-alkylaryl, —N(H)alkyl, —N(H)aryl, —N(H)-alkylaryl, —N(alkyl)$_2$, —C(O)N(H)alkyl, —C(O)N(alkyl)$_2$, —N(H)C(O)alkyl, —N(H)C(O)Oalkyl, —N(H)C(O)Oaryl, —N(H)C(O)Oalkylaryl, —N(H)C(O)Oheteroaryl, —N(H)C(O)Oalkylheteroaryl, —N(H)C(O)Ocycloalkyl, —N(H)C(O)N(H)alkyl, —N(H)C(O)N(alkyl)$_2$, —N(H)C(O)N(H)aryl, —N(H)C(O)N(H)alkylaryl, —N(H)C(O)N(H)heteroaryl, —N(H)C(O)N(H)alkylheteroaryl, —N(H)C(O)N(H)cycloalkyl, —S-alkyl, —S-aryl, —S-alkylaryl, —S(O)$_2$alkyl, —S(O)alkyl, —C(O)alkyl, —CH$_2$NH$_2$, —CH$_2$N(H)alkyl, or —CH$_2$N(alkyl)$_2$, -alkyl, -cycloalkyl, -aryl, -heteroaryl, -heterocyclyl, -alkylcycloalkyl -alkylaryl, -alkylheteroaryl, or -alkylheterocyclyl, wherein a hydrogen atom bound to any -aryl or -heteroaryl carbon atom is optionally replaced by R$^{11}$ and a hydrogen atom bound to any nitrogen atom is optionally replaced by R$^1$; and each R$^{11}$ is independently —OH, —SH, —F, —Cl, —Br, —I, —NO$_2$, —CN, —NH$_2$, —CO$_2$H, —C(O)NH$_2$, —N(H)C(O)H, —N(H)C(O)NH$_2$, -alkyl, -cycloalkyl, -perfluoroalkyl, —O-alkyl, —O-aryl, —O-alkylaryl, —N(H)alkyl, —N(H)aryl, —N(H)-alkylaryl, —N(alkyl)$_2$, —C(O)N(H)alkyl, —C(O)N(alkyl)$_2$, —N(H)C(O)alkyl, —N(H)C(O)N(H)alkyl, —N(H)C(O)N(alkyl)$_2$, —S-alkyl, —S-aryl, —S-alkylaryl, —S(O)$_2$alkyl, —S(O)alkyl, —C(O)alkyl, —CH$_2$NH$_2$, —CH$_2$N(H)alkyl, or —CH$_2$N(alkyl)$_2$;

provided that if one R$^3$ is —H, then the other R$^3$ is not —H.

Another preferred embodiment D of the present invention provides a compound of formula I, wherein Y is:

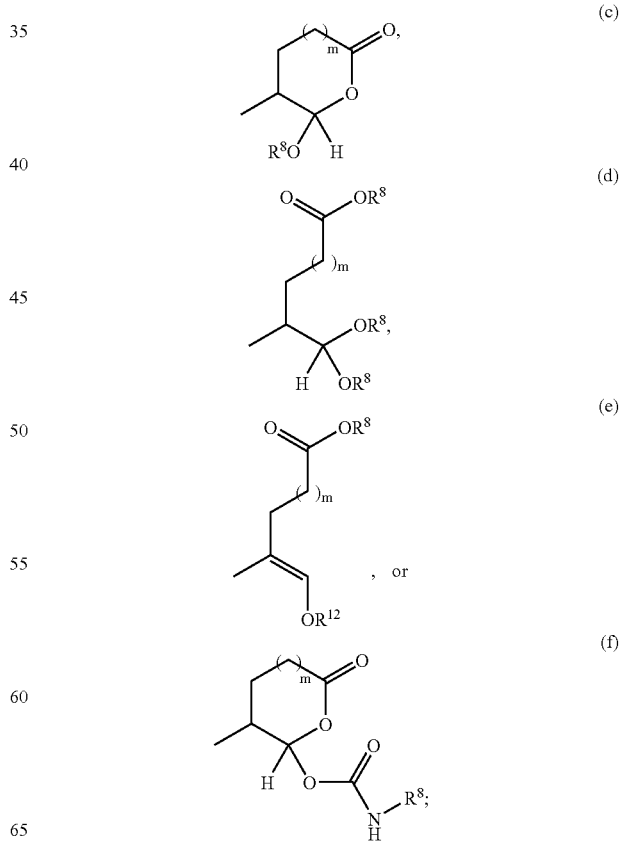

$R^{12}$ is —C(O)alkyl, —C(O)cycloalkyl, —C(O)alkenyl, —C(O)alkynyl, —C(O)alkylaryl, —C(O)alkylheteroaryl, —C(O)heterocyclyl, or —C(O)alkylheterocyclyl;

the other substituents are as described above except that both of the $R^3$ groups may be —H.

In any of embodiments A-D, preferred compounds are those wherein:

$R^1$ is —C(O)$R^8$ or —C(O)C(O)$R^8$;

$R^2$ and one $R^3$ are both —H and the other $R^3$ is an amino acid side chain, —$R^8$, alkenyl-$R^9$, or alkynyl-$R^9$; or $R^4$ and one $R^5$ together with the atoms to which they are bound form a ring system selected from:

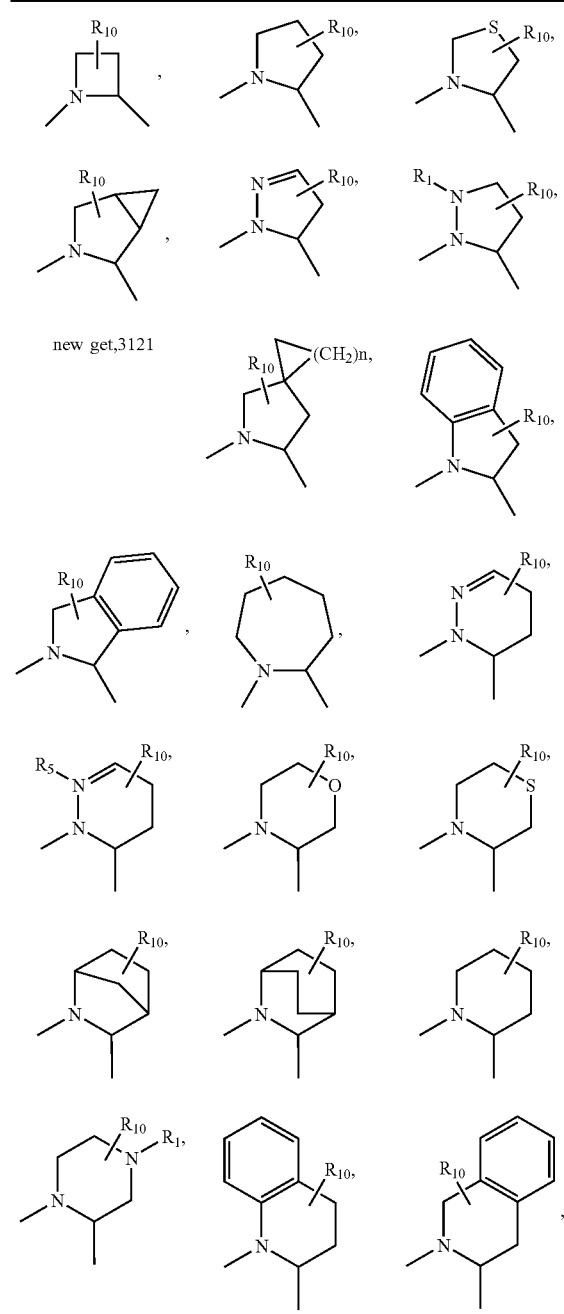

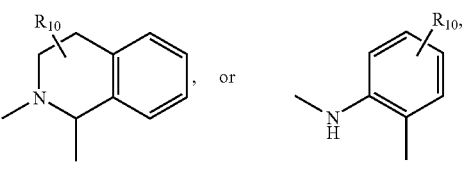

provided that each of the ring systems are optionally substituted with one or more $R^{10}$ groups.

Alternatively, preferred compounds of embodiments A-D are those wherein $R^3$ is —H and the other $R^3$ is methyl, isopropyl, tert-butyl, —CH$_2$S$R^8$, —CH$_2$SO$_2$$R^8$, —CH$_2$CH$_2$S$R^8$, —CH$_2$CH$_2$SO$_2$$R^8$.

More preferred compounds of embodiments A-D are those wherein $R^4$ and one $R^5$ together with the atoms to which they are bound form the ring system:

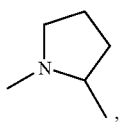

and the other $R^5$ is H; or one $R^3$ is —H and the other $R^3$ is methyl.

Alternatively, more preferred compounds of embodiments A-D are those wherein $R^4$ and one $R^5$ together with the atoms to which they are bound form the ring system:

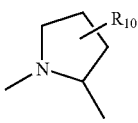

and the other $R^5$ is H.

In the above alternative embodiment, $R^{10}$ is preferably, 4-fluoro or 4,4-difluoro.

Most preferred compounds of this invention are those wherein $R^3$ is methyl; and $R^4$ and one $R^5$ together with the atoms to which they are bound form the ring system:

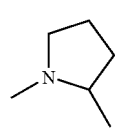

and the other $R^5$ is H.

Alternatively, most preferred compounds of embodiments A-D are those wherein $R^3$ is methyl; and $R^4$ and one $R^5$ together with the atoms to which they are bound form the ring system:

and

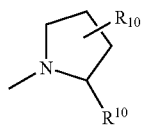

the other R⁵ is H; and is 4-fluoro or 4,4-difluoro.

Preferred compounds of embodiments (B) or (D) are those wherein Y is:

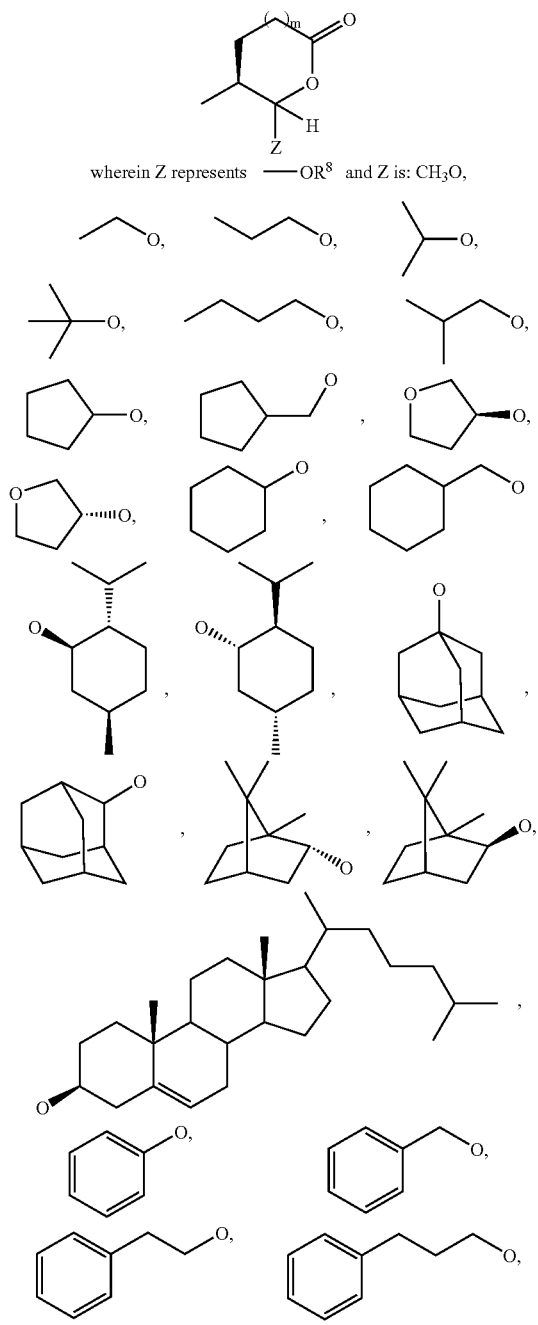

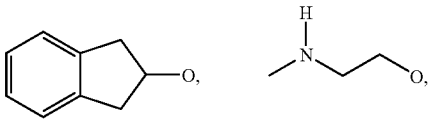

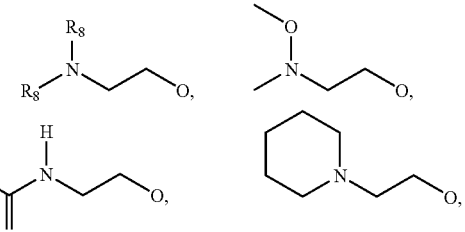

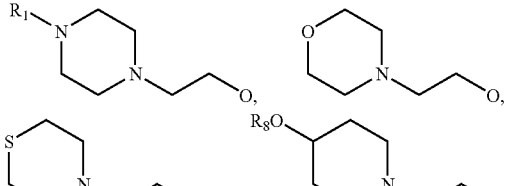

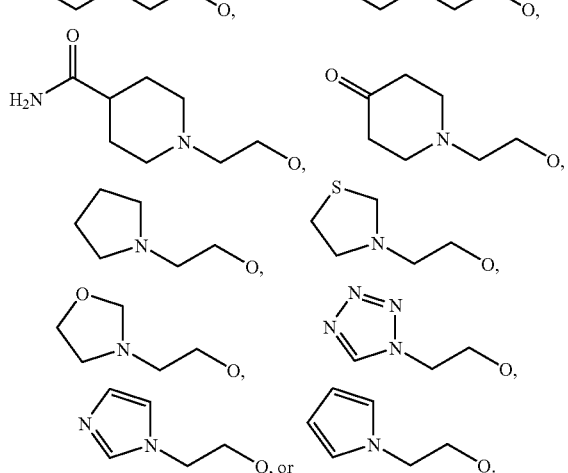

Specific compounds of this invention include, but are not limited to, Examples 5a-5bd, 7a-7at, 9a-9g, 15a-15f, 16a-16b, 17a-17e, 18a-18f, 20a-20t, 23a-23i, 24a-24e, 25a-25e, 26a-26h, 27a-27n, 28a-28c, 29a-29s, 32a-32e, 34, G1, G2, 41, 42, 45, 46, 51, 52, 56, 57, 60, 61, 64, 65, 68, 69, 72, 73, 76-93, 98a-z, aa-az, and ba-bb, 101, 102a, 102b, 108a-d, 110, 111, 116a-h, 120a and b, 121, 122 a-v, and 123 a-c.

The compounds of this invention may contain one or more "asymmetric" carbon atoms and thus may occur as racemates and racemic mixtures, single enantiomers, diastereomeric mixtures and individual diastereomers. Each stereogenic carbon may be of the R or S configuration. Although specific compounds and scaffolds exemplified in this application may be depicted in a particular stereochemical configuration, compounds and scaffolds having either the opposite stereochemistry at any given chiral center or mixtures thereof are also envisioned.

All such isomeric forms of these compounds are expressly included in the present invention, as well as pharmaceutically acceptable derivative thereof.

The term "pharmaceutically acceptable derivative" means any pharmaceutically acceptable salt, ester, or salt of such ester, of a compound of this invention or any other compound which, upon administration to a recipient, is capable of providing (directly or indirectly) a compound of this invention or an active metabolite or residue thereof.

Pharmaceutically acceptable salts of the compounds of this invention include, for example, those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, formic, benzoic, malonic, naphthalene-2-sulfonic and benzenesulfonic acids. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium), alkaline earth metal (e.g., magnesium), ammonium and $N-(C_{1-4}alkyl)_4^+$ salts.

This invention also envisions the "quaternization" of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

When multiply substituted, each substituent may be picked independently of any other substituent as long as the combination of substituents results in the formation of a stable compound.

Combinations of substituents and variables envisioned by this invention are only those that result in the formation of stable compounds. The term "stable", as used herein, refers to compounds which possess stability sufficient to allow manufacture and administration to a mammal by methods known in the art. Typically, such compounds are stable at a temperature of 40° C. or less, in the absence of moisture or other chemically reactive conditions, for at least a week.

Preferred compounds of this invention may be readily absorbed by the bloodstream of patients upon oral administration. This oral availability makes such compounds excellent agents for orally-administered treatment and prevention regimens against IL-1-, apoptosis-, IGIF-, or IFN-γ-mediated diseases.

It should be understood that the compounds of this invention may exist in various equilibrium forms, depending on conditions including choice of solvent, pH, and others known to the practitioner skilled in the art. All such forms of these compounds are expressly included in the present invention. In particular, many of the compounds of this invention, especially those which contain aldehyde or ketone groups and carboxylic acid groups in Y, may take hemi-acetal or hydrated forms. For example, compounds of embodiment A are in a hemiacetal form when Y is:

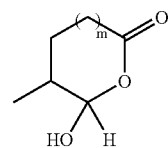

Depending on the choice of solvent and other conditions known to the practitioner skilled in the art, compounds of this invention may also take hydrated, acyloxy acetal, acetal, or enol forms. For example, compounds of this invention are in hydrated forms when Y is:

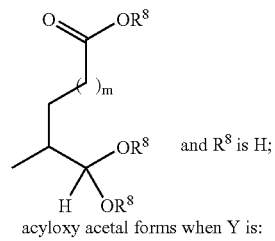

and $R^8$ is H;

acyloxy acetal forms when Y is:

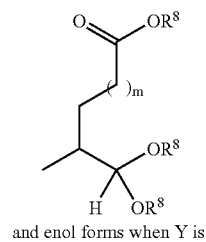

acetal forms when Y is and $R^8$ is other than H:

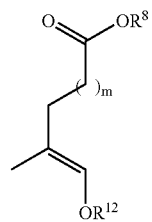

and enol forms when Y is:

In addition, it should be understood that the equilibrium forms of the compounds of this invention may include tautomeric forms. All such forms of these compounds are expressly included in the present invention.

The compounds of formula I may be synthesized using conventional techniques. Advantageously, these compounds are conveniently synthesized from readily available starting materials.

Compounds of this invention may be prepared using the processes described herein. As can be appreciated by the skilled practitioner, these processes are not the only means by which the compounds described and claimed in this application may be synthesized. Further methods will be evident to those of ordinary skill in the art. Additionally, the various synthetic steps described herein may be performed in an alternate sequence or order to give the desired compounds.

It should be understood that the compounds of this invention may be modified by appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion. In addition, the compounds may be altered to pro-drug form such that the desired compound is created in the body of the patient as the result of the action of metabolic or other biochemical processes on the pro-drug. Such pro-drug forms typically demonstrate little or no activity in in vitro assays. Some examples of pro-drug forms include ketal, acetal, oxime, imine and hydrazone forms of compounds which contain ketone or aldehyde groups, especially where they occur in the Y group of the compounds of-this invention. Other examples of pro-drug forms include the hemi-ketal, hemi-acetal, acyloxy ketal, acyloxy acetal, ketal, acetal and enol forms that are described herein.

Compositions and Methods

The compounds of this invention are caspase inhibitors, and in particular ICE inhibitors. Accordingly, these compounds are capable of targeting and inhibiting events in IL-1-, apoptosis-, IGIF-, and IFN-γ-mediated diseases, and, thus, the ultimate activity of that protein in inflammatory diseases, autoimmune diseases, destructive bone, proliferative disorders, infectious diseases, and degenerative diseases. For example, the compounds of this invention inhibit the conversion of precursor IL-1β to mature IL-1β by inhibiting ICE. Because ICE is essential for the production of mature IL-1, inhibition of that enzyme effectively blocks initiation of IL-1-mediated physiological effects and symptoms, such as inflammation, by inhibiting the production of mature IL-1. Thus, by inhibiting IL-1β precursor activity, the compounds of this invention effectively function as IL-1 inhibitors.

Compounds of this invention also inhibit conversion of pro-IGIF into active, mature IGIF by inhibiting ICE. Because ICE is essential for the production of mature IGIF, inhibition of ICE effectively blocks initiation of IGIF-mediated physiological effects and symptoms, by inhibiting production of mature IGIF. IGIF is in turn essential for the production of IFN-γ. ICE therefore effectively blocks initiation of IFN-γ-mediated physiological effects and symptoms, by inhibiting production of mature IGIF and thus production of IFN-γ.

The compounds of this invention are surprisingly bioavailable when compared with peptidyl inhibitors, such as those described in, for example, EP 618 223, EP 623 592, WO 93/09135, WO 93/16710, U.S. Pat. No. 5,434,248, WO 95/35308, or WO 96/33209. Thus, the pharmaceutical compositions and methods of this invention will be useful for controlling caspase activity in vivo. The compositions and methods of this invention will therefore be useful for controlling IL-1, IGIF, or IFN-γ levels in vivo and for treating or reducing the advancement, severity or effects of IL-1-, apoptosis-, IGIF-, or IFN-γ-mediated conditions, including diseases, disorders or effects.

Pharmaceutical compositions of this invention comprise a compound of formula I or a pharmaceutically acceptable salt thereof and a pharmaceutically acceptable carrier. Such compositions may optionally comprise an additional therapeutic agent. Such agents include, but are not limited to, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound.

The term "pharmaceutically acceptable carrier" refers to a non-toxic carrier that may be administered to a patient, together with a compound of this invention, and which does not destroy the pharmacological activity thereof.

Pharmaceutically acceptable carriers that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, wool fat and self-emulsifying drug delivery systems (SEDDS) such α-tocopherol, polyethyleneglycol 1000 succinate, or other similar polymeric delivery matrices.

In pharmaceutical composition comprising only a compound of embodiments A-D as the active component, methods for administering these compositions may additionally comprise the step of administering to the subject an additional agent. Such agents include, but are not limited to, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound.

The term "pharmaceutically effective amount" refers to an amount effective in treating or ameliorating an IL-1-, apoptosis-, IGIF-, or IFN-γ-mediated disease in a patient. The term "prophylactically effective amount" refers to an amount effective in preventing or substantially lessening IL-1-, apoptosis-, IGIF-, or IFN-γ-mediated diseases in a patient.

The compounds of this invention may be employed in a conventional manner for controlling IGIF and IFN-γ levels in vivo and for treating diseases or reducing the advancement or severity of effects which are mediated by IL-1, apoptosis, IGIF, or IFN-γ. Such methods of treatment, their dosage levels and requirements may be selected by those of ordinary skill in the art from available methods and techniques.

For example, a compound of this invention may be combined with a pharmaceutically acceptable adjuvant for administration to a patient suffering from an IL-1-, apoptosis-, IGIF-, or IFN-γ-mediated disease in a pharmaceutically acceptable manner and in an amount effective to lessen the severity of that disease.

Alternatively, the compounds of this invention may be used in compositions and methods for treating or protecting individuals against IL-1, apoptosis-, IGIF, or IFN-γ mediated diseases over extended periods of time. The compounds may be employed in such compositions either alone or together with other compounds of this invention in a manner consistent with the conventional utilization of enzyme. inhibitors in pharmaceutical compositions. For example, a compound of this invention may be combined with pharmaceutically acceptable adjuvants conventionally employed in vaccines and administered in prophylactically effective amounts to protect individuals over an extended period of time against IL-1-, apoptosis-, IGIF, or IFN-γ mediated diseases.

The compounds of formula I may also be co-administered with other caspase or ICE inhibitors to increase the effect of therapy or prophylaxis against various IL-1-, apoptosis-, IGIF-, or IFN-γ mediated diseases.

In addition, the compounds of this invention may be used in combination either conventional anti-inflammatory agents or with matrix metalloprotease inhibitors, lipoxygenase inhibitors and antagonists of cytokines other than IL-1β.

The compounds of this invention can also be administered in combination with immunomodulators (e.g., bropirimine, anti-human alpha-interferon antibody, IL-2, GM-CSF, methionine enkephalin, interferon-alpha, diethyldithiocarbamate, tumor necrosis factor, naltrexone and EPO), with prostaglandins, or with antiviral agents (e.g., 3TC, polysulfated polysaccharides, ganiclovir, ribavirin, acyclovir, alpha interferon, trimethotrexate and fancyclovir) or prodrugs of these or related compounds to prevent or combat IL-1-mediated disease symptoms such as inflammation.

When the compounds of this invention are administered in combination therapies with other agents, they may be administered sequentially or concurrently to the patient. Alternatively, pharmaceutical or prophylactic compositions according to this invention comprise a combination of a compound of formula I and another therapeutic or prophylactic agent.

The pharmaceutical compositions of this invention may be administered orally, parenterally, by inhalation spray, topically, rectally, nasally, buccally, vaginally or via an implanted reservoir. We prefer oral administration. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as those described in Pharmacopeia Helvetica, or a similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and solutions and propylene glycol are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical -composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-administered transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 100 mg/kg body weight per day, preferably between 0.5 and about 75 mg/kg body weight per day and most preferably between about 1 and 50 mg/kg body weight per day of the active ingredient compound are useful in a monotherapy for the prevention and treatment of IL-1-, apoptosis-, IGIF-, and IFN-γ mediated diseases, including inflammatory diseases, autoimmune diseases, destructive bone disorders, proliferative disorders, infectious diseases, degenerative diseases, necrotic diseases, inflammatory peritonitis, osteoarthritis, acute pancreatitis, chronic pancreatitis, asthma, adult respiratory distress syndrome, glomerulonephritis, rheumatoid arthritis, systemic lupus erythematosus, scleroderma, chronic thyroiditis, Graves' disease, autoimmune gastritis, insulin-dependent diabetes mellitus (Type I), autoimmune hemolytic anemia, autoimmune neutropenia, thrombocytopenia, chronic active hepatitis, myasthenia gravis, inflammatory bowel disease, Crohn's disease, psoriasis, atopic dermatitis, graft vs. host disease, osteoporosis, multiple myeloma-related bone disorder, leukemias and related disorders, myelodysplastic syndrome, acute myelogenous leukemia, chronic myelogenous leukemia, metastatic melanoma, Kaposi's sarcoma, multiple myeloma, sepsis, septic shock, Shigellosis, Alzheimer's disease, Parkinson's disease, cerebral ischemia, myocardial ischemia, spinal muscular atrophy, multiple sclerosis, AIDS-related encephalitis, HIV-related encephalitis, aging, alopecia, neurological damage due to stroke, ulcerative collitis, infectious hepatitis, juvenile diabetes, lichenplanus, acute dermatomyositis, eczema, primary cirrhosis, uveitis, Behcet's disease, atopic skin disease, pure red cell aplasia, aplastic anemia, amyotrophic lateral sclerosis, nephrotic syndrome and systemic diseases or diseases with effects localized in the liver or other organs having an inflammatory or apoptotic component caused by excess dietary alcohol intake or viruses, such as HBV, HCV, HGV, yellow fever virus, dengue fever virus, and Japanese encephalitis virus.

Typically, the pharmaceutical compositions of this invention will be administered from about 1 to 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of a compound of formula I and one or more additional therapeutic or prophylactic agents, both the compound and the additional agent should be present at dosage levels of between about 10% to 80% of the dosage normally administered in a monotherapy regime.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence or disease symptoms.

As the skilled artisan will appreciate, lower or higher doses than those recited above may be required. Specific dosage and treatment regimens for any-particular patient will depend upon a variety of factors, including the activity of the specific compound employed, the age, body weight, general health status, sex, diet, time of administration, rate of excretion, drug combination, the severity and course of the disease, and the patient's disposition to the disease and the judgment of the treating physician.

IL-1 or apoptosis mediated diseases which may be treated or prevented by the compounds of this invention include, but are not limited to, inflammatory diseases-, autoimmune diseases, proliferative disorders, infectious diseases, and degenerative diseases. The apoptosis-mediated diseases which may be treated or prevented by the compounds of this invention include degenerative diseases.

IL-1 or apoptosis mediated inflammatory diseases which may be treated or prevented include, but are not limited to, osteoarthritis, acute pancreatitis, chronic pancreatitis, asthma, and adult respiratory distress syndrome. Preferably the inflammatory disease is osteoarthritis or acute pancreatitis.

IL-1 or apoptosis mediated autoimmune diseases which may be treated or prevented include, but are not limited to, glomerulonephritis, rheumatoid arthritis, systemic lupus erythematosus, scleroderma, chronic thyroiditis, Graves' disease, autoimmune gastritis, insulin-dependent diabetes mellitus (Type I), autoimmune hemolytic anemia, autoimmune neutropenia, thrombocytopenia, chronic active hepatitis, myasthenia gravis, multiple sclerosis, inflammatory bowel disease, Crohn's disease, psoriasis, atopic dermatitis and graft vs. host disease. Preferably the autoimmune disease is rheumatoid arthritis, inflammatory bowel disease, Crohn's disease, psoriasis, or atopic dermatitis.

IL-1 or apoptosis mediated destructive bone disorders which may be treated or prevented include, but are not limited to, osteoporosis and multiple myeloma-related bone disorder.

IL-1 or apoptosis mediated proliferative diseases which may be treated or prevented include, but are not limited to, leukemias and related disorders, such as myelodysplastic syndrome, acute myelogenous leukemia, chronic myelogenous leukemia, metastatic melanoma, Kaposi's sarcoma, and multiple myeloma.

IL-1 or apoptosis mediated infectious diseases which may be treated or prevented include, but are not limited to, sepsis, septic shock, and Shigellosis.

IL-1 or apoptosis mediated degenerative or necrotic diseases which may be treated or prevented by the compounds of this invention include, but are not limited to, Alzheimer's disease, Parkinson's disease, cerebral ischemia, and myocardial ischemia.

Preferably, the degenerative disease is Alzheimer's disease.

IL-1 or apoptosis-mediated degenerative diseases which may be treated or prevented by the compounds of this invention include, but are not limited to, Alzheimer's disease, Parkinson's disease, cerebral ischemia, myocardial ischemia, spinal muscular atrophy, multiple sclerosis, AIDS-related encephalitis, HIV-related encephalitis, aging, alopecia, and neurological damage due to stroke.

Other diseases having an inflammatory or apoptotic component may be treated or prevented by the compounds of this invention. Such diseases may be systemic diseases or diseases with effects localized in the liver or other organs and may be caused by, for example, excess dietary alcohol intake or viruses, such as HBV, HCV, HGV, yellow fever virus, dengue fever virus, and Japanese encephalitis virus.

IGIF- or IFN-γ-mediated diseases which may be treated or prevented by the compounds of this invention include, but are not limited to, inflammatory, infectious, autoimmune, proliferative, neurodegenerative and necrotic conditions.

IGIF- or IFN-γ-mediated inflammatory diseases which may be treated or prevented include, but are not limited to osteoarthritis, acute pancreatitis, chronic pancreatitis, asthma, rheumatoid arthritis, inflammatory bowel disease, Crohn's disease, ulcerative collitis, cerebral ischemia, myocardial ischemia and adult respiratory distress syndrome. Preferably, the inflammatory disease is rheumatoid arthritis, ulcerative collitis, Crohn's disease, hepatitis or adult respiratory distress syndrome.

IGIF- or IFN-γ-mediated infectious diseases which may be treated or prevented include, but are not limited to infectious hepatitis, sepsis, septic shock and Shigellosis.

IGIF- or IFN-γ-mediated autoimmune diseases which may be treated or prevented include, but are not limited to glomerulonephritis, systemic lupus erythematosus, scleroderma, chronic thyroiditis, Graves' disease, autoimmune gastritis, insulin-dependent diabetes mellitus (Type I), juvenile diabetes, autoimmune hemolytic anemia, autoimmune neutropenia, thrombocytopenia, myasthenia gravis, multiple sclerosis, psoriasis, lichenplanus, graft vs. host disease, acute dermatomyositis, eczema, primary cirrhosis, hepatitis, uveitis, Behcet's disease, atopic skin disease, pure red cell aplasia, aplastic anemia, amyotrophic lateral sclerosis and nephrotic syndrome. Preferably, the autoimmune disease is glomerulonephritis, insulin-dependent diabetes mellitus (Type I), juvenile diabetes, psoriasis, graft vs. host disease or hepatitis.

More preferred diseases which may be treated or prevented include rheumatoid arthritis, inflammatory bowel disease, including Crohn's disease and ulcerative colitis, inflammatory peritonitis, septic shock, pancreatitis, traumatic brain injury, organ transplant rejection, osteoarthritis, asthma, psoriasis, Alzeheimer's disease, atopic dermatitis, or leukemias and related disorders, such as myelodysplastic syndrome or multiple myeloma.

Accordingly, one embodiment of this invention provides a method for treating or preventing an IL-1 or apoptosis mediated disease in a subject comprising the step of administering to the subject any compound, pharmaceutical composition, or combination described herein and a pharmaceutically acceptable carrier.

Another embodiment of this invention provides a method for decreasing IGIF production in a subject comprising the step of administering to the subject any compound, pharmaceutical composition, or combination described herein and a pharmaceutically acceptable carrier.

Yet another embodiment of this invention provides a method for decreasing IFN-γ production in a subject comprising the step of administering to the subject any compound, pharmaceutical composition, or combination described herein and a pharmaceutically acceptable carrier.

Although this invention focuses on the use of the compounds disclosed herein for preventing and treating IL-1, apoptosis-, IGIF, and IFN-γ-mediated diseases, the compounds of this invention can also be used as inhibitory agents for other cysteine proteases.

The compounds of this invention are also useful as commercial reagents which effectively bind to caspases or other cysteine proteases including, but not limited to ICE. As commercial reagents, the compounds of this invention, and their derivatives, may be used to block proteolysis of a target peptide in biochemical or cellular assays for ICE and ICE homologs or may be derivatized to bind to a stable resin as a tethered substrate for affinity chromatography applications. These and other uses which characterize commercial cysteine protease inhibitors will be evident to those of ordinary skill in the art.

In order that this invention be more fully understood, the following examples are set forth. These examples are for the purpose of illustration only and are not to be construed as limiting the scope of the invention in any way.

General Methods

Analytical HPLC Conditions:
Column: C-18, Particle size: 5μ, Pore size: 100 Å,
Column size: 4.6×150 mm
Solvent A: 0.1% TFA/1% MeCN/98.9% water
Solvent B: 0.1% TFA/99.9% MeCN
Gradient: A to B over 20 min at a flow rate of 1 mL/min
Column: Cyano, Particle size: 5μ, Pore size: 100 Å,
Column size: 4.6×150 mm
Solvent A: 0.1% TFA/1% MeCN/98.9% water
Solvent B: 0.1% TFA/99.9% MeCN
Gradient: A/B=99%/1% to 50%/50% over 20 min at a flow rate of 1 mL/min HPLC Mass Spectral Analysis Mass Spectral Analysis: All mass spectral data were collected using a Micromass Quattro II triple quadrupole mass spectrometer (Beverly, Mass.) equipped with a cross-flow electrospray ionization source. The mass spectrometer was coupled to a HPLC system manufactured by Hewlett-Packard (HP1100). The autosampler for the system was a Gilson 215 (Middleton, Wis.) liquid handler. All of the equipment was controlled by the MassLynx software package purchased from Micromass.

Mass spectral analysis was performed by liquid chromatography-MS to determine purity and confirm molecular weight simultaneously. In instances where the sample purity had been determined by other means, a flow injection analysis (FIA) was used instead of the full chromatography analysis. In all cases, both positive and negative ion spectra were collected.

Mass Spectrum Acquisition Conditions: For all experiments, the mass spectrometer was configured in electrospray mode with the cross-flow counter electrode. A flow splitter was used to reduce the flow from the HPLC to 40% of the original flow. The inlet temperature was set to 140° C. and the drying gas flow was set to maximize signal. The resolution of the mass spectrometer was adjusted to 0.65 amu FWHM and data was collected in centroid mode. In positive ion mode, the cone voltage was set to 25V, the capillary voltage was. 3.8 kV. In negative ion mode, the cone voltage was set to 25 V and the capillary voltage was set to 3.5 kV. In both positive and negative ion mode, the time to acquire a full spectrum was 1 s with a switching time of 0.25 seconds between scans. The mass range scanned for molecules with an expected molecular weight of less than 350 amu was 70-500 m/z while for molecules with a expected mass of more than 350 amu the mass to charge ratio scanned was 200-1000 m/z.

Chromatography Conditions: Liquid chromatography was performed using a YMC AQ C18 column (150 mm×3 mm with 5 μm particle and a 120 Å pore size). For all analysis, MeCN with 0.2% formic acid was combined with water with 0.2% formic acid to form the elution gradient. The gradient profile consisted of starting with 15% MeCN:water and increasing the amount of MeCN linearly over ten minutes to 90%. That concentration was held constant for 2 minutes before returning to initial conditions. During the entire analysis the flow rate was 0.9 mL/min.

Flow Injection Conditions: A 1:1 mixture of the water to MeCN (both with 0.2% formic acid added) was used to acquire the FIA data. The flow rate was set to 0.3 ml/min.

$^1$H NMR

All $^1$H NMR spectra were acquired using a Bruker Instruments AMX-500 NMR spectrometer in the solvent given.

Synthetic Methods

General Procedure for the Preparation of Compounds of Formula I, Embodiment C (Schemes I-VI)

Procedure for the Preparation of Analogs 5a-5bd mmol), and O-benzotriazole-N,N,N,N'-tetramethyluronium hexafluorophosphate (HBTU) (1.1 eq, 2.24 g, 5.90 mmol). Compound 1 was prepared according to the literature procedure of A. M. Murphy et al, *J. Am. Chem. Soc.*, 114, pp. 3156-3157 (1992). The mixture was rotated at room temperature overnight using a wrist arm shaker.

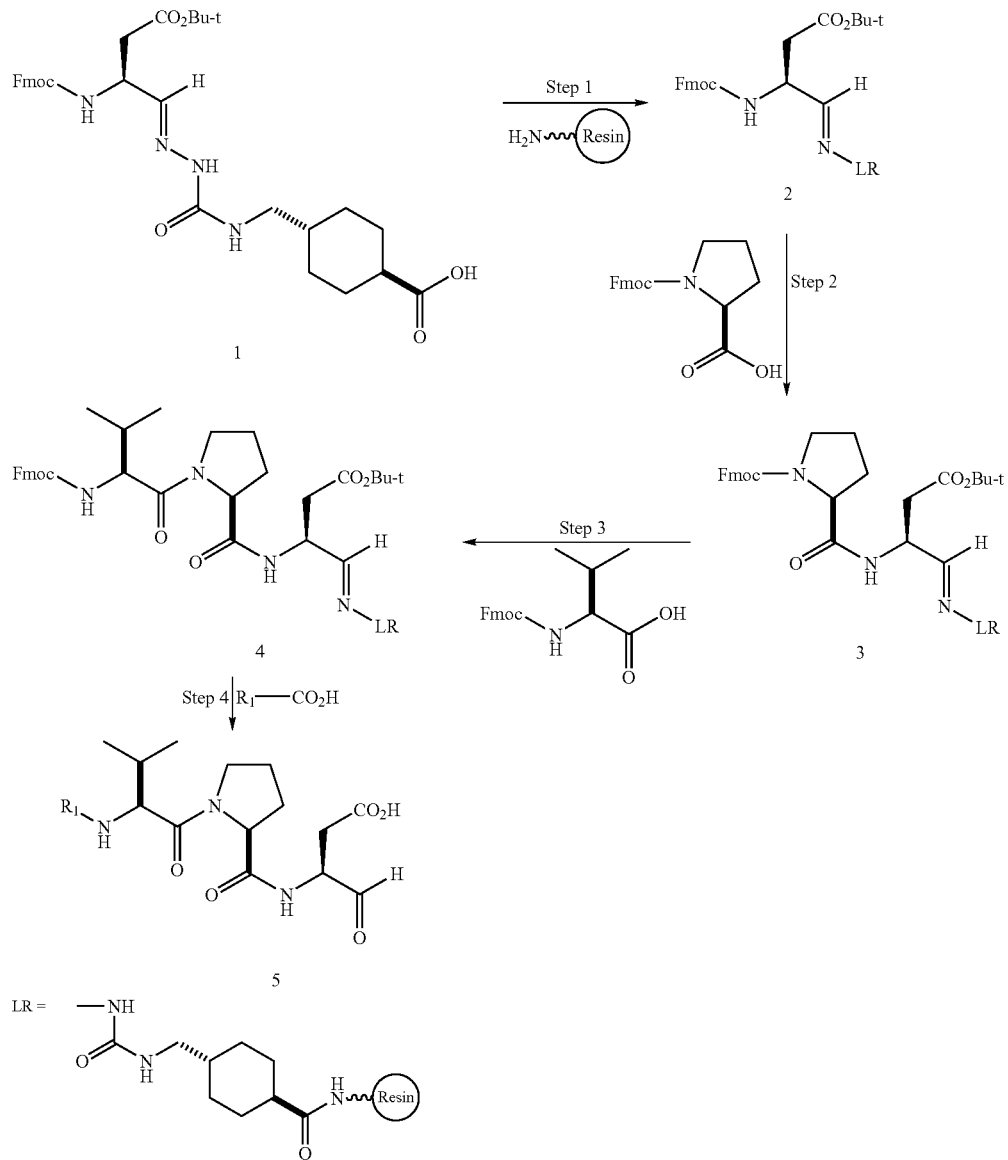

In Schemes I-VIII, the variable LR refers to the linker-resin and is defined as shown above in Scheme I.

Step 1: A 6.7 g portion (0.8 mmol/gram loading, 5.36 mmol) of 4-methyl benzhydrylamine hydrochloride salt resin (Scheme I) was washed with DMF (3×50 mL), 10% DIEA/DMF (3×50 mL) and N-methylpyrrolidinone (NMP) (3×50 mL). To a suspension of the washed resin in 25 mL of NMP was added successively compound 1 (1.1 eq, 3.5 g, 5.90 mmol) DIEA (3.33 eq, 3.1 mL, 17.70 mmol), 1-hydroxybenzotriazole hydrate (HOBt) (1.1 eq, 797 mg, 5.90

The resulting mixture was filtered, and the resin was rinsed with DMF then treated with 12 mL of a 20% solution of acetic anhydride in DMF for 30 minutes at room temperature. The mixture was filtered, and the resin was washed successively with DMF (2×50 mL), $CH_3OH$ (50 mL), 1:1 DMF/$CH_2Cl_2$ (2×5 mL), $CH_3OH$ (50 mL) and $CH_2Cl_2$ (3×50 mL). After drying in vacuo, 9.0 grams of resin 2 were obtained (0.48 mmol/gram loading).

Step 2: To 4.5 g of resin 2 (0.48 mmol/gram, 2.16 mmol) was added 25 mL of a 20% solution of piperidine in DMF.

The suspension was rotated at room temperature for 5 minutes and drained. The procedure was repeated over 20 minutes. The resin was then washed successively with DMF (2×40 mL), CH₃OH (40 mL), CH₂Cl₂ (2×40 mL), CH₃OH (40 mL) and NMP (40 mL). To a suspension of resin in 40 mL of NMP was added successively 2.92 g of N-Fmoc-proline (4 eq, 8.64 mmol), 3.0 mL of DIEA (8 eq, 17.28 mmol), 1.17 g of HOBt (4 eq, 8.64 mmol) and 3.27 g of HBTU (4 eq, 8.64 mmol). The mixture was rotated at room temperature overnight and drained. This coupling procedure was repeated over 3 hours. The resin was then washed successively with DMF (2×40 mL), CH₃OH (40 mL), 1:1 DMF/CH₂Cl₂ (2×40 mL), CH₃OH (40 mL) and CH₂Cl₂ (3×40 mL)), and briefly dried in vacuo to afford resin 3.

Step 3: A suspension of resin 3 in 25 mL of a 20% solution of piperidine in DMF was rotated at room temperature for 5 minutes. The suspension was drained. The procedure was repeated over 20 minutes. The resin was washed successively with DMF (2×40 mL), —CH₃OH (40 mL), CH₂Cl₂ (2×40 mL), CH₃OH (40 mL) and NMP (2×40 mL). To a suspension of resin in 40 mL of NMP was added successively 2.93 g of N-Fmoc-valine (4 eq, 8.64 mmol), 3.0 mL of DIEA (8 eq, 17.28 mmol), 1.17 g of HOBt (4 eq, 8.64 mmol) and 3.27 g of HBTU (4 eq, 8.64 mmol). The mixture was rotated at room temperature overnight and drained. This coupling procedure was repeated over 3 hours. The resin was then washed successively with DMF (2×40 mL), CH₃OH (40 mL), 1:1 DMF/CH₂Cl₂ (2×40 mL), CH₃OH (40 mL) and CH₂Cl₂ (3×40 mL), and dried in vacuo to afford resin 4 (0.45 mmol/gram).

Step 4: To a 0.05 mmol portion of resin 4 was added 2 mL of a 20% solution of piperidine in DMF. The suspension was rotated at room temperature for 5 minutes, and drained. The procedure was repeated over 20 minutes. The resulting resin was washed successively with DMF (3×5 mL), CH₃OH (5 mL), and NMP (3×5 mL). The desired carboxylic acid was then added (4 eq, 0.2 mmol), followed by 0.8 mL of a 0.25M solution of HOBt in NMP, 0.14 mL of DIEA (8 eq, 0.4 mmol) and 0.8 mL of a 0.25M solution of HBTU in NMP. The mixture was rotated at room temperature overnight and drained. The resin was washed successively with DMF (2×5 mL), CH₃OH (5 mL), 1:1 DMF/CH₂Cl₂ (2×5 mL), CH₃OH (5 mL) and CH₂Cl₂ (3×5 mL), and dried in vacuo. A 2 mL portion of a 95% solution of TFA in water was then added to the resin. The mixture was stirred at room temperature for one hour, and filtered. The filtrate was evaporated, and the residue was taken up in acetonitrile-water and purified by preparative HPLC to afford compounds 5a-5bd.

Product yield, analytical HPLC conditions, HPLC retention time, product purity, and mass spectral data obtained for examples 5a-5bd, 7a-7at, 9a-9g, 15a-15f, 16a-16b, 17a-17e, 18a-18f, 20a-20t, 23a-23i, 24a-24e, 25a-25e, 26a-26h, 27a-27n, 28a-28c, 29a-29s, 32a-32e are provided in Table 1 unless noted otherwise.

TABLE 1

Physical Data for Selected Examples

| Ex. | Yield (mg) | HPLC Gradient/ time (min) | RT (min) | Purity (%) | Mass Spec (M + H or M + Na) |
|---|---|---|---|---|---|
| 5a | 1.0 | 5-45%/10' | 4.66 | 92 | 475.2 |
| 5b | 1.0 | 5-45%/10' | 6.86 | 85 | 457.2 |
| 5c | 4.0 | 5-45%/10' | 5.98 | 85 | 469.2 |
| 5d | 1.5 | 5-45%/10' | 6.82 | 95 | 467.5 |
| 5e | 1.0 | 5-45%/10' | 5.52 | 95 | 418.2 |
| 5f | 0.6 | 5-45%/10' | 4.28 | 93 | 434.2 |
| 5g | 6.4 | 10-60%/10' | 8.57 | 97 | 504.7 (+Na) |
| 5h | 15.6 | 10-60%/10' | 4.51 | 99 | 459.2 |
| 5i | 6.6 | 5%-90%/10' | 9.34 | 90 | 506.1 |
| 5j | 5.1 | 5%-90%/10' | 10.04 | 95 | 506.1 |
| 5k | 10.7 | 5%-90%/10' | 8.64 | 85 | 520.1 |
| 5l | 6.6 | 5%-90%/10' | 8.72 | 85 | 540.1 |
| 5m | 6.8 | 5%-90%/10' | 7.89 | 85 | 502.0 |
| 5n | 1.9 | 5%-0%/10' | 6.46 | 85 | 494.1 |
| 5o | 3.8 | 5%-90%/10' | 7.04 | 85 | 506.1 |
| 5p | 6.8 | 5%-90%/10' | 11.62 | 95 | 576.0 |
| 5q | 2.2 | 5%-90%/10' | 9.72 | 90 | 508.1 |
| 5r | 3.8 | 5%-90%/10' | 7.27 | 85 | 462.1 |
| 5s | 4.3 | 5%-90%/10' | 6.46 | 90 | 470.1 |
| 5t | 5.9 | 5%-60%/9' 60%-90%/2' | 10.27 | 90 | 486.2 |
| 5u | 3.1 | 5%-60%/9' 60%-90%/2' | 9.09 | 80 | 522.1 |
| 5v | 1.0 | 5%-60%/9' 60%-90%/2' | 11.63 | 85 | 502.2 |
| 5w | 10.3 | 5%-60%/9' 60%-90%/2' | 8.75 | 95 | 470.2 |
| 5x | 8.8 | 5%-60%/9' 60%-90%/2' | 8.88 | 95 | 565.1 |
| 5y | 6.6 | 5%-60%/9' 60%-90%/2' | 12.32 | 95 | 518.2 |
| 5z | 10.2 | 5%-60%/9' 60%-90%/2' | 12.63 | 95 | 502.2 |
| 5aa | 2.5 | 5%-60%/9' 60%-90%/2' | 9.57 | 95 | 554.1 |
| 5ab | 7.8 | 5%-60%/9' 60%-90%/2' | 10.54 | 85 | 538.2 |
| 5ac | 1.4 | 5%-60%/9' 60%-90%/2' | 9.28 | 95 | 476.2 |
| 5ad | 5.3 | 5%-60%/9' 60%-90%/2' | 6.51 | 85 | 469.2 |
| 5ae | 4.3 | 5%-60%/9' 60%-90%/2' | 9.81 | 95 | 551.1 |
| 5af | 0.9 | 5%-60%/9' 60%-90%/2' | 9.98 | 90 | 547.4 |
| 5ag | 5.7 | 5%-60%/9' 60%-90%/2' | 10.31 | 90 | 526.2 |
| 5ah | 1.4 | 5%-60%/9' 60%-90%/2' | 8.13 | 85 | 542.1 |
| 5ai | 10.9 | 10%-90%/10' | 5.88 | 85 | 584.2 |
| 5aj | 4.2 | 10%-90%/10' | 5.89 | 90 | 556.2 |
| 5ak | 7.8 | 10%-90%/10' | 5.54 | 85 | 568.3 |
| 5al | 8.4 | 10%-90%/10' | 6.25 | 95 | 516.2 |
| 5am | 7.6 | 10%-90%/10' | 6.49 | 95 | 474.3 |
| 5an | 6.2 | 10%-90%/10' | 6.00 | 95 | 500.2 |
| 5ao | 9.4 | 10%-90%/10' | 6.68 | 95 | 581.3 |
| 5ap | 6.4 | 10%-90%/10' | 4.30 | 90 | 500.3 |
| 5aq | 5.2 | 10%-90%/10' | 6.45 | 95 | 559.2 |
| 5ar | 1.4 | 10%-90%/10' | 5.38 | 90 | 561.3 |
| 5as | 16.2 | 10%-90%/10' | 4.25 | 95 | 475.2 |
| 5at | 15.4 | 10%-90%/10' | 6.68 | 95 | 560.3 |
| 5au | 5.9 | 10%-90%/10' | 6.70 | 90 | 498.3 |
| 5av | 4.1 | 10%-90%/10' | 5.13 | 85 | 531.2 |
| 5aw | 5.5 | 10%-90%/10' | 6.53 | 85 | 570.3 |
| 5ax | 14.0 | 10%-90%/10' | 6.26 | 90 | 557.3 |
| 5ay | 10.4 | 10%-90%/10' | 6.52 | 90 | 510.3 |
| 5az | 9.2 | 10%-90%/10' | 5.96 | 95 | 522.3 |
| 5ba | 8.5 | 10%-90%/10' | 6.69 | 95 | 562.3 |
| 5bb | 4.6 | 10%-90%/10' | 6.00 | 85 | 520.2 |
| 5bc | 8.8 | 10%-90%/10' | 4.96 | 90 | 546.2 |
| 5bd | 8.2 | 10%-90%/10' | 8.01 | 95 | 536.3 |
| 7a | 2.1 | 5-45%/10' | 5.28 | 86 | 440.2 |
| 7b | 1.7 | 5-45%/10' | 4.12 | 94 | 390.2 |
| 7c | 0.5 | 5-45%/10' | 4.04 | 94 | 434.2 |
| 7d | 1.1 | 5-45%/10' | 4.29 | 95 | 441.2 |
| 7e | 1.1 | 5-45%/10' | 3.28 | 98 | 447.2 |
| 7f | 1.0 | 5-45%/10' | 3.96 | 97 | 420.2 |
| 7g | 11.0 | 10%-90%/10' | 4.00 | 95 | 483.4 |
| 7h | 6.0 | 10%-90%/10' | 4.90 | 95 | 439.3 |
| 7i | 12.0 | 10%-90%/10' | 6.40 | 95 | 474.3 |
| 7j | 6.6 | 10%-90%/10' | 4.50 | 95 | 461.4 |
| 7k | 4.0 | 10%-90%/10' | 5.40 | 95 | 480.4 |
| 7l | 8.6 | 10%-90%/10' | 2.61 | 95 | 435.3 |
| 7m | 6.0 | 10%-90%/10' | 4.29 | 95 | 438.4 |

TABLE 1-continued

| | | | | | |
|---|---|---|---|---|---|
| 7n | 15.4 | 10%-90%/10' | 2.00 | 85 | 433.4 |
| 7o | 8.4 | 10%-90%/10' | 4.01 | 90 | 470.0 |
| 7p | 3.0 | 10%-90%/10' | 4.61 | 95 | 434.4 |
| 7q | 5.7 | 10%-90%/10' | 3.89 | 95 | 434.3 |
| 7r | 8.8 | 10%-90%/10' | 2.94 | 95 | 425.3 |
| 7s | 10.5 | 10%-90%/10' | 3.89 | 90 | 433.4 |
| 7t | 6.9 | 10%-90%/10' | 2.45 | 85 | 419.3 |
| 7u | 11.6 | 10%-90%/10' | 1.98 | 85 | 433.3 |
| 7v | 4.6 | 10%-90%/10' | 4.60 | 95 | 489.4 |
| 7w | 13.8 | 10%-90%/10' | 4.20 | 95 | 453.3 |
| 7x | 6.0 | 10%-90%/10' | 3.90 | 95 | 483.2 |
| 7y | 12.0 | 10%-90%/10' | 5.40 | 95 | 489.2 |
| 7z | 10.0 | 10%-90%/10' | 5.40 | 95 | 517.2 |
| 7aa | 11.0 | 10%-90%/10' | 5.30 | 95 | 453.8 |
| 7ab | 10.0 | 10%-90%/10' | 5.60 | 95 | 595.1 |
| 7ac | 3.9 | 10-60%/10' | 4.59 | 88 | 469.2 |
| 7ad | 13.0 | 5-45%/10' | 4.48 | 88 | 415.2 |
| 7ae | 4.9 | 5-45%/10' | 4.37 | 88 | 426.2 |
| 7af | 20.6 | 5-45%/10' | 4.68 | 86 | 405.3 |
| 7ag | 14.9 | 5-45%/10' | 4.78 | 82 | 406.3 |
| 7ah | 9.5 | 5-45%/10' | 7.40 | 91 | 447.3 (+Na) |
| 7ai | 10.8 | 5-45%/10' | 9.21 | 95 | 480.8 (+Na) |
| 7aj | 8.3 | 5-45%/10' | 9.14 | 92 | 481.1 (+Na) |
| 7ak | 13.6 | 5-45%/10' | 8.05 | 96 | 464.8 (+Na) |
| 7al | 8.1 | 5-45%/10' | 7.04 | 91 | 448.8 (+Na) |
| 7am | 7.8 | 5-45%/10' | 8.54 | 90 | 480.4 (+Na) |
| 7an | 4.3 | 5-45%/10' | 7.48 | 88 | 460.9 (+Na) |
| 7ao | 13.5 | 5-45%/10' | 7.45 | 92 | 460.7 (+Na) |
| 7ap | 2.5 | 5-45%/10' | 6.52 | 93 | 440.3 (+Na) |
| 7aq | 1.4 | 5-45%/10' | 3.30 | 84 | 405.2 |
| 7ar | 15.10 | 5-45%/10' | 3.79 | 97 | 413.30 |
| 7as | 15.70 | 5-45%/10' | 5.50 | 88 | 441.30 |
| 7at | 22.20 | 5-45%/10' | 4.49 | 94 | 415.30 |
| 9a | 0.5 | 10-60%/10' | 7.08 | 98 | 527.4 (+Na) |
| 9b | 1.2 | 10-60%/10' | 8.31 | 93 | 570.5 (+Na) |
| 9c | 2.5 | 10-60%/10' | 8.46 | 97 | 569.6 |
| 9d | 1.2 | 10-60%/10' | 7.22 | 85 | 562.1 |
| 9e | 0.4 | 10-60%/10' | 7.86 | 95 | 543.2 (+Na) |
| 9f | 4.3 | 10-60%/10' | 8.11 | 96 | 542.5 |
| 9g | 2.1 | 10-60%/10' | 7.18 | 93 | 526.3 |
| 15a | 1.0 | 10%-60%/10' | 5.76 | 95 | 477.6 |
| 15b | 3.9 | 10%-60%/10' | 6.32 | 91 | 483.8 |
| 15c | 2.9 | 10%-90%/10' | 3.30 | 85 | 463.3 |
| 15d | 1.3 | 10%-90%/10' | 4.26 | 95 | 531 |
| 15e | 1.0 | 10%-90%/10' | 3.10 | 85 | 482.3 |
| 15f | 1.2 | 10%-90%/10' | 3.60 | 95 | 484.6 |
| 16a | 2.5 | 10%-90%/10' | 2.80 | 95 | 456.3 |
| 16b | 6.0 | 10%-90%/10' | 1.90 | 95 | 454.2 |
| 17a | 1.0 | 10%-90%/10' | 3.30 | 85 | 496.8 |
| 17b | 1.1 | 10%-90%/10' | 3.62 | 85 | 498.3 |
| 17c | 2.3 | 10%-90%/10' | 5.80 | 95 | 573.2 |
| 17d | 1.6 | 10%-90%/10' | 1.60 | 95 | 525.1 |
| 17e | 1.5 | 10%-90%/10' | 2.62 | 95 | 526.3 |
| 18a | 1.0 | 10%-90%/10' | 3.90 | 95 | 528.3 |
| 18b | 1.2 | 10%-90%/10' | 5.27 | 95 | 562.3 |
| 18c | 2.2 | 10%-90%/10' | 4.09 | 95 | 499.2 |
| 18d | 1.5 | 10%-90%/10' | 3.78 | 95 | 498.3 |
| 18e | 1.2 | 10%-90%/10' | 4.78 | 95 | 541.3 |
| 18f | 7.1 | 10%-90%/10' | 3.84 | 98 | 526.1 |
| 20a | 2.0 | 5-45%/10' | 6.95 | 91 | 483.2 |
| 20b | 1.3 | 5-45%/10' | 7.58 | 99 | 482.2 |
| 20c | 2.5 | 10%-90%/10' | 5.89 | 85 | 483.3 |
| 20d | 4.3 | 10%-90%/10' | 4.09 | 90 | 471.3 |
| 20e | 3.6 | 10%-90%/10' | 4.65 | 95 | 455.3 |
| 20f | 12.2 | 10%-90%/10' | 3.25 | 95 | 518.3 |
| 20g | 12.1 | 10%-90%/10' | 5.01 | 90 | 487.2 |
| 20h | 3.3 | 10%-90%/10' | 4.30 | 90 | 533.2 |
| 20i | 5.0 | 10%-90%/10' | 4.16 | 90 | 485.2 |
| 20j | 1.3 | 10%-90%/10' | 3.45 | 85 | 531.2 |
| 20k | 9.7 | 10%-90%/10' | 5.41 | 90 | 516.2 |
| 20l | 3.8 | 10%-90%/10' | 3.73 | 85 | 504.2 |
| 20m | 6.6 | 10%-90%/10' | 4.52 | 90 | 488.2 |
| 20n | 1.8 | 10%-90%/10' | 2.85 | 90 | 551.2 |
| 20o | 7.0 | 10%-90%/10' | 4.70 | 95 | 520.2 |
| 20p | 1.2 | 10%-90%/10' | 4.00 | 95 | 566.2 |
| 20q | 2.3 | 10%-90%/10' | 4.93 | 95 | 481.3 |
| 20r | 3.6 | 10%-90%/10' | 4.45 | 95 | 519.3 |
| 20s | 3.0 | 10%-90%/10' | 4.18 | 95 | 552.2 |
| 20t | 6.0 | 10%-90%/10' | 3.80 | 90 | 517.4 |
| 23a | 21.0 | 10-60%/10' | 8.11 | 99 | 495.4 |
| 23b | 25.0 | 10-60%/10' | 8.94 | 99 | 539.8 (+Na) |
| 23c | 26.0 | 10-60%/10' | 8.55 | 99 | 539.9 (+Na) |
| 23d | 12.6 | 10%-90%/10' | 3.90 | 85 | 453.3 |
| 23e | 8.3 | 10%-90%/10' | 5.16 | 85 | 501.3 |
| 23f | 12.5 | 10%-90%/10' | 3.41 | 80 | 425.3 |
| 23g | 1.5 | 10%-90%/10' | 3.34 | 85 | 452.3 |
| 23h | 8.4 | 10%-90%/10' | 3.84 | 90 | 451.3 |
| 23i | 9.0 | 10%-90%/10' | 3.78 | 85 | 469.4 |
| 24a | 1.1 | 10-60%/12' | 8.76 | 90 | 480.5 |
| 24b | 3.1 | 10-60%/10' | 5.14 | 90 | 375.4 |
| 24c | 7.2 | 10-60%/10' | 10.33 | 96 | 531.0 |
| 24d | 3.4 | 10-60%/10' | 6.51 | 95 | 426.5 (+Na) |
| 24e | 6.9 | 10-60%/10' | 7.22 | 99 | 455.5 |
| 25a | 1.9 | 5-45%/10' | 5.38 | 85 | 455.5 |
| 25b | 1.5 | 5-45%/10' | 6.90 | 97 | 483.2 |
| 25c | 1.0 | 5-45%/10' | 8.09 | 94 | 497.2 |
| 25d | 12.8 | 5-45%/10' | 5.75 | 88% | 453.3 |
| 25e | 9.5 | 5-45%/10' | 7.76 | 90% | 495.2 |
| 26a | 10.2 | 5-45%/10' | 7.36 | 95 | 455.1 (+Na) |
| 26b | 1.1 | 5-45%/10' | 7.38 | 89 | 476.3 |
| 26c | 13.8 | 5-45%/10' | 8.13 | 98 | 483.2 |
| 26d | 2.3 | 5-45%/10' | 10.35 | 99 | 503.0 |
| 26e | 12.8 | 5-45%/10' | 11.11 | 99 | 523.2 |
| 26f | 13.2 | 10-60%/10' | 12.11 | 99 | 545.0 |
| 26g | 0.7 | 10-60%/10' | 10.89 | 87 | 523.2 |
| 26h | 4.4 | 10-60%/10' | 11.62 | 99 | 545.8 |
| 27a | 5.0 | 10%-90%/10' | 4.42 | 95 | 475.3 |
| 27b | 16.4 | 10-60%/10' | 5.20 | 92 | 505.1 |
| 27c | 2.7 | 5-45%/10' | 7.50 | 82 | 476.6 (+Na) |
| 27d | 1.6 | 5-45%/12' | 8.70 | 90 | 503.2 |
| 27e | 4.4 | 5-45%/12' | 7.80 | 82 | 489.2 |
| 27f | 1.2 | 5-45%/12' | 6.95 | 85 | 476.3 |
| 27g | 2.5 | 5-45%/12' | 6.67 | 82 | 510.1 |
| 27h | 1.1 | 5-45%/12' | 8.49 | 95 | 524.1 |
| 27i | 0.9 | 5-45%/12' | 7.34 | 90 | 484.3 |
| 27j | 4.3 | 5-45%/12' | 5.77 | 82 | 470.3 |
| 27k | 1.3 | 5-45%/12' | 5.33 | 95 | 551.1 |
| 27l | 16.6 | 5-45%/10' | 5.90 | 91 | 477.2 |
| 27m | 7.0 | 5-45%/10' | 7.70 | 93 | 494.2 |
| 27n | 15.1 | 5-45%/10' | 3.99 | 86 | 466.2 |
| 28a | 1.2 | 5-45%/10' | 5.91 | 86 | 487.1 |
| 28b | 0.5 | 5-45%/10' | 6.86 | 98 | 486.1 |
| 28c | 1.5 | 5-45%/10' | 7.47 | 93 | 515.1 |
| 29a | 4.5 | 5-45%/12' | 8.21 | 98 | 392 |
| 29b | 28.0 | 5-45%/12' | 11.80 | 96 | 443.3 |
| 29c | 1.7 | 5-45%/10' | 3.73 | 97 | 415.2 |
| 29d | 1.7 | 5-45%/10' | 4.62 | 89 | 414.2 |
| 29e | 0.6 | 5-45%/10' | 4.94 | 85 | 436.2 |
| 29f | 1.1 | 5-45%/10' | 6.23 | 97 | 442.2 |
| 29g | 1.7 | 5-45%/10' | 6.39 | 90 | 457.2 |
| 29h | 0.7 | 5-45%/10' | 3.56 | 92 | 408.2 |
| 29i | 0.7 | 5-45%/10' | 6.50 | 96 | 431.2 |
| 29j | 0.4 | 5-45%/10' | 7.24 | 89 | 445.2 |
| 29k | 1.6 | 5-45%/10' | 7.07 | 90 | 456.2 |
| 29l | 0.9 | 5-45%/10' | 3.08 | 99 | 408.2 |
| 29m | 1.5 | 10-60%/10' | 6.68 | 90 | 406.3 |
| 29n | 6.4 | 10-60%/10' | 4.27 | 87% | 422.3 |
| 29o | 8.4 | 10-60%/10' | 4.42 | 86% | 422.3 |
| 29p | 13.2 | 10-60%/10' | 5.62 | 83% | 450.3 |
| 29q | 15.1 | 5-45%/10' | 3.79 | 97% | 413.3 |
| 29r | 15.7 | 5-45%/10' | 5.50 | 88% | 441.3 |
| 29s | 19.9 | 5-45%/10' | 4.30 | 95% | 394.3 |
| 32a | 7.7 | 5-60%/20' | 14.2 | 90 | 469.3 |
| 32b | 4.0 | 5-60%/20' | 13.4 | 85 | 485.1 (+Na) |
| 32c | 2.5 | 5-60%/20' | 11.1 | 90 | 459.3 |
| 32d | 3.0 | 5-60%/20' | 8.19 | 95 | 471.3 |
| 32e | 4.9 | 5-60%/20' | 14.2 | 90 | 486.2 |

TABLE 1-continued
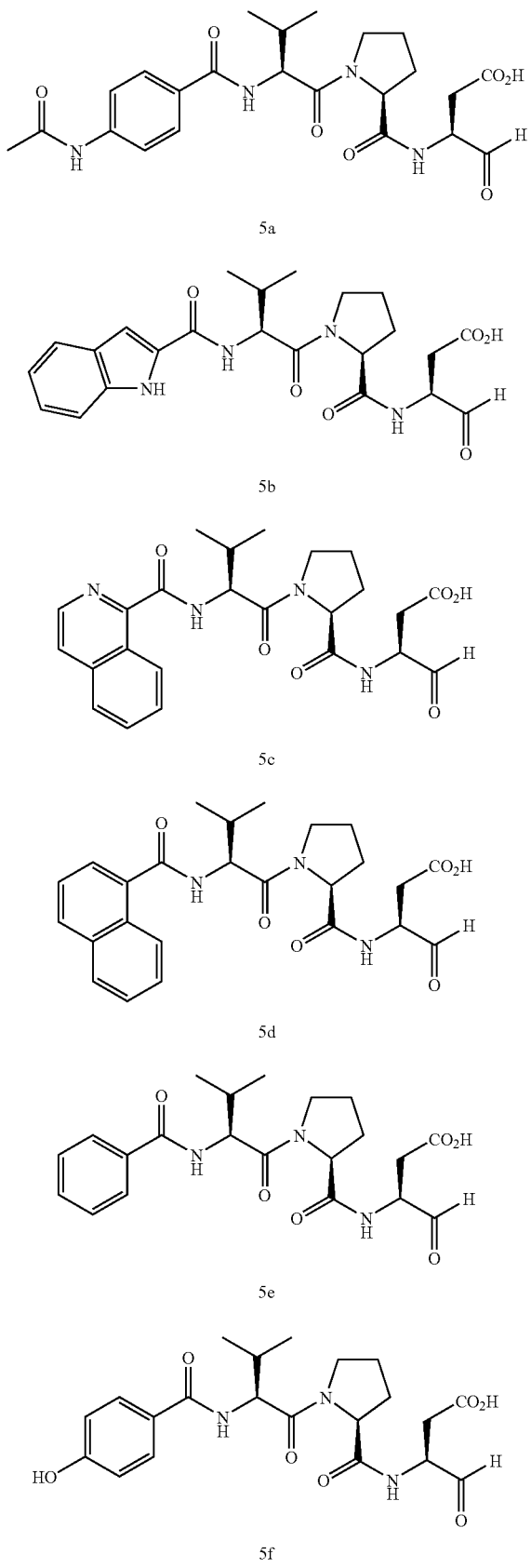
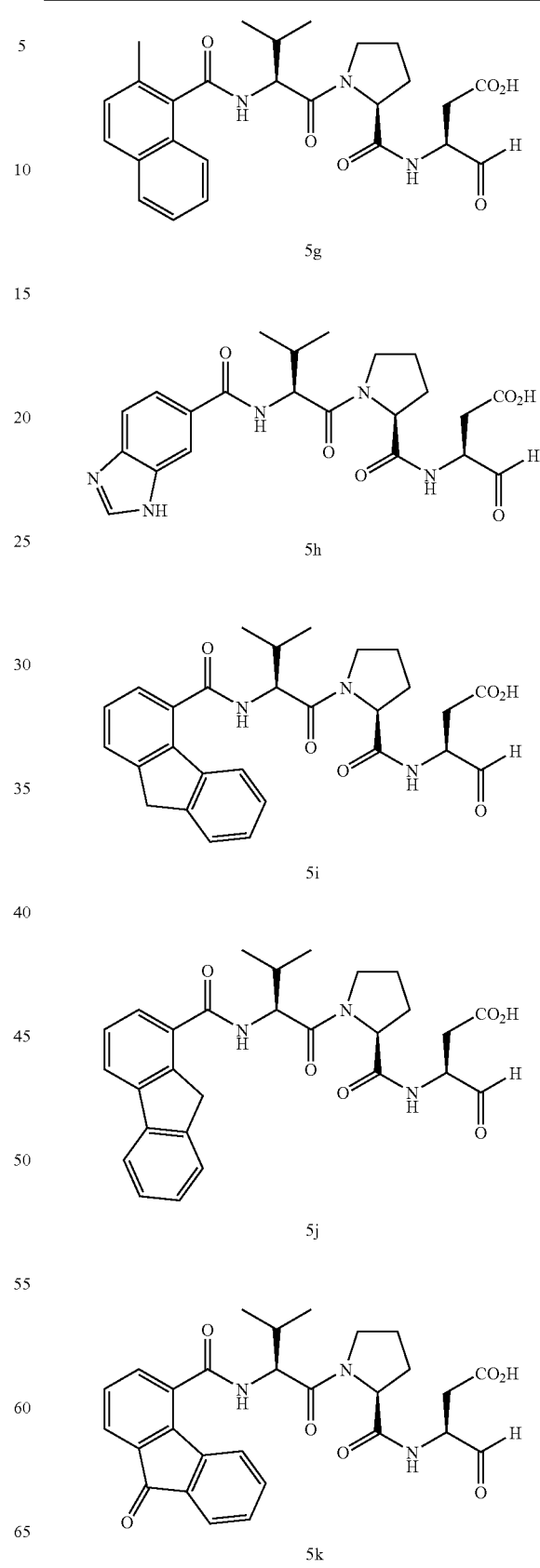

TABLE 1-continued
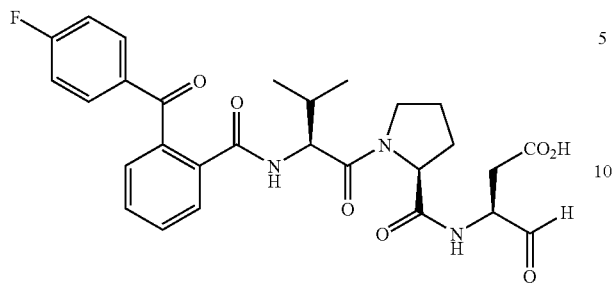
5l
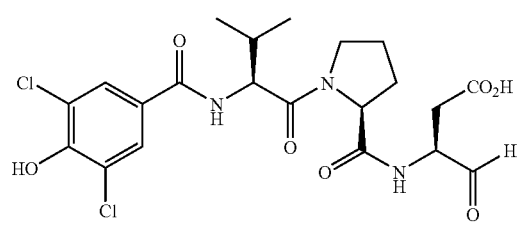
5m
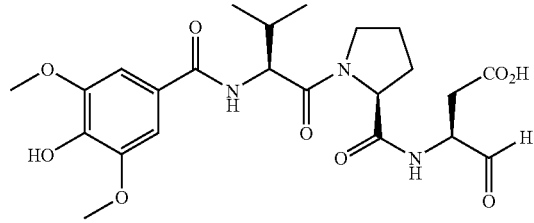
5n
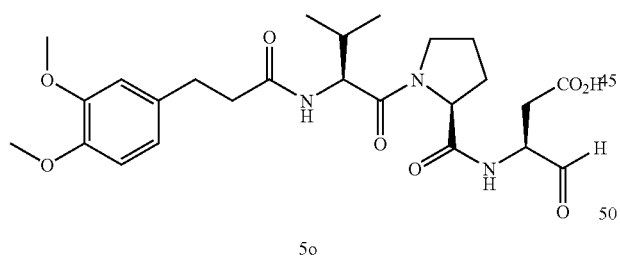
5o
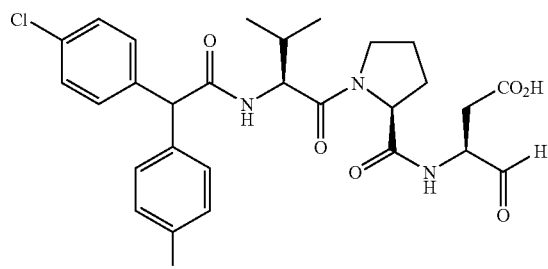
5p
TABLE 1-continued
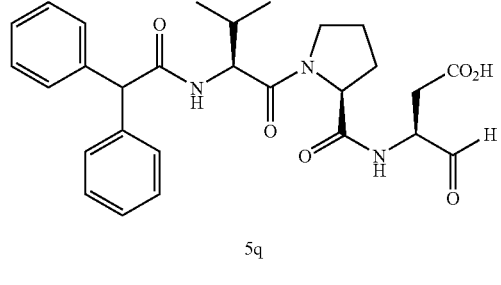
5q
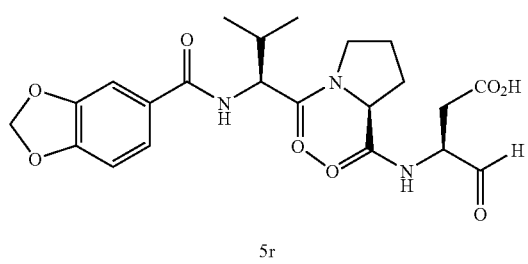
5r
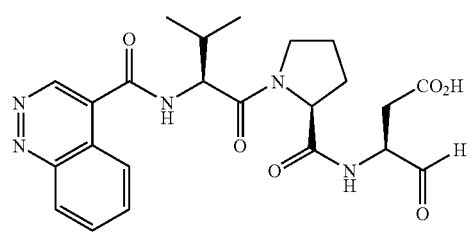
5s
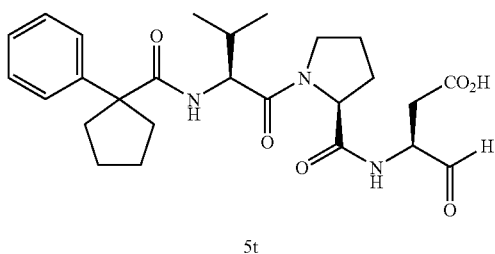
5t
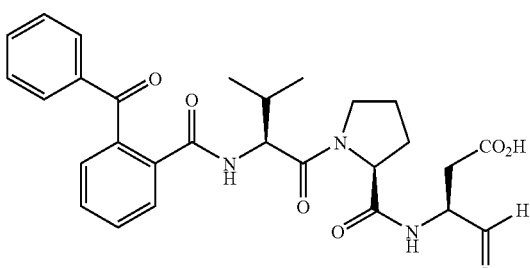
5u TABLE 1-continued
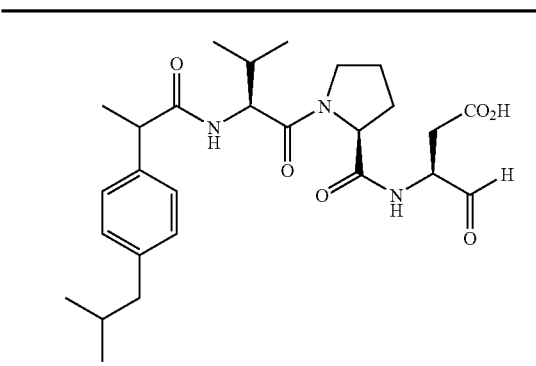
5v
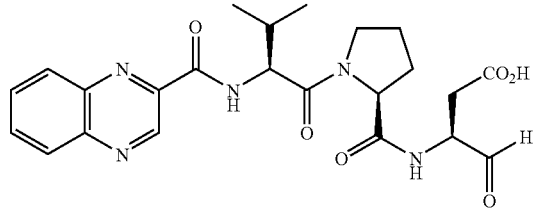
5w
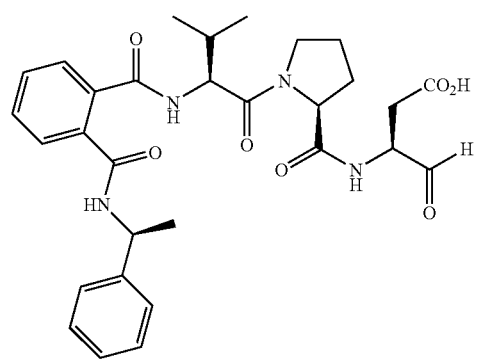
5x
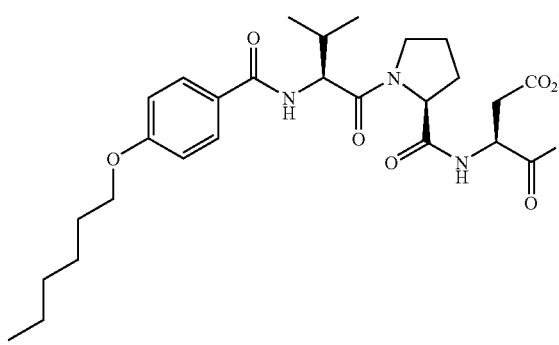
5y
TABLE 1-continued
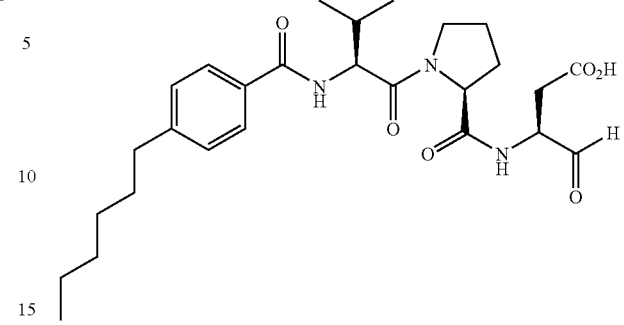
5z
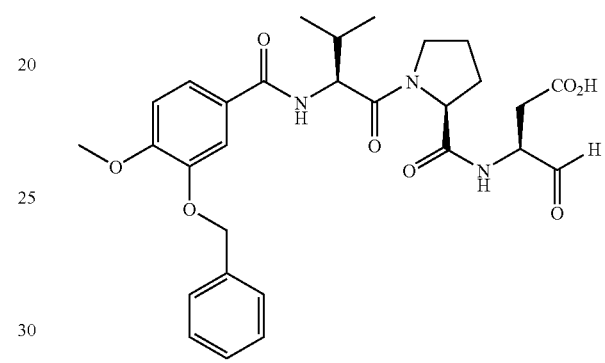
5aa
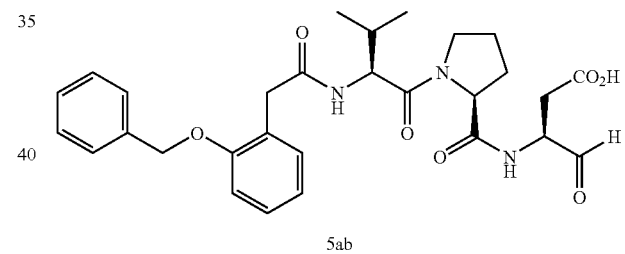
5ab
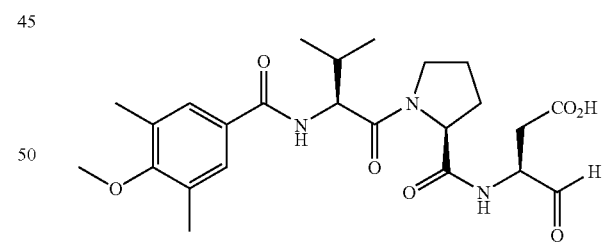
5ac
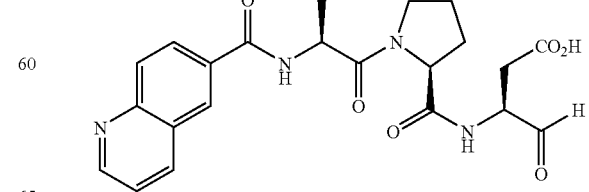
5ad TABLE 1-continued
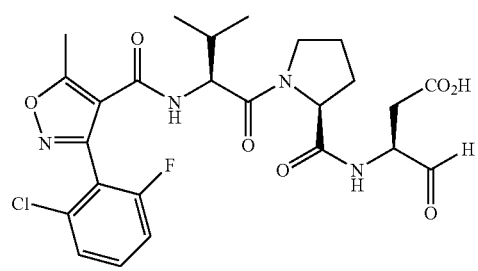
5ae
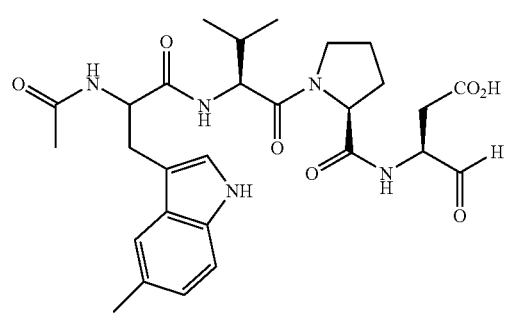
5af
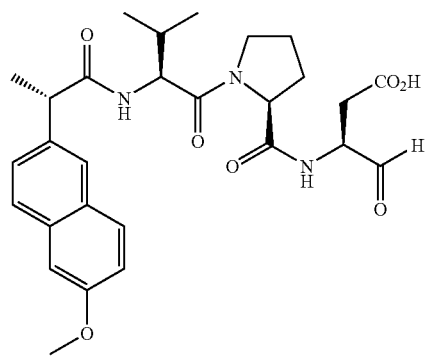
5ag
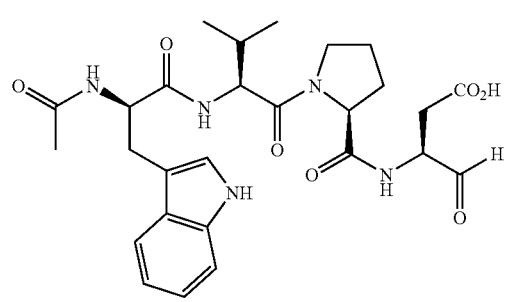
5ah
TABLE 1-continued
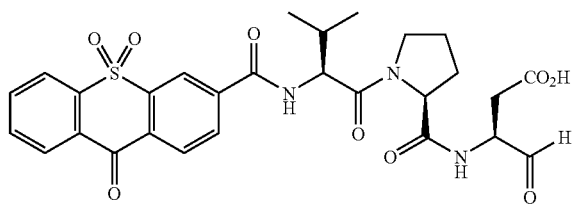
5ai
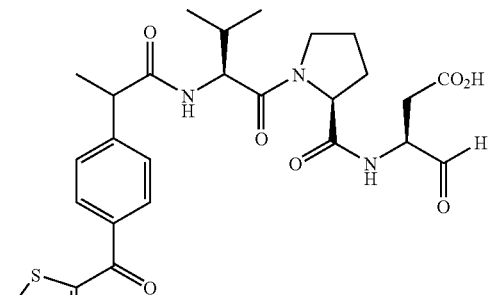
5aj
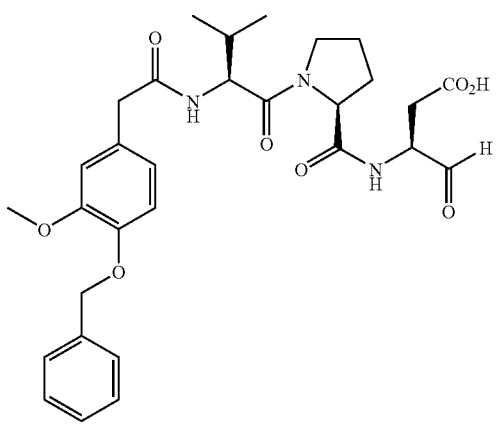
5ak
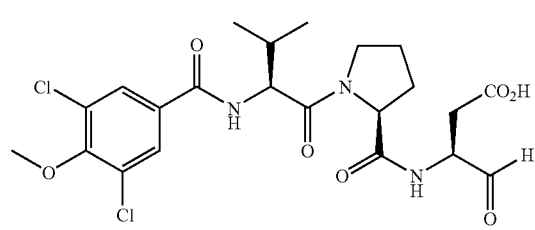
5al
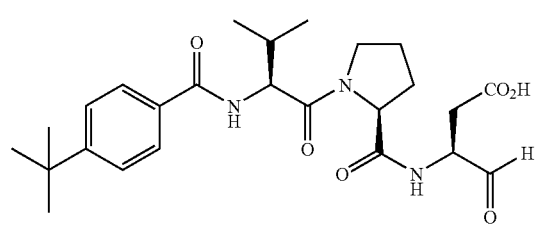
5am TABLE 1-continued
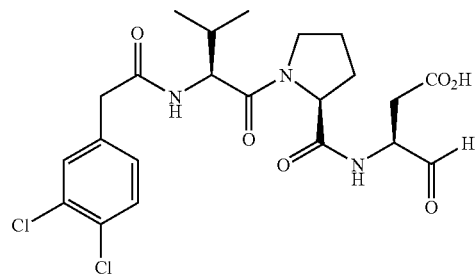
5an
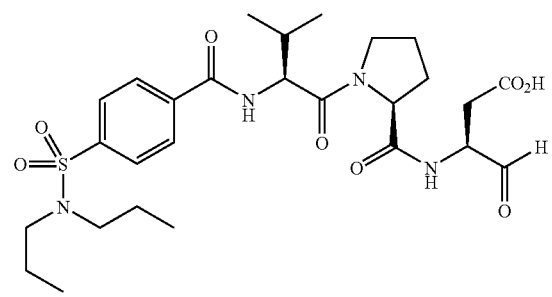
5ao
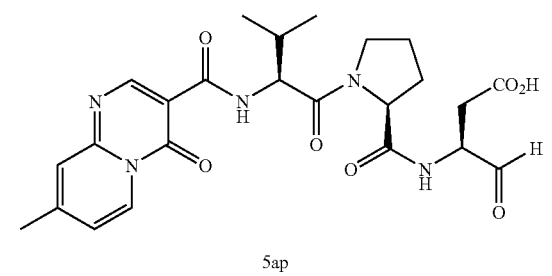
5ap
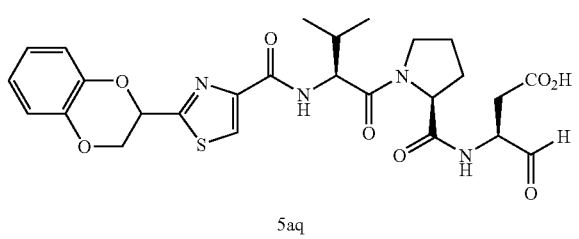
5aq
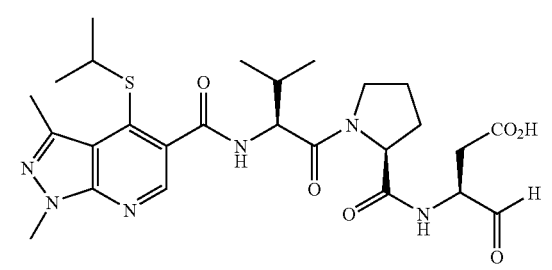
5ar
TABLE 1-continued
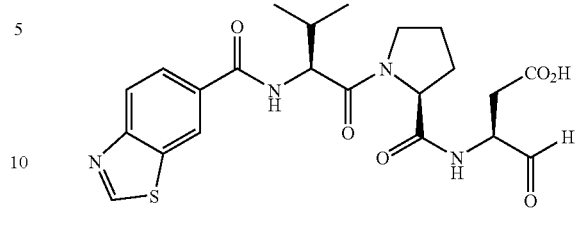
5as
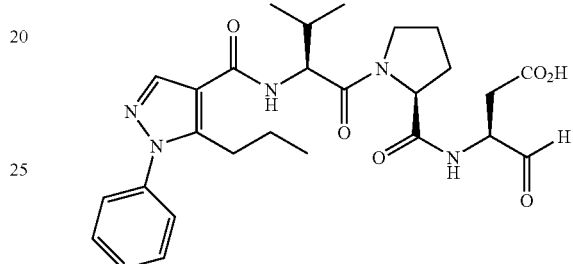
5at
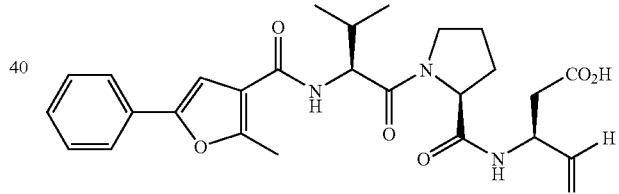
5au
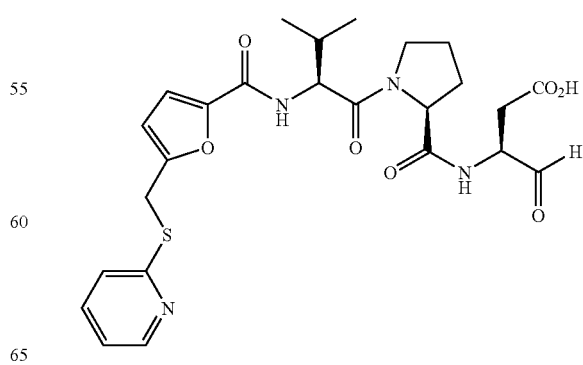
5av TABLE 1-continued
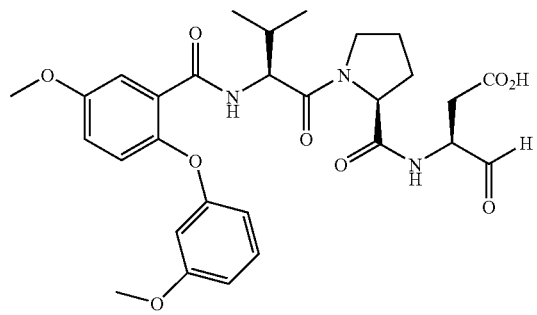
5aw
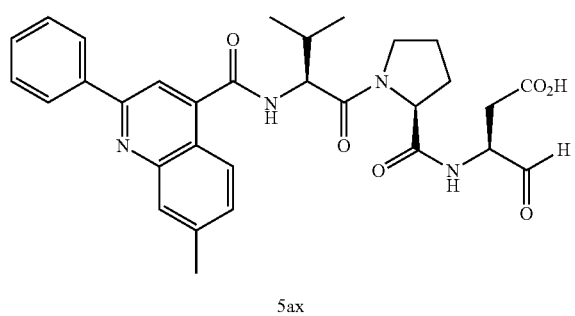
5ax
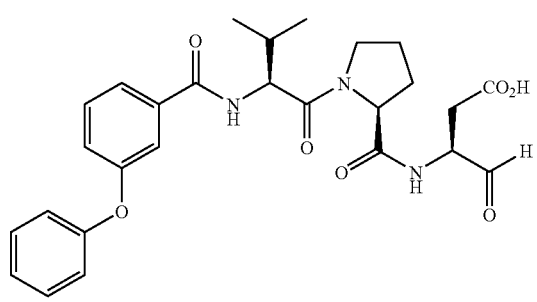
5ay
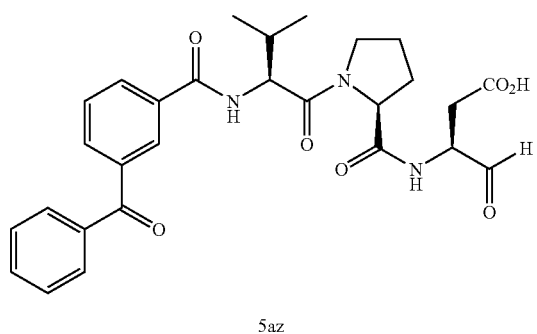
5az
TABLE 1-continued
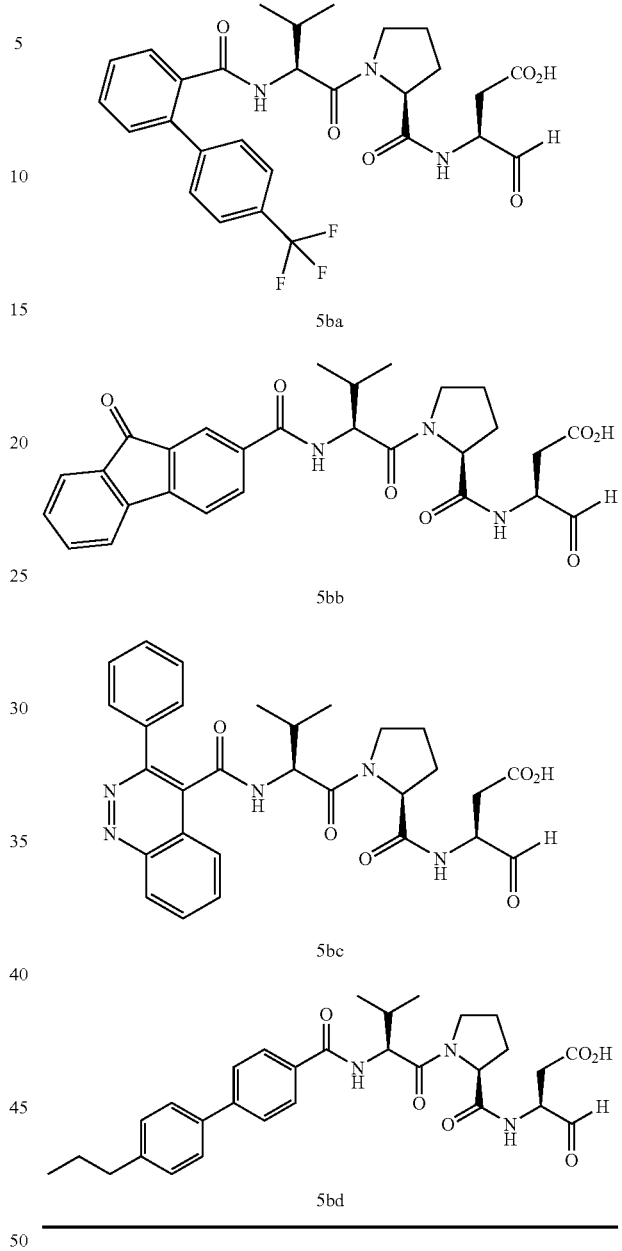
Procedure for the Preparation of Analogs 7a-7at
Scheme II
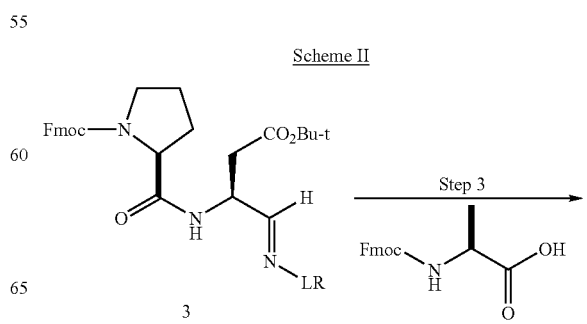
3

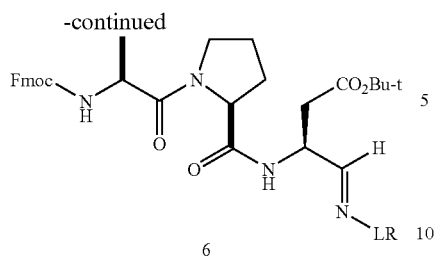

5

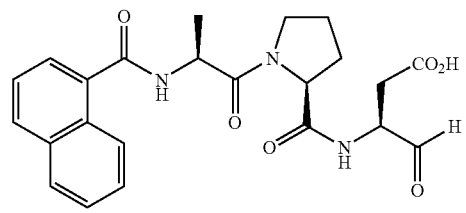
7a

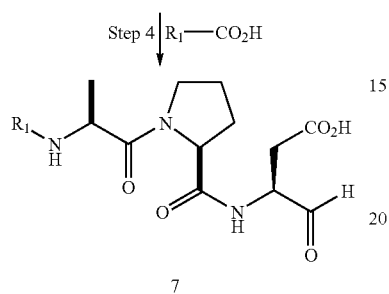

Step 4 | R₁—CO₂H

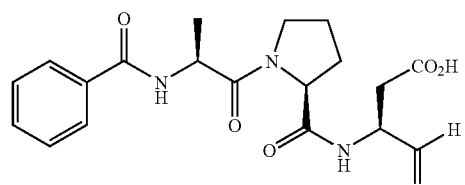
7b

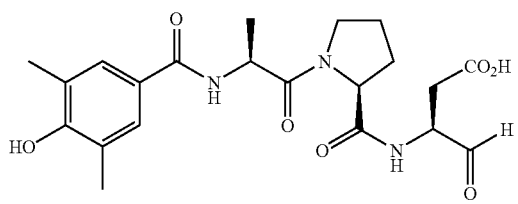
7c

Analogs of 7a-7at were prepared as described above in Scheme I only substituting Fmoc-alanine for Fmoc-valine in Step 3 (Scheme II).

Step 3: A suspension of resin 3 (3.5 g, 1.75 mmol) in 20 mL of a 20% solution of piperidine in DMF was rotated at room temperature for 5 minutes. The suspension was drained. The procedure was repeated over 20 minutes. The resin was washed successively with DMF (2×30 mL), CH₃OH (30 mL), CH₂Cl₂ (2×30 mL), CH₃OH (30 mL) and NMP (2×30 mL). To a suspension of resin in 30 mL of NMP was added successively 1.44 g of N-Fmoc-alanine (4 eq, 7.0 mmol), 2.4 mL of DIEA (8 eq, 14.0 mmol), 0.95 g of HOBt (4 eq, 7.0 mmol) and 2.66 g of HBTU (4 eq, 7.0 mmol). The mixture was rotated at room temperature overnight and drained. This coupling procedure was repeated over 3 hours. The resin was then washed successively with DMF (2×30 mL), CH₃OH (30 mL), 1:1 DMF/CH₂Cl₂ (2×30 mL), CH₃OH (30 mL) and CH₂Cl₂ (3×30 mL), and dried in vacuo to afford resin 6 (0.50 mmol/gram).

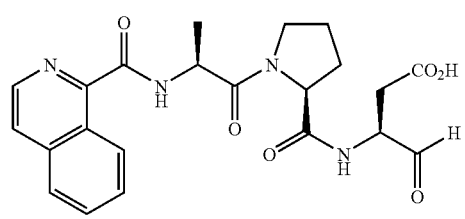
7d

Step 4: To a 0.125 mmol portion of resin 6 was added 5 mL of a 20% solution of piperidine in DMF. The suspension was rotated at room temperature for 5 minutes, and drained. The procedure was repeated over 20 minutes. The resulting resin was washed successively with DMF (3×5 mL), CH₃OH (5 mL), and NMP (3×5 mL). The desired carboxylic acid was then added (4 eq, 0.6 mmol), followed by 2.0 mL of a 0.25M solution of HOBt in NMP, 0.35 mL of DIEA (8 eq, 1.0 mmol) and 2.0 mL of a 0.25M solution of HBTU in NMP. The mixture was rotated at room temperature overnight and drained. The resin was washed successively with DMF (3×5 mL), CH₃OH (5 mL), 1:1 DMF/CH₂Cl₂ (2×5 mL), CH₃OH (5 mL) and CH₂Cl₂ (3×5 mL), and dried in vacuo. A 5 mL portion of a 95% solution of TFA in water was then added to the resin. The mixture was stirred at room temperature for one hour, and filtered. The filtrate was evaporated, and the residue was dissolved in acetonitrile-water and purified by preparative HPLC to afford compounds 7a-7at.

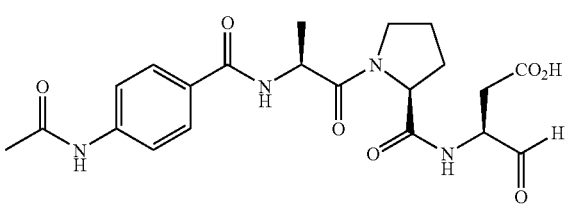
7e

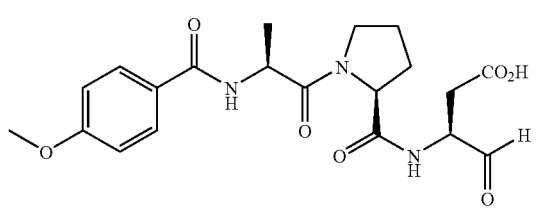
7f

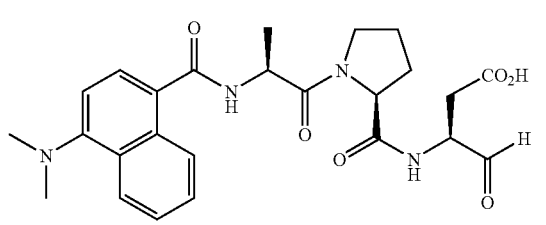
7g

-continued
7h
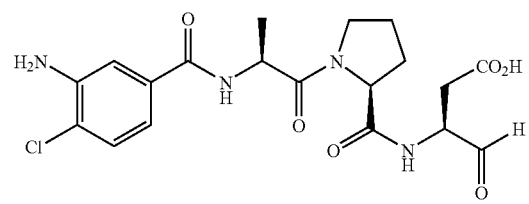
7i
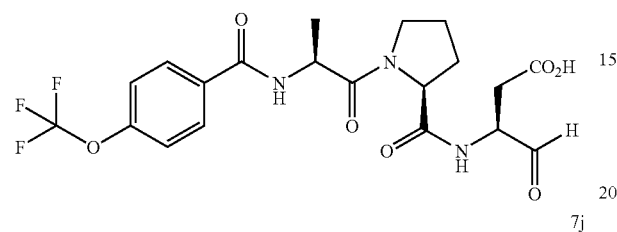
7j
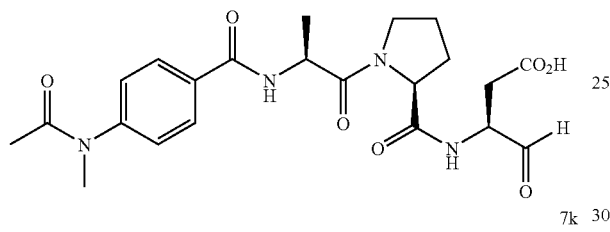
7k
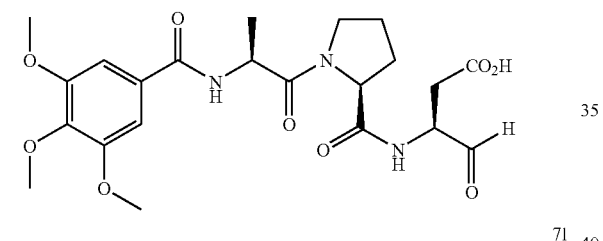
7l
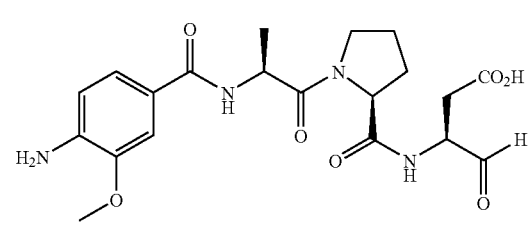
7m
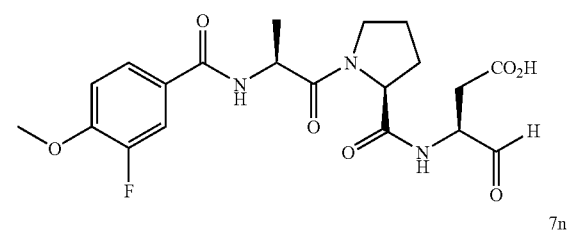
7n
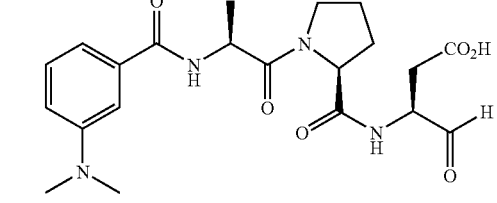
-continued
7o
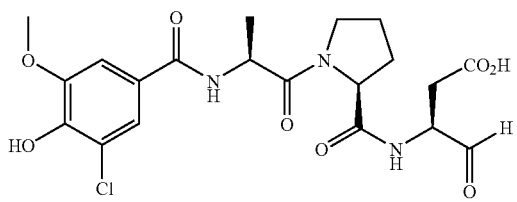
7p
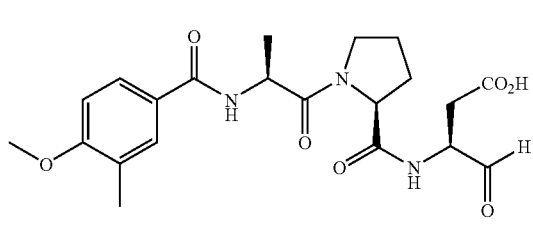
7q
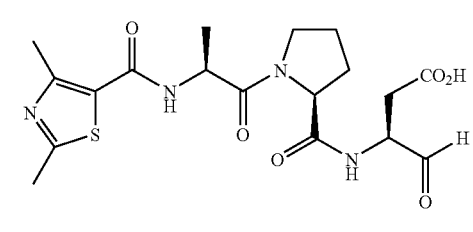
7r
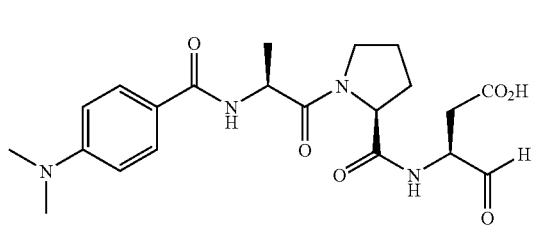
7s
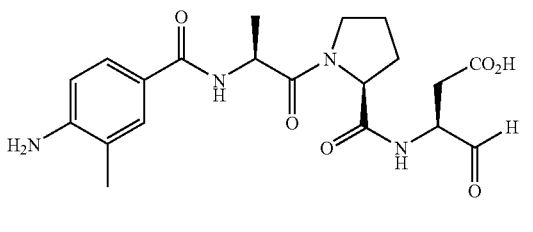
7t
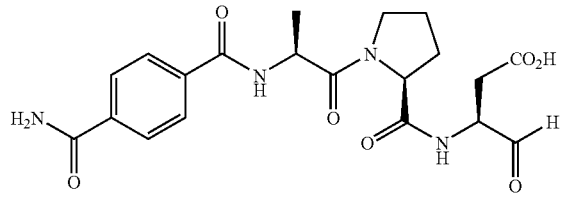
7u 7v
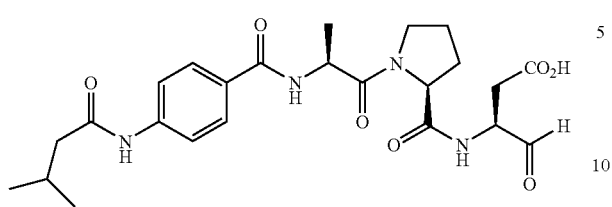
7ab
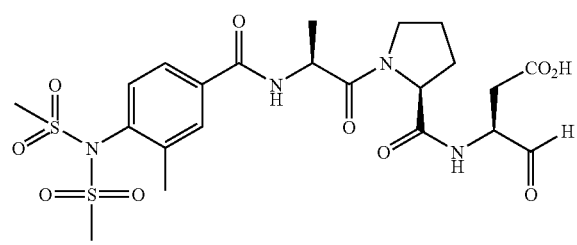
7w
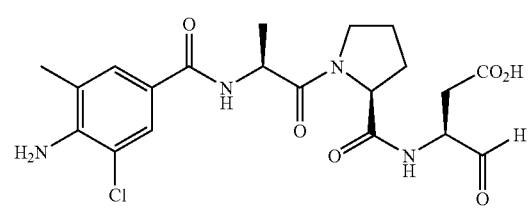
7ac
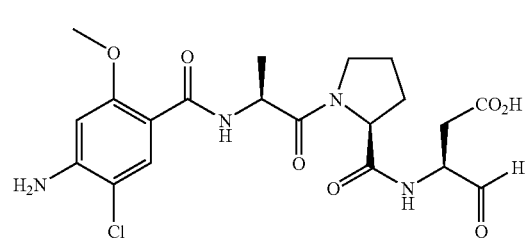
7x
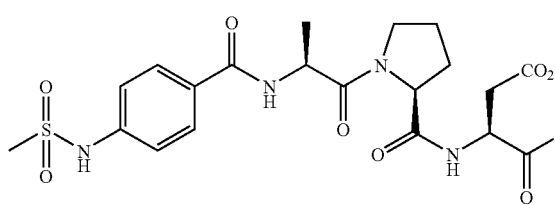
7ad
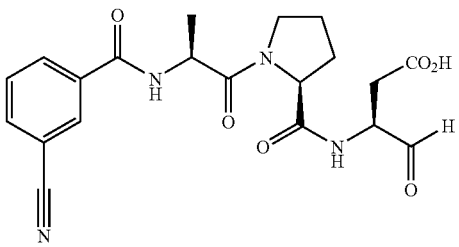
7y
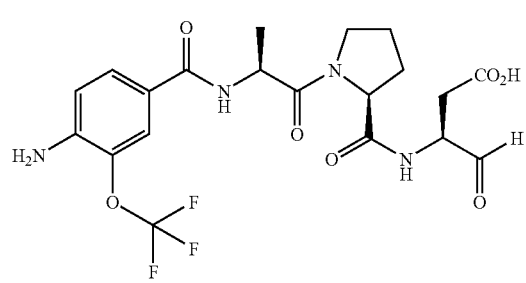
7ae
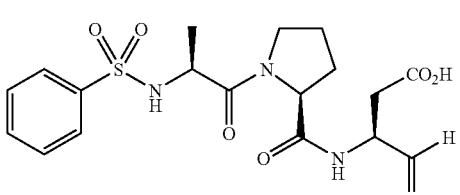
7af
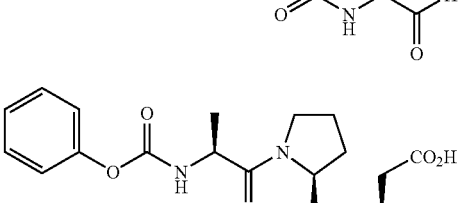
7z
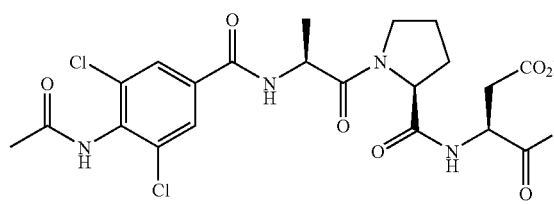
7ag
7aa
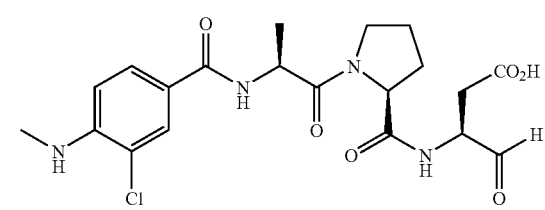
7ah
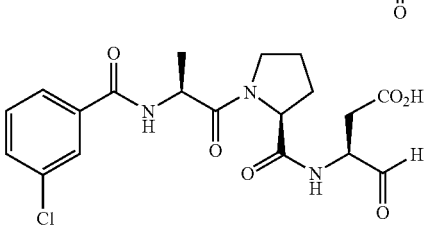

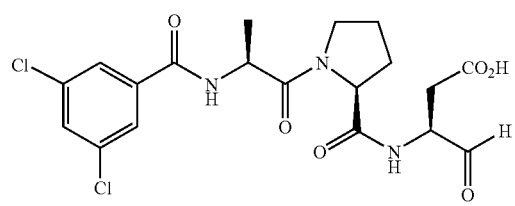
7ai
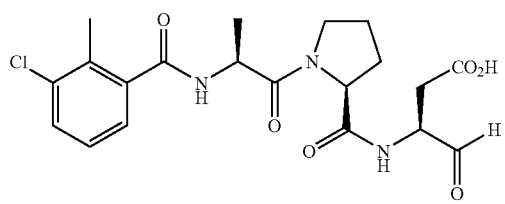
7ao
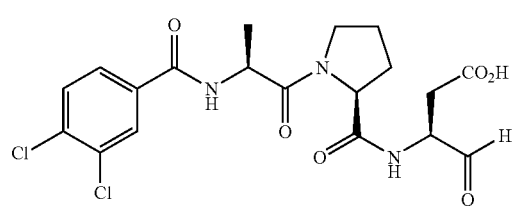
7aj
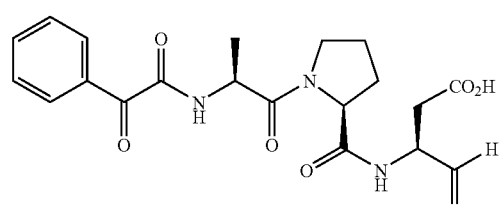
7ap
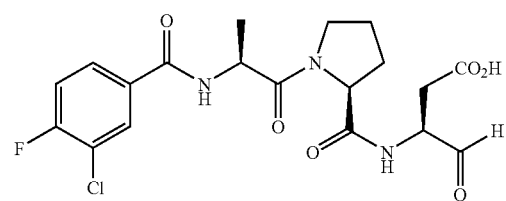
7ak
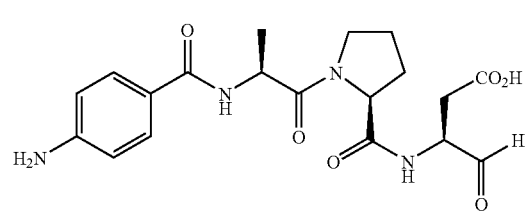
7aq
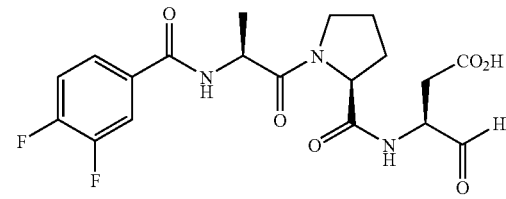
7al
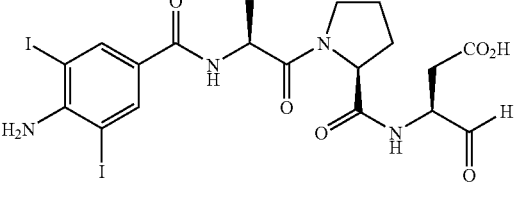
7ar
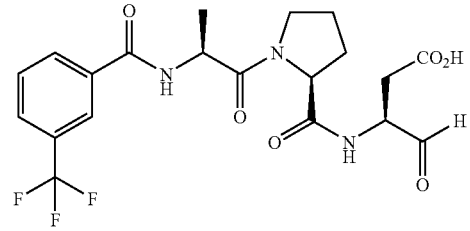
7am
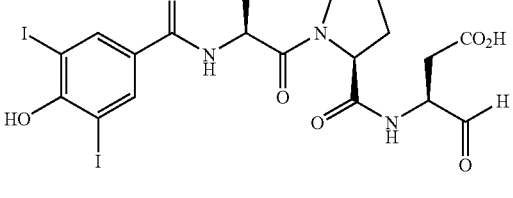
7as
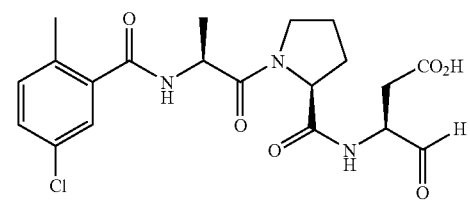
7an
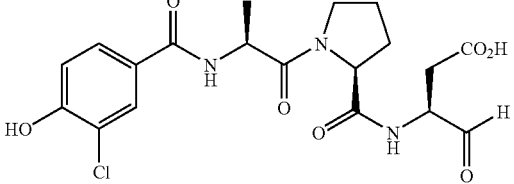
7at Procedure for the Preparation of Analogs 9a-9g Scheme III

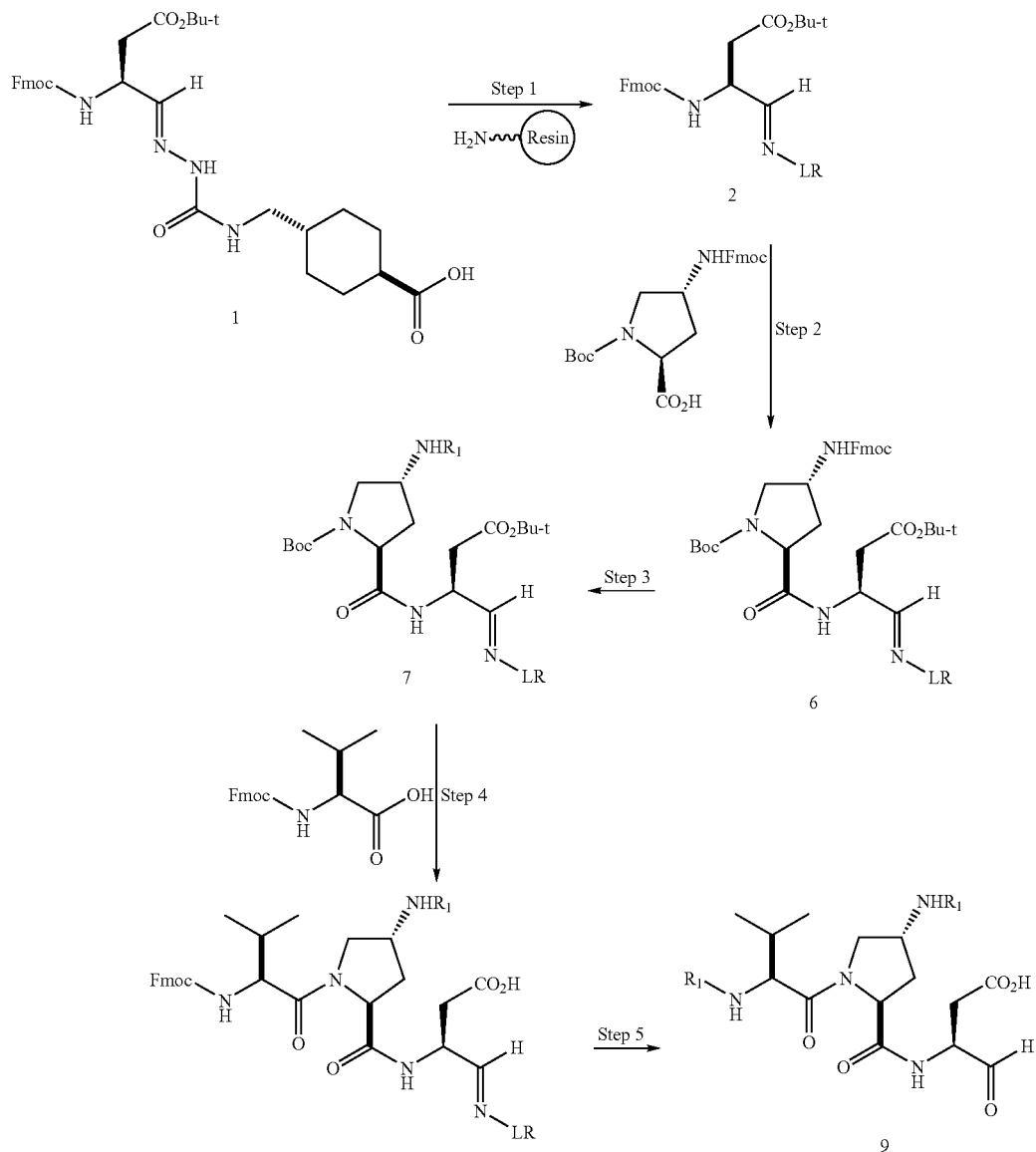

Step 1: A 10.0 g portion (0.75 mmol/gram loading, 7.5 mmol) AgroPore-aminomethyl resin (catalog number 800047) was washed with DMF (3×40 mL), 10% DIEA/DMF (3×40 mL), DMF and NMP (3×40 mL). To above resin was added successively compound 1 (0.87 eq, 3.88 g, 6.55 mmol), HBTU (1.14 eq, 3.13 g, 8.25 mmol), HOBt (1.14 eq, 1.26 g, 8.25 mmol), and NMP (40 mL). The reagents were then mixed by bubbling nitrogen through the bottom of the flask for two minutes at room temperature. N,N-diisopropylethylamine (3.33 eq, 4.35 mL, 25 mmol) was added and the resulting suspension mixed at room temperature overnight, filtered, then washed successively with NMP (3×40 mL) and DMF (3×40 mL). The resin was then treated with 50 mL of a 20% solution of acetic anhydride in DMF for 38 minutes at room temperature. The mixture was filtered, and the resin was washed successively with NMP (3×40 mL) $CH_2Cl_2$ (3×40 mL), 1:1 $CH_3OH/CH_2Cl_2$ (3×40 mL), and $CH_3OH$ (3×40 mL). After drying in vacuo, 13.76 grams of resin 2 were obtained (0.35 mmol/gram loading).

Step 2: Seven reaction vessels were each charged with 181 mg of resin 2 (0.48 mmol/gram, 0.063 mmol) then washed with $CH_2Cl_2$ (3×1 mL) and NMP (3×1 mL). Then each vessel was treated with 1 mL of a 25% solution of piperidine in DMF and mixed (vortex) at room temperature for 15 minutes. This procedure was repeated in triplicate. Each vessel was then washed three times with NMP (3×1 mL). The vessels were then treated with 500 μl of a solution of 0.4 M (2S,4R)-Fmoc-4-amino-1-Boc-pyrrolidine-2-carboxylic acid/0.4 M HOBt/NMP, 500 μl of a solution of 0.4 M HBTU/NMP, and 250 μl of a solution of 1.6 M DIEA/

NMP and mixed for 3 hours at room temperature. After mixing, the vessels were drained and the procedure was repeated.

Step 3: The resulting resin was washed with NMP (3×1 mL) and then treated with 1 mL of a 25% solution of piperidine in DMF and mixed (vortex) at room temperature for 15 minutes. The procedure was repeated in triplicate. The resulting resin was washed with NMP (3×1 mL) then treated with either acetic anhydride, or isopropyl isocyanate, or methane sulphonyl chloride, or methyl chloroformate. For acetic anhydride: add 300 μl of a 1.6 M DIEA/NMP solution and 1 mL of a solution of 0.5 M acetic anhydride/0.125 M DIEA/0.015 M HOBt in NMP. For isopropyl isocyanate: add 300 μl of a 1.6 M DIEA/NMP solution and 1 mL of a solution of 1 M isopropyl isocyanate in NMP. For methane sulphonyl chloride: add 600 βl of a solution of 1 M pyridine in $CH_2Cl_2$ and 600 μl of a solution of 1M methane sulphonyl chloride in $CH_2Cl_2$. For methyl chloroformate: add 500 μl of a 1.6 M DIEA/NMP solution and 1 mL of a solution of 0.7 M methyl chloroformate in $CH_2Cl_2$ The resulting suspensions were mixed for 6 hours at room temperature: the solvent drained and the coupling procedure repeated.

Step 4: The resulting resin was washed with NMP (3×1 mL) then treated with a 1:1 mixture of TFA/$CH_2Cl_2$ at room temperature for 30 minutes. The resulting resin was then washed with $CH_2Cl_2$ (3×1 mL) and NMP (3×1 mL). The resin was then treated with 500 μl of a solution of 0.4 M Fmoc-valine-carboxylic acid/0.4 M HOBt/NMP, 500 μl of a solution of 0.4 M HBTU/NMP, and 250 μl of a solution of 1.6 M DIEA/NMP and mixed for 3 hours at room temperature. After mixing, the vessels were drained and the coupling procedure was repeated.

Step 5: The resulting resin was washed with NMP (3×1 mL) then treated with 1 mL of a 25% solution of piperidine in DMF and mixed (vortex) at room temperature for 15 minutes. This procedure was repeated in triplicate. The resulting resin was washed with NMP (3×1 mL) then treated with either 500 μl of a solution of 0.4 M 1-isoquinoline carboxylic acid/0.4 M HOBt/NMP or 500 μl of a solution of 0.4 M p-anisic acid acid/0.4 M HOBt/NMP. The resulting mixtures were treated with 500 μl of a solution of 0.4 M HBTU/NMP and 250 μl of a solution of 1.6 M DIEA/NMP then mixed for 3 hours at room temperature, the solvent drained and the procedure repeated. The resulting resin was treated with 1.5 mL of a 95% solution of TFA in water and stirred at room temperature for one hour then filtered. The filtrate was evaporated, and the residue was taken up in a 2:1:2 mixture of DMF/acetonitrile/water and purified by preparative HPLC to afford compounds 9a-9g.

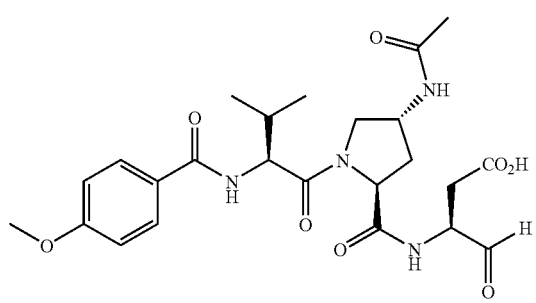

9a

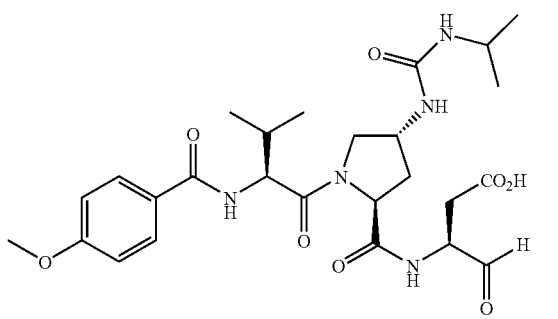

9b

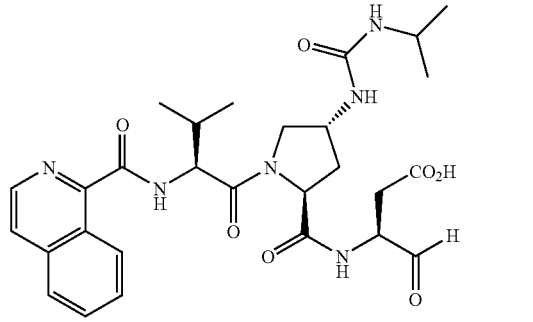

9c

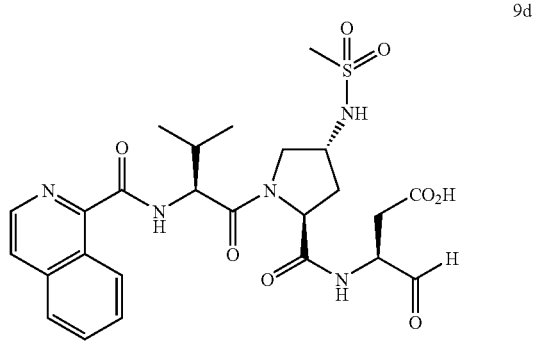

9d

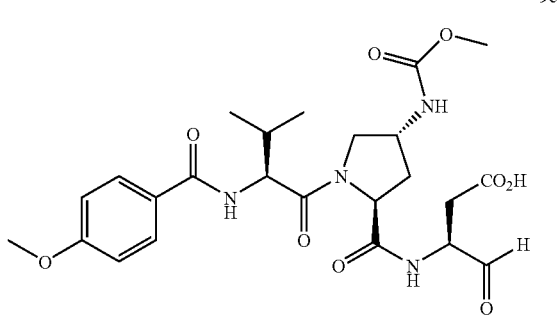

9e

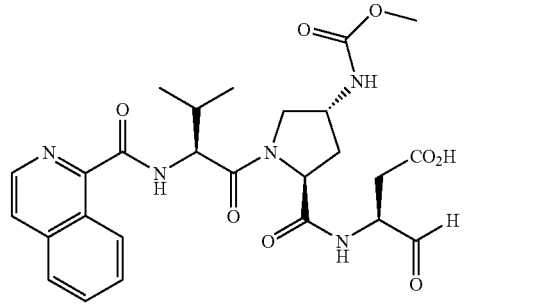

9f

-continued

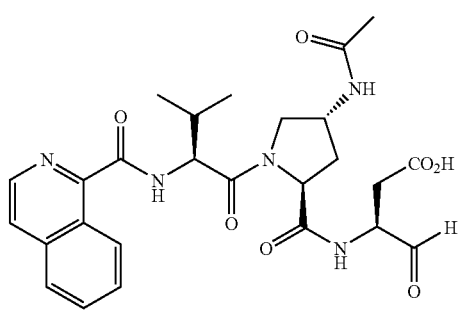

Procedure for the Synthesis of Analogs 15-18

Preparation of Analogs 15 and 16 (Scheme IV)

Synthesis of 2-(S)-piperazine-1,2,4-tricarboxylic acid 4-tert-butyl ester 1-(9H-fluoren-9-ylmethyl) ester To a solution of 2-(S)-piperazine carboxylic acid (Lonza) (3 g, 15 mmol) in 1:1 H$_2$O:dioxane (30 mL) was added a solution of (Boc)$_2$O in dioxane (3.3 g, 15 mmol, in 5 mL dioxane) while maintaining the pH at 11 with 1N NaOH. The pH was maintained over 3 hours at room temperature. The solution was adjusted to pH 9.5 with 1N HCl, cooled to 0° C. and treated with Fmoc-Cl (3.87 g, 15 mmol). The pH was maintained at 9.5 for 1 hour and the mixture stirred at room temperature overnight. The resulting suspension was filtered and the filtrate treated with 1N KHSO$_4$ to pH 2 then extracted with ethyl acetate (2×75 mL). The organic layer

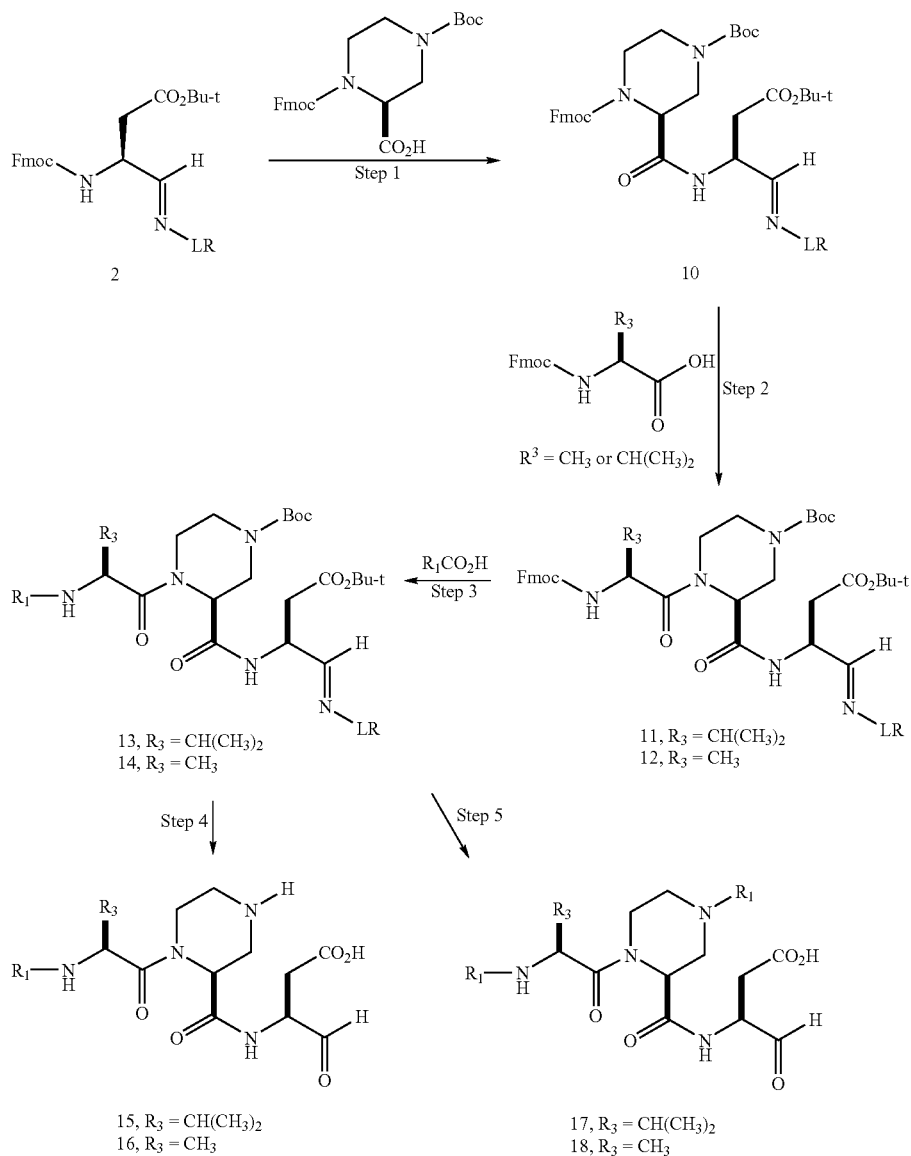

was dried with brine and MgSO₄ filtered, and concentrated to give colorless oil. The oil was dissolved in ethyl acetate and added to hexane to give 3.5 g (51% yield) of white solid after isolation. $^1$H NMR (500 MHz, DMSO-d$_6$) δ 1.55 (s, 9H) 2.80-3.5 (m, 3H), 3.8-4.9 (m, 5H), 5.7 (bs, 1H), 7.3 (m, 2H), 7.3-7.9 ppm (m, 8H), LC/MS (ES⁻) m/e 451.3 (M−H).

Step 1: To 5 g of resin 2 (0.375 mmol/gram 1.82 mmol) was added 25 mL of a 20% solution of piperidine in DMF. The suspension was rotated at room temperature for 5 minutes and drained. The procedure was repeated over 20 minutes. The resin was then washed successively with DMF (2×50 mL), CH₃OH (50 ML), CH₂Cl₂ (2×50 mL), CH₃OH (50 mL) and NMP (50 mL). To a suspension of resin in 25 mL of NMP was added successively 3.5 g of N-Fmoc-Boc piperazine carboxlyic acid (4 eq, 7.48 mmol), 1.0 mL of DIEA (8 eq, 14.96 mmol), 1.01 g of HOBt (4 eq, 7.48 mmol) and 2.83 g of HBTU (4 eq, 7.48 mmol). The mixture was rotated at room temperature overnight and drained. This coupling procedure was repeated over 3 hours. The resin was then washed successively with DMP (2×50 mL), CH₃OH (50 mL), 1:1 DMF/CH₂Cl₂ (2×50 mL), CH₃OH (1×50 mL) and CH₂Cl₂ (3×50 mL), and briefly dried in vacuo to afford resin 10.

Step 2: To 5 g (0.335 mmol/gram loading, 1.675 mmol) of 10 was added 25 mL of a 20% solution of piperidine in DMP. The suspension was rotated at room temperature for 5 minutes and drained. The procedure was repeated over 20 minutes. The resin-was then washed successively with DMF (2×50 mL), CH₃OH (50 mL), CH₂Cl₂ (2×50 mL), CH₃OH (50 mL) and NMP (2×50 mL). To a suspension of resin in 25 mL of NMP was added successively 2.08 g of N-Fmoc-valine or N-Fmoc-alanine (4 eq, 6.7 mmol), 1.17 mL of DIEA (4 eq, 6.7 mmol), 0.905 g of HOBt (4 eq, 6.7 mmol) and 1.38 g of HBTU (4 eq, 3.66 mmol). The mixture was rotated at room temperature overnight and drained. This coupling procedure was repeated over 3 hours. The resin was then washed successively with DMF (2×50 mL), CH₃OH (50 mL), 1:1 DMF/CH₂Cl₂ (2×50 mL), CH₃OH (50 mL) and CH₂Cl₂ (3×50 mL), and dried in vacuo to afford resin 11 or 12 respectively (0.35 mmol/gram, 5 g).

Step 3: To a 1.5 g (0.165 mmol) portion of resin 11 or 12 was added 2 mL of a 20% solution of piperidine in DMF. The suspension was rotated at room temperature for 5 minutes, and drained. The procedure was repeated over 20 minutes. The resulting resin was washed successively with DMF (3×15 mL), CH₃OH (15 mL), and NMP (3×15 mL). The desired carboxylic acid was then added (4 eq, 0.66 mmol), followed by 0.25 g HOBt (0.66 mmol), 0.12 mL of DIEA (4 eq, 0.66 mmol) and 0.89 g (0.66 mmol) HBTU in NMP. The mixture was rotated at room temperature overnight and drained. The resin was washed successively with DMF (2×15 mL), CH₃OH (15 mL), 1:1 DMF/CH₂Cl₂ (2×15 mL), CH₃OH (15 mL) and CH₂Cl₂ (3×15 mL), and dried in vacuo to afford 13 or 14.

Step 4: A 2 mL portion of a 95% solution of TFA in water was then added to the resin. The mixture was stirred at room temperature for one hour, and filtered. The filtrate was evaporated, and the residue was taken up in acetonitrile-water and purified by preparative HPLC to afford compounds 15 and 16.

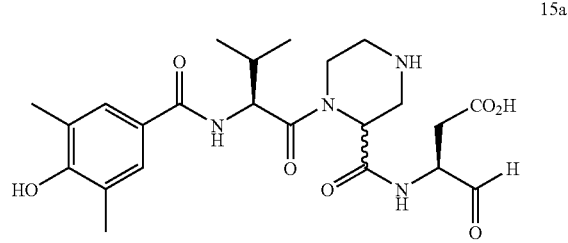

15a

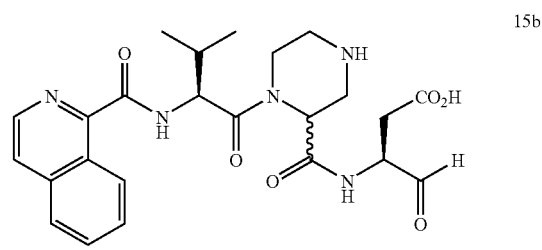

15b

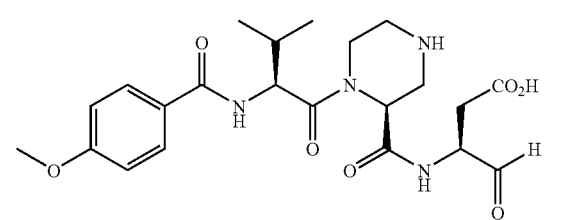

15c

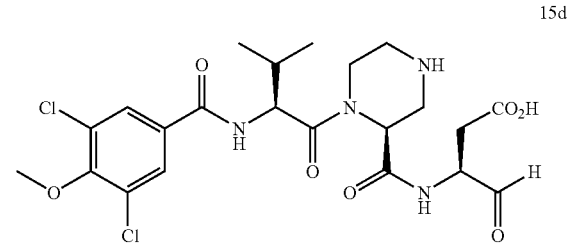

15d

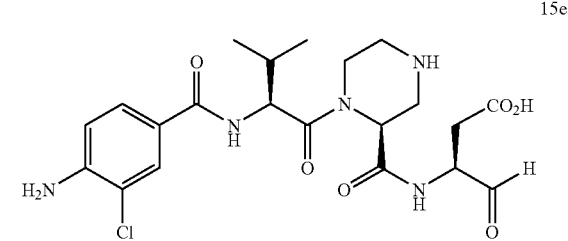

15e

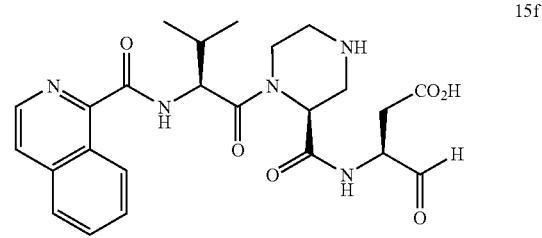

15f

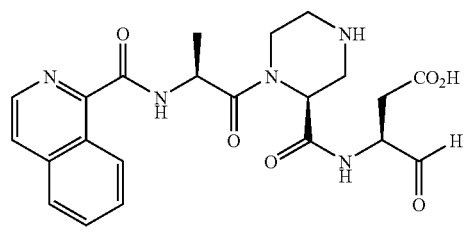

16a

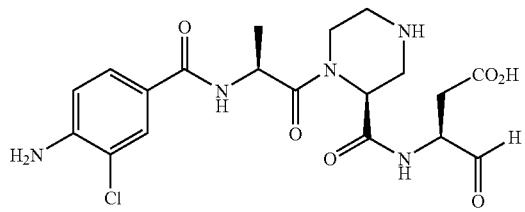

16b

Procedure for the Synthesis of Analogs 17 and 18
(See Scheme IV)

Step 5: Resin 13 or 14 was treated with 2 mL 25% TF/CH$_2$Cl$_2$ for 30 min and washed with DMF (2×5 mL), 10% DIEA/CH$_2$Cl$_2$ (2×5 mL) DMF/CH$_2$Cl$_2$ (2×5 mL), CH$_3$OH (5 mL) and CH$_2$Cl$_2$ (3×5 mL) and dried for five minutes. The resulting resin was washed with NMP (3×1 mL) then treated with acetic anhydride, or methoxacetic acid, or 2-propanesulfonyl chloride, or isopropyl isocyanate, or methane sulphonyl chloride, or methyl chloroformate according to the procedure used to prepare analogs 9 (Scheme III). Compounds 17 and 18 were obtained as described in Step 4 for compounds 15 and 16.

Compounds 17a and 17b were prepared by reductive amination using Na(OAc)$_3$BH and HCHO (38% in H$_2$O, 0.2 mL) and CH$_3$COOH (0.02 mL) prior to Step 4 and compound 18c was prepared by treatment with phosgene followed by ammonia prior to Step 4.

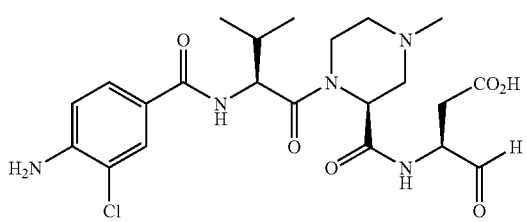

17a

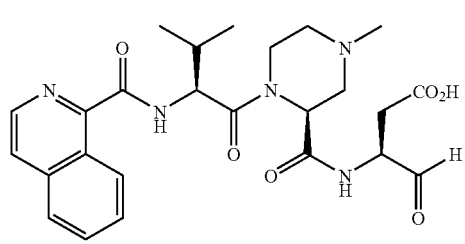

17b

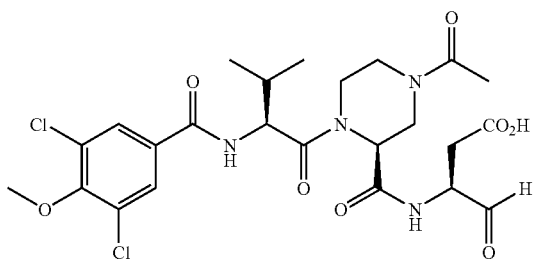

17c

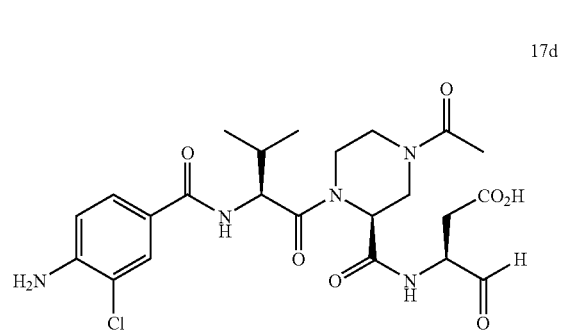

17d

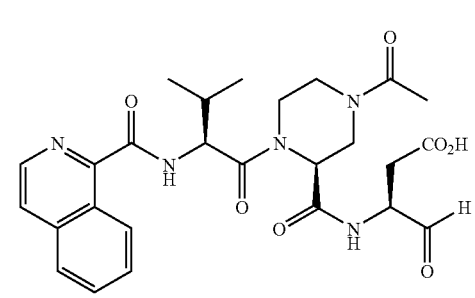

17e

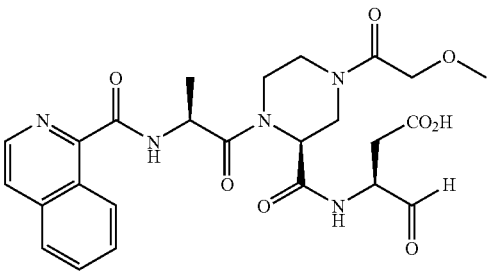

18a

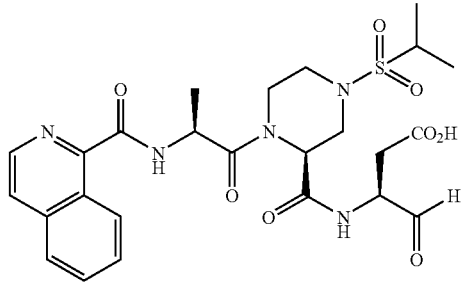

18b

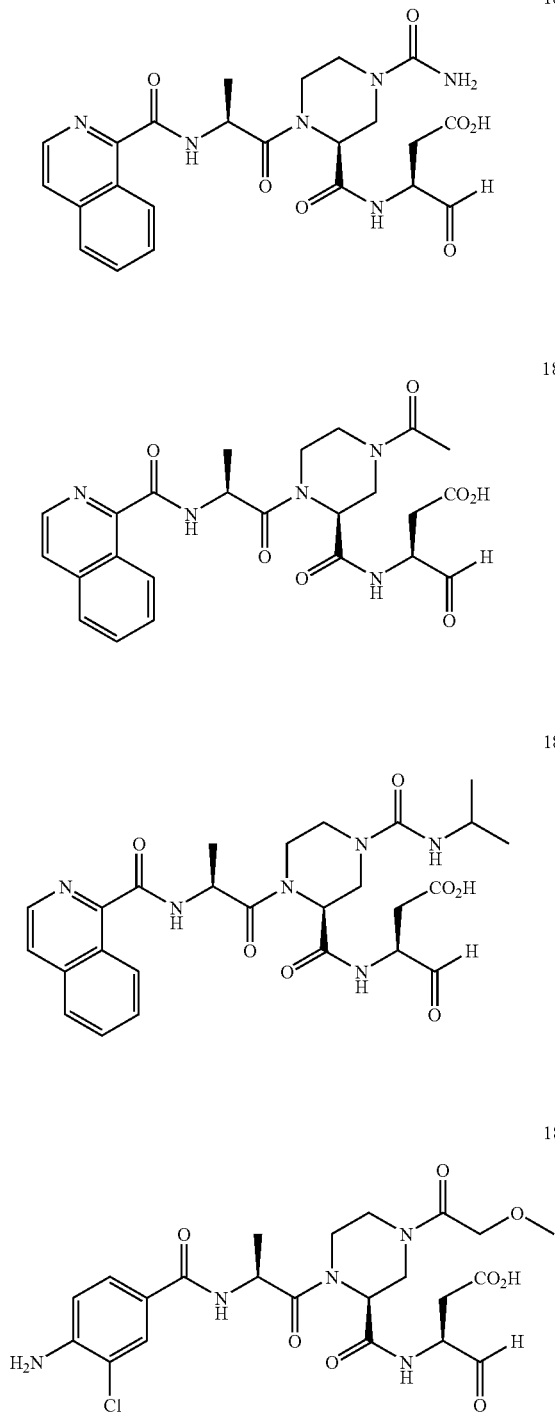

Procedure for the Preparation of Analogs 20

Compounds 20a-20t were prepared according to the procedure described for compounds 5 (Scheme I) only substituting the appropriate Fmoc-amino acid for Fmoc-Valine in Step 3 (Scheme V).

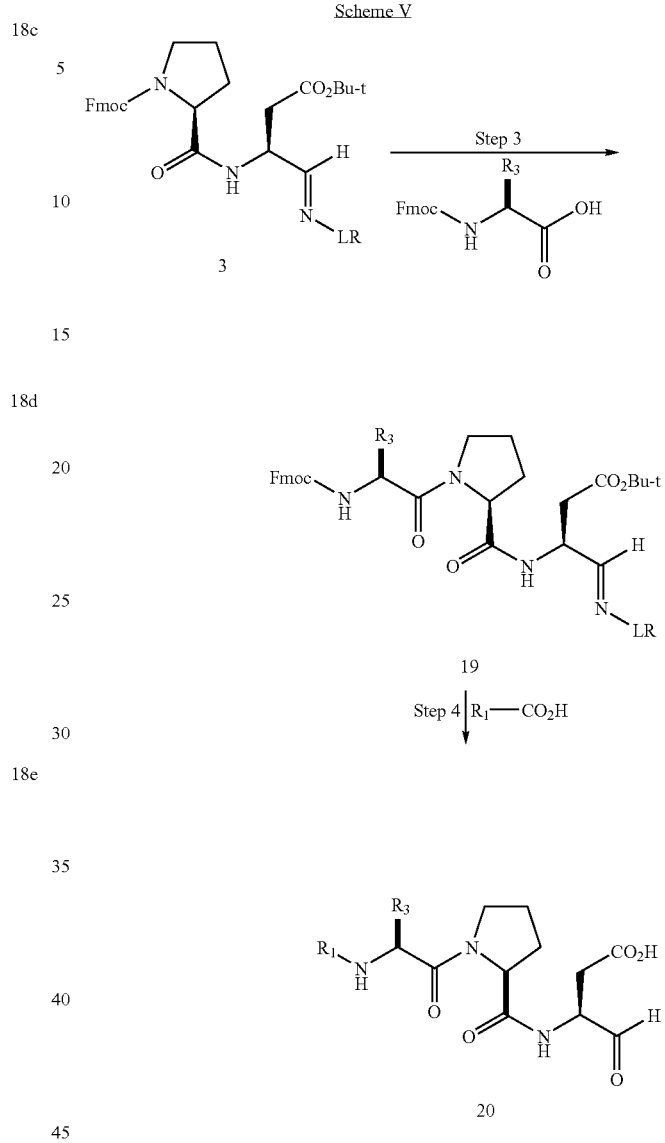

Scheme V

Preparation of 3-({1-[2-(4-amino-3-chloro-benzoylamino)-3-methylsulfonyl-propionyl]-pyrrolidine-2-carbonyl}-amino)-4-oxo-butyric acid (20i)

A suspension of 0.132 mmol of resin 3 in 4 mL of 20% piperidine in DMF was rotated at room temperature for 5 minutes, and the mixture was drained. The procedure was repeated over 20 minutes. The resin was washed successively with DMF (twice), $CH_3OH$ (once), $CH_2Cl_2$ (twice), $CH_3OH$ (once) and NMP (twice). To a suspension of the resin in 4 mL of NMP was added successively 189 mg of N-Fmoc-methyl cysteine (4 eq, 0.528 mmol), 0.185 mL of DIEA (8 eq, 1.056 mmol), 71 mg of HOBt (4 eq, 0.528 mmol) and 200 mg of HBTU (4 eq, 0.528 mmol). The mixture was rotated at room temperature overnight and drained. This coupling procedure was repeated over 3 hours. The resin was then washed successively with DMF (twice), $CH_3OH$ (once), and 1:1 $DMF/CH_2Cl_2$ (twice), $CH_3OH$ (once) and $CH_2Cl_2$ (three times), and dried in vacuo.

A suspension of 100 mg of this resin in 2 mL of 20% piperidine in DMF was rotated at room temperature for 5 minutes, and drained. The procedure was repeated over 20 minutes. The resin was washed successively with DMF (twice), CH$_3$OH (once), CH$_2$Cl$_2$ (twice), CH$_3$OH (once) and NMP (twice). To a suspension of resin in 2 mL of NMP was added successively 38 mg of 4-amino-3-chlorobenzoic acid (4 eq, 0.2 mmol), 0.140 mL of DIEA (8 eq, 0.4 mmol), 27 mg of HOBt (4 eq, 0.2 mmol) and 76 mg of HBTU (4 eq, 0.4 mmol). The mixture was rotated at room temperature overnight and drained. The resin was then washed successively with DMF (twice), CH$_3$OH (once), and 1:1 DMF/CH$_2$Cl$_2$ (twice), CH$_3$OH (once) and CH$_2$Cl$_2$ (three times), and dried in vacuo. The resin was then treated with 2 mL of 95% TFA in water for 1 h. The suspension was filtered, the filtrate was concentrated in vacuo and purified by preparative HPLC to afford the title compound (20i).

Preparation of 3-({1-[2-(3,5-dichloro-4-hydroxy-benizoylamino)-4-methanesulfonyl-butyryl]-pyrrolidine-2-carbonyl}-amino)-4-oxo-butyric acid (20p)

Compound 20p was prepared according to the procedure used for the preparation of 20i using N-Fmoc-methionine as the first component coupled to resin 3, and 3,5-dichloro-4-hydroxybenzoic acid as the second component.

Preparation of 3-[(1-{2-[(isoquinoline-1-carbonyl)-amino]-3-methanesulfonyl-propionyl}-pyrrolidine-2-carbonyl)-amino]-4-oxo-butyric acid (20r)

N-Fmoc methyl cysteine was oxidized to the corresponding sulfone using the method of B. M. Trost and D. P. Curran, *Tetrahedron Lett.* 22, pp. 1287-190 (1981). To a solution of 0.714 g (2 mmol) of N-Fmoc methyl cysteine in 24 mL of a 1:1 solution of CH$_3$OH—water stirred at 0° C. was added 3.68 g (3 eq, 6 mmol) of Oxone™. The mixture was stirred at room temperature for 48 h, diluted with water, acidified to pH 2 using 6N HCl, and extracted with three 100 mL portions of ethyl acetate. The combined organic extracts were dried (MgSO$_4$) and concentrated in vacuo to afford 0.700 g (89% yield) of sulfone: $^1$H NMR (DMSO-d$_6$, 500 MHz) δ 2.97 (s, 3H), 3.49-3.59 (m, 2H), 4.25 (m, 1H), 4.30-4.38 (m, 2H), 4.46 (m, 1H), 7.33 (t, 2H), 7.42 (t, 2H), 7.70-8.00 (m, 4H); exact mass calculated for C$_{19}$H$_{19}$NO$_6$S m/e 389.09, found m/e 390.2.

A suspension of 0.250 mmol of resin 3 in 10 mL of 20% piperidine in DMF was rotated at room temperature for 5 minutes, and the mixture was drained. The procedure was repeated over 20 minutes. The resin was washed successively with DMF (twice), CH$_3$OH (once), CH$_2$Cl$_2$ (twice), CH$_3$OH (once) and NMP (twice). To a suspension of the resin in 6 mL of NMP was added successively 200 mg of N-Fmoc-methyl cysteine sulfone (4 eq, 0.50 mmol) 0.175 mL of DIEA (8 eq, 1.00 mmol), 70 mg of HOBt (4 eq, 0.50 mmol) and 188 mg of HBTU (4 eq, 0.50 mmol). The mixture was rotated at room temperature overnight and drained. This coupling procedure was repeated over 3 hours. The resin was washed successively with DMF (twice), CH$_3$OH (once), 1:1 DMF/CH$_2$Cl$_2$ (twice), CH$_3$OH (once) and CH$_2$Cl$_2$ (three times), and dried in vacuo.

A suspension of 150 mg of this resin in 4 mL of 20% piperidine in DMF was rotated at room temperature for 5 minutes, and drained. The procedure was repeated over 20 minutes. The resin was washed successively with DMF (twice), CH$_3$OH (once), CH$_2$Cl$_2$ (twice), CH$_3$OH (once) and NMP (twice). To a suspension of resin in 3 mL of NMP was added successively 52 mg of 1-isoquinolinecarboxylic acid (4 eq, 0.3 mmol), 0.104 mL of DIEA (8 eq, 0.6 mmol), 37 mg of HOBt (4 eq, 0.3 mmol) and 104 mg of HBTU (4 eq, 0.3 mmol). The mixture was rotated at room temperature overnight and drained. The resin was washed successively with DMF (twice), CH$_3$OH (once), and 1:1 DMF/CH$_2$Cl$_2$ (twice), CH$_3$OH (once) and CH$_2$Cl$_2$ (three times), and dried in vacuo. The resin was then treated with 2 mL of 95% TFA in water for 1 hour. The suspension was filtered, the filtrate was concentrated in vacuo and purified by preparative HPLC to afford the title compound (20r).

Preparation of 3-({1-[2-(3,5-dichloro-4-hydroxy-benzoylamino)-3-methanesulfonyl-propionyl]-pyrrolidine-2-carbonyl}-amino)-4-oxo-butyric acid (20s)

Compound 20s was prepared according to the procedure used for the preparation of 20i, using 3,5-dichloro-4-hydroxybenzoic acid in place of 1-isoquinolinecarboxylic acid.

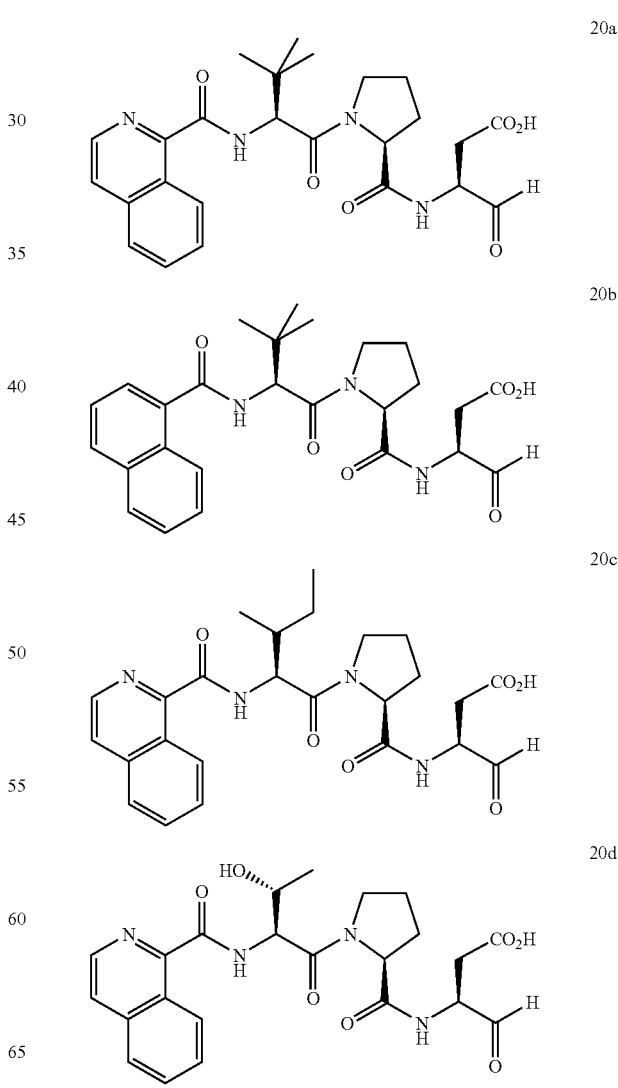

-continued
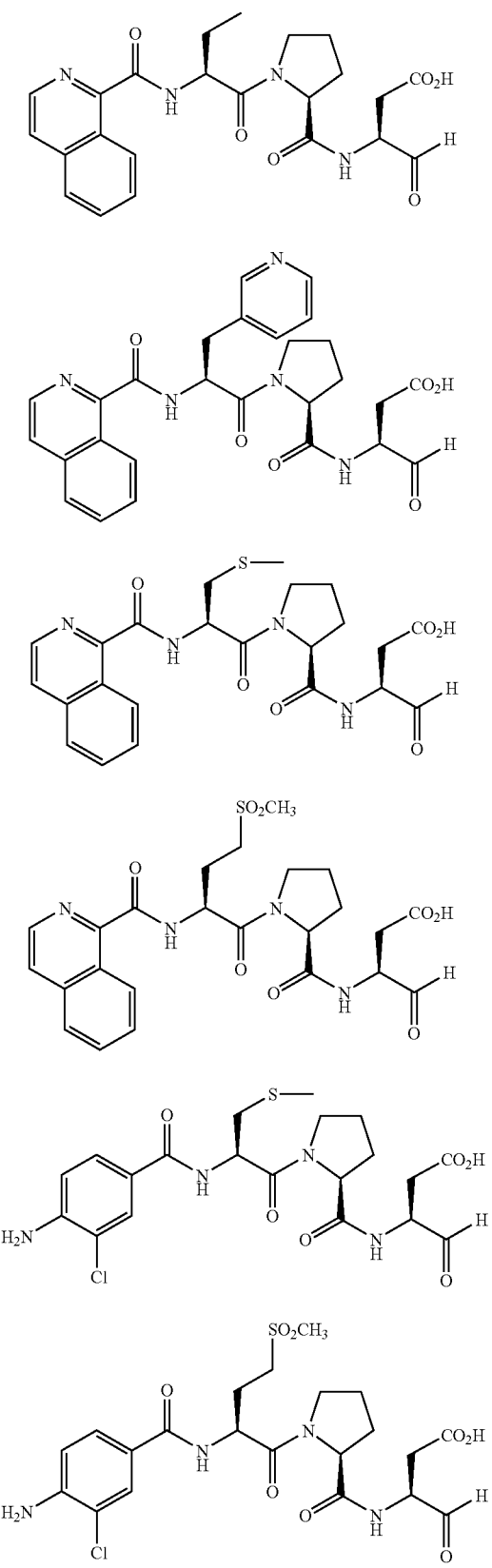
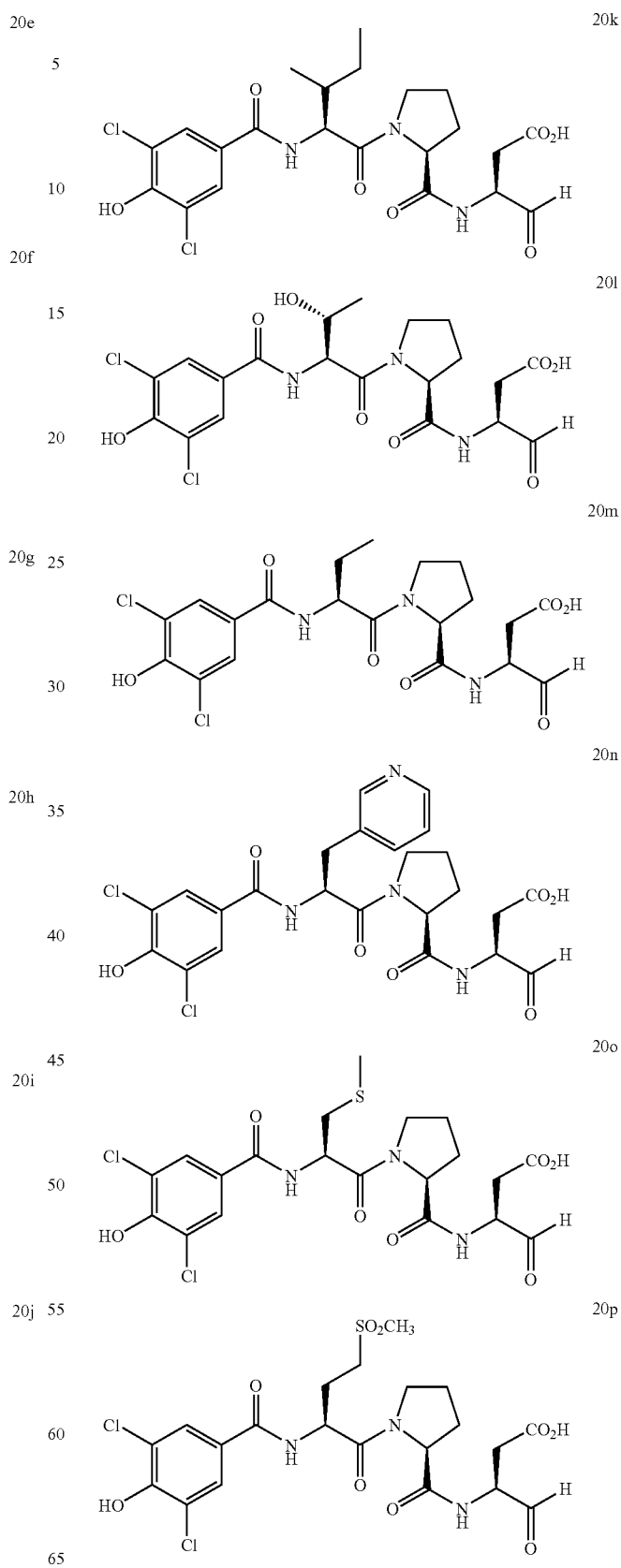

-continued
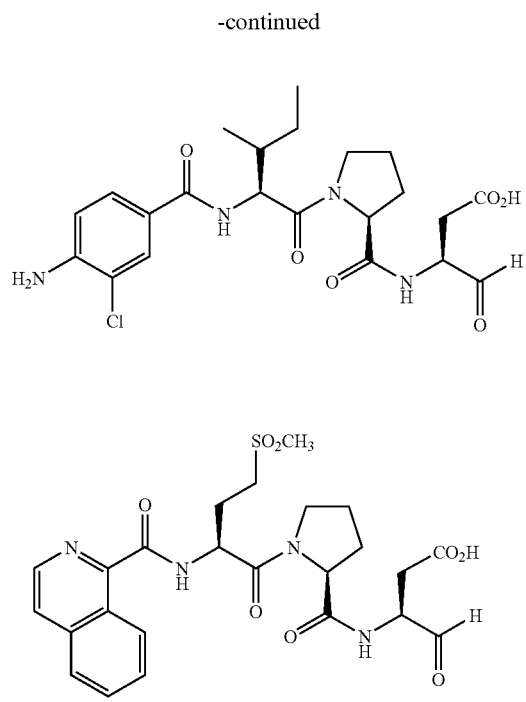
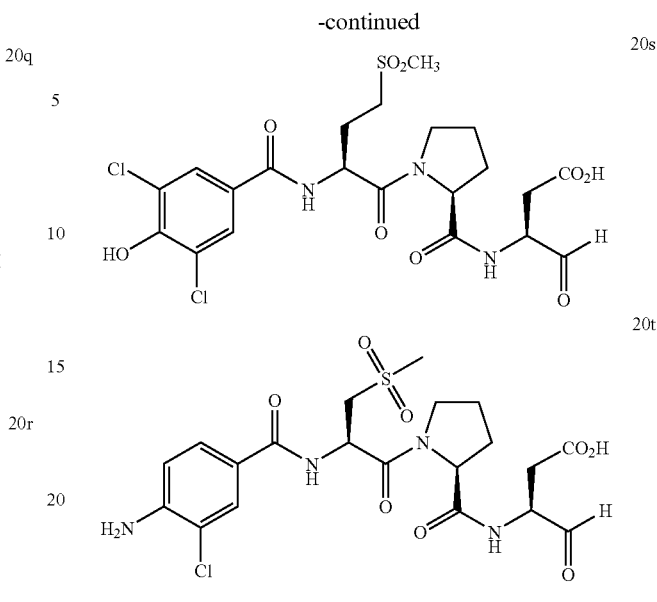
Procedure for the Preparation of Analogs 23
Compounds 23a-23i were prepared according to the procedure described for compounds 7 (Scheme II) only substituting the appropriate Fmoc-amino acid for Fmoc-proline in Step 2 (Scheme VI).
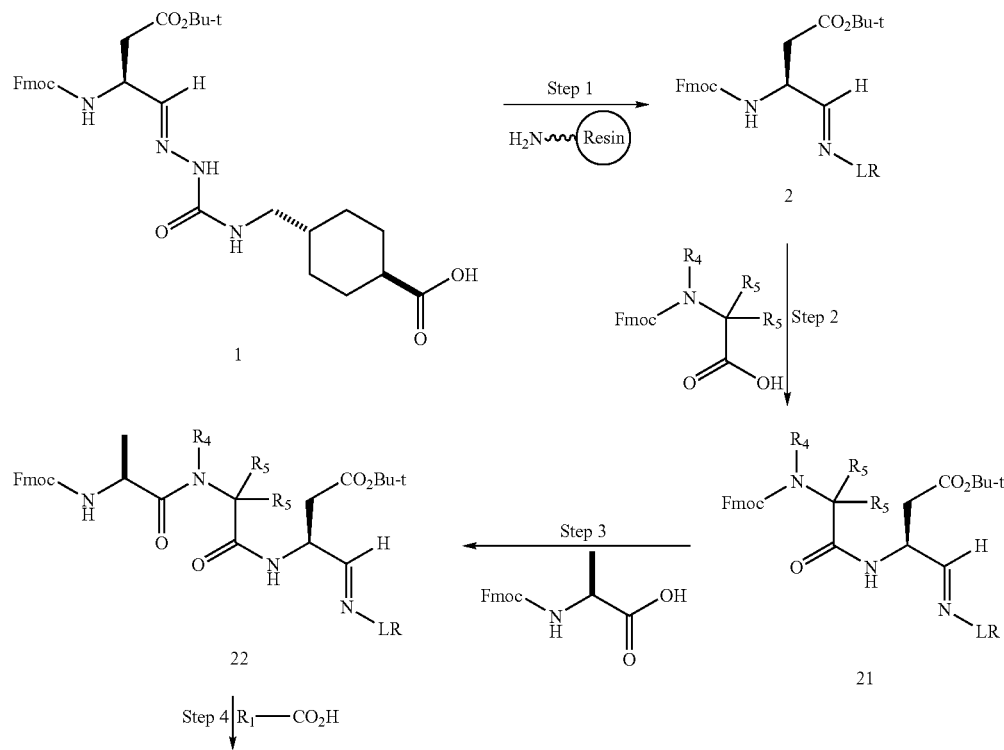

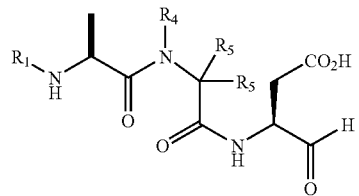

23

Preparation of 3-({2-[2-(4-Amino-3-chloro-benzoylamino)-propionyl]-4-methyl-3,4-dihydro-2H-pyrazole-3-carbonyl}-amino)-4-oxo-butyric acid (23g)

Compound 23g was prepared according to the procedure described for compounds 7 only substituting 4-methyl-4,5-dihydro-pyrazole-1,5-dicarboxylic acid 1-(9H-fluoren-9-yl-methyl) ester for Fmoc-proline (Scheme II) in Step 2.

Preparation of 4-methyl-4,5-dihydro-pyrazole-1,5-dicarboxylic acid 1-(9H-fluoren-9-ylmethyl)ester To a solution of 650 mg (2 mmol) of (10,10-dimethyl-3,3-dioxo-$\lambda^6$-thia-4-aza-tricyclo[5.2.1.0$^{0,0}$]dec-4-yl)-(4-methyl-3,4-dihydro-2H-pyrazol-3-yl)-methanone (*J. Am. Chem. Soc.*, 119, pp. 8379-8380 (1997)) in 6 mL of water and 14 mL of THF stirred at 0° C. was added 420 mg (10 mmol, 5 eq) of lithium hydroxide. The mixture was stirred at 0° C. for 2 hours and at room temperature for 30 minutes, diluted with 20 mL of water and washed with ether (20 mL). The pH of the solution was then adjusted to 9, and a solution of 519 mg (2 mmol, 1 eq) of Fmoc-Cl in 3 mL of dioxane was added. The mixture was stirred at room temperature overnight, washed with ether, acidified to pH 2-3 and extracted with 3 40-mL portions of ethyl acetate. The combined organic extracts were washed with brine, dried (MgSO$_4$) and concentrated in vacuo to afford 690 mg (98% yield) of a colorless foam which was identified as the title compound. $^1$H NMR (DMSO-d$_6$, 500 MHz) δ 1.2 (d, 3H), 3.2 (m, 1H), 4.2-4.6 (m, 3H), 7.1 (s, 1H), 7.2-7.5 (m, 5H) 7.7-8.0 (m, 4H). Exact mass calculated for C$_{20}$H$_{18}$N$_2$O$_4$ m/e 350.13, found m/e 351.3

Preparation of 3-({1-[2-(4-amino-3-chloro-benzoylamino)-propionyl]-4-methoxy-pyrrolidine-2-carbonyl}-amino)-4-oxo-butyric acid (23i)

Compound 23i was prepared according to the procedure described for compounds 7 only substituting N-Fmoc-4-methoxyproline for Fmoc-proline (Scheme II) in Step 2.

Preparation of N-Fmoc-4-methoxyproline

To a solution of 735 mg (3 mmol) of N-Boc-4-hydroxyproline methyl ester in 20 mL of THF stirred at 0° C. was added 79 mg (1.1 eq, 3.3 mmol) of 60% sodium hydride in mineral oil. The mixture was stirred at 0° C. for 1 hour, and methyl iodide (0.56 mL, 3 eq, 9 mmol) was added. The mixture was stirred at room temperature overnight, quenched by addition of saturated aqueous ammonium chloride, diluted with water, and extracted with three 80 mL portions of ethyl acetate. The combined organic extracts were washed with brine, dried (MgSO$_4$), and concentrated in vacuo to afford a pale yellow oil. The oil was taken up in 9 mL of CH$_3$OH and 3 mL of water, and 378 mg (3 eq, 9 mmol) of lithium hydroxide was added. The mixture was stirred at room temperature overnight, diluted with water, acidified to pH 3 and extracted with three 80 mL portions of ethyl acetate. The combined organic extracts were washed with brine, dried (MgSO$_4$) and concentrated in vacuo. The residual oil was taken up in 10 mL of TFA and the solution was stirred at room temperature for 2 hours, and concentrated in vacuo. The residual oil was diluted with 6 mL of 10% aqueous sodium carbonate and 3 mL of dioxane, and a solution of 9-fluorenylmethyl chloroformate (779 mg, 1 eq, 3 mmol) in 5 mL of dioxane was added. The mixture was stirred at room temperature overnight, diluted with water, acidified to pH 3 and extracted with three 80 mL portions of ethyl acetate. The combined organic extracts were washed with brine, dried (MgSO$_4$) and concentrated in vacuo to afford an oil, which was purified by column chromatography over silica gel eluted with CH$_2$Cl$_2$/CH$_3$OH 20:1, to afford 600 mg (55%) of N-Fmoc-4-methoxyproline: exact mass calculated for C$_{21}$H$_{21}$NO$_5$ m/e 367.14 found m/e 368.4.

To a 0.125 mmol portion of resin 2 was added 4 mL of 20% piperidine in DMF. The mixture was rotated at room temperature for 5 minutes and drained. The procedure was repeated over 20 minutes: The resin was washed successively with DMF (twice), CH$_3$OH (once), CH$_2$Cl$_2$ (twice), CH$_3$OH (once) and NMP (twice). To a suspension of the resin in 4 mL of NMP was added successively 184 mg of N-Fmoc-4-methoxyproline (4 eq, 0.50 mmol), 0.175 mL of DIEA (8 eq, 1.00 mmol), 70 mg of HOBt (4 eq, 0.50 mmol) and 188 mg of HBTU (4 eq, 0.50 mmol). The mixture was rotated at room temperature overnight and drained. This coupling procedure was repeated over 3 hours. The resin was washed successively with DMF (twice), CH$_3$OH (once), 1:1 DMF/CH$_2$Cl$_2$ (twice), CH$_3$OH (once) and CH$_2$Cl$_2$ (three times), and dried in vacuo.

To the resin was added 4 mL of 20% piperidine in DMF. The mixture was rotated at room temperature for 5 minutes and drained. The procedure was repeated over 20 minutes. The resin was washed successively with DMF (twice), CH$_3$OH (once), CH$_2$Cl$_2$ (twice), CH$_3$OH (once) and NMP (twice). To a suspension of the resin in 4 mL of NMP was added successively 156 mg of N-Fmoc-alanine (4 eq, 0.50 mmol), 0.175 mL of DIEA (8 eq, 1.00 mmol), 70 mg of HOBt (4 eq, 0.50 mmol) and 188 mg of HBTU (4 eq, 0.50 mmol). The mixture was rotated at room temperature overnight and drained. This coupling procedure was repeated over 3 hours. The resin was washed successively with DMF (twice), CH$_3$OH (once), 1:1 DMF/CH$_2$Cl$_2$ (twice), CH$_3$OH (once) and CH$_2$Cl$_2$ (three times), and dried in vacuo.

To the resin was added 4 mL of 20% piperidine in DMF. The mixture was rotated at room temperature for 5 minutes and drained. The procedure was repeated over 20 minutes. The resin was washed successively with DMF (twice), CH$_3$OH (once), CH$_2$Cl$_2$ (twice), CH$_3$OH (once) and NMP (twice). To a suspension of the resin in 4 mL of NMP was added successively 80 mg of 4-amino-3-chlorobenzoic acid (4 eq, 0.50 mmol), 0.175 mL of DIEA (8 eq, 1.00 mmol), 70 mg of HOBt (4 eq, 0.50 mmol) and 188 mg of HBTU (4 eq, 0.50 mmol). The mixture was rotated at room temperature overnight and drained. The resin was washed successively with DMF (twice), $CH_3OH$ (once), 1:1 $DMF/CH_2Cl_2$ (twice), $CH_3OH$ (once) and $CH_2Cl_2$ (three times), and dried in vacuo.

The resin was treated with 4 mL of 95% TFA in water for 1 hour. The mixture was filtered. The filtrate was concentrated in vacuo to afford an oil, which was purified by HPLC to afford the title compound (23i).

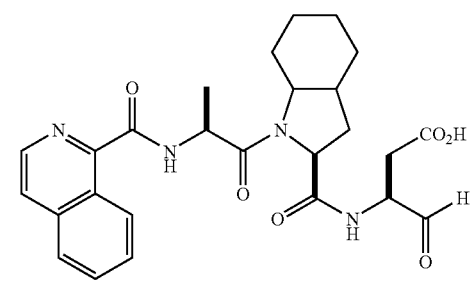

23a

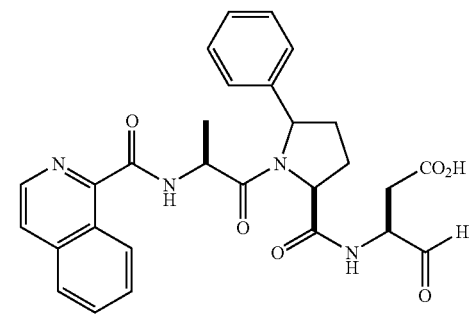

23b

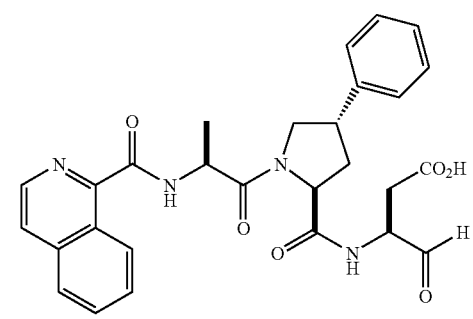

23c

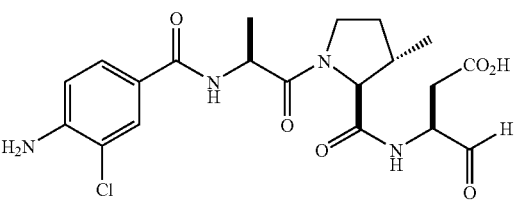

23d

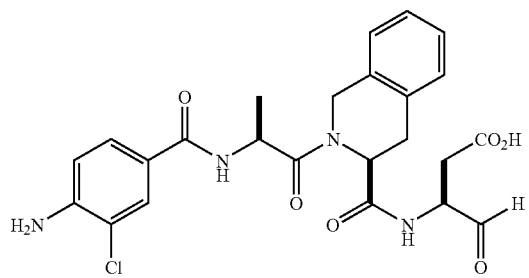

23e

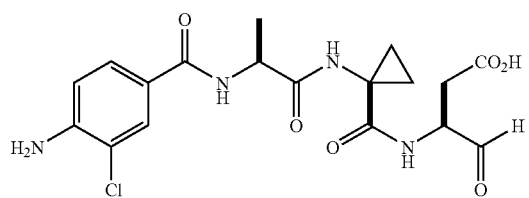

23f

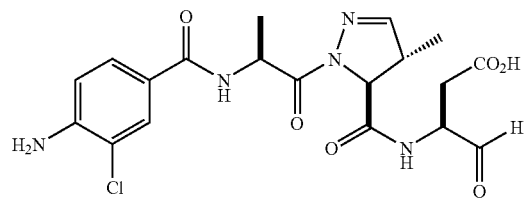

23g

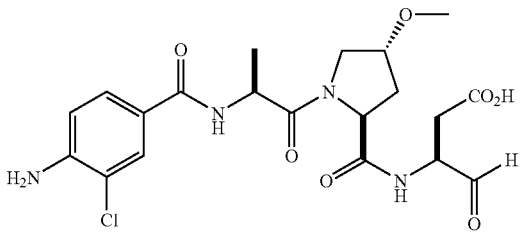

23i

Procedure for the Preparation of Analogs 24a-e

Compounds 24a-24e were prepared according to the procedures described for compounds 5 (Scheme I) only substituting either Fmoc-azetidine carboxylic acid or trans-2-phenyl-Fmoc-azetidine carboxylic acid for Fmoc-proline in Step 2.

24a
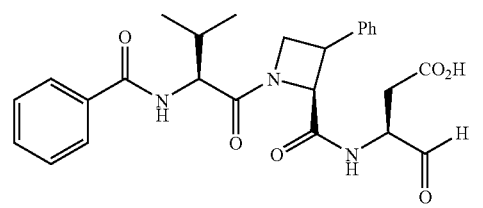

24b
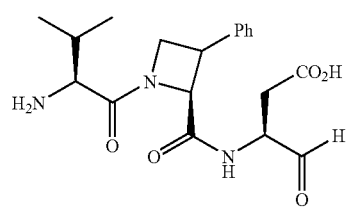

24c
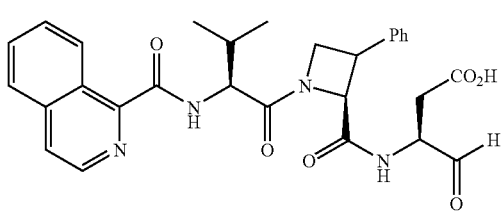

24d
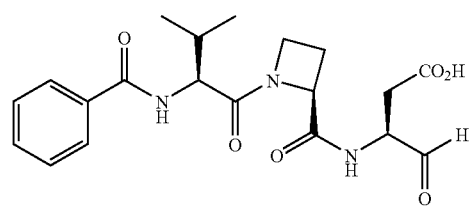

24r
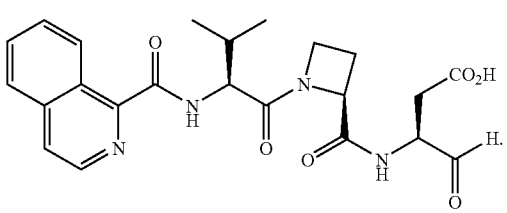

Procedure for the Preparation of Analogs 25

Compounds 25a-25e were prepared according to the procedures described for compounds 5 and 7 (Scheme I and Scheme II) only substituting Fmoc-2(S)-pipecolic acid for Fmoc-proline in Step 2 and coupling either Fmoc-valine or Fmoc-alanine or Fmoc-tert-leucine in Step 3.

25a
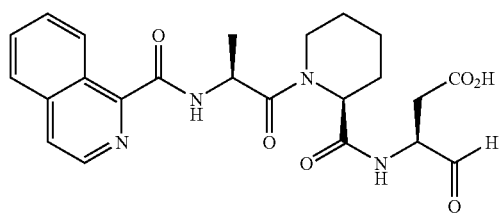

25b
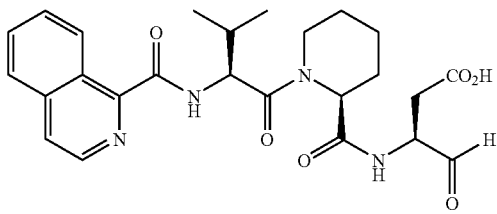

25c
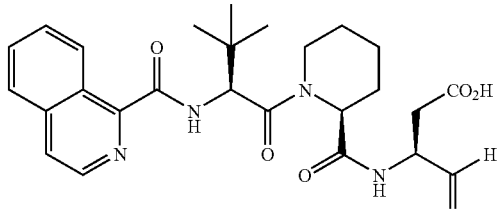

25d
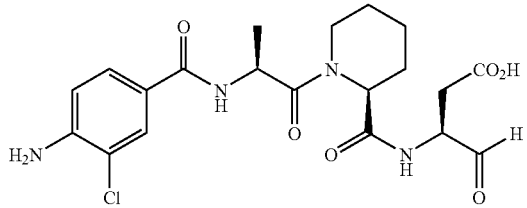

25e
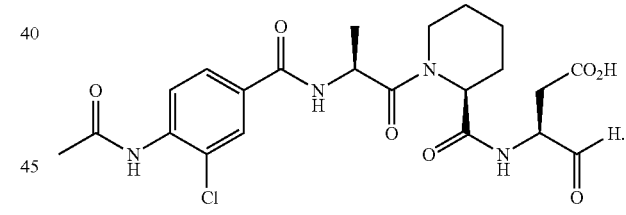

Procedure for the Preparation of Analogs 26a-h

Compounds 26a-26h were prepared according to the procedure described for compounds 23 (Scheme VI) only substituting Fmoc-valine for Fmoc-alanine in Step 3.

26a
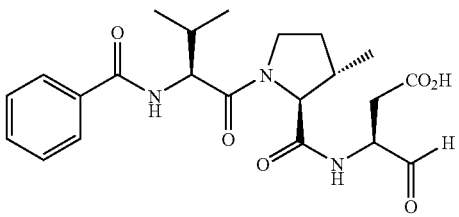

-continued

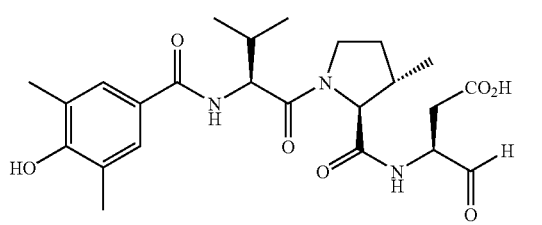
26b

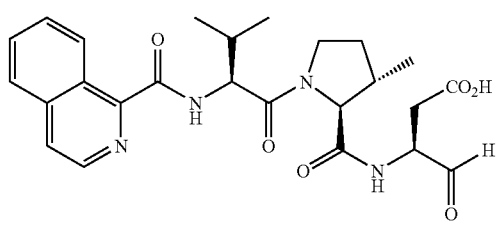
26c

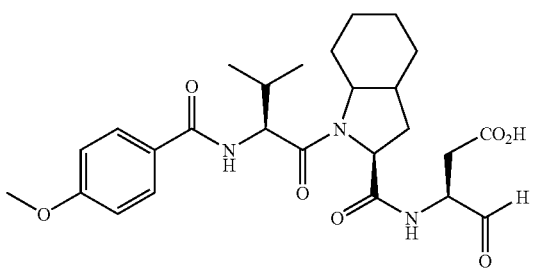
26d

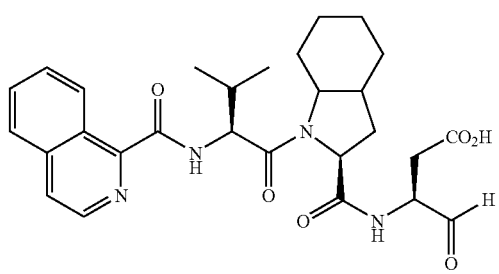
26e

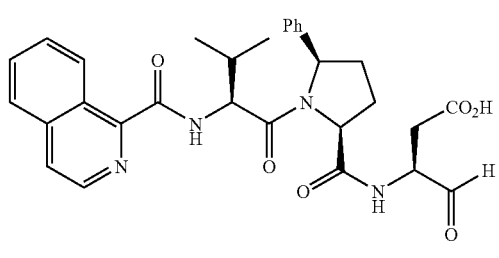
26f

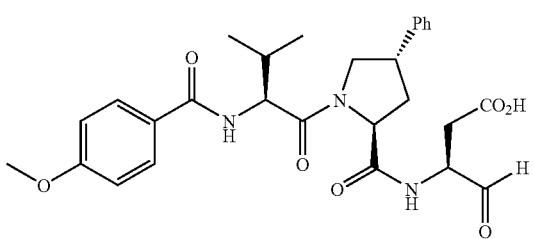
26g

-continued

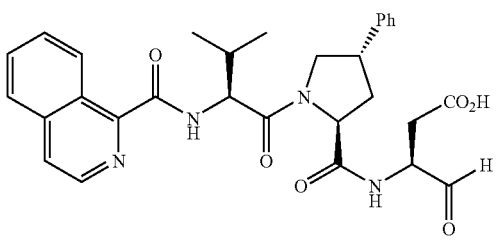
26h

Procedure for the Preparation of Analogs 27

Compounds 27a-27n were prepared according to the procedure described for compounds 7 (Scheme II) only substituting Fmoc-4,4-difluoroproline for Fmoc-proline in Step 2.

Preparation of N-Boc 4,4-difluoroproline methyl ester

To a solution of 9.63 mL (7.2 mmol) of oxalyl chloride in 10.6 mL of $CH_2Cl_2$ stirred at −78° C. was added a solution of 0.94 mL (13.2 mmol) of methyl sulfoxide in 15 mL of $CH_2Cl_2$. The solution was stirred at −78° C. for 30 min. A solution of 1.47 g (6 mmol) of N-Boc-4-hydroxyproline methyl ester in 19 mL of $CH_2Cl_2$ was then added dropwise. The mixture was stirred at −78° C. for 1.5 h, and 3.34 mL (24 mmol) of triethylamine was added. The solution was allowed to warm up to room temperature and stirred overnight. It was then diluted with 100 mL of $CH_2Cl_2$, washed successively with 100 mL of water, 100 mL of 1N HCl, and 100 mL of brine, dried ($MgSO_4$) and concentrated in vacuo. The residue was purified by column chromatography over silica gel (eluted with ethyl acetate/hexanes, 1:3), to afford 1.294 g (89% yield) of N-Boc-4-oxo-proline methyl ester. $^1$H NMR (500 MHz, $CDCl_3$) δ 1.45 (m, 9H), 2.60 (m, 1H), 2.95 (m, 1H), 3.75 (m, 3H), 3.90 (m, 2H), 4.80 (m, 1H).

To a solution of 808 mg (3.33 mmol) of N-Boc-4-oxo-proline methyl ester in 13 mL of $CH_2Cl_2$ stirred at 0° C. was added 0.88 mL (7.19 mmol, 2.2 eq) of DAST. The mixture was stirred at 0° C. for 2 hours, at room temperature for 16 hours, and poured into ice water. The mixture was stirred at room temperature for 2 hours. The organic phase was separated, washed with water, dried ($MgSO_4$) and concentrated in vacuo. The residue was purified by column chromatography over silica gel (eluted with ethyl acetate-hexanes, 1:8), to afford 754 mg (79% yield) of difluorinated derivative as a pale yellow oil. $^1$H NMR (500 MHz, $CDCl_3$) δ 1.50 (m, 9H), 2.45 (m, 1H), 2.70 (m, 1H), 3.75 (m, 3H), 3.80 (m, 2H), 4.50 (m, 1H).

Preparation of N-Fmoc-4,4-difluoroproline

To a solution of 754 mg (2.85 mmol) of N-Boc 4,4-difluoroproline methyl ester in 5 mL of THF stirred at 0° C. was added a solution of 179 mg (4.27 mmol) of lithium hydroxide in 5 mL of water. The solution was stirred at 0° C. for 3 h, at room temperature for 1 hour, diluted with water, extracted with ether, acidified to pH 2-3, and extracted with two 30 mL portions of ethyl acetate. The combined organic extracts were washed with brine, dried ($MgSO_4$) and concentrated in vacuo to afford 652 mg (91%) of acid as a pale yellow solid.

A solution of 652 mg (2 mmol) of N-Boc-4,4-difluoro-proline in 10 mL of 1;1 TFA/CH$_2$Cl$_2$ was stirred at 0° C. for 45 min, and concentrated in vacuo. The residue was taken up in 3 mL of dioxane, and 5 mL of 10% aqueous sodium carbonate was added, followed by a solution of 675 mg (1 eq) of Fmoc-Cl in 5 mL of dioxane. The mixture was stirred at room temperature for 16 h, diluted with 20 mL of water, extracted with 2 20-mL portions of diethyl ether, acidified to pH 2, and extracted with three 30-mL portions of ethyl acetate. The combined organic extracts were washed with 50 mL of brine, dried (MgSO$_4$) and concentrated in vacuo. The residue was purified by column chromatography over silica gel (eluted with CH$_2$Cl$_2$/CH$_3$OH 10:1), to afford 850 mg (88%) of N-Fmoc-4,4-difluoroproline as a brownish solid. $^1$H NMR (500 MHz, CDCl$_3$) δ 2.55 (m, 1H) 2.95 (m, 1H), 3.80 (m, 2H), 4.20 (m, 1H), 4.30 (m, 2H), 4.55 (m, 1H), 7.32 (m, 2H), 7.45 (m, 2H), 7.70 (m, 2H), 7.90 (m, 2H). Exact mass calculated for C$_{20}$H$_{17}$F$_2$NO$_4$ m/e 373.11, found m/e 374.4.

-continued

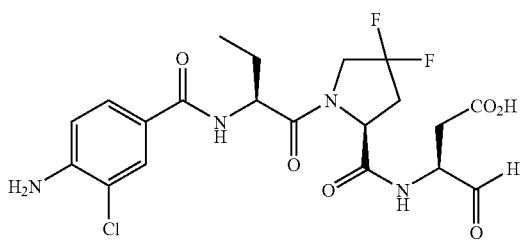

27e

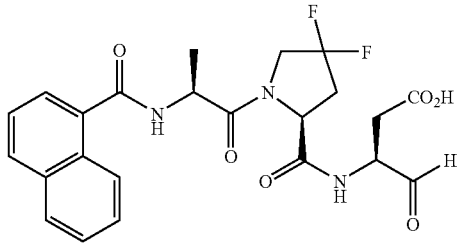

27f

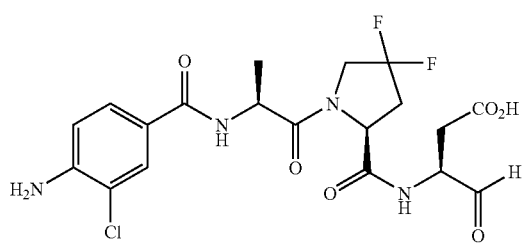

27a

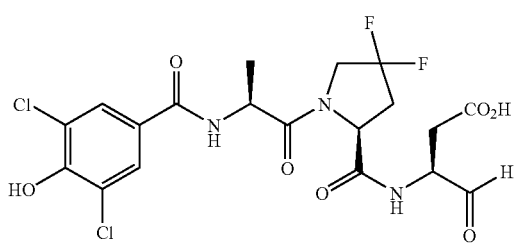

27g

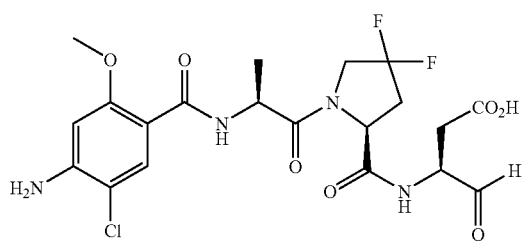

27b

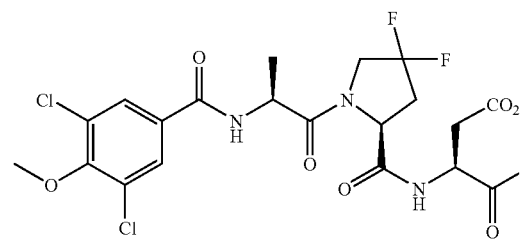

27h

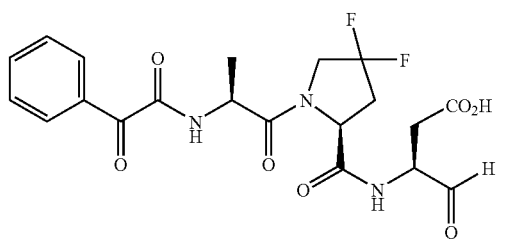

27c

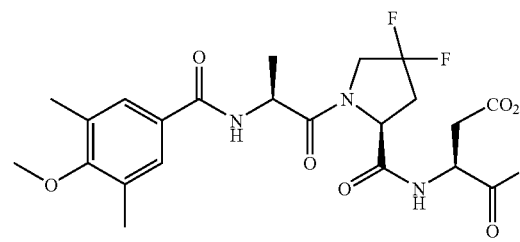

27i

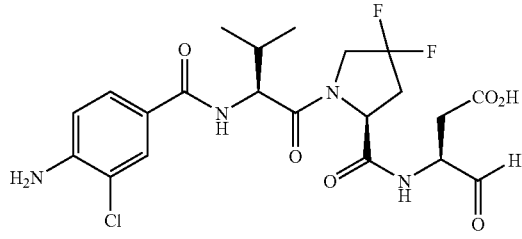

27d

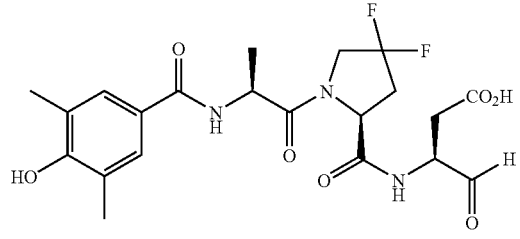

27j

-continued

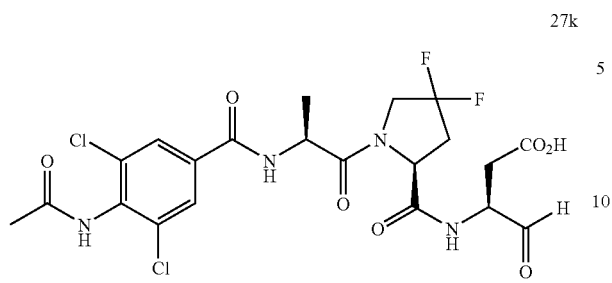
27k

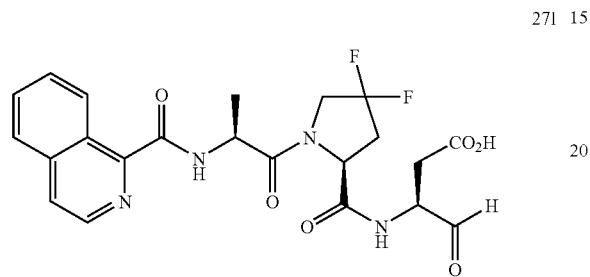
27l

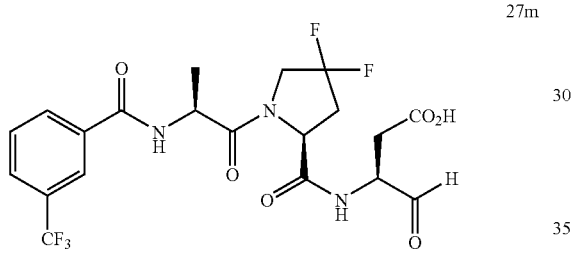
27m

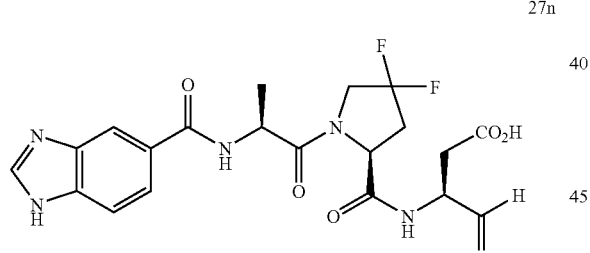
27n

Compounds 28a-28c were prepared according to the procedure described for compounds 5 and 7 (Scheme I and Scheme II) only substituting Fmoc-dimethylthioproline for Fmoc-proline in Step 2.

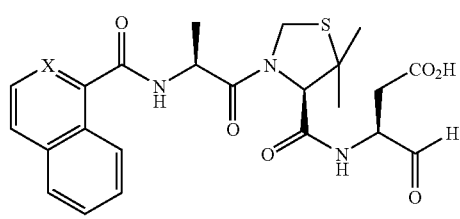

28a, X = N
28b, X = C

-continued

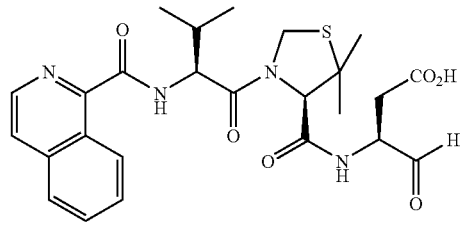
28c

General Procedures for the Preparation of Compounds of Embodiment A Formula I (Schemes VII-VIII)

Compounds of Embodiment A Formula I where $R_4$=H and one $R_5$=H

Procedure for the Preparation of Analogs 29

Compounds 29a-29s were prepared according to the procedure described for compounds 5 (Scheme I) only substituting Fmoc-alanine for Fmoc-proline in Step 2 and using either Fmoc-valine or Fmoc-alanine or Fmoc-tert-leucine in Step 3.

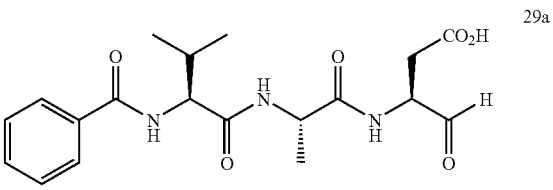
29a

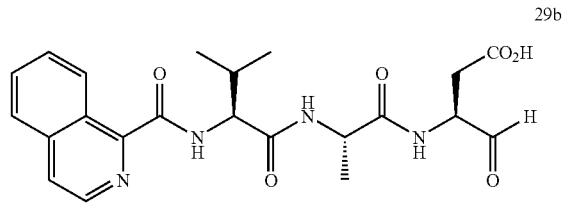
29b

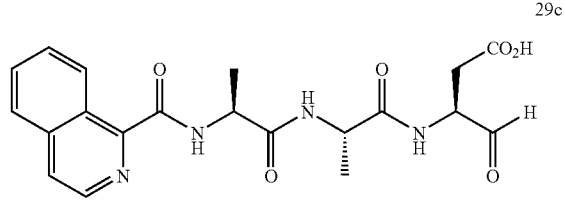
29c

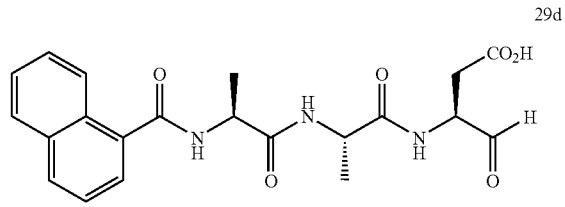
29d

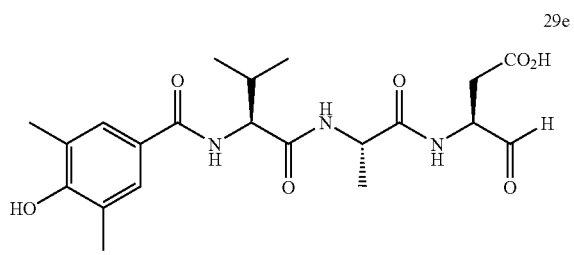
29e
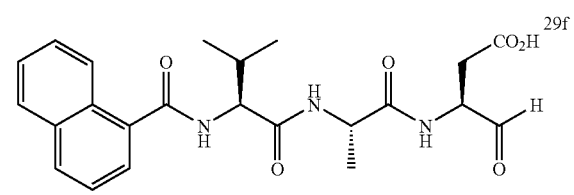
29f
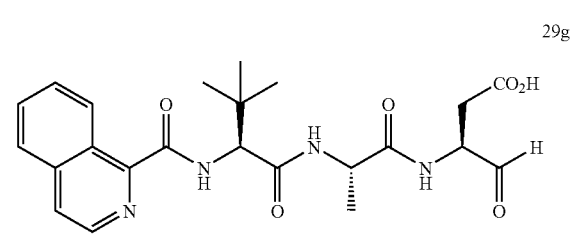
29g
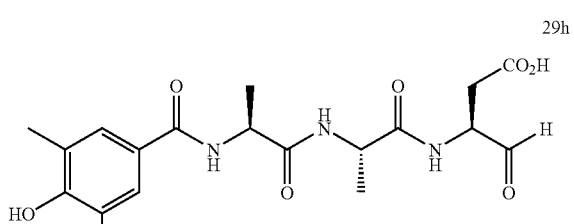
29h
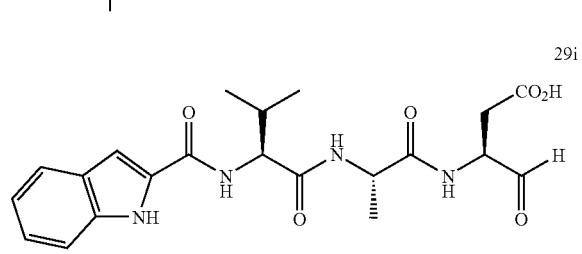
29i
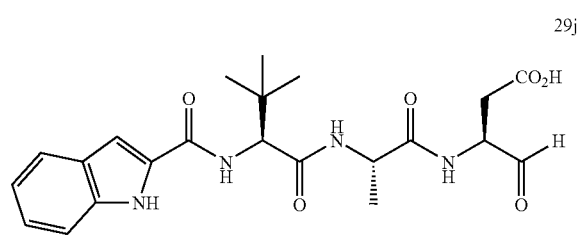
29j
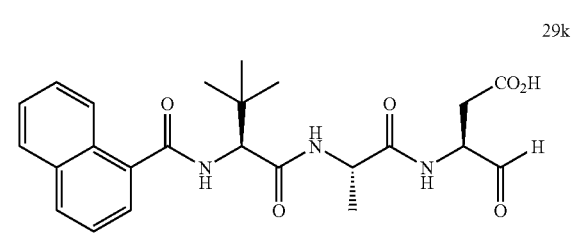
29k
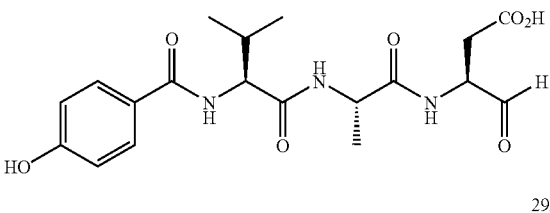
29l
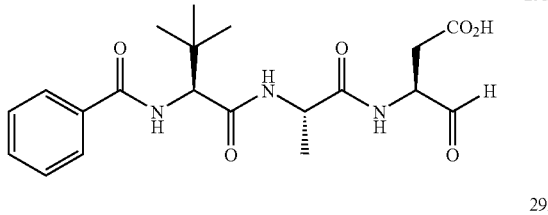
29m
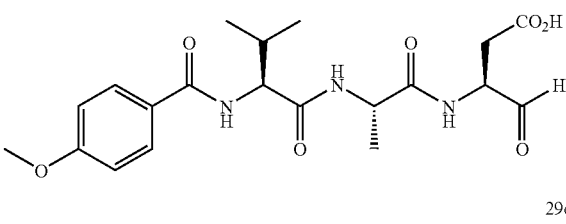
29n
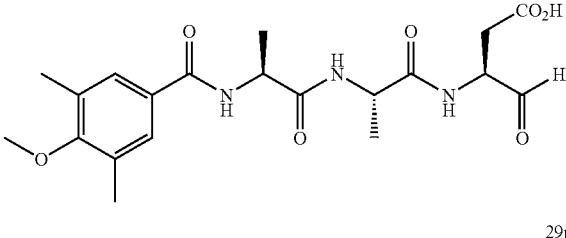
29o
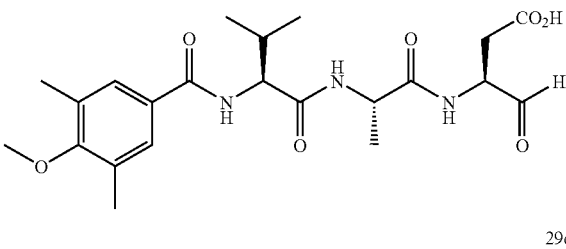
29p
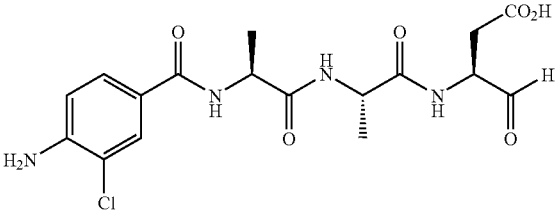
29q
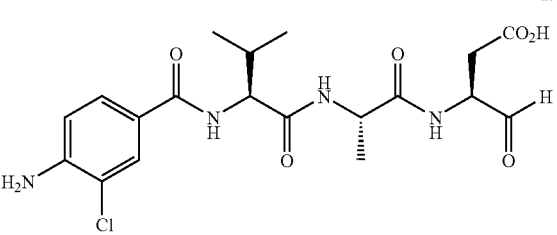
29r

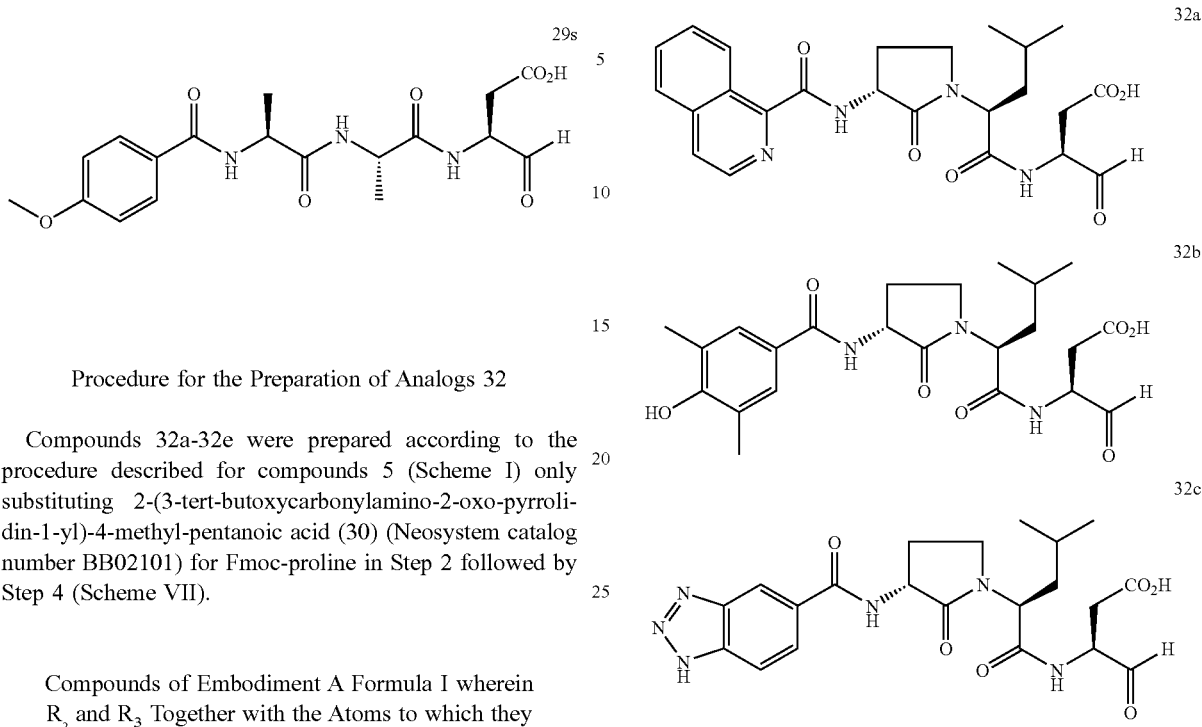

Procedure for the Preparation of Analogs 32

Compounds 32a-32e were prepared according to the procedure described for compounds 5 (Scheme I) only substituting 2-(3-tert-butoxycarbonylamino-2-oxo-pyrrolidin-1-yl)-4-methyl-pentanoic acid (30) (Neosystem catalog number BB02101) for Fmoc-proline in Step 2 followed by Step 4 (Scheme VII).

Compounds of Embodiment A Formula I wherein $R_2$ and $R_3$ Together with the Atoms to which they are Bound Form a 5 Membered Ring

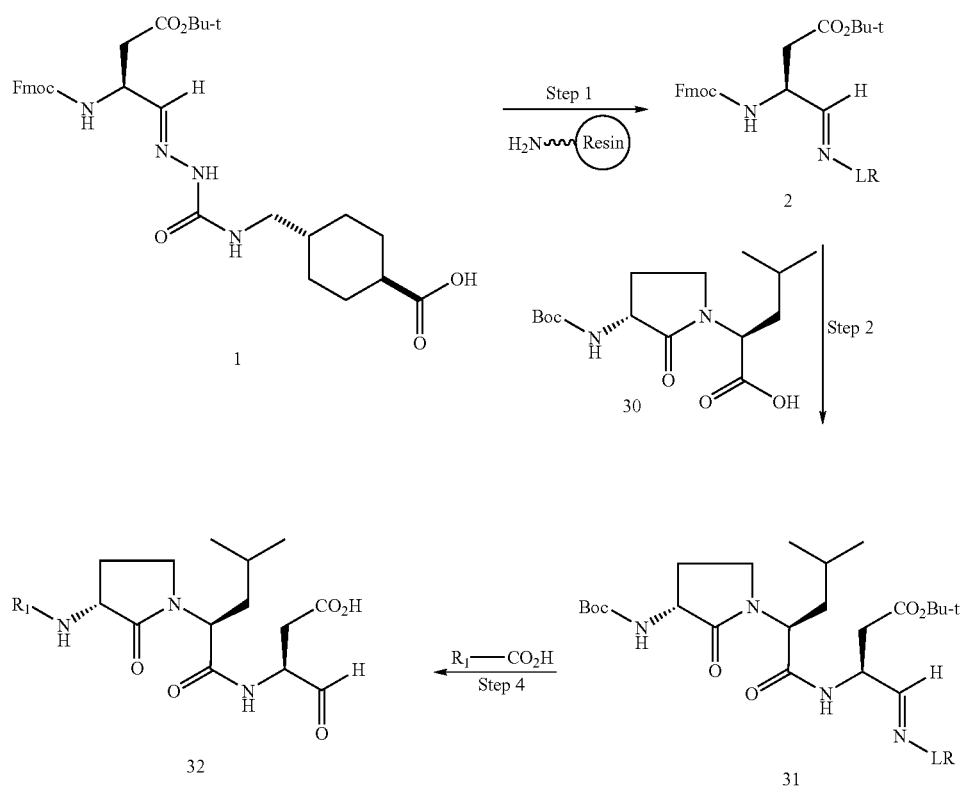

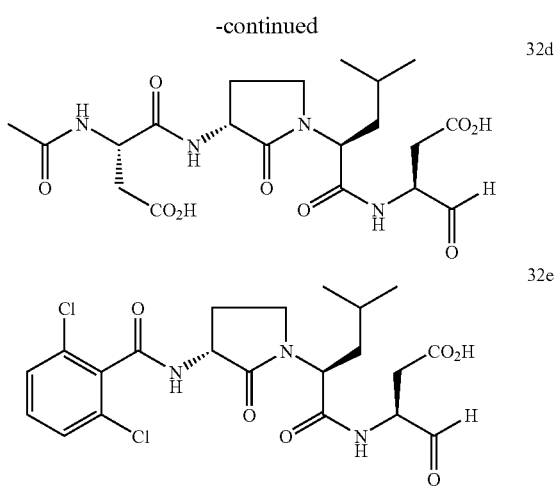

Compound of Embodiment A Formula I wherein X=N—CH₃

Scheme VIII

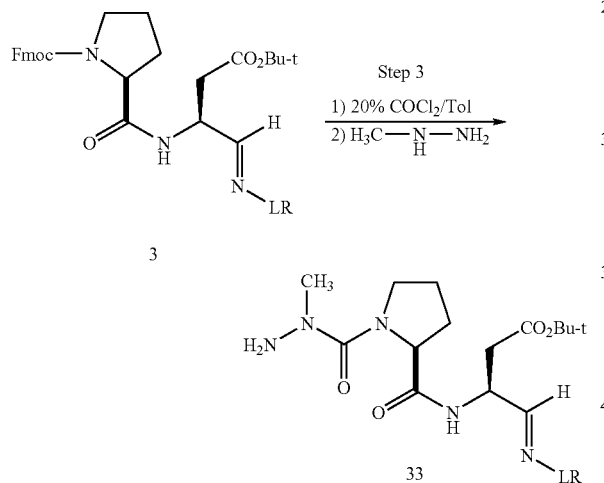

temperature for 5 minutes and drained. The procedure was repeated over 20 minutes. The resin was washed successively with DMF (twice), CH₃OH (once), 1:1 DMF/CH₂Cl₂ (twice), CH₃OH (once) and CH₂Cl₂ (three times), and briefly dried. To the resin was added 5 mL of dry CH₂Cl₂, 0.128 mL of DIEA (3eq, 0.75 mmol) and 0.400 mL of a 20% solution of phosgene in toluene (3 eq, 0.75 mmol). The suspension was rotated at room temperature for 1.5 hours. The mixture was drained, and the resin was washed with CH₂Cl₂ several times. To a suspension of resin in 5 mL of CH₂Cl₂ was added 0.133 mL of methyl hydrazine (10 eq, 2.5 mmol). The mixture was rotated at room temperature overnight and drained. The resin was washed successively with DMF (twice), CH₃OH (once), 1:1 DMF/CH₂Cl₂ (twice), CH₃OH (once) and CH₂Cl₂ (three times), and dried in vacuo.

To a 0.075 mmol portion of the resin in 3 mL of NMP was added successively 52 mg of 1-isoquinolinecarboxylic acid (4 eq, 0.3 mmol), 0.19 mL of DIEA (8 eq, 0.6 mmol), 37 mg of HOBt (4 eq, 0.3 mmol) and 104 mg of HBTU (4 eq, 0.3 mmol). The mixture was rotated at room temperature overnight and drained. The resin was washed successively with DMF (twice), CH₃OH (once), 1:1 DMF/CH₂Cl₂ (twice), CH₃OH (once) and CH₂Cl₂ (three times), and dried in vacuo.

The resin was treated with 4 mL of 95% TFA in water for 1 hour. The mixture was filtered. The filtrate was concentrated in vacuo to afford an oil, which was purified by HPLC to afford the title compound (34).

Compounds of Embodiment A Formula I wherein $R_3=R_3=H$

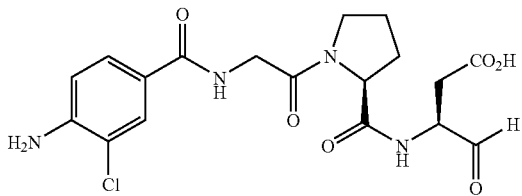

3-({1-[(4-Amino-3-chloro-benzoylamino)-acetyl]-pyrrolidine-2-carbonyl}-amino)-4-oxo-butyric acid (G1)

Prepared as described for compounds 7 only substituting Fmoc-glycine for Fmoc-alanine in Step 3 (Scheme II) to afford 4.3 mg of the title compound. LC-MS (ES⁺) m/e=425.2 (M+H).

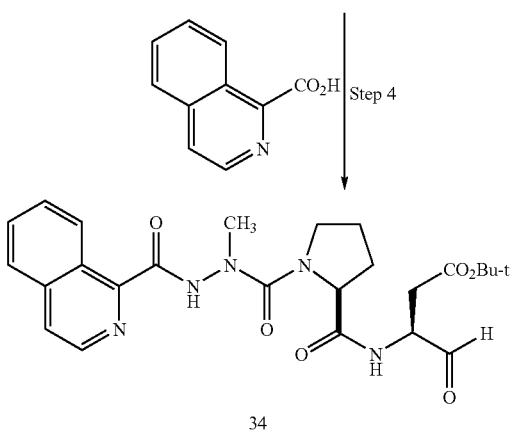

Preparation of 3-({1-[N-(isoquinoline-1-carbonyl)-N-methyl-hydrazinocarbonyl]-pyrrolidine-2-carbonyl}-amino)-4-oxo-butyric acid (34)

A suspension of 0.250 mmol of resin 3 (Scheme VIII) in 10 mL of 20% piperidine in DMF was rotated at room

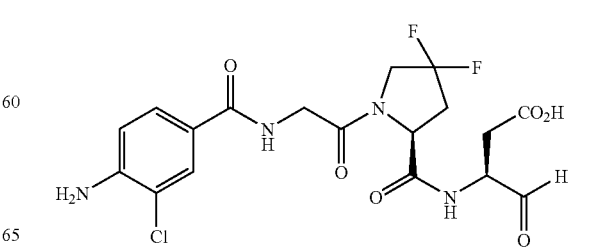

3-({1-[(4-Amino-3-chloro-benzoylamino)-acetyl]-4,
4-difluoro-pyrrolidine-2-carbonyl}-amino)-4-oxo-
butyric acid (G2)

Prepared as described for compounds 7 and 27 only substituting Fmoc-glycine for Fmoc-alanine in Step 3 (Scheme II) to afford 10.0 mg of the title compound. LC-MS (ES+) m/e=461.2 (M+H).

General Procedures for the Preparation of
Compounds of Embodiment C Formula I and
Embodiment D and Formula I wherein Y=C
(Schemes IX-XXII)

Scheme IX

Route A

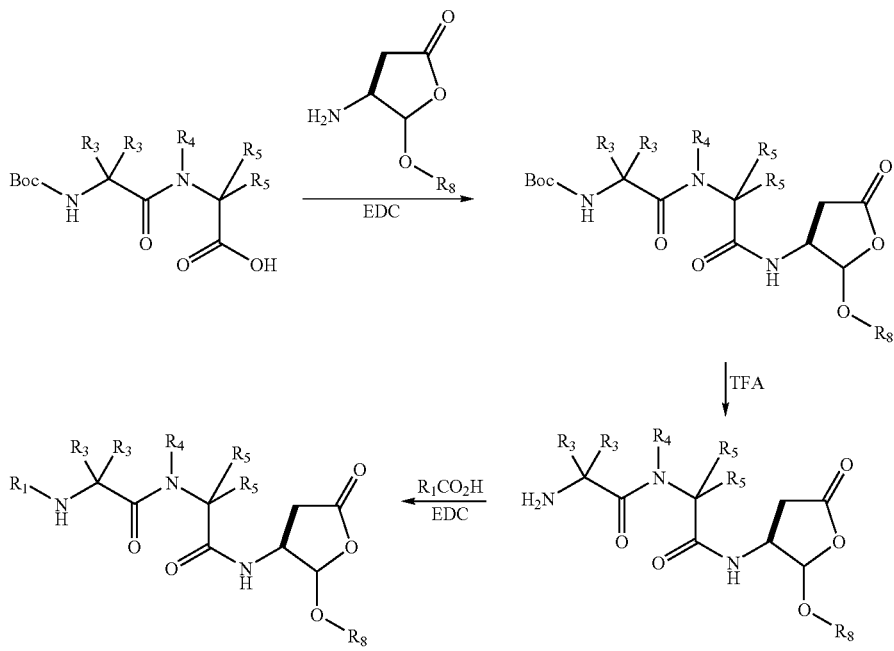

Route B

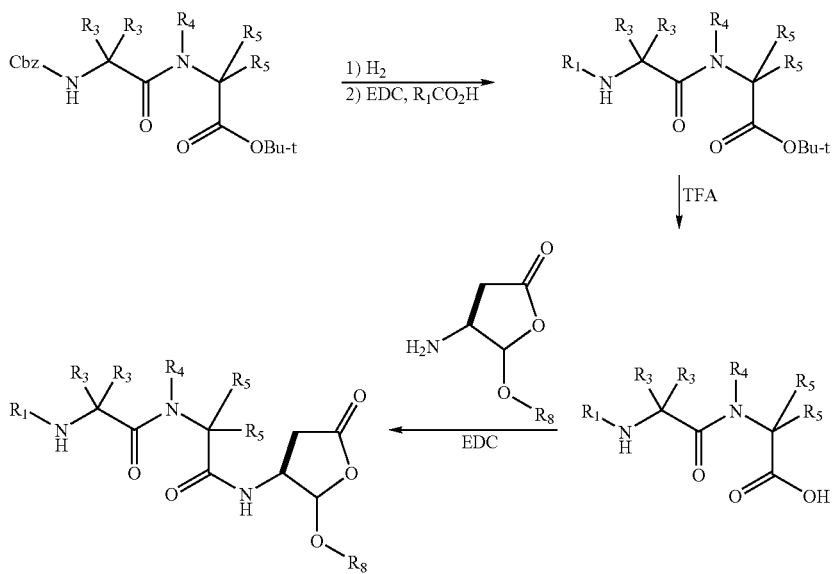

Sources for Selected Ring Systems

| Structure | Reference |
|---|---|
| (3-phenyl-azetidine-2-carboxylate, N-acetyl) | Blythin, D. J., *J. Org. Chem.*, 59, pp. 6098-6100 (1994). |
| (1-methyl-2-acetyl-hexahydropyridazine-3-carboxylate) | Decicco, C. P. et al., *Syn. Lett.*, pp. 615-616, (1995). |
| (2,5-dimethyl-thiadiazoline-carboxylate) | Bennion, C. et al., *J. Med. Chem.*, 34, pp. 439-447 (1991); Jensen, K. A. et al., *Acta Chemica Scand.*, 13, pp. 1097-1103 (1961). |

-continued

Sources for Selected Ring Systems

| Structure | Reference |
|---|---|
| (N-acetyl-dimethyl-thiazolidine-carboxylate) | commercially available |
| (1-methyl-pyrazoline-carboxylate) | Mish, M. R., *J. Am. Chem. Soc.*, 119, pp. 8379-8380 (1997). |
| (1-methyl-tetrahydropyridazine-carboxylate) | Xi, N. et al., *J. Am. Chem. Soc.*, 120 pp. 80-86 (1998). |
| (1,4-dimethyl-piperazine-2-carboxylic acid) | Merour, J. Y. et al., *Tetrahedron Lett.*, 32, pp. 2469-2470 (1991); Rossen, K., *Tetrahedron Lett.*, 36, pp. 6419-6422 (1995). |

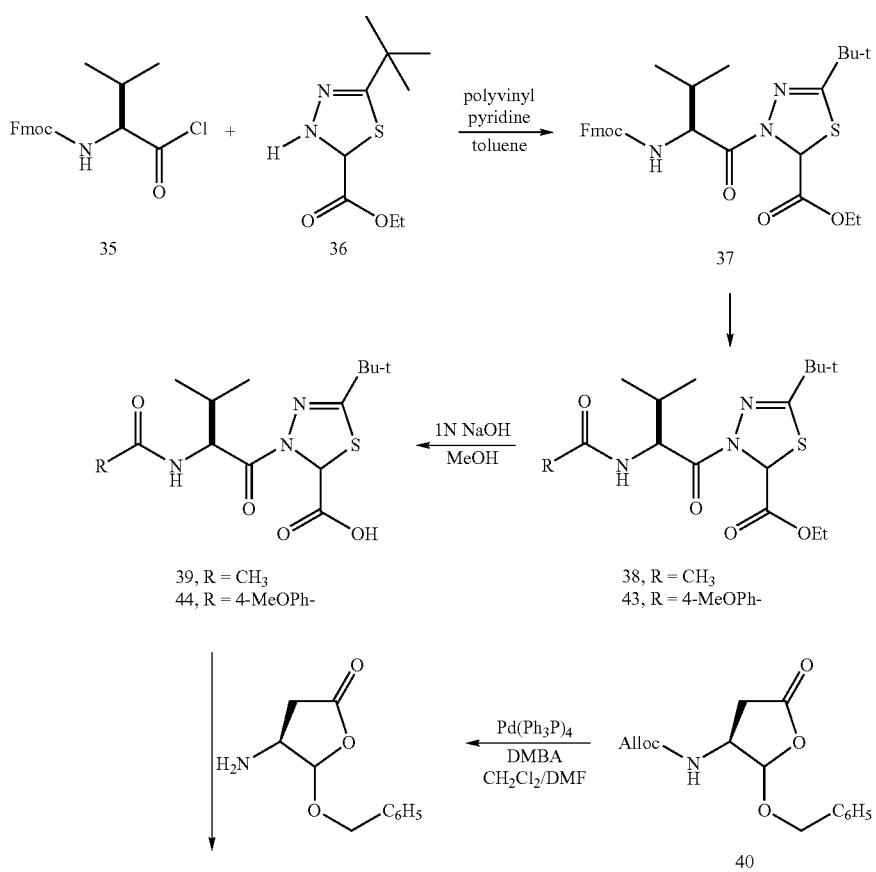

Scheme X

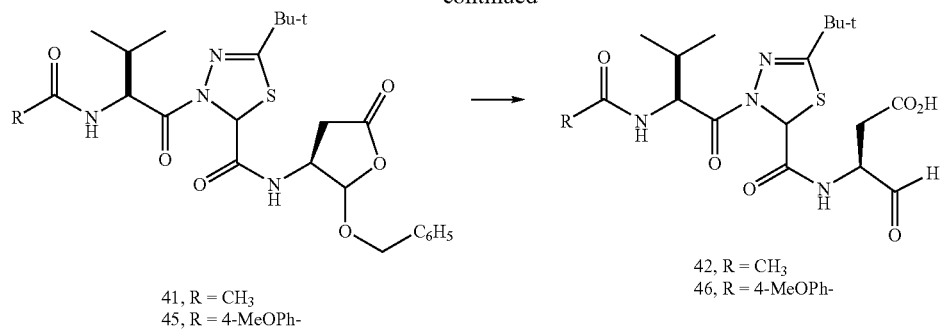

41, R = CH₃
45, R = 4-MeOPh-

42, R = CH₃
46, R = 4-MeOPh- 5-tert-Butyl-3-[2-(9H-fluoren-9-ylmethoxycarbony-lamino)-3-methyl butyryl]-2,3-dihydro-[1,3,4]thia-diazole-2-carboxylic acid ethyl ester (37)

A stirred suspension of polyvinylpyridine (2.63 g, 25 mmol) in a solution of 5-tert-butyl-2,3-dihydro-[1,3,4]thia-diazole-2-carboxylic acid ethyl ester (36) (*J. Med. Chem.,* 34, p. 439 (1991)), (2.16 g, 10 mmol) in dry toluene was treated with the dropwise addition of (1-chlorocarbonyl-2-methyl-propyl)-carbamic acid 9H-fluoren-9-ylmethyl ester (4.76 g, 12.1 mmol) in 20 mL of anhydrous toluene. After stirring for 16 hours, the suspension was filtered and the filtrate was washed with saturated sodium bicarbonate solution. The organic layer was separated, washed with water, dried over anhydrous sodium sulfate, and evaporated to give a yellow oil. Purification by flash chromatography eluting with 9/1 hexane/ethyl acetate gave 2.66 g (49% yield) of the title compound (37) as a clear, viscous oil. ¹H NMR (500 MHz, CD₃OD) δ 0.89 (d, 1.5H), 0.93 (d, 1.5H), 1.00 (d, 1.5H), 1.06 (d, 1.5H), 1.22 (t, 3H), 1.28 (s, 9H), 2.12-2.22 (m, 0.5H), 2.32-2.42 (m, 0.5H), 4.18-4.28 (m, 2H), 4.31-4.45 (m, 2H), 4.96-5.01 (m, 0.5H), 5.02-5.10 (m, 0.5H), 5.52 (d, 0.5H), 5.61 (d, 0.5H), 6.10 (s, 0.5H), 6.13 (s, 0.5H), 7.27-7.34 (m, 2H), 7.35-7.42 (m, 2H), 7.56-7.64 (m, 2H), 7.73-7.78 (m, 2H).

3-(2-Acetylamino-3-methylbutyryl)-5-tert-butyl-2,3-dihydro-[1,2,4]thiadiazole-2-carboxylic acid ethyl ester (38)

To a solution of (37) (Scheme IX) (0.508 g, 0.94 mmol) in CH₃CN (10 mL) was added diethylamine (1 mL). The solution was stirred at room temperature for 2 hours, the solvent removed in vacuo and the resultant oil azeotroped with CH₂Cl₂ (4×). The crude oil was dissolved in CH₂Cl₂ (5 mL) and triethylamine (0.26 mL, 1.86 mmol) and acetyl chloride (80 µl, 1.1 mmol) were added. The solution was stirred at room temperature under an N₂ atmosphere for 2 hours. The solvent was evaporated, and the crude material dissolved in EtOAc and washed with 0.5N NaHSO₄ (2×), saturated NaHCO₃ (2×) and brine and was dried over anhydrous Na₂SO₄, filtered and evaporated to give a yellow oil. Purification by flash column chromatography on silica gel using hexanes/EtOAc (95/5 to 90/10%) yielded the product as a yellow oil (0.301 g, 89% yield). ¹H-NMR (500 MHz, CDCl₃) δ 0.88 (dd, 3H), 0.99 (dd, 3H), 1.16-1.45 (m, 12H), 2.02 (s, 3H), 2.09-2.19 (m, 0.5H), 2.30-2.40 (m, 0.5H), 4.12-4.29 (m, 2H), 5.20-5.27 (m, 0.5H), 5.30-5.36 (m, 0.5H), 6.60 (s, 0.5H), 6.90 (s, 0.5H), 6.20-6.31 (m, 1H).

Analytical HPLC (C18 column),(mixture of diastereomers) 7.77, 7.98 min. LC-MS (ES⁺) m/e=358.3 (M+H).

3-(2-Acetylamino-3-methylbutyryl)-5-tert-butyl-2,3-dihydro-[1,2,4]thiadiazole-2-carboxylic acid (39)

To a solution of 38 (0.301 g, 0.84 mmol) in MeOH (10 mL) was added 1N NaOH solution (1.7 mL, 1.7 mmol). The reaction was stirred at room temperature for 2 hours and solvent was evaporated. The residue was dissolved in EtOAc and washed with 0.5N NaHSO₄ (2×) and brine and was dried over anhydrous Na₂SO₄, filtered and evaporated to give the title compound as a yellow solid (0.277 g, quantitative).

Preparation of 2-(Benzyloxy-5-oxo-tetrahydro-furan-3-yl)-carbamic acid allyl ester (40)

Compound 40 was prepared from 3-allyloxycarbony-lamino-4-hydroxy-butyric acid tert-butyl ester by a modification of the procedure described in *Bioorg. Med. Chem. Lett.* Vol. 2, No. 6, pp. 613-618, (1992).

To a solution of DMSO (27.52 g, 352 mmol) in CH₂Cl₂ (240 mL) at −78° C. was added oxalyl chloride (24.4 g, 192 mmol). After 15 min, a solution of 3-allyloxycarbony-lamino-4-hydroxy-butyric acid tert-butyl ester (41.44 g, 160 mmol) in CH₂Cl₂ (100 mL) was slowly added and the mixture was stirred at −78° C. for an additional 1.5 hours. DIEA (62.0 g, 480 mmol) was added and the mixture allowed to warm to room temperature for 15 min. The resulting solution was diluted with CH₂Cl₂ (300 mL), washed with 0.5 N NaHSO₄ (500 mL×2), water (300 mL×2), and brine (400 mL×2). The organic layer was dried over anhydrous Na₂SO₄, filtered and concentrated in vacuo to 200 mL volume. To this solution was added, benzyl alcohol (48 g, 444 mmol), followed by 3 Å molecular sieves (30 g) and p-toluenesufonic acid (0.8 g). The reaction mixture was allowed to stir for 4 days and TFA (96 mL) was added. The resulting suspension was stirred for one hour then evaporated in vacuo. Ethyl acetate (500 mL) was added and the mixture was filtered through Celite. The filtrate was washed with saturated NaHCO₃ (500 mL×2), water (400 mL×2), and brine (300 mL×2). The organic solution was dried over anhydrous Na₂SO₄, filtered and evaporated in vacuo to give 90 g of pale yellow oil, which was stirred with hexane (400 mL×2) to give 31 g of crude product from the lower layer residue. Chromatography using ethyl acetate/hexane (4/96 to 22/78) afforded 6.97 g of anti-2-(benzyloxy-5-oxo-tet-rahydro-furan-3-yl)-carbamic acid allyl ester (higher Rf), 4.53 g of syn diastereomer and 12.97 g of the mixture of the diastereomers (overall yield 53%). ¹H-NMR (500 MHz, CDCl$_3$) for anti diastereomer: δ 2.41-2.45 (m, H), 3.02-3.07 (m, H), 4.28 (br, H), 4.50-4.80 (m, 3H), 4.80-5.15 (m, 2H), 5.24-5.32 (m, 2H), 5.48 (s, H), 5.88-6.00 (m, H), 7.31-7.56 (m, 5H); for syn diastereomer: δ 2.49-2.53 (m, H), 2.83-2.89 (m, H), 4.57-4.65 (m, 4H), 4.87-4.90 (m, H), 5.12-5.30 (m, 3H), 5.52-5.53 (d, H), 5.88-6.00 (m, H), 7.31-7.39 (m, 5H); retention time on analytical HPLC: 10.49 min for anti diastereomer and 10.37 min for syn diastereomer; LC-MS: m/z=292 (M+H$^+$).

3-(2-Acetylamino-3-methylbutyryl)-5-tert-butyl-2,3-dihydro-[1,2,4]thiadiazole-2-carboxylic acid (2-benzyloxy-5-oxo-tetrahydrofuran-3-yl)-amide (41)

To a solution of (2-benzyloxy-5-oxo-tetrahydrofuran-3-yl)-carbamic acid allyl ester (40) (0.385 g, 1.32 mmol) in DMF (2 ml) and CH$_2$Cl$_2$ (2 ml) was added DMBA (0.456 g, 2.92 mmol) and Pd(PPh$_3$)$_4$ (0.136 g, 0.12 mmol) and the solution was stirred at room temperature for 15 min. A solution of (39) in CH$_2$Cl$_2$ (4.5 ml) and DMF (0.5 ml) was added, followed by HOBT (0.168 g, 1.24 mmol) and EDC (0.256 g, 1.33 mmol). The reaction was stirred at room temperature for 18 hours under N$_2$. The solvent was evaporated. The crude material was dissolved in EtOAc and washed with 0.5N NaHSO$_4$ (2×), saturated NaHCO$_3$ (2×) and brine and was dried over anhydrous Na$_2$SO$_4$, filtered and evaporated to give a yellow solid. Purification by flash column chromatography gave the title compound (41) as a mixture of diastereomers (374 mg, 88% yield) $^1$H-NMR (500 MHz, CDCl$_3$) δ 0.75-1.05 (m, 6H), 1.19-1.34 (m, 9H), 1.93-2.08 (m, 3H), 2.19-2.50 (m, 2H), 2.80-3.03 (m, 1H), 4.56-4.93 (m, 3H), 5.02-5.20 (m, 1H) 5.46-5.56 (m, 1H), 5.95-6.16 (m, 2H), 6.86-6.95 (m, 1H), 7.20-7.43 (m, 5H). Analytical HPLC (C18 column), (mixture of diastereomers) 8.58 min. LC-MS (ES$^+$) m/e=519.2 (M+H).

Preparation of 3-{[3-(2-acetylamino-3-methyl-butyryl)-5-tert-butyl-2,3-dihydro-[1,3,4]thiadiazole-2-carbonyl]-amino)-4-oxo-butyric acid (42)

A 45 mg (0.087 mmol) sample of 41 was hydrolyzed according to method A (see Scheme XXIII) to give 17 mg (45% yield) of the title compound. Analytical HPLC (C18 column): 5.15 min. LC-MS (ES$^+$) m/e=429.3 (M+H).

5-tert-Butyl-3-[2-(4-methoxy-benzoylamino)-3-methyl-butyryl]-2,3-dihydro-[1,3,4]thiadiazole-2-carboxylic acid ethyl-ester (43)

Was prepared by the method reported above for compound 38 using anisoyl chloride to give 216 mg (50%) of the title compound as an amorphous solid. $^1$H NMR (500 MHz, CDCl$_3$) δ 0.92 (d, 1.5H), 0.98 (d, 1.5H), 1.03 (d, 1.5H), 1.07 (d, 1.5H), 1.21 (t, 3H), 1.28 (s, H), 2.21-2.28 (m, 0.5H), 2.41-2.48 (m, 0.5H), 3.83 (s, 3H), 4.15-4.28 (m, 2H), 5.41-5.46 (m, 0.5H), 5.48-5.53 (m, 0.5H), 6.08 (s, 0.5H), 6.13 (s, 0.5H), 6.75 (d, 0.5H), 6.85 (d, 0.5H), 6.91 (d, 2H), 7.59 (d, 2H)

5-tert-Butyl-3-[2-(4-methoxy-benzoylamino)-3-methyl-butyryl]-2,3-dihydro-[1,3,4]thiadiazole-2-carboxylic acid (44)

Prepared by the procedure described for 39 to give 180 mg (quantitative) of the title compound as a white solid. $^1$H NMR (500 MHz, CDCl$_3$) δ 0.92 (d, 1.5H), 0.96 (d, 1.5H), 1.03 (d, 1.5H), 1.07 (d, 1.5H), 2.22-2.30 (m, 0.5H), 2.37-2.45 (m, 0.5H), 3.83 (s, 1.5H) 3.84 (s, 1.5H), 5.41-5.48 (m, 1H), 6.14 (s, 0.5H), 6.15 (s, 0.5H), 6.87-6.95 (m, 2H), 7.75-7.83 (m, 3H)

5-tert-Butyl-3-[2-(4-methoxy-benzoylamino)-3-methyl-butyryl]-2,3-dihydro-[1,3,4]thiadiazole-2-carboxylic acid (2-benzyloxy-5-oxo-tetrahydro-furan-3-yl)-amide (45a and 45b)

Was prepared by the procedure reported for compound 41 to give the crude title compound as 4 diastereomers. The crude material was purified by flash chromatography, eluting with a gradient of CH$_2$Cl$_2$ to CH$_2$Cl$_2$/ethyl acetate (6/4) to give 31 mg of the higher R$_f$ component as a single diastereomer (45a). Analytical HPLC (Microsorb C18 column) 19.87 min. $^1$H NMR (500 MHz, CDCl$_3$) (single diastereomer) δ 1.04 (d, 3H), 1.14 (d, 3H), 1.28 (s, 9H), 2.77 (d, 0.5H), 2.81 (d, 0.5H), 2.90 (d, 0.5H), 2.95 (d, 0.5H), 3.84 (s, 3H), 4.44-4.49 (m, 1H), 4.53 (d, 1H), 4.85 (d, 1H), 5.02-5.08 (m, 1H), 6.37 (s, 1H), 6.41 (d, 1H), 6.93 (d, 2H), 7.26-7.40 (m, 5H), 7.75 (d, 2H), 7.92-7.96 (m, 1H).

The lower R$_f$ fraction contained 185 mg of a solid as a 3:1:2 mixture of diastereomers (45b). Analytical HPLC: Microsorb C18 column. 19.00, 19.26, 20.02 mins, $^1$H NMR (500 MHz, CDCl$_3$) (3:1:2 mixture of 3 diastereomers) δ 0.89 (d, 2.25H), 0.98 (d, 0.75H), 1.02 (d, 0.5H) 1.03 (d, 1.5H), 1.08 (d, 0.25H), 1.10 (d, 0.75H), 1.16 (s, 0.75H), 1.17 (s, 2.25H), 1.23 (s, 0.375H), 1.24 (s, 1.125H), 1.28 (s, 1.125H), 1.29 (s, 3.375H), 2.12-2.18 (m, 0.33H), 2.32-2.42 (m, 0.67H), 2.43-2.51 (m, 0.5H), 2.61-2.67 (m, 0.5H), 2.84-2.92 (m, 0.5H), 2.96-3.07 (m, 0.5H), 3.85 (s, 3H), 4.58-4.71 (m, 2H), 4.81 (d, 0.16H), 4.86 (d, 0.32H), 4.91 (d, 0.52H), 5.09-5.13 (m, 0.33H), 5.14-5.18 (m, 0.67H), 5.35 (dd, 1H), 5.46 (s, 0.16H), 5.53 (d, 0.32H), 5.58-5.62 (d, 0.52H), 6.17 (s, 0.52H), 6.20 (s, 0.16H), 6.34 (s, 0.32H), 6.50 (d, 0.32H), 6.62 (d, 0.16H), 6.67 (d, 0.52H), 6.86 (d, 0.33H), 6.91 (d, 0.67H), 6.94 (d, 1.0H), 7.24-7.43 (m, 5H), 7.61 (d, 1H), 7.70 (d, 0.33H), 7.71 (d, 0.67H), 7.76 (d, 1H).

Preparation of 3-({5-tert-butyl-3-[2-(4-methoxy-benzoylamino)-3-methyl-butyryl]-2,3-dihydro-[1,3,4]thiadiazole-2-carbonyl)-amino)-4-oxo-butyric acid (46a)

A 30 mg sample of 45a was hydrolyzed according to method B (see Scheme XXIII) to give 8 mg (30% yield) of the desired product. Analytical HPLC (Microsorb C-18 column, acetonitrile/water, with TFA buffer) 12.85 min, $^1$H NMR (500 MHz, CD$_3$OD) δ 0.98-1.1 (m, 6H), 1.28 (s, 9H), 2.20-2.31 (m, 1H) 2.40-2.48 (m, 1H), 2.6-2.72 (m, 1H), 3.84 (s, 3H), 4.18-4.26 (m, 1H), 4.56-4.62 (m, 1H), 5.25-5.32 (m, 1H), 6.24-6.28 (m, 1H), 6.98 (d, 2H), 7.85 (d, 2H).

Preparation of 3-({5-tert-butyl-3-[2-(4-methoxy-benizoylamino)-3-methyl-butyryl]-2,3-dihydro-[1,3,4]thiadiazole-2-carbonyl}-amino)-4-oxo-butyric acid (46b)

A 30 mg sample of 45b (mixture of 3 diastereomers) was hydrolyzed according to method B (see Scheme XXIII) to give 22 mg (84% yield) of the desired product as a 3:2 mixture of diastereomers. Analytical HPLC (Microsorb cyano column) 7.08, 7.78 min. $^1$H NMR (500 MHz, CD$_3$OD) δ 0.98-1.08 (m, 4H), 1.09-1.12 (m, 2H), 1.29 & 1.31 (2 singlets, 9H), 2.23-2.30 (m, 0.5H), 2.36-2.55 (m, 1.5H), 2.62-2.72 (m, 1H), 3.85 (s, 3H), 4.18-4.27 (m, 1H), 4.58-4.65 (m, 1H), 5.27-5.33 (m, 1H), 6.23-6.27 (m, 1H), 7.00 (d, 2H), 7.70-7.88 (m, 2H).

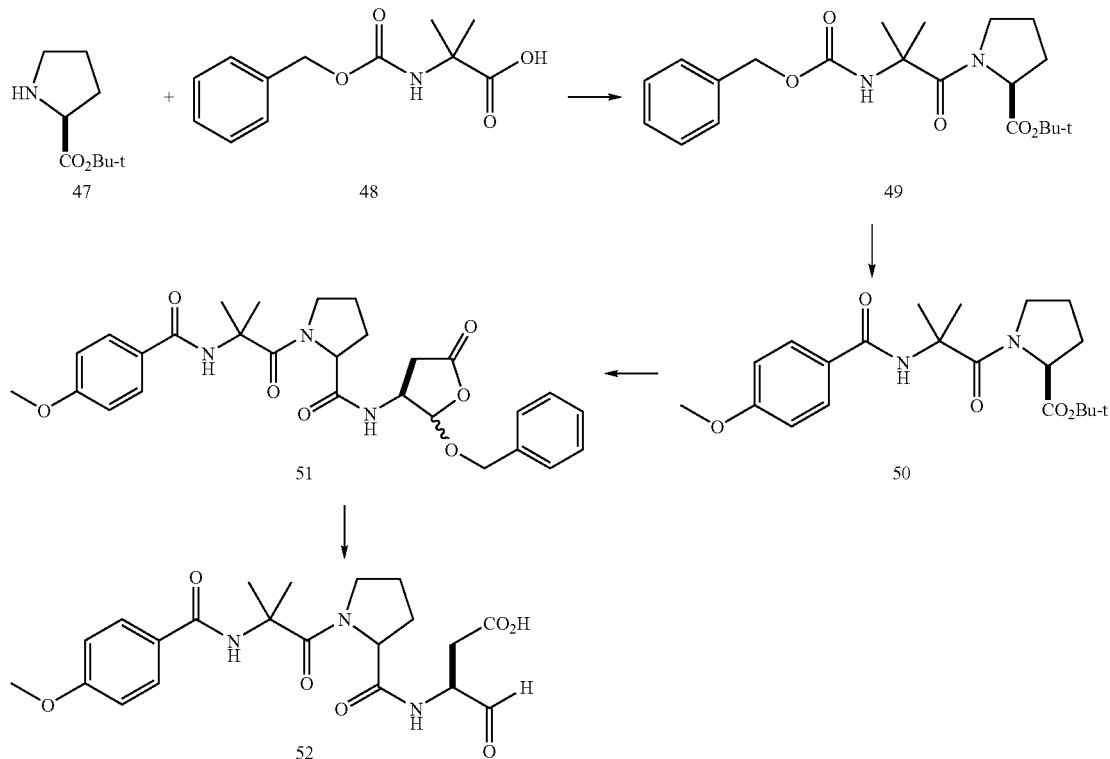

Scheme XI

1-(2-Benzyloxycarbonylamino-2-methyl-propionyl)-pyrrolidine-2-carboxylic acid tert-butyl ester (49)

To a solution of proline-tert-butyl ester (47) (2.00 g, 12 mmol, in CH$_2$Cl$_2$ (15 ml) was added N-carbobenzyloxy-2-methylalanine (3.05 g, 13 mmol), HOBT (2.36 g, 17 mmol) and EDC (3.43 g, 18 mmol) and the solution was stirred at room temperature under N$_2$ for 48 hours. The solvent was evaporated, the crude material dissolved in EtOAc and washed with 0.5N NaHSO$_4$ (2×), saturated NaHCO$_3$ (2×) and brine and was dried over anhydrous Na$_2$SO$_4$, filtered and evaporated to give a white solid (4.68 g, 100%). $^1$H-NMR (500 MHz, CDCl$_3$) δ 1.20-2.15 (m, 4H), 1.43 (s, 9H), 1.59 (d, 6H), 3.21-3.79 (m, 2H), 4.35 (br s, 1H), 4.82-5.19 (m, 3H), 5.74 (br s, 1H), 7.17-7.49 (m, 5H). Analytical HPLC (C18 column) 10.66 min. LC-MS (ES$^+$) m/e=391.3 (M+H).

1-[2-(4-Methoxy-benzoylamino)-2-methyl-propionyl]-pyrrolidine-2-carboxylic acid tert-butyl ester (50)

To solution of 49 (1.00 g, 2.56 mmol) in MeOH (20 ml) was added 10% Pd/C (200 mg) and the mixture was stirred under H$_2$ for 2 hours. The mixture was filtered through 0.45 μm PTFE filter and the solvent removed in vacuo to yield a colorless oil. This oil was dissolved in CH$_2$Cl$_2$ (25 mL) and DIEA (660 μl, 3.79 mmol) and p-anisoyl chloride (480 mg, 2.8 mmol) were added. The solution was stirred at room temperature under N$_2$ for 18 hours. The solvent was removed in vacuo and the oil dissolved in EtOAc. The organic phase was washed with 0.5N NaHSO$_4$ (2×), water, saturated NaHCO$_3$ (2×) and brine. The organic phase was dried over Na$_2$SO$_4$, filtered and evaporated to give a white solid which was purified by flash column chromatography, eluting with CH$_2$Cl$_2$/MeOH (99/1 to 98/2%) to give the title compound as a white solid (655 mg, 65% yield). $^1$H-NMR (500 MHz, CDCl$_3$) δ 1.47 (s, 9H), 1.68-2.24 (m, 5H), 1.80 (d, 6H), 3.55-3.68 (m, 1H), 3.72-3.93 (m, 1H), 3.84 (s, 3H), 4.43-4.55 (m, 1H), 6.90 (d, 2H), 7.60 (br s, 1H), 7.77 (d, 2H) Analytical HPLC (C18 column)8.98 min.

1-[2-(4-Methoxy-benzoylamino)-2-methyl-propionyl]-pyrrolidine-2-carboxylic acid (2-benzyloxy-5-oxo-tetrahydro-furan-3-yl)-amide (51)

To a solution of 50 (325 mg, 0.83 mmol) in dioxane (5 mL) was added triethylamine (463 μl, 3.32 mmol) and TMS-triflate (642 μl, 3.32 mmol) and the solution was stirred at 100° C. for 5 hours, then at room temperature for 18 hours. The reaction was diluted with water, adjusted to pH 8 with saturated NaHCO$_3$ and extracted with Et$_2$O, dried over Na$_2$SO4, filtered and evaporated to give a white solid (230 mg, 83% yield) which was used directly in the next step.

To a solution of (2-benzyloxy-5-oxo-tetrahydrofuran-3-yl)-carbamic acid allyl ester (40) (1.027 g, 3.5 mmol) in CH$_2$Cl$_2$ (20 ml) was added DMBA (543 mg, 3.48 mmol) and Pd(PPh$_3$)$_4$ (280 mg, 0.24 mmol) and the solution was stirred at room temperature under N$_2$ for 20 minutes. A solution of 1-[2-(4-methoxy-benzoylamino)-2-methyl-propionyl]-pyrrolidine-2-carboxylic acid (818 mg, 2.45 mmol) in $CH_2Cl_2$ (5 ml) was added, followed by HOBT (0.534 g, 3.95 mmol) and EDC (738 mg, 3.84 mmol). The reaction was stirred at room temperature for 18 hours under $N_2$. The solvent was evaporated, the crude material dissolved in EtOAc and washed with 0.5N $NaHSO_4$ (2×), saturated $NaHCO_3$ (2×) and brine and was dried over anhydrous $Na_2SO_4$, filtered and evaporated to give a yellow solid. Purification by flash column chromatography, eluting with ethyl acetate/hexanes (20/80 to 50/50%), gave the product as pale yellow solid (760 mg, 61% yield). $^1$H-NMR (500 MHz, $CD_3OD$) δ 1.53 (d, 6H), 1.65-1.93 (m, 3H), 1.96-2.14 (m, 1H), 2.60 (dd, 0.1H), 2.77 (dd, 0.85H), 2.94 (dd, 0.85H), 3.04-3.11 (m, 0.2H), 3.42-3.52 (m, 1H), 3.57-3.67 (m, 1H), 3.84 (s, 3H), 4.38-4.76 (m, 3H), 4.84 (d, 1H), 5.64-5.70 (m, 1H), 6.96-7.03 (m, 2H), 7.23-7.43 (m, 5H), 7.78-7.97 (m, 2H). Analytical HPLC (C18 column) 13.32, 14.37 min. LC-MS (ES$^+$) m/e=524.3 (M+H).

Preparation of 3-((1-[2-(4-methoxy-benzoylamino)-2-methyl-propionyl)-pyrrolidine-2-carbonyl}-amino)-4-oxo-butyric acid (52)

A 61 mg (0.14 mmole) sample of 51 was hydrolyzed according to method C (see Scheme XXIII) to afford 30 mg (60% yield) of the title compound: Analytical HPLC (C18 column) 6.79 min. LC-MS (ES$^+$) m/e=434.3 (M+H).

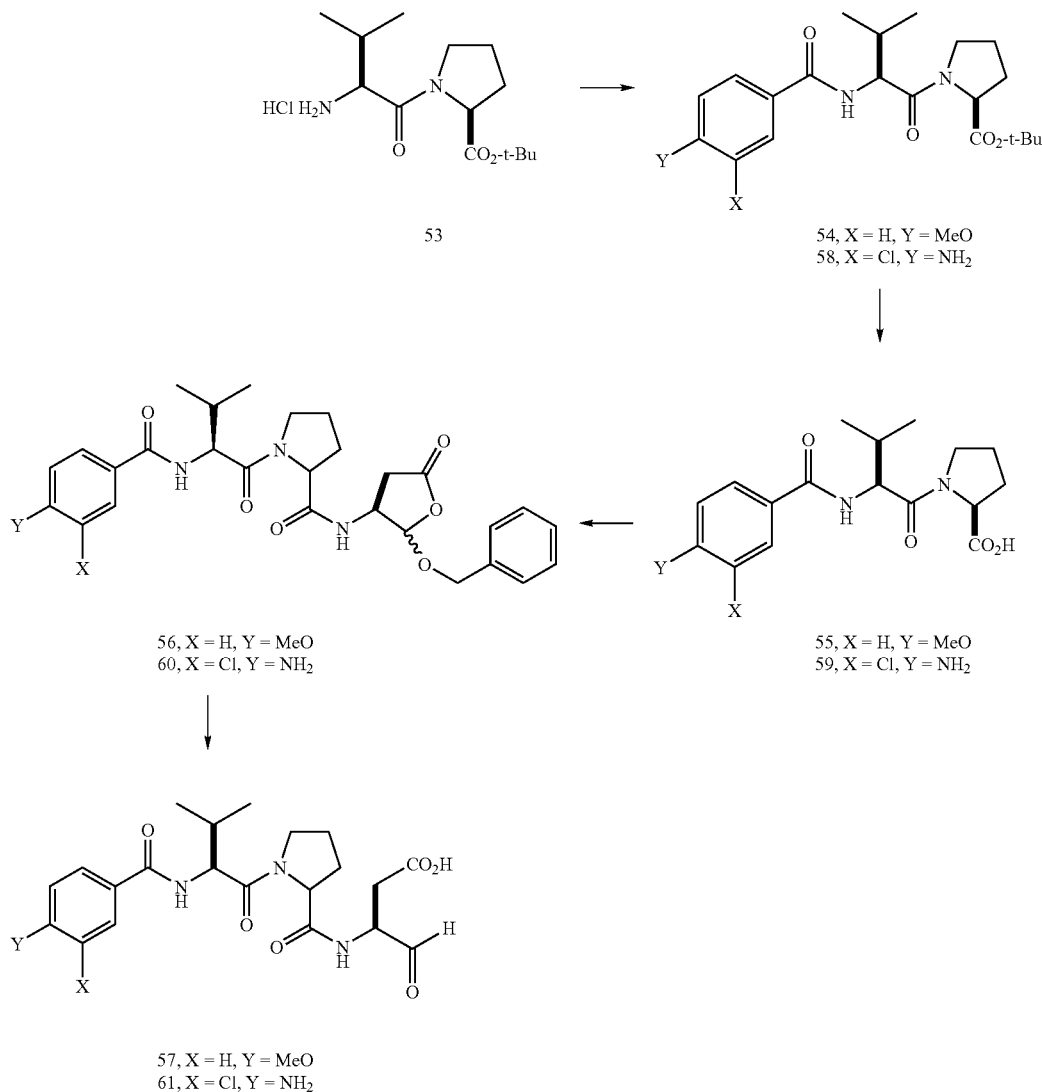

1-[2-(4-Methoxy-benzoylamino)-3-methylbutyryl]-pyrrolidine-2-carboxylic acid tert-butyl ester (54)

To a suspension of H-val-pro-OtBu.HCl (53) (2.011 g, 7.44 mmol) in $CH_2Cl_2$ (20 ml) was added DIEA (3.2 ml, 18.4 mmol) followed by a solution of 4-methoxy-benzoyl chloride (1.26 g, 7.4 mmol) in $CH_2Cl_2$ (5 ml). The solution was stirred at room temperature under nitrogen for 1 hour then concentrated. The resulting oil was dissolved in EtOAc and washed with 0.5N $KHSO_4$ (2×), saturated $NaHCO_3$ (2×) and brine, then concentrated in vacuo to give the title compound as a white solid (2.814 g, 94% yield). $^1$H-NMR (500 MHz, CDCl$_3$) δ 1.05 (dd, 6H), 1.46 (s, 9H), 1.88-2.29 (m, 5H), 3.65-3.74 (m, 1H), 3.81-3.92 (m, 1H), 3.85 (s, 3H), 4.32-4.42 (m, 1H), 4.81-4.91 (m, 1H), 6.79-6.86 (m, 1H), 6.91 (d, 2H), 7.78 (d, 2H). Analytical HPLC (cyano column) 10.18 min.

1-[2-(4-Methoxy-benzoylamino)-3-methylbutyryl]-pyrrolidine-2-carboxylic acid (2-benzyloxy-5-oxo-tetrahydrofuran-3-yl)amide (56)

A 1.079 g (2.67 mmol) sample of 54 was dissolved in 15% TFA in CH$_2$Cl$_2$ (40 mL) and stirred at room temperature for 4 hours. The solvent was concentrated in vacuo to give 55 as a white solid (0.93 g, 100%) which was used in the next step.

To a solution of 40 (1.796 g, 6.17 mmol) in CH$_2$Cl$_2$ (20 ml) was added DMBA (1.119 g, 7.17 mmol) and Pd(PPh$_3$)$_4$ (0.683 g, 0.59 mmol) and the solution stirred at room temperature for 20 minutes. A solution of 55 (0.928 g, 2.67 mmol) in CH$_2$Cl$_2$ (17 ml) and DMF (2 ml) was added, followed by HOBT (0.811 g, 6.01 mmol) and EDC (1.16 g, 6.04 mmol). The reaction was stirred at room temperature for 18 hours under N$_2$. The solvent was evaporated, the crude material dissolved in EtOAc and washed with 0.5N NaHSO$_4$ (2×), saturated NaHCO$_3$ (2×) and brine and was dried over anhydrous Na$_2$SO$_4$, filtered and evaporated to give a yellow solid. Purification by flash chromatography eluting with ethyl acetate/CH$_2$Cl$_2$ (10/90 to 40/60%) gave the title compound as pale yellow solid (910 mg, 63% yield). $^1$H-NMR (500 MHz, CDCl$_3$) δ 0.96 (dd, 6H), 1.84-2.19 (m, 4H), 2.25-2.38 (m, 1H), 2.45 (dd, 1H), 2.80-2.98 (m, 1H), 3.60-3.72 (m, 1H), 3.82-3.95 (m, 1H), 3.86 (s, 3H), 4.26-4.95 (m, 6H), 5.41 (s, 0.2H) 5.53 (d, 0.8H), 6.67-6.77 (m, 1H), 6.88-6.99 (d, 2H) 7.22-7.57 (m, 5H), 7.71-7.82 (d, 2H). Analytical HPLC (cyano column) (mixture of 2 diastereomers) 9.21 min. LC-MS (ES$^+$) m/e=538.3 (M+H).

3-({1-[2-(4-Methoxy-benzoylamino)-3-methyl-butyryl]-pyrrolidine-2-carbonyl}-amino)-4-oxo-butyric acid (57)

A 125 mg (0.23 mmol) sample of 56 was hydrolyzed according to method A (see Scheme XXIII) to afford 60 mg (58% yield) of the title compound: Analytical HPLC 5.71 min. LC-MS (ES$^+$) m/e=448.2 (M+H).

Preparation of 4-Amino-3-chloro-benzoic acid

A suspension of 4-amino-3-chlorobenzonitrile (4.82 g, 31.58 mmol) was heated to reflux in 6N HCl (140 ml). The precipitate dissolved upon heating to give a colorless solution. Upon further heating the solution became cloudy. After 9 hours the reaction was cooled to room temperature. The resulting precipitate was filtered, then dissolved in THF and the solvent evaporated. The residue was repeatedly concentrated from toluene to give a white solid (3.18 g, 59% yield). $^1$H-NMR (500 MHz, CD$_3$OD:CDCl$_3$ 1:4) δ 6.80 (d, 1H), 7.75 (dd, 1H), 7.94 (d, 1H). Analytical HPLC (cyano column) 8.73 min.

1-[2-(4-Amino-3-chloro-benzoylamino)-3-methylbutyryl]-pyrrolidine-2-carboxylic acid tert-butyl ester (58)

To a suspension of 53 (1.707 g, 6.31 mmol) in CH$_2$Cl$_2$ (25 ml) at 0° C. was added DIEA (3.2 ml, 18.4 mmol) followed by a solution of 4-amino-3-chlorobenzoic acid (1.298 g, 7.56 mmol), HOBT (1.005 g, 7.44 mmol) and EDC (1.456 g, 7.58 mmol). The resulting mixture was stirred at 0° C. for 15 minutes then allowed to warm to room temperature and stir for 18 hours. The solvent was evaporated and the resulting oil dissolved in EtOAc, washed with 0.5N NaHSO$_4$ (2×), saturated NaHCO$_3$ (2×) and brine to give a white solid (2.68 g). Flash chromatography using MeOH/CH$_2$Cl$_2$ (1/99 to 2/98%) gave 2.04 g (76% yield) of 58 as a white solid. $^1$H-NMR (500 MHz, CDCl$_3$) δ 1.05 (dd, 6H), 1.47 (s, 9H), 1.86-2.29 (m, 5H), 3.62-3.78 (m, 1H), 3.78-3.94 (m, 1H), 4.39 (dd, 1H), 4.79-4.89 (dd, 1H), 6.73 (d, 1H), 6.78 (d, 1H), 7.52 (dd, 1H), 7.75 (d, 1H). Analytical HPLC (cyano column) 16.18 min. LC-MS (ES$^+$) m/e=424.3 (M+H).

1-[2-(4-Amino-3-chloro-benxoylamino)-3-methylbutyryl]-pyrrolidine-2-carboxylic acid (2-benzyloxy-5-oxo-tetrahydro-furan-3-yl)-amide (60)

A 0.632 g (1.49 mmol) sample of 59 was dissolved in 50% TFA in CH$_2$Cl$_2$ (20 mL) and the solution stirred at room temperature for 2 hours. Residual TFA was removed by repeated concentration from CH$_2$Cl$_2$ (3×) to give the product as a white solid.

A 385 mg (1.04 mmol) sample was allowed to react with 40 by the method used for compound 56. The title compound (60) was isolated as a yellow solid (265 mg, 45% yield) $^1$H-NMR (500 MHz, CD$_3$OD) δ 0.89-1.12 (m, 6H), 1.72-2.26 (m, 5H), 2.49 (dd, 0.25H), 2.60 (dd, 0.7H), 2.80 (dd, 0.75H), 2.96-3.09 (m, 0.3H), 3.64-3.77 (m, 1H), 3.94-4.10 (m, 1H), 4.20-4.74 (m, 4H), 4.76-4.95 (m, 1H), 5.51 (s, 0.5H), 5.61-5.70 (m, 1.5H), 6.79 (dd, 1H), 7.23-7.43 (m, 5H), 7.48-7.61 (m, 1.4H), 7.68-7.81 (m, 1H), 7.99-8.12 (m, 0.6H). Analytical HPLC (cyano column) (mixture of 2 diastereomers) 14.90, 15.20 min. LC-MS (ES$^+$) m/e=557.2 (M+H).

3-((1-[2-(4-Amino-3-chloro-benzoylamino)-3-methyl-butyryl]-pyrrolidine-2-carbonyl}-amino)-4-oxo-butyric acid (61)

A 45 mg (0.08 mmol) sample of 60 was hydrolyzed according to method A (see Scheme XXIII) to afford 30 mg (80% yield) of the title compound: $^1$H NMR (500 MHz, CD$_3$OD) δ 1.06 (dd, 6H), 1.78-2.38 (m, 5H), 2.38-2.86 (m, 2H), 3.62-3.83 (m, 1H), 4.12-4.76 (m, 4H), 7.04-7.21 (m, 1H), 7.58-8.01 (m, 2H); Analytical HPLC 8.16 min. LC-MS (ES$^+$) m/e=467.3 (M+H).

Scheme XIII

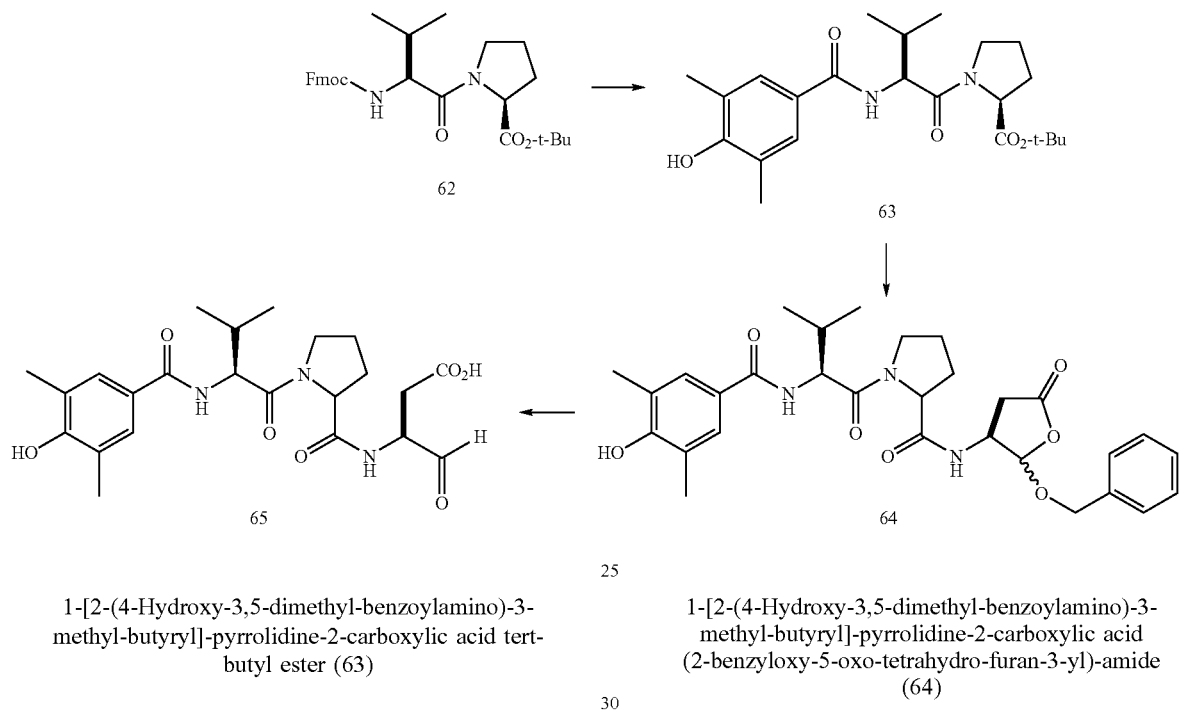

1-[2-(4-Hydroxy-3,5-dimethyl-benzoylamino)-3-methyl-butyryl]-pyrrolidine-2-carboxylic acid tert-butyl ester (63)

To a solution of 62 (prepared from 53 and Fmoc-Cl) (600 mg, 1.22 mmol) in anhydrous DMF (10 ml) was added diethylamine (3 ml). The solution was stirred at room temperature under $N_2$ for 3 hours and the solvent was evaporated. The resulting oil was dissolved in $CH_2Cl_2$ (8 ml) and 3,5-dimethyl-4-hydroxybenzoic acid (0.302 g, 1.82 mmol), HOBT (338 mg, 2.5 mmol) and EDC (0.456 g, 2.43 mmol) were added and the solution stirred at room temperature under $N_2$ for 18 hours. The solvent was concentrated in vacuo and the resulting oil dissolved in EtOAc, washed with 0.5N $NaHSO_4$ (2×), saturated $NaHCO_3$ (2×) and brine to give the crude product as a white solid (0.80 g). Flash chromatography eluting with $MeOH/CH_2Cl_2$ (1/99 to 2/98%) gave 380 mg (75% yield) of a white solid. $^1$H-NMR (500MHz, $CDCl_3$) δ 1.06 (dd, 6H), 1.47 (s, 9H), 1.90-2.32 (m, 5H), 2.24 (s, 6H), 3.65-3.75 (m, 1H), 3.84-3.92 (m, 1H), 4.36-4.42 (m, 1H), 4.82-4.88 (m, 1H), 5.53-5.61 (m, 1H), 6.77-6.85 (m, 1H), 7.42 (s, 2H). Analytical HPLC (cyano column) 17.53 min. LC-MS ($ES^+$) m/e=419.3 (M+H).

1-[2-(4-Hydroxy-3,5-dimethyl-benzoylamino)-3-methyl-butyryl]-pyrrolidine-2-carboxylic acid (2-benzyloxy-5-oxo-tetrahydro-furan-3-yl)-amide (64)

Prepared from 63 and 40 by the method used to prepare 56 to give title compound (64) as a pale yellow solid (352 mg, 72% yield). $^1$H-NMR (500 MHz, $CD_3OD$) δ 0.83-1.28 (m, 6H), 1.66-2.37 (m, 3H), 2.23 (s, 6H), 2.48-2.54 (m, 0.2H), 2.61 (ddd, 0.8H), 2.72 (ddd, 0.9H), 3.01-3.09 (m, 1H), 3.66-3.76 (m, 1H), 3.95-4.07 (m, 1H), 4.48-4.73 (m, 3H), 4.75-4.92 (m, 1H), 5.45-5.48 (m, 0.1H), 5.61-5.64 (m, 0.1H), 5.64-5.70 (m, 0.8H), 7.21-7.62 (m, 6H), 7.88-8.04 (m, 1H). Analytical HPLC (cyano column) (mixture of 2 diastereomers) 17.73 min. LC-MS ($ES^+$) m/e=552.3(M+H).

3-({1-[2-(4-Hydroxy-3,5-dimethyl-benzoylamino)-3-methyl-butyryl]-pyrrolidine-2-carbonyl}-amino)-4-oxo-butyric acid (65)

A 160 mg (0.29 mmol) sample of 64 was hydrolyzed according to method A (see Scheme XXIII) to afford 13.1 mg (10% yield) of the title compound: Analytical HPLC (cyano column) 10.28 min. LC-MS ($ES^+$) m/e=462.2 (M+H).

Scheme XIV

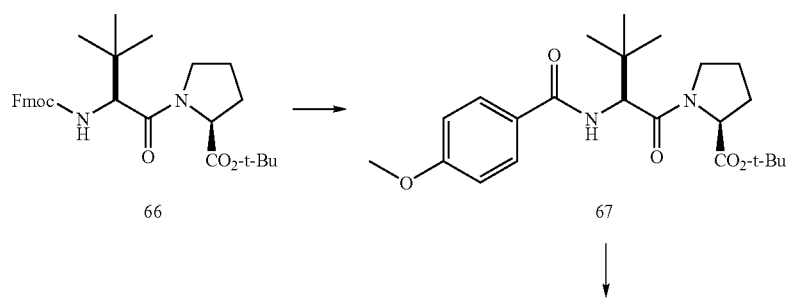

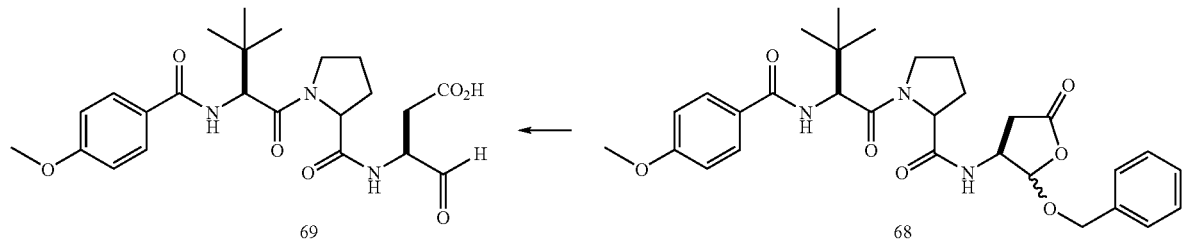

1-[2-(2-9H-Fluoren-9-yl-acetylamino)-3,3-dimethyl-butyryl]-pyrrolidine-2-carboxylic acid tert-butyl ester (66)

To a solution of H-pro-OtBu (53) (1.033 g, 6.0 mmol, II, Scheme 5) in $CH_2Cl_2$ (20 ml) and DMF (5 ml) was added Fmoc-tLeu-OH (2.337 g, 6.60 mmol, I, Scheme 5), HOBT (1.63 g, 12.1 mmol) and EDC (2.30 g, 12.0 mmol) and the solution stirred at room temperature under $N_2$ for 18 hours. The solvent was removed in vacuo, and the residue dissolved in EtOAc then washed with 0.5N $NaHSO_4$ (2×), saturated $NaHCO_3$ (2×) and brine. The organic layer was dried over anhydrous $Na_2SO_4$ and evaporated to give a pale yellow solid (3.65 g). Flash chromatography using EtOAc/hexanes (10/90 to 20/80%) give the title compound (66) (2.25 g, 74% yield). $^1$H-NMR (500 MHz, CDCl3) δ 1.09 (s, 9H), 1.47 (s, 9H), 1.79-2.28 (m, 3H) 3.62-3.72 (m, 1H), 3.76-3.83 (m, 1H), 4.18-4.43 (m, 4H), 5.48-5.67 (m, 1H), 7.28-7.44 (m, 4H), 7.55-7.64 (m, 2H), 7.72-7.82 (m, 2H). Analytical HPLC (cyano column) 11.95 min. LC-MS (ES$^+$) m/e=507.3 (M+H).

1-[2-(4-Methoxy-benzoylamino)-3,3-dimethyl-butyryl]-pyrrolidine-2-carboxylic acid tert-butyl ester (67)

To a solution of 66 (0.503 g, 0.99 mmol) in DMF (8 ml) was added diethylamine (2.5 ml) and the solution stirred at room temperature for 1 hour and the solvent evaporated. The resulting residue was repeatedly concentrated from $CH_2Cl_2$ (3×). The resulting oil was dissolved in $CH_2Cl_2$ (9 mL) and DIEA (260 µl, 1.49 mmol) and 4-methoxy-benzoyl chloride (190 mg, 1.05 mmol) was added. The solution was stirred under $N_2$ for 18 hours and the solvent concentrated in vacuo. The residue was dissolved in EtOAc and washed with 0.5N $NaHSO_4$ (2×), saturated $NaHCO_3$ (2×) and brine then dried over anhydrous $Na_2SO_4$ and evaporated to give a white solid (0.529 g). Flash chromatography on silica gel using MeOH/$CH_2Cl_2$ (1/99 to 2/98%) gave the title compound (2.25 g, 74% yield). $^1$H-NMR (500 MHz, $CD_3OD$) δ 1.01 (s, 1.4H), 1.11 (s, 7.6H), 1.73-2.25 (m, 4H), 2.47-2.77 (m, 1H), 2.81 (dd, 0.7H), 2.91-3.11 (m, 0.3H), 3.61-4.03 (m, 3H), 3.84 (s, 3H), 4.29-4.49 (m, 1H), 4.49-5.00 (m, 5H), 5.46 (s, 0.15H), 5.58-5.73 (m, 0.85H), 6.94-7.04 (m, 2H), 7.27-7.41 (m, 4H), 7.61-7.73 (m, 1H), 7.74-7.84 (m, 2H). Analytical HPLC (cyano column) 13.10 min.

1-[2-(4-Methoxy-benzoylamino)-3,3-dimethyl-butyryl]-pyrrolidine-2-carboxylic acid (2-benzyloxy-5-oxo-tetrahydro-furan-3-yl)-amide (68)

To a solution of 67 (0.90 g, 1.74 mmol) in $CH_2Cl_2$ (25 ml) was added 2,6-lutidine (2.1 ml, 18.0 mmol) and TMS-triflate (2.3 ml, 11.9 mmol) and the reaction stirred at room temperature under $N_2$ for 1.5 hours. The resulting mixture was diluted with $CH_2Cl_2$, washed with 10% $NaHCO_3$ (2×) and brine then dried over $Na_2SO_4$, filtered and evaporated. The residue was dissolved in $CH_2Cl_2$ then treated with DIEA (0.6 ml, 3.5 mmol) and 4-methoxy-benzoyl chloride (0.355 g, 2.09 mmol) and allowed to stir under $N_2$ at room temperature for 18 hours. The crude product was purified by flash chromatography, eluting with $CH_2Cl_2$/MeOH (99/1) to yield the title compound (274 mg, 28% yield). $^1$H-NMR (500 MHz, $CD_3OD$) δ 1.01 (s, 1.4H), 1.11 (s, 7.6H), 1.73-2.25 (m, 4H), 2.47-2.77 (m, 1H), 2.81 (dd, 0.7H), 2.91-3.11 (m, 0.3H), 3.61-4.03 (m, 3H), 3.84 (s, 3H), 4.29-4.49 (m, 1H), 4.49-5.00 (m, 5H), 5.46 (s, 0.15H), 5.58-5.73 (m, 0.85H), 6.94-7.04 (m, 2H), 7.27-7.41 (m, 4H), 7.61-7.73 (m, 1H), 7.74-7.84 (m, 2H). Analytical HPLC (cyano column) (mixture of 2 diastereomers) 17.03, 17.39 min. LC-MS (ES$^+$) m/e=552.3 (M+H).

3-({1-[2-(4-Methoxy-benzoylamino)-3,3-dimethyl-butyryl]-pyrrolidine-2-carbonyl}-amino)-4-oxo-butyric acid (69)

A 117 mg (0.21 mmol) sample of 68 was hydrolyzed according to method C (see Scheme XXIII) to afford 40 mg (41% yield) of the title compound: Analytical HPLC 7.16 min. LC-MS (ES$^+$) m/e=462.3 (M+H).

Scheme XV

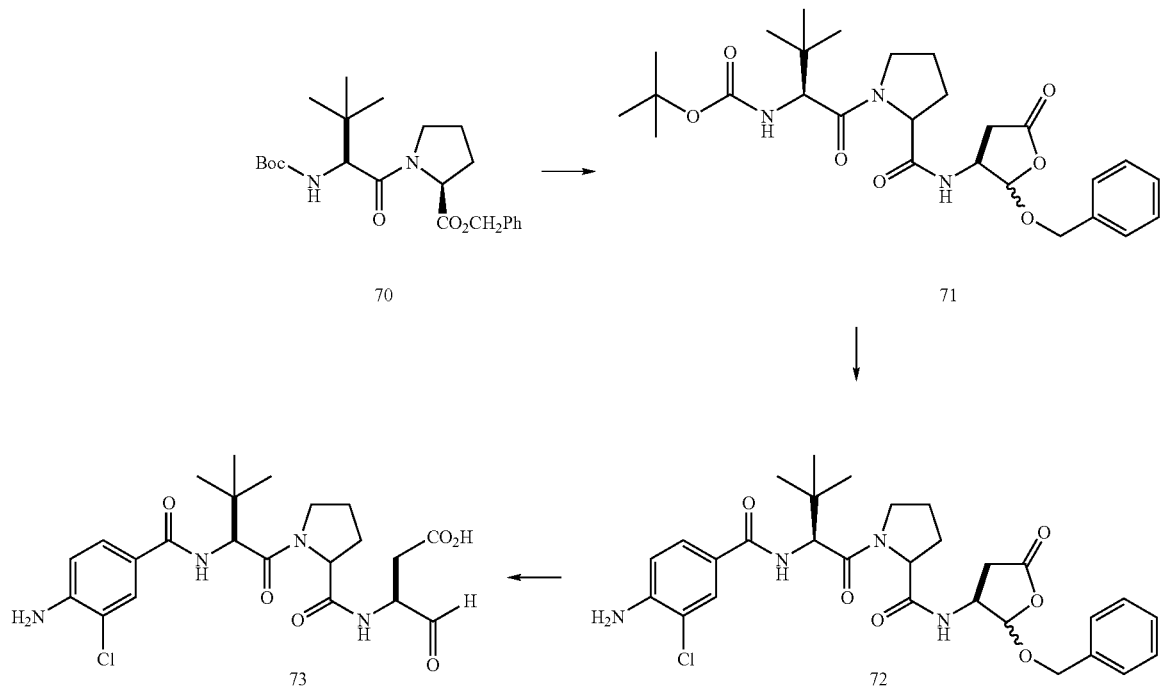

1-(2-tert-Butoxycarbonylamino-3,3-dimethyl-butyryl)-pyrrolidine-2-carboxylic acid benzyl ester (70)

To a suspension of H-pro-OBzl.HCl (2.00 g, 8.66 mmol) in CH$_2$Cl$_2$ (20 ml) was added DIEA (2.25 ml, 12.92 mmol) to give a colorless solution. Boc-tLeu-OH (1.95 g, 9.52 mmol), HOBT (1.76 g, 13.03 mmol) and EDC (2.49 g, 12.95 mmol) were added and the solution stirred under N$_2$ at room temperature for 18 hours. Removed solvent in vacuo, dissolved in EtOAc and washed with H$_2$O, 0.5N NaHSO$_4$ (2×), saturated NaHCO$_3$ (2×) and brine. Dried over anhydrous Na$_2$SO$_4$ and evaporated to give the title compound. (3.57 g, 99% yield). $^1$H-NMR (500 MHz, CDCl$_3$) δ 0.99 (s, 9H), 1.40 (s, 9H), 1.88-2.33 (m, 4H), 3.58-3.90 (m, 2H), 4.21-4.35 (d, 1H), 4.53-4.66 (m, 1H), 5.04-5.38 (m, 3H), 7.14-7.42 (m, 5H). LC-MS (ES$^+$) m/e=419.4 (M+H).

{1-[2-(2-Benzyloxy-5-oxo-tetrahydro-furan-3-ylcarbamoyl)-pyrrolidine-1-carbonyl]-2,2-dimethyl-propyl}-carbamic acid tert-butyl ester (71)

An 871 mg (2.08 mmol) sample of 70 was dissolved in MeOH (15 mL) and 10% Pd/C (200 mg) added. The suspension was stirred under H$_2$ for 1 hour then filtered through Celite and the solvent evaporated. This resulting residue was reacted with 40 according to the procedure used to prepare 56 to give 889 mg (71% yield) of the title compound (71). $^1$H-NMR (500 MHz, CDCl$_3$) δ 0.93 (s, 9H), 1.44 (s, 9H), 1.78-2.18 (m, 4H), 2.29-2.49 (m, 2H), 2.76-3.04 (m, 1H), 3.50-3.70 (m, 1H), 3.70-3.85 (m, 1H), 4.20-4.37 (m, 1H), 4.49-4.78 (m, 3H), 4.78-4.98 (m, 1H), 5.12-5.26 (m, 1H), 5.40-5.59 (m, 1H), 7.10-7.78 (m, 5H). Analytical HPLC (cyano column) 11.17 min. LC-MS (ES$^+$) m/e=518.3 (M+H).

1-[2-(4-Amino-3-chloro-benzoylamino)-3,3-dimethyl-butyryl]-pyrrolidine-2-carboxylic acid (2-benzyloxy-5-oxo-tetrahydro-furan-3-yl)-amide (72)

A solution of 456 mg (0.088 mmol) of 71 in CH$_2$Cl$_2$ (20 ml) was treated with anhydrous TFA (5 mL) then stirred at room temperature under N$_2$ for 1 hour and evaporated to dryness. The residue was repeatedly concentrated from CH$_2$Cl$_2$ (3×) then dried under vacuum. The resulting residue was dissolved in CH$_2$Cl$_2$ (20 ml), cooled to 0° C., then treated with DIEA (1.3 ml, 8 eq, 2.46 mmol) followed by 4-amino-3-chloro-benzoic acid (202 mg, 1.17 mmol), HOBT (1833 mg, 1.35 mmol), and EDC (279 mg, 1.45 mmol). The resulting mixture was allowed to warm to room temperature and stir for 18 hours. The solvent was removed in vacuo and the residue dissolved in EtOAc then washed with distilled water (3×), 0.5N NaHSO$_4$ (2×), saturated NaHCO$_3$ (2×) and brine. The organic layer was dried over Na$_2$SO$_4$, filtered and evaporated to give a residue that was purified by flash chromatography, eluting with CH$_2$Cl$_2$/MeOH (99/1 to 97/3%), affording 285 mg (57% yield) of the title compound (72) as a yellow solid.

$^1$H-NMR (500 MHz, CD$_3$OD) δ 0.91-1.24 (m, 9H), 1.70-2.27 (m, 4H), 2.47-2.85 (m, 1.5H), 2.99-3.13 (m, 0.5H), 3.39-3.53 (m, 0.5H), 3.60-3.78 (m, 1.5H), 3.85-4.04 (m, 1H), 4.24-4.47 (m, 2H), 4.53-4.97 (m, 4H), 5.46 (s, 0.3H), 3.88-4.02 (m, 0.1H), 5.60-5.69 (m, 0.6H), 6.80 (d, 1H), 7.22-7.77 (m, 7H). Analytical HPLC (cyano column) (mixture of 2 diastereomers) 15.90, 16.23 min. LC-MS (ES$^+$) m/e=571.2 (M+H).

3-({1-[2-(4-Amino-3-chloro-benzoylamino)-3,3-dimethyl-butyryl]-pyrrolidine-2-carbonyl}-amino)-4-oxo-butyric acid (73)

A 40 mg (0.07 mmol) sample of 72 was hydrolyzed according to method A (see Scheme XXIII) to afford 25 mg (74% yield) of the title compound: Analytical HPLC (cyano column) 10.66 min. LC-MS (ES+) m/e=481.3 (M+H). 3H), 1.42 (s, 9H), 1.69-2.29 (m, 4H), 2.45-2.67 (m, 0.9H), 2.71-2.86 (m, 0.5H), 2.99-3.10 (m, 0.6H), 3.49-3.84 (m, 2H), 4.24-4.45 (m, 2.5H), 4.57-4.73 (m, 1.5H), 4.76-4.92 (m, 1H), 5.45 (s, 0.45H), 5.63-5.68 (m, 0.55H), 7.25-7.40 (m, 5H). Analytical HPLC (cyano column) (mixture of 2 diastereomers) 15.99, 16.33 min. LC-MS (ES+) m/e=476.3 (M+H).

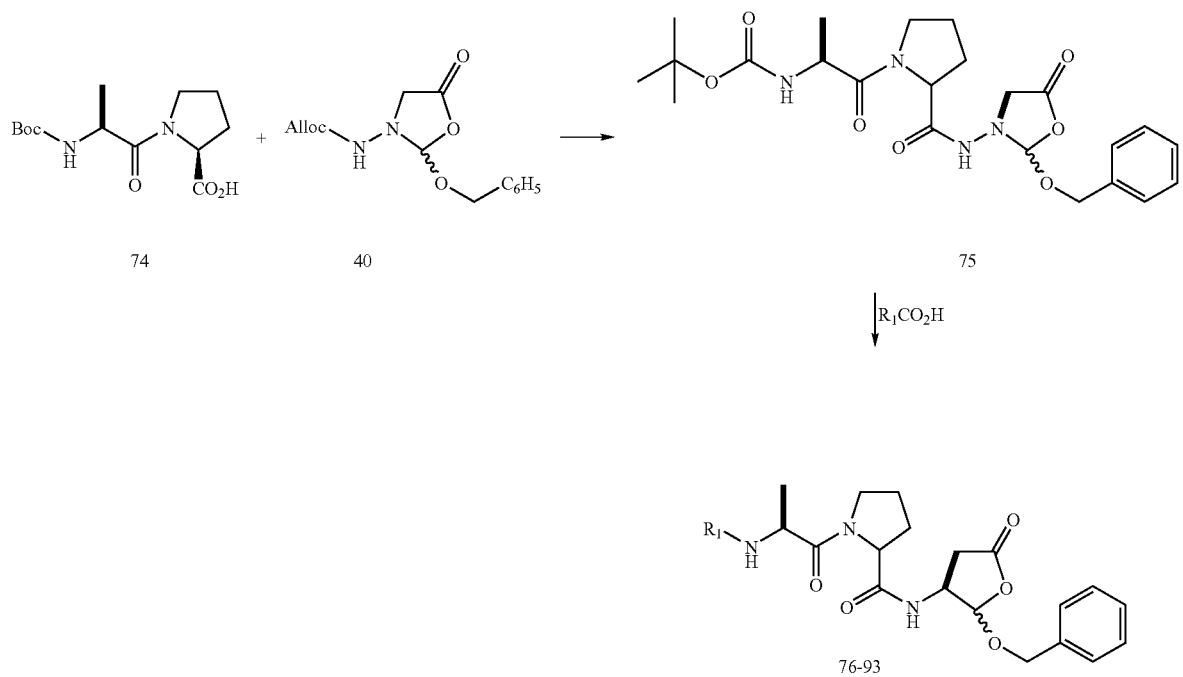

{2-[2-(2-Benzyloxy-5-oxo-tetrahydro-furan-3-ylcarbamoyl)-pyrrolidin-1-yl]-1-methyl-2-oxo-ethyl}-carbamic acid tert-butyl ester (75)

To a solution of 40 (6.69 g, 23.0 mmol) in anhydrous CH$_2$Cl$_2$ was added 1,3-dimethylbarbituric acid (DMBA) (3.97 g, 25.4 mmol) and Pd(PPh$_3$)$_4$ (1.12 g, 0.97 mmol). The solution was stirred under N$_2$ at room temperature for 15 min, cooled to 0° C., followed by the addition of Boc-ala-pro-OH (BaChem) (5.087 g, 17.8 mmol), HOBT (3.60 g, 26.7 mmol) and EDC (5.12 g, 26.7 mmol). The resulting solution was allowed to warm to room temperature and stir under N$_2$ for 18 hours. The solvent was concentrated in vacuo and the residue dissolved in EtOAc, then washed with 0.5N NaHSO$_4$ (2×), saturated NaHCO$_3$ (2×) and brine. The organic layer was dried over anhydrous Na$_2$SO$_4$ and evaporated to give an orange oil (12.23 g). Flash column chromatography on silica gel using CH$_2$Cl$_2$/EtOAc (80/20 to 60/40) gave the title compound 75 as a yellow solid (7.28 g, 86% yield). $^1$H-NMR (500 MHz, CD$_3$OD) δ 1.19-1.31 (m,

[1-[2-(4-Amino-3-chloro-benzoylamino)-propionyl]-pyrrolidine-2-carboxylic acid (2-benzyloxy-5-oxo-tetrahydro-furan-3-yl)-amide] (76)

A 1.899 g (3.99 mmol) sample of 75 in CH$_2$Cl$_2$ (20 ml) was treated with anhydrous TFA (5 ml) then stirred at room temperature under N$_2$ for 1 hour and evaporated to dryness. The residue was repeatedly concentrated from CH$_2$Cl$_2$ (3×) then dried under vacuum. The resulting residue was dissolved in CH₂Cl₂ (20 ml), cooled to 0° C., then treated with DIEA (5.6 ml, 8 eq, 32.1 mmol), 4-amino-3-chloro-benzoic acid (0.910 g, 5.3 mmol), HOBT (0.824 g, 6.1 mmol), and EDC (1.197 g, 6.23 mmol). The resulting mixture was warmed to room temperature and stirred for 18 hours. The solvent was removed in vacuo and the residue dissolved in EtOAc then washed with distilled water (3×), 0.5N NaHSO₄ (2×), saturated NaHCO₃ (2×) and brine. The organic layer was dried over Na₂SO₄, filtered and evaporated to give a residue that was purified by flash chromatography using CH₂Cl₂/MeOH (99/1 to 97/3%). The title compound was obtained as a white solid (1.221 g, 58% yield). ¹H-NMR (500 MHz, CD₃OD) δ 1.15 (d, 0.25H), 1.29-1.60 (m, 2.75H), 2.41-2.54 (m, 0.5H), 2.55-2.70 (m, 0.5H), 2.77 (dd, 0.5H), 3.03 (ddd, 0.5H), 3.59-3.75 (m, 1H), 3.75-3.98 (m, 1H), 4.26-5.01 (m, 5H), 5.41-5.57 (m, 1H), 5.60-5.76 (m, 0.5H), 6.70-6.92 (m, 0.5H), 7.15-7.48 (m, 5H), 7.48-7.68 (m, 1H), 7.68-7.88 (m, 1H), 8.15-8.34 (m, 1H). Analytical HPLC (cyano column) (mixture of 2 diastereomers) 14.44, 14.89 min. LC-MS (ES⁺) m/e=529.3 (M+H).

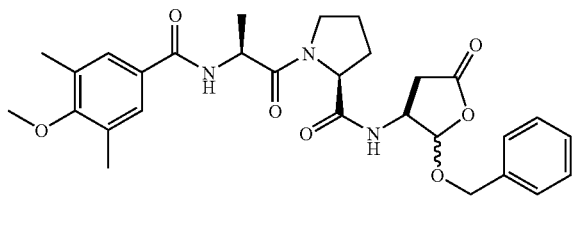

[1-[2-(4-Methoxy-3,5-dimethyl-benzoylamino)-propionyl]-pyrrolidine-2-carboxylic acid (2-benzyloxy-5-oxo-tetrahydro-furan-3-yl)-amide] (77)

Was synthesized from 75 and 3,5-dimethyl-4-methoxy benzoic acid according to the procedure used to prepare 76 to afford the title compound (1.18 g, 44% yield). ¹H-NMR (500 MHz, CD₃OD) δ 1.40 (m, 3H), 1.67-2.41 (m, 4H), 2.28 (s, 6H), 2.48 (ddd, 0.5H), 2.62 (dd, 0.5H), 2.78 (ddd, 0.5H), 3.04 (ddd, 0.5H), 3.62-3.94 (m, 3H), 3.71 (s, 3H), 4.21-4.51 (m, 2H), 4.59-4.85 (m, 4H), 5.46 (s, 0.25H), 5.52 (s, 0.25H), 5.63 (d, 0.4H), 5.67 (d, 0.1H), 7.17-7.45 (m, 5H), 7.45-7.65 (m, 2H). Analytical HPLC (cyano column) (mixture of 2 diastereomers) 15.06, 15.39 min. LC-MS (ES⁺) m/e=538 (M+H).

Preparation of 4-Acetylamino-3-chlorobenzoic acid

To a solution of 4-amino-3-chloro-benzoic acid (10.0 g, 58.3 mmol) in anhydrous THF (100 mL) was added acetyl chloride (20.7 ml, 291.1 mmol) and the solution stirred at room temperature for 48 hours. The solvent was evaporated and the product precipitated from hexanes then filtered and dried to give a white solid (11.73 g, 94% yield). ¹H-NMR (500 MHz, CD₃OD) δ 2.28 (s, 3H), 7.92 (dd, 1H), 7.99-8.16 (m, 2H). Analytical HPLC (cyano column) 7.84 min.

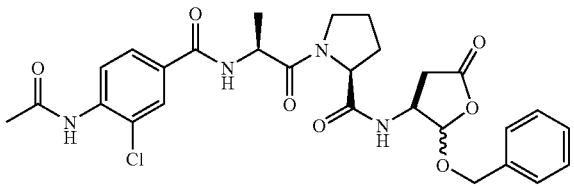

1-[2-(4-Acetylamino-3-chloro-benzoylamino)-propionyl]-pyrrolidine-2-carboxylic acid (2-benzyloxy-5-oxo-tetrahydro-furan-3-yl)-amide (78)

Prepared from 75 and 4-acetylamino-3-chloro-benzoic acid according to the procedure used to prepare 76 to afford the title compound (146 mg, 19% yield). ¹H-NMR (500 MHz, CD₃OD) δ 1.28-1.52 (m, 3H), 1.68-2.38 (m, 4H), 2.20 (s, 3H), 2.41-2.88 (m, 1.5H), 2.96-3.10 (m, 0.5H), 2.96-3.10 (m, 0.5H), 3.43-3.75 (m, 1H), 3.80-3.96 (m, 1H), 4.25-5.00 (m, % H), 5.42-5.54 (m, 0.5H), 5.63-5.78 (m, 0.5H), 7.13-7.48 (m, 05H), 7.79-8.14 (m, 2.5H), 8.56-8.70 (m, 0.5H). Analytical HPLC (cyano column) (mixture of 2 diastereomers) 8.64 min. LC-MS (ES⁺) m/e=571.2 (M+H).

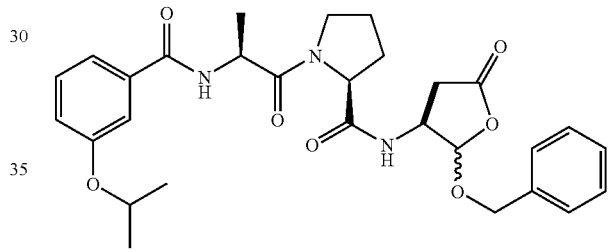

1-[2-(3-Isopropoxy-benzoylamino)-propionyl]-pyrrolidine-2-carboxylic acid (2-benzyloxy-5-oxo-tetrahydro-furan-3-yl)-amide (79)

Prepared from 75 and 3-isopropoxybenzoic acid according to the procedure used to prepare 76 to afford the title compound (120 mg, 58% yield). ¹H-NMR (500 MHz, CD₃OD) δ 1.27 (d, 6H), 1.33-1.52 (m, 3H), 1.69-2.31 (m, 4H), 2.49 (dd, 0.3H), 2.63 (dd, 0.7H), 2.78 (dd, 0.7H), 3.03 (dd, 0.3H), 3.43-3.73 (m, 1H), 3.78-3.94 (m, 1H), 4.27-4.47 (m, 2H), 4.47-4.87 (m, 4H), 5.47 (s, 0.7H), 5.53 (d, 0.3H), 5.64 (d, 0.8H), 5.72 (d, 0.2H), 6.98-7.12 (m, 1H), 7.19-7.47 (m, 9H). Analytical HPLC (cyano column) (mixture of 2 diastereomers) 14.54, 14.85 min. LC-MS (ES⁺) m/e=538 (M+H).

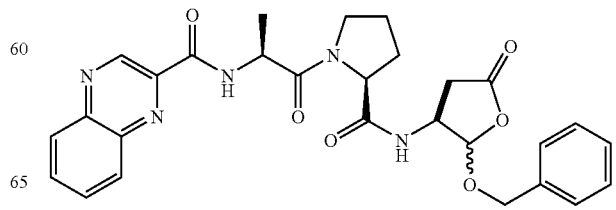

Quinoxaline-2-carboxylic acid {2-[2-(2-benzyloxy-5-oxo-tetrahydrofuran-3-ylcarbamoyl)-pyrrolidin-1-yl]-1-methyl-2-oxo-ethyl}-amide (80)

Prepared from 75 and 2-quinoxaline carboxylic acid according to the procedure used to prepare 76 to afford the title compound (122 mg, 60% yield). $^1$H-NMR (500 MHz, CD$_3$OD) δ 1.12-1.67 (m, 3H), 1.68-2.34 (m, 4H), 2.35-2.70 (m, 0.85H), 2.70-2.95 (m, 0.75H), 3.06 (dd, 0.4H), 3.41-3.49 (m, 2H), 4.18-5.03 (m, 6H), 5.47 (d, 0.5H), 5.55 (d, 2H), 5.67 (dd, 1H), 5.71 (dd, 0.3H), 7.03-7.53 (m, 5H), 7.80-8.06 (m, 2H), 8.06-8.34 (m, 2H), 9.43-9.48 (m, 1H). Analytical HPLC (cyano column) (mixture of 2 diastereomers) 9.06 min. LC-MS (ES$^+$) m/e=532.3 (M+H).

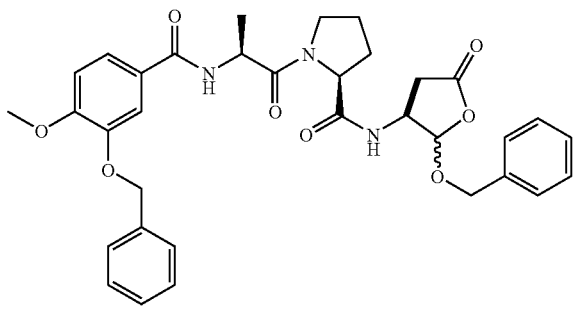

81

1-[2-(3-Benzyloxy-4-methoxy-benzoylamino)-propionyl]-pyrrolidine-2-carboxylic acid (2-benzyloxy-5-oxo-tetrahydro-furan-3-yl)-amide (81)

Prepared from 75 and 3-benzyloxy-4-methoxy benzoic acid according to the procedure used to prepare 76 to afford the title compound (142 mg, 58% yield). $^1$H-NMR (500 MHz, CD$_3$OD) δ 1.14 (d, 0.3H), 1.27-1.52 (m, 2.7H), 1.66-2.30 (m, 4H), 2.47 (dd, 0.4H), 2.59 (dd, 0.6H), 2.77 (dd, 0.6H), 3.02 (dd, 0.4H), 3.41-3.72 (m, 1H), 3.72-3.99 (m, 2H), 3.86 (s, 3H), 4.19-4.86 (m, 5H), 4.99-5.15 (m, 2H), 5.45 (m, 0.8H), 5.65 (m, 1.2H), 6.98 (dd, 1H), 7.11-7.63 (m, 12H). Analytical HPLC (cyano column) (mixture of 2 diastereomers) 12.28, 12.44 min. LC-MS (ES$^+$) m/e=616.3 (M+H).

4-Allyloxy-3,5-dimethyl-benzoic acid

A mixture of 4-hydroxy-3,5-dimethyl-benzoic acid (3.32 g, 20 mmol), allyl bromide (7.26 g, 60 mmol), benzyltriethylammonium chloride (455 mg, 2 mmol) and K$_2$CO$_3$ (6.9 g, 50 mmol) in DMF (50 mL) was stirred at room temperature for 16 hours. The mixture was diluted with ethyl acetate (200 mL), washed with water, brine. The organic layer was dried over Na$_2$SO$_4$, filtered and evaporated in vacuo to give 5.3 g of the ester as an oil. The ester was refluxed with NaOH (5 g, 125 mmol) in water/methanol (50 mL/50 mL) for 6 hours. The mixture was evaporated in vacuo to remove methanol and the resulted solution was diluted with water (200 mL), washed with ethyl acetate/hexane (30 mL/70 mL). The aqueous layer was acidified at 0° C. with concentrated HCl solution to pH 2. The resulted precipitate was collected by filtration and washed with water, dried over high vacuum to afford 3.86 g (yield 94%) of the title compound. $^1$H-NMR (500 MHz, CDCl$_3$): δ 2.33 (s, 6H), 4.35-4.37 (m, 2H), 5.28-5.30 (m, H), 5.42-5.46 (m, H), 6.07-6.15 (m, H), 7.79 (s, 2H); retention time on analytical HPLC: 11.28 min; LC-MS: m/z=205 (M−H$^+$)

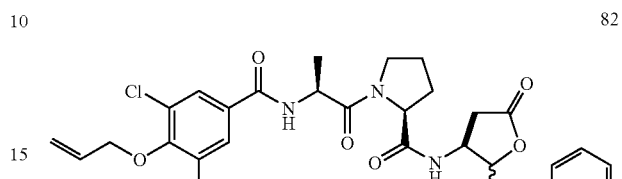

82

1-[2-(4-Allyloxy-3,5-dichloro-benzoylamino)-propionyl]-pyrrolidine-2-carboxylic acid (2-benzyloxy-5-oxo-tetrahydro-furan-3-yl)-amide (82)

Prepared from 75 and 4-allyloxy-3,5-dichloro-benzoic acid according to the procedure used to prepare 76 to afford the title compound (208 mg. 47% yield). $^1$H-NMR (500 MHz, CDCl$_3$) δ 1.05-1.58 (m, 3H), 1.68-3.21 (m, 7H), 3.39-3.90 (m, 3H), 4.05-5.01 (m, 6H), 5.22-5.62 (m, 3H), 6.04-6.25 (m, 1H), 6.94-7.63 (m, 8H). Analytical HPLC (cyano column) (mixture of 2 diastereomers) 9.69, 9.89 min. LC-MS (ES$^+$) m/e=604.2 (M+H).

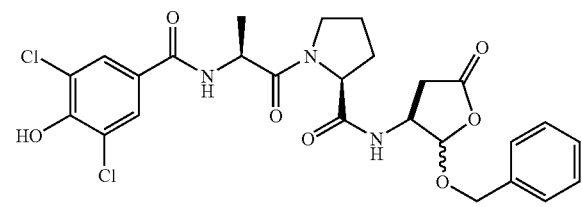

83

1-[2-(3,5-Dichloro-4-hydroxy-benzoylamino)-propionyl]-pyrrolidine-2-carboxylic acid (2-benzyloxy-5-oxo-tetrahydro-furan-3-yl)-amide (83)

A 140 mg sample of 82 (0.23 mmol) was dissolved in CH$_2$Cl$_2$ (4 mL) and treated with DMBA (35.4 mg, 0.26 mmol) and Pd(PPh$_3$)$_4$ (32 mg, 0.028 mmol). The solution was stirred at 0° C. for 15 mins, warmed to room temperature for 2 hours, then diluted with CH$_2$Cl$_2$ and washed with water (2×) and brine. The solvent was concentrated in vacuo and the residue purified by flash chromatography on silica gel using MeOH/CH$_2$Cl$_2$ (1/99 to 3/97) to give the title compound (93.2 mg, 71% yield). $^1$H-NMR (500 MHz, CD$_3$OD) δ 1.16 (d, 0.25H), 1.28-1.49 (m, 2.75H), 1.63-2.33 (m, 4H), 2.48 (dd, 0.4H), 3.39-3.59 (m, 0.2H), 3.60-3.73 (m, 0.8H), 3.73-3.96 (m, 1H), 4.24-4.48 (m, 2H), 4.57-4.92 (m, 7H), 5.44 (s, 0.4H), 5.50 (d, 0.4H), 5.64 (d, 0.8H), 5.75 (d, 0.5H), 7.16-7.43 (m, 5H), 7.78-7.89 (m, 1.6H), 8.40-8.63

(m, 0.4H). Analytical HPLC (cyano column) (mixture of 2 diastereomers) 11.57, 11.82 min. LC-MS (ES+) m/e=564.1 (M+H).

7.21-7.43 (m, 5H), 7.49-7.83 (m, 2.8H), 7.88-8.04 (m, 1.8H), 8.45-8.54 (m, 0.8H), 8.97-9.06 (m, 0.6H). Analytical HPLC (mixture of 2 diastereomers) 15.71, 16.04 min. LC-MS (ES+) m/e=531.2 (M+H).

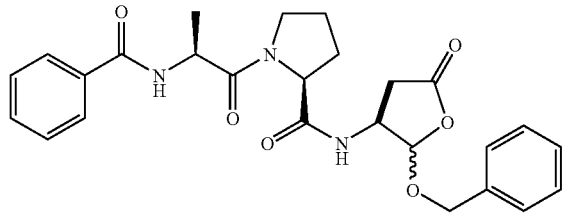

84

1-(2-Benzoylamino-propionyl)-pyrrolidine-2-carboxylic acid (2-benzyloxy-5-oxo-tetrahydro-furan-3-yl)-amide (84)

Prepared from 75 and benzoyl chloride according to the procedure used to prepare 76 to afford the title compound as a colorless oil (8 mg, 38% yield). $^1$H-NMR (500 MHz, CD$_3$OD) δ 1.35-1.54 (m, 3H), 1.72-2.30 (m, 4H), 2.42-2.70 (m, 1.3H), 2.74-2.84 (m, 0.5H), 3.03 (dd, 0.2H), 3.41-3.75 (m, 2H), 3.81-3.96 (m, 1H), 4.22-4.86 (m, 4H), 5.46 (s, 0.3H), 5.51-5.54 (m, 0.1H), 5.66 (d, 0.5H), 5.72 (d, 0.1H), 7.20-7.57 (m, 7H), 7.77-7.89 (m, 2H), 8.42-8.67 (m, 1H). Analytical HPLC (cyano column) (mixture of 2 diastereomers) 15.23, 15.67 min. LC-MS (ES+) m/e=481.2 (M+H).

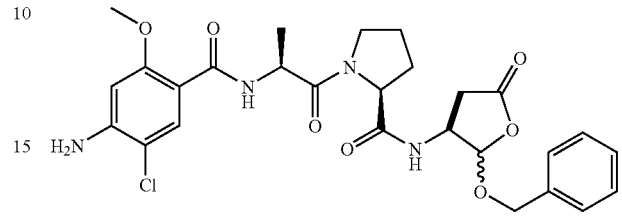

86

1-[2-(4-Amino-5-chloro-2-methoxy-benzoylamino)-propionyl]-pyrrolidine-2-carboxylic acid (2-benzyloxy-5-oxo-tetrahydro-furan-3-yl)-amide (86)

Prepared from 75 and 4-amino-5-chloro-2-methoxy benzoic acid according to the procedure used for 76 to afford the title compound (330 mg, 61% yield). $^1$H-NMR (500 MHz, CD$_3$OD) δ 1.22 (d, 0.25H), 1.29-1.50 (m, 0.75H), 1.68-2.36 (m, 4H), 2.38-2.89 (m, 1.5H), 2.94-3.14 (m, 0.5H), 3.37-3.98 (m, 6H), 4.27-4.98 (m, 6H), 5.44-5.50 (m, 0.4H), 5.53-5.56 (s, 0.1H), 5.60-5.75 (m, 0.5H), 6.50 (s, 1H), 7.17-7.45 (m, 4H), 7.73-7.90 (m, 1H), 8.49-8.70 (m, 1H). Analytical HPLC (cyano column) (mixture of 2 diastereomers) 16.39, 16.82 min. LC-MS (ES+) m/e=559.2 (M+H).

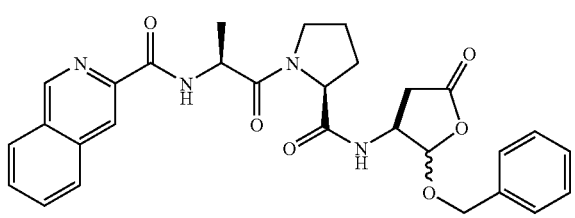

85

Isoquinoline-1-carboxylic acid {2-(2-benzyloxy-5-oxo-tetrahydro-furan-3-ylcarbamoyl)-pyrrolidin-1-yl]-1-methyl-2-oxo-ethyl}-amide (85)

Prepared from 75 and 1-isoquinolinecarboxylic acid according to the procedure used to prepare 76 to afford the title compound (732 mg, 53% yield). $^1$H-NMR (500 MHz, CD$_3$OD) δ 1.22-1.56 (m, 3H), 1.70-2.34 (m, 4H), 2.43-2.71 (m, 0.9H), 2.73-2.89 (m, 0.5H), 3.06 (ddd, 0.6H), 3.42-3.81 (m, 2H), 3.84-4.01 (m, 1H), 4.29-5.00 (m, 5H), 5.47 (d, 0.65H), 5.55 (s, 0.3H), 5.67 (d, 0.8H), 5.72 (d, 0.25H),

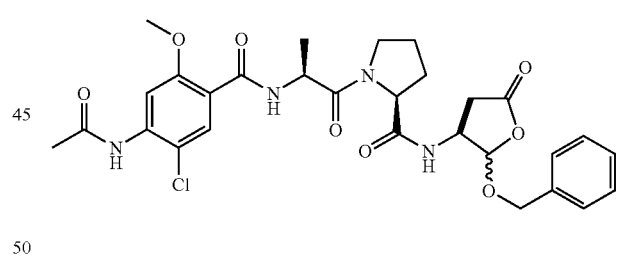

87

1-[2-(4-Acetylamino-5-chloro-2-methoxy-benzoylamino)-propionyl]-pyrrolidine-2-carboxylic acid (2-benzyloxy-5-oxo-tetrahydro-furan-3-yl)-amide (87)

Prepared from 75 and 4-acetylamino-5-chloro-2-methoxy benzoic acid according to the procedure used for 76 to afford the title compound (364 mg, 64% yield). $^1$H-NMR (500 MHz, CD$_3$OD) δ 1.20-1.27 (m, 0.25), 1.35-1.49 (m, 0.75H), 1.72-2.30 (m, 4H), 2.23 (s, 3H), 2.42-2.58 (m, 0.6H), 2.59-2.68 (m, 0.5H), 2.73-2.86 (m, 0.7H), 2.99-3.11 (m, 0.7H), 3.41-4.07 (m, 5H), 4.29-4.97 (m, 5H), 4.79-5.56 (m, 0.5H), 5.65-5.73 (m, 0.5H), 7.18-7.44 (m, 4.3H), 7.90-8.09 (m, 2H), 8.71-8.85 (m, 0.7H). Analytical HPLC (cyano column) (mixture of 2 diastereomers) 15.61, 16.01 min. LC-MS (ES⁺) m/e=601.1 (M+H).

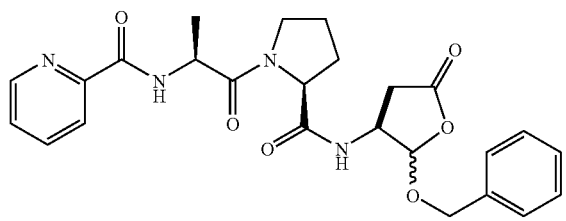

88

Pyridine-2-carboxylic acid {2-[2-(2-benzyloxy-5-oxo-tetrahydro-furan-3-ylcarbamoyl)-pyrrolidin-1-yl]-1-methyl-2-oxo-ethyl}-amide (88)

Prepared from 75 and pyridine-2-carboxylic acid according to the procedure used for 76 to afford the title compound (233 mg, 42% yield). ¹H-NMR (500 MHz, CD₃OD) δ 1.30-1.59 (m, 3H), 1.68-2.36 (m, 4H), 2.39-2.57 (m, 0.6H), 2.57-2.69 (m, 0.35H), 2.71-2.87 (m, 0.4H), 3.05 (dd, 0.65H), 3.39-3.93 (m, 3H), 4.24-4.99 (m, 5H), 5.49-5.55 (m, 0.8H), 5.63-5.77 (m, 1.2H), 7.17-7.46 (m, 5H), 7.49-7.60 (m, 1H), 7.89-7.99 (m, 1H), 8.03-8.12 (m, 1H), 8.58-8.67 (m, 1H). Analytical HPLC (cyano column) (mixture of 2 diastereomers) 8.63 min. LC-MS (ES⁺) m/e=481.3 (M+H).

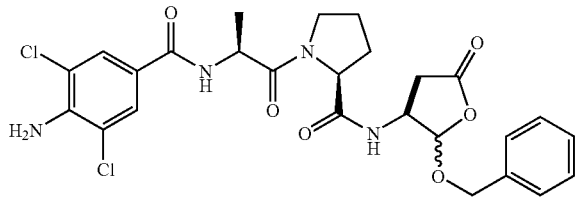

89

[1-[2-(4-Amino-3,5-dichloro-benzoylamino)-propionyl]-pyrrolidine-2-carboxylic acid (2-benzyloxy-5-oxo-tetrahydro-furan-3-yl)-amide] (89)

Prepared from 75 and 3,5-dichloro-4-aminobenzoic acid according to the procedure used for 76 to afford the title compound (162 mg, 70% yield). ¹H-NMR (500 MHz, CD₃OD) δ 1.21-1.58 (m, 3H), 1.58-2.37 (m, 4H), 2.37-3.13 (m, 2H), 3.43-3.74 (m, 1.5H), 3.77-3.94 (m, 1H), 4.28-4.51 (m, 1.5H), 4.50-5.01 (m, 3H), 5.41-5.77 (m, 1H), 7.15-7.49 (m, 5H), 7.66-7.88 (m, 2H). Analytical HPLC (cyano column) (mixture of 2 diastereomers) 8.36 min. LC-MS (ES⁺) m/e=563.2 (M+H).

90

1-[2-(4-Methoxy-benzoylamino)-propionyl]-pyrrolidine-2-carboxylic acid (2-benzyloxy-5-oxo-tetrahydro-furan-3-yl)-amide (90)

Prepared from 75 and 4-methoxy-benzoylchloride according to the procedure used for 76 to afford the title compound (404 mg, 50%). ¹H-NMR (500 MHz, CD₃OD) δ 1.19 (d, 0.3H), 1.29-1.58 (m, 2.7H), 1.58-2.38 (m, 4H), 2.43-2.69 (m, 1H), 2.74-2.86 (m, 0.6H), 2.99-3.11 (m, 0.4H), 3.39-3.75 (m, 1.5H), 3.77-3.94 (m, 1H), 3.84 (s, 3H), 4.29-4.94 (m, 4.5H), 5.45-5.55 (m, 4.5H), 5.63-5.71 (m, 0.5H), 5.73 (d, 0.1H), 6.85-7.09 (m, 2H), 7.19-7.44 (m, 4H), 7.73-7.92 (m, 2H), 8.26-8.44 (m, 1H). Analytical HPLC (cyano column) (mixture of 2 diastereomers) 15.18, 15.65 min. LC-MS (ES⁺) m/e=510.2 (M+H).

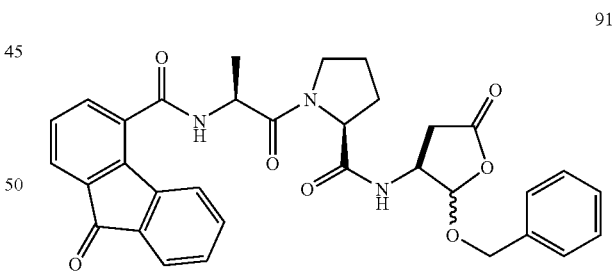

91

1-{2-[(9-Oxo-9H-fluorene-4-carbonyl)-amino]-propionyl}-pyrrolidine-2-carboxylic acid (2-benzyloxy-5-oxo-tetrahydro-furan-3-yl)-amide (91)

Prepared from 75 and 9-oxo-9H-fluorene-carboxylic acid according to the procedure used for 76 to afford the title compound (403 mg, 44% yield). ¹H-NMR (500 MHz, CDCl₃) δ 1.38-1.59 (m, 3H), 1.75-2.37 (m, 4H), 2.43-2.59 (m, 0.65H), 2.59-2.72 (m, 0.35H), 2.79-2.89 (m, 0.35H), 3.01-3.11 (m, 0.65H), 3.68-3.86 (m, 1H), 3.92-4.09 (m, 1H), 4.35-5.03 (m, 7H), 5.42-5.90 (m, 1H), 7.06-8.00 (m, 12H). Analytical HPLC (cyano column) (mixture of 2 diastereomers) 12.30 min. LC-MS (ES+) m/e=582.1 (M+H).

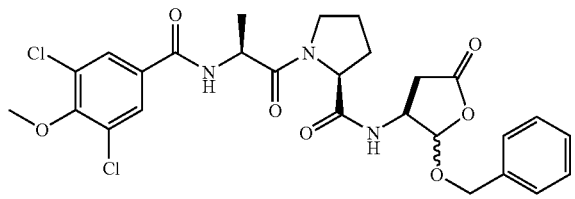

1-[2-(3,5-Dichloro-4-methoxy-benzoylamino)-propionyl]-pyrrolidine-2-carboxylic acid (2-benzyloxy-5-oxo-tetrahydro-furan-3-yl)-amide (92)

Prepared from 75 and 3,5-dichloro-4-methoxy-benzoic acid according to the procedure used for 76 to afford the title compound (364 mg. 46% yield). $^1$H-NMR (500 MHz, CD$_3$OD) δ 1.17 (d, 0.25H), 1.28-1.53 (m, 2.75H), 1.64-2.33 (m, 4H), 2.39-2.94 (m, 1.5H), 2.94-3.12 (m, 0.5H), 3.41-3.74 (m, 2H), 3.74-4.00 (m, 1H), 3.91 (s, 3H), 4.26-5.02 (m, 5H), 5.42-5.81 (m, 1H), 7.08 (d, 0.4H), 7.21-7.43 (m, 4.6H), 7.53-7.69 (m, 0.8H), 7.85-7.97 (m, 1.2H). Analytical HPLC (cyano column) (mixture of 2 diastereomers) 10.79 min. LC-MS (ES+) m/e=578.2 (M+H).

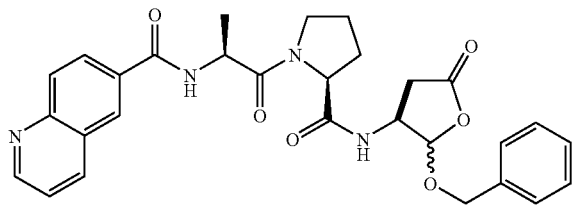

Quinoline-6-carboxylic acid {2-(2-benzyloxy-5-oxo-tetrahydro-furan-3-ylcarbamoyl)-pyrrolidin-1-yl]-1-methyl-2-oxo-ethyl}-amide (93)

Prepared from 75 and 6-quinolinecarboxylic acid according to the procedure used for 76 to afford the title compound (344 mg, 71% yield). $^1$H-NMR (500 MHz, CD$_3$OD) δ 1.11-1.58 (m, 3H), 1.69-2.40 (m, 4H), 2.42-3.15 (m, 2H), 3.80-4.01 (m, 1H), 4.29-4.99 (m, 5H), 5.44-5.54 (m, 0.5H), 5.63-5.73 (d, 0.4H), 5.73-5.79 (d, 0.1H), 7.18-7.43 (m, 5H), 7.56-7.67 (m, 1H), 8.08 (d, 1H), 8.13-8.25 (m, 1H), 8.40-8.56 (m, 2H), 8.88-8.99 (m, 1H). Analytical HPLC (cyano column) (mixture of 2 diastereomers) 10.27, 10.50 min. LC-MS (ES+) m/e=531.2 (M+H).

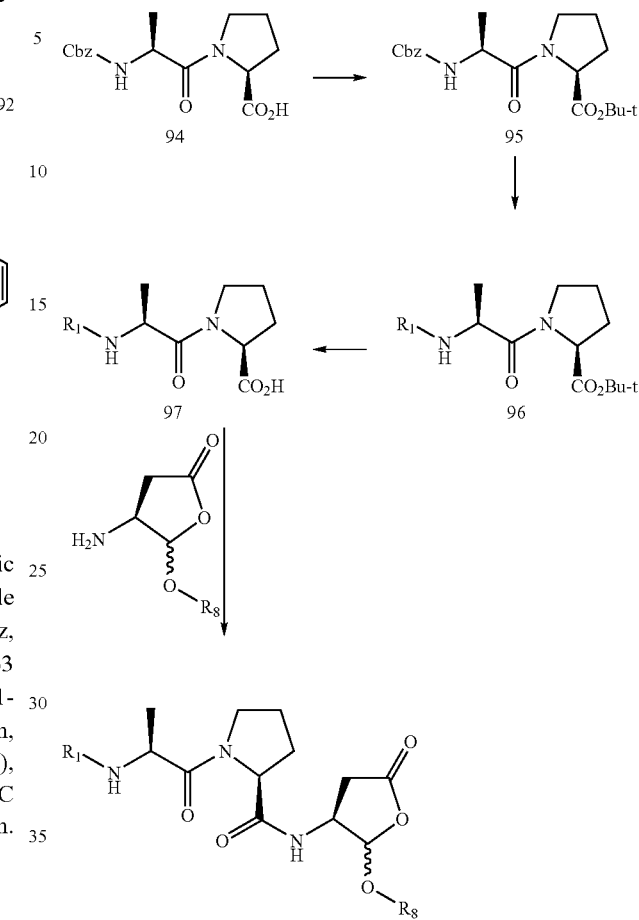

1-(2-Benzyloxycarbonylamino-propionyl)-pyrrolidine-2-carboxylic acid tert-butyl ester (95)

Prepared according to the method described in Pierre Chevallet, Patrick Garrouste, Barbara Malawaska & Jean Martinez in Tetrahedron Letters, Vol. 34, pp. 7409-7412, (1993). A mixture of Cbz-ala-pro-OH (10.0 g, 31.2 mmol), tert-butyl bromide (180 g, 1.31 mol), benzyltriethylammonium chloride (7.11 g, 31.2 mmol) and K$_2$CO$_3$ (180 g, 1.30 mol) in N,N-dimethylacetamide (DMA) (225 mL) was stirred at 55° C. for 24 hours. The reaction mixture was cooled to room temperature and diluted with one liter of ice-water, extracted with ethyl acetate (200 mL×3). The organic layer was dried over anhydrous Na$_2$SO$_4$, filtered and evaporated in vacuo to give 14 g of oil, which was purified by flash chromatography using hexane/ethyl acetate (95/5 to 50/50) to afford 11.73 g (yield 99.7%) of the title compound as a clear oil. $^1$H-NMR (500 MHz, CDCl$_3$): δ 1.25-1.50 (m, 12H), 1.85-2.25 (m, 4H), 3.42-3.70 (m, 2H), 4.25-4.57 (m, 2H), 5.07-5.11 (m, 2H), 5.69 (d, H), 7.28-7.38 (m, 5H); retention time on analytical HPLC: 11.07 min; LC-MS: m/z=377 (M+H+).

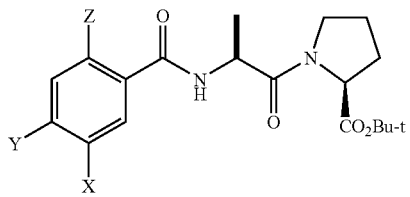

96a, X = Cl, Y = NH$_2$, Z = H
96b, X = Cl, Y = AcNH, Z = H
96c, X = Cl, Y = AcNH, Z = CH$_3$O

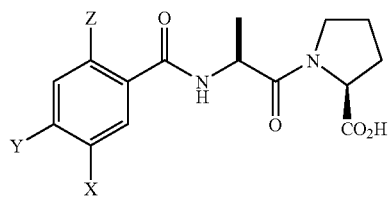

97a, X = Cl, Y = NH$_2$, Z = H
97b, X = Cl, Y = AcNH, Z = H
97c, X = Cl, Y = AcNH, Z = CH$_3$O

1-[2-(4-Amino-3-chloro-benzoylamino)-propionyl]-pyrrolidine-2-carboxylic acid tert-butyl ester (96a)

To a solution of 95 (10.50 g, 27.9 mmol) in MeOH (100 ml) was added a suspension of 10% Pd/C (5.00 g) in EtOAc (50 ml). The mixture was stirred under H$_2$ for 48 hours, filtered through celite and the solvent evaporated to yield a waxy solid. This was dissolved in CH$_2$Cl$_2$ (100 ml) and DMF (50 ml) and the solution cooled to 0° C. 4-Amino-3-chlorobenzoic acid (5.82 g, 27.2 mmol), DIEA (14.58 mL, 83.7 mmol), HOBT (3.77 g, 27.9 mmol) and EDC (6.68 g, 34.8 mmol) were added and the solution stirred at 0° C. for 15 mins then at room temperature for 24 hours. The reaction mixture was diluted with EtOAc, washed with NaHSO$_4$ (2×), 10% NaHCO$_3$ (2×) and brine then dried over MgSO$_4$, filtered and evaporated. The crude product was purified by flash column chromatography, using CH$_2$Cl$_2$/MeOH (99/1 to 97/3%) to yield the title compound as a white solid (7.75 g, 70% yield). $^1$H-NMR (500 MHz, CD$_3$OD) δ 1.27-1.67 (m, 12H), 1.82-2.14 (m, 4H), 3.48-3.85 (m, 2H), 4.26-4.53 (m, 3H), 4.81-4.98 (m, 1H), 6.71 (d, 1H), 7.15 (m, 1H), 7.50 (dd, 1H), 7.75 (d, 1H). Analytical HPLC 10.83 min. LC-MS (ES$^+$) m/e=396.3 (MH$^+$).

1-[2-(4-Amino-3-chloro-benzoylamino)-propionyl]-pyrrolidine-2-carboxylic acid (97a)

Prepared from 96a by treatment with TFA/CH$_2$Cl$_2$. After complete reaction, the solvent is removed in vacuo and the residue repeatedly concentrated from toluene. The resulting residue was dried under vacuum to a constant weight.

1-[2-(4-Acetylamino-3-chloro-benzoylamino)-propionyl]-pyrrolidine-2-carboxylic acid tert-butyl ester (96b)

Prepared from 95 and 4-acetylamino-3-chlorobenzoic acid according to the method used for 96a to afford the title compound as a white solid (9.18 g, 77% yield). $^1$H-NMR (500 MHz, CD$_3$OD) δ 1.30-1.62 (m, 12H), 1.85-2.16 (m, 3H), 2.16-2.44 (m, 1H), 2.27 (s, 3H), 3.47-3.83 (m, 2H), 4.34-4.54 (m, 1H), 4.89 (m, 1H), 7.27-7.39 (m, 1H), 7.59-7.71 (m, 2H), 7.83-7.97 (m, 1H), 8.47 (d, 1H). Analytical HPLC 9.43 min.

1-[2-(4-Acetylmino-3-chloro-benzoylamino)-propionyl]-pyrrolidine-2-carboxylic acid (97b)

Prepared from 96b by treatment with TFA/CH$_2$Cl$_2$. After complete reaction, the solvent is removed in vacuo and the residue repeatedly concentrated from toluene. The resulting residue was dried under vacuum to a constant weight.

4-Acetylamino-5-chloro-2-methoxy-benzoic acid

4-Acetylamino-5-chloro-2-methoxy-benzoic acid methyl ester (2.09 g, 8.11 mmol) was dissolved in MeOH (110 ml) and LiOH solution (25.48 mmol in 30 ml, 1:1 MeOH:H$_2$O) added and the solution stirred at room temperature for 6 hours. The solvent was concentrated in vacuo, EtOAc added and the organic phase was washed with 0.5N HCl then extracted with saturated NaHCO$_3$ (2×). The aqueous phase was acidified with 12N HCl to pH 1 and the resulting precipitate extracted into CH$_2$Cl$_2$. The combined extracts were dried over anhydrous Na$_2$SO$_4$, filtered and evaporated to give the title compound as a white solid (0.933 g, 50% yield). $^1$H-NMR (500 MHz, CDCl3). δ 2.31 (s, 3H), 4.10 (s, 3H), 7.78-7.92 (br s, 1H), 8.17 (s, 1H), 8.45 (s, 1H). Analytical HPLC 5.62 min.

1-[2-(4-Acetylamino-5-chloro-2-methoxy-benzoylamino)-propionyl]-pyrrolidine-2-carboxylic acid tert-butyl ester (96c)

To a solution of 95 (1.534 g, 4.07 mmol) in MeOH (40 ml) was added 10% Pd/C (650 mg) and the mixture stirred under H$_2$ for 2 hours. The suspension was filtered through celite and evaporated to give a yellow oil. This was allowed to react with 4-acetyl-5-chloro-2-methoxy benzoic acid following the procedure used for the preparation of 96a to give the title compound (497 mg, 52% yield). $^1$H-NMR (500 MHz, CD$_3$OD) δ 1.46 (d, 3H), 1.49 (s, 9H), 1.80-2.01 (m, 3H), 2.19-2.40 (m, 1H), 2.22 (s, 3H), 3.58-3.72 (m, 1H), 3.78-3.89 (m, 1H), 3.98-4.09 (s, 3H), 4.31-4.45 (s, 1H), 4.78-4.95 (m, 1H), 7.89-8.10 (m, 2H). Analytical HPLC 11.31 min.

1-[2-(4-Acetylamino-5-chloro-2-methoxy-benzoylamino)-propionyl]-pyrrolidine-2-carboxylic acid (97c)

Prepared from 96c by treatment with TFA/CH$_2$Cl$_2$. After complete reaction, the solvent is removed in vacuo and the

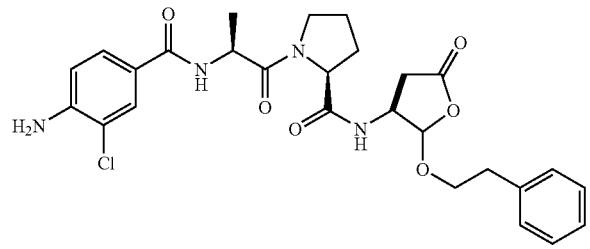

1-[2-(4-Amino-3-chloro-benzoylamino)-propionyl]-pyrrolidine-2-carboxylic acid (5-oxo-2-phenethyloxy-tetrahydro-furan-3-yl)-amide (98a)

To a solution of (5-oxo-2-phenethyloxy-tetrahydro-furan-3-yl)-carbamic acid allyl ester (194 mg, 0.54 mmol) (prepared as described for (40) using phenethyl alcohol) in anhydrous CH$_2$Cl$_2$ (5 mL) at 0° C. was added DMBA (196 mg, 1.26 mmol) and Pd(PPh$_3$)$_4$ (32 mg, 0.03 mmol). The solution was stirred for 15 min and a solution of 97a (prepared from 96a by treatment with TFA in CH$_2$Cl$_2$) (166 mg, 0.49 mmol) and DIEA (680 µl, 3.90 mmol) in CH$_2$Cl$_2$ (2 mL) was added followed by HOBT (98 mg, 0.73 mmol) and EDC (122 mg, 0.63 mmol). The solution was stirred at 0° C. for 15 min then at room temperature for 18 hours. The solvent was removed in vacuo and the residue dissolved in EtOAc then washed with 0.5N NaHSO$_4$ (2×), saturated NaHCO$_3$ (2×) and brine. Dried over anhydrous Na$_2$SO$_4$ and evaporated to give an orange solid which was purified by flash column chromatography, using CH$_2$Cl$_2$/MeOH (99/1 to 97/3%) to yield the title compound as a white solid (190 mg, 73% yield). $^1$H-NMR (500 MHz, CD$_3$OD) δ 1.29 (d, 0.6H), 1.41 (d, 2.4H), 1.78 (m, 1H), 2.08 (m, 3H), 2.56 (m, 1H), 2.77 (dd, 1H), 2.94 (t, 2H), 3.53 (m, 0.3H), 3.67 (m, 0.8H), 3.85 (m, 2H), 3.96-4.08 (m, 1H), 4.40 (m, 2H), 4.62 (m, 1H), 4.67-4.79 (m, 1H), 5.57 (d, 0.7H), 5.60 (d, 0.3H), 6.78 (dd, 1H), 7.21 (m, 5H), 7.58 (m, 1H), 7.79 (m, 1H), 8.26 (d, 1H). Analytical HPLC 14.52 min. LC-MS (ES$^+$) m/e=543.2 (MH$^+$).

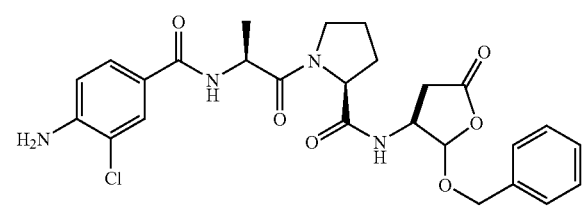

1-[2-(4-Amino-3-chloro-benzoylamino)-propionyl]-pyrrolidine-2-carboxylic acid (2-benzyloxy-5-oxo-tetrahydro-furan-3-yl)-amide (98b)

Was prepared from the syn diastereomer of (2-benzyloxy-5-oxo-tetrahydro-furan-3-yl)-carbamic acid allyl ester (40) and 97a following the method used for 98a. The title compound was isolated as a pale yellow solid (720 mg, 51% yield). $^1$H-NMR (500 MHz, CD$_3$OD) δ 1.16 (d, 0.5H), 1.40 (d, 2.5H), 1.64-2.25 (m, 4H), 2.61 (dd, 1H), 2.79 (dd, 1H), 3.37-3.59 (m, 1H), 3.59-3.74 (m, 1H), 3.77-3.92 (m, 1H), 4.29-4.47 (m, 1H), 4.47-5.02 (m, 4H), 5.48 (s, 0.5H), 5.66 (d, 1H), 5.68 (d, 0.5H), 6.79 (d, 1H), 7.17-7.52 (m, 5H), 7.48-7.62 (m, 1H), 7.68-7.83 (m, 1H). Analytical HPLC 15.98 min. LC-MS (ES$^+$) m/e=529.2 (MH$^+$).

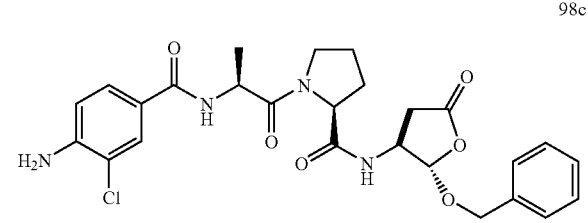

1-[2-(4-Amino-3-chloro-benzoylamino)-propionyl]-pyrrolidine-2-carboxylic acid (2-benzyloxy-5-oxo-tetrahydro-furan-3-yl)-amide (98c)

Prepared from the anti-(2-benzyloxy-5-oxo-tetrahydro-furan-3-yl)-carbamic acid allyl ester (40) and 97a following the method used for 98a. The title compound was isolated as a white solid (186.6 mg, 46% yield). $^1$H-NMR (500 MHz, CD$_3$OD) δ 1.30-1.52 (m, 3H), 1.76-2.33 (m, 4H), 2.41-2.59 (m, 1H), 2.90 (dd, 0.15H), 3.04 (dd, 0.85H), 3.44-3.75 (m, 1.5H), 3.82-3.95 (m, 1H), 4.27-4.42 (m, 2H), 4.42-4.56 (m, 0.5H), 4.56-4.86 (m, 4H), 5.42-5.55 (m, 1H), 6.79 (d, 1H), 7.21-7.42 (m, 4.6H), 7.54-7.63 (m, 1.4H), 7.76-7.83 (m, 0.65H), 8.60-8.68 (m, 0.35H). Analytical HPLC 15.19 min. LC-MS (ES$^+$) m/e=529.3 (MH$^+$).

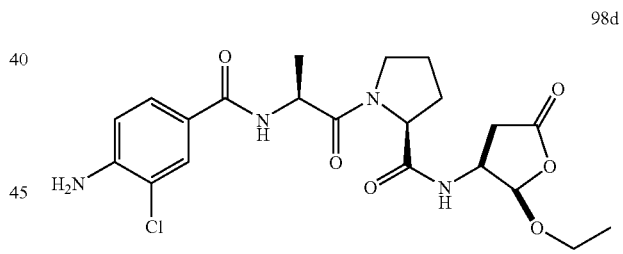

2-(Ethoxy-5-oxo-tetrahydro-furan-3-yl)-carbamic acid allyl ester

Prepared from 3-allyloxycarbonylamino-4-hydroxy-butyric acid tert-butyl ester as described for (40) using ethanol. Chromatography using hexane/ethyl acetate (95/5 to 80/20) gave 0.94 g of anti-2-(ethoxy-5-oxo-tetrahydro-furan-3-yl)-carbamic acid allyl ester (higher Rf), 1.96 g of syn diastereomer (lower Rf) and 8.08 g of the mixture of the diastereomers (total overall yield 60%). $^1$H-NMR (500 MHz, CDCl$_3$) for the anti diastereomer: δ 1.13-1.31 (m, 3H), 2.31-2.45 (m, 1H), 2.92-3.08 (m, 1H), 3.52-3.72 (m, 1H), 3.78-3.92 (m, 1H), 4.10-4.25 (m, 1H), 4.45-4.70 (m, 2H), 5.00 (bs, 1H), 5.12-5.45 (m, 3H), 5.80-5.95 (m, 1H); for syn diastereomer 1.13-1.35 (m, 3H), 2.38-2.50 (m, 1H), 2.75-2.92 (m, 1H), 3.60-3.73 (m, 1H), 3.82-3.95 (m, 1H), 4.40-4.70 (m, 3H), 5.10-5.52 (m, 4H), 5.80-5.94 (m, 1H); LC-MS: m/z=230 (M+H$^+$) for both diastereomers.

1-[2-(4-Amino-3-chloro-benzoylamino)-propionyl]-pyrrolidine-2-carboxylic acid (2-ethoxy-5-oxo-tetrahydro-furan-3-yl)-amide (98d)

Prepared from (2-ethoxy-5-oxo-tetrahydro-furan-3-yl)-carbamic acid allyl ester and 97a following the method used for 98a. The title compound was isolated as a white solid (175 mg, 77% yield). $^1$H-NMR (500 MHz, CD$_3$OD) δ 1.13 (t, 0.5H), 1.23 (t, 2.5H), 1.36 (d, 0.5H), 1.44 (d, 2.5H), 1.75-2.38 (m, 4H), 2.56 (dd, 1H), 2.76 (dd, 1H), 3.45-3.97 (m, 5H), 4.47 (dd, 1H), 4.59-4.67 (m, 1H), 4.74 (q, 1H), 5.55 (d, 0.2H), 5.56 (d, 0.8H), 6.75-6.82 (m, 1H), 7.56 (dd, 1H), 7.77 (d, 1H), 8.39 (d, 1H). Analytical HPLC 8.17 min. LC-MS (ES$^+$) m/e=467.4 (MH$^+$).

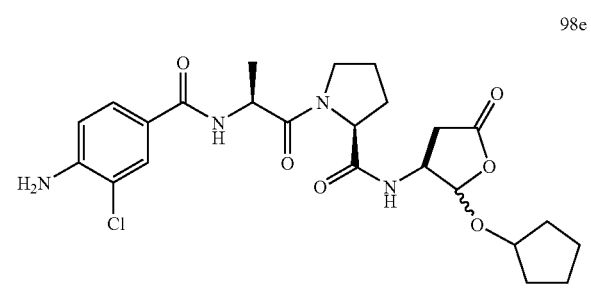

98e (2-Cyclopentyloxy-5-oxo-tetrahydro-furan-3-yl)-carbamic acid allyl ester

Prepared from 3-allyloxycarbonylamino-4-hydroxy-butyric acid tert-butyl ester as described for 40 using cyclopentanol to afford the title compound as a mixture of diastereomers. Flash column chromatography using hexanes/EtOAc (90/10 to 80/20) afforded the syn diastereomer of the title compound: syn diastereomer $^1$H NMR (500 MHz, CDCl$_3$) δ 1.5-2.0 (m, 8H), 2.45 (dd, 1H), 2.81 (dd, 0.9H), 3.0 (dd, 0.1H), 4.31 (m, 1H), 4.59 (m, 4H), 5.23 (m, 1H), 5.32 (m, 1H), 5.45 (s, 0.1H), 5.51 (s, 0.9H), 5.92 (m, 1H) ppm; anti diastereomer $^1$H-NMR (500 MHz, CDCl$_3$) δ 1.50 (m, 2H), 1.67 (m, 6H), 2.36 (d, 1H), 2.8 (dd, 0.08H), 2.96 (dd, 0.92H), 4.13 (m, 1H), 4.25 (m, 1H), 4.55 (br, 2H), 5.20 (d, 1H), 5.30 (m, 2H), 5.43 (s, 0.92H), 5.5 (d, 0.08H), 5.89 (s, 1H) ppm.

1-[2-(4-Amino-3-chloro-benzoylamino)-propionyl]-pyrrolidine-2-carboxylic acid (2-cyclopentyloxy-5-oxo-tetrahydro-furan-3-yl)-amide (98e)

Prepared from (2-cyclopentyloxy-5-oxo-tetrahydro-furan-3-yl)-carbamic acid allyl ester and 97a following the method used for 98a to give the title compound (280 mg, 51% yield). $^1$H-NMR (500 MHz, CD$_3$OD) δ 1.38 (d, 0.5H), 1.44 (d, 2.5H), 1.49-2.35 (m, 12H), 2.47 (dd, 0.7H), 2.56 (dd, 0.3H), 2.75 (dd, 0.3H), 2.81-2.88 (m, 0.1H), 2.97 (dd, 0.6H), 3.47-3.76 (m, 0.2H), 3.82-3.96 (m, 1H), 4.10-4.40 (m, 2H), 4.40-4.46 (m, 1H), 5.44 (d, 0.5H), 5.50 (d, 0.2H), 5.65 (d, 0.3H), 6.79 (d, 1H), 7.54-7.64 (m, 1H), 7.78 (d, 1H), 8.21-8.31 (m, 1H). Analytical HPLC 15.02, 15.34 min. LC-MS (ES$^+$) m/e=507.3 (MH$^+$)

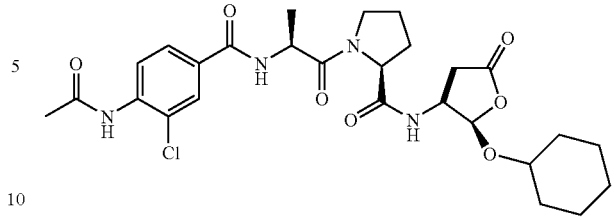

(2-Cyclohexyloxy-5-oxo-tetrahydro-furan-3-yl)-carbamic acid allyl ester

Prepared from 3-allyloxycarbonylamino-4-hydroxy-butyric acid tert-butyl ester as described for 40 using cyclohexanol to afford the title compound as a mixture of diastereomers (pale yellow oil) (4.62 g, 85% yield). Flash column chromatography using hexanes/EtOAc (90/10 to 80/20) gave 394 mg (7% yield) of the syn diastereomer of the title compound. $^1$H NMR (500 MHz, CDCl$_3$) δ 1.11-2.09 (m, 10H), 2.35-2.61 (dd, 1H), 2.72-2.98 (dd, 1H), 3.60-3.83 (m, 1H), 4.32-4.72 (m, 3H), 5.06-5.43 (m, 2H), 5.60 (d, 1H), 5.82-6.03 (m, 1H).

1-[2-(4-Acetylamino-3-chloro-benzoylamino)-propionyl]-pyrrolidine-2-carboxylic acid (2-cyclohexyloxy-5-oxo-tetrahydro-furan-3-yl)-amide (98f)

Prepared from syn-(2-cyclohexyloxy-5-oxo-tetrahydro-furan-3-yl)-carbamic acid allyl ester and 97b following the method used for 98a to give the title compound (121 mg, 33% yield). $^1$H-NMR (500 MHz, CD$_3$OD) δ 1.06-1.61 (m, 9H), 1.61-2.37 (m, 7H), 2.22 (s, 3H), 2.52-2.81 (m, 2H), 3.49-3.78 (m, 2H), 3.84-3.97 (m, 1H), 4.42-4.57 (m, 1H), 4.57-4.69 (m, 1H), 5.67-5.81 (m, 1H), 7.72-7.89 (m, 1H), 7.89-8.12 (m, 2H). Analytical HPLC 9.84 min. LC-MS (ES$^+$) m/e=563.3 (MH$^+$).

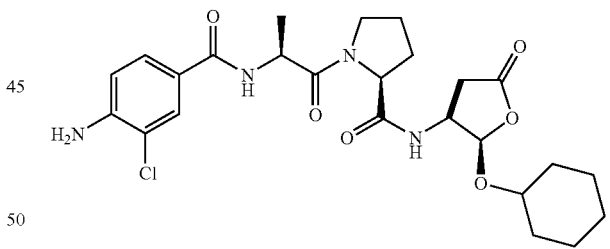

1-[2-(4-Amino-3-chloro-benzoylamino)-propionyl]-pyrrolidine-2-carboxylic acid (2-cyclohexyloxy-5-oxo-tetrahydro-furan-3-yl)-amide (98g)

Prepared from syn-(2-cyclohexyloxy-5-oxo-tetrahydro-furan-3-yl)-carbamic acid allyl ester and 97a following the method used for 98a to give the title compound (153 mg, 47% yield). $^1$H-NMR (500 MHz, CD$_3$OD) δ 1.06-2.38 (m, 14H), 1.42 (d, 3H), 2.50-2.66 (m, 1H), 2.69-2.82 (dd, 1H), 3.06-3.75 (m, 2H), 3.80-3.94 (m, 1H), 4.40-4.52 (m, 1H), 4.57-4.65 (m, 1H), 4.70-4.80 (m, 1H), 5.72 (d, 1H), 6.71 (m, 1H), 7.50-7.63 (m, 1H), 7.78 (d, 0.6H), 8.42 (d, 0.4H). Analytical HPLC 10.30 min. LC-MS (ES$^+$) m/e=521.2 (MH$^+$).

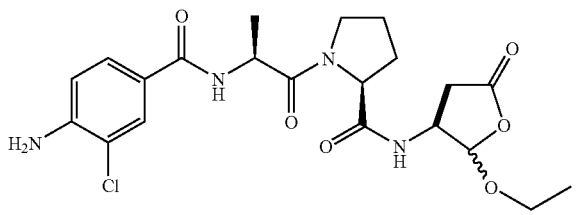

98h

1-[2-(4-Amino-3-chloro-benzoylamino)-propionyl]-pyrrolidine-2-carboxylic acid (2-ethoxy-5-oxo-tetrahydro-furan-3-yl)-amide (98h)

Prepared from (2-ethoxy-5-oxo-tetrahydro-furan-3-yl)-carbamic acid allyl ester and 97a following the method used for 98a. The title compound was isolated as a white solid (195 mg, 82% yield). $^1$H-NMR (500 MHz, CD$_3$OD) δ 1.32-1.55 (m, 3H), 1.58-1.77 (m, 3H), 1.98-2.54 (m, 4H), 2.68-2.76 (d, 0.3H), 2.79-2.89 (m, 0.7H), 2.96-3.10 (m, 0.7H), 3.18-3.27 (dd, 0.3H), 3.72-4.18 (m, 4H), 4.46-5.12 (m, 3H), 5.60 (s, 0.4H), 5.74-5.84 (m, 0.6H), 7.03 (d, 0.8H), 7.75-7.86 (m, 1H), 8.01 (d, 0.7H), 8.35 (d, 0.3H), 8.74 (d, 0.2H). Analytical HPLC 8.31 min. LC-MS (ES$^+$) m/e=467.3 (MH$^+$).

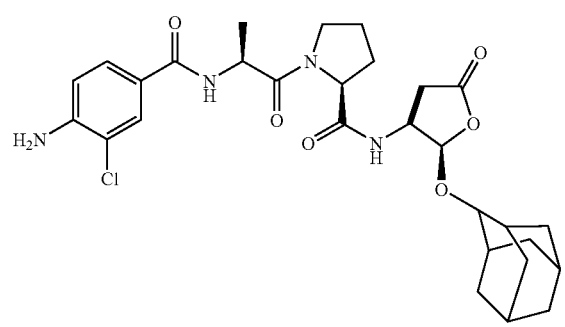

98i

[5-Oxo-2-(tricyclo[3.3.1.1$^{o,o}$]dec-2-yloxy)-tetrahydro-furan-3-yl]-carbamic acid allyl ester Prepared from 3-allyloxycarbonylamino-4-hydroxy-butyric acid tert-butyl ester as described for 40 using 2-adamantanol (6.21 g, 5 equivalents) to afford the title compound as a pale yellow oil (1.52 g, 61% yield). $^1$H NMR (500 MHz, CDCl$_3$). δ 1.38-2.22 (m, 14H), 2.40 (d, 0.2H), 2.53 (dd, 0.7H), 2.87 (dd, 0.7H), 2.87 (dd, 0.8H), 3.00-3.12 (m, 0.3H), 3.84-3.97 (m, 1H), 4.40-4.71 (m, 3H), 5.18-5.44 (m, 2H), 5.53-5.69 (m, 1H), 5.82-6.02 (m, 1H).

1-[2-(4-Amino-3-chloro-benzoylamino)-propionyl]-pyrrolidine-2-carboxylic acid [5-oxo-2-(tricyclo[3.3.1.1$^{o,o}$]dec-2-yloxy)-tetrahydro-furan-3-yl]amide (98i)

Prepared from [5-oxo-2-(tricyclo[3.3.1.1$^{o,o}$]dec-2-yloxy)-tetrahydro-furan-3-yl]-carbamic acid allyl ester and 97a following the method used for 98a. The title compound was isolated as a white solid (76 mg, 13% yield). $^1$H-NMR (500 MHz, CD$_3$OD) δ 1.38-2.22 (m, 14H), 2.40 (d, 0.2H), 2.53 (dd, 0.7H), 2.87 (dd, 0.8H), 3.00-3.12 (m, 0.3H), 3.84-3.97 (m, 1H), 4.40-4.71 (m, 3H), 5.18-5.44 (m, 2H), 5.53-5.69 (m, 1H), 5.82-6.02 (m, 1H). Analytical HPLC. 11.89 min. LC-MS (ES$^+$) m/e=573.2 (MH$^+$).

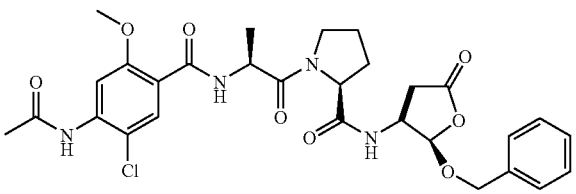

98j

1-[2-(4-Acetylamino-5-chloro-2-methoxy-benzoylamino)-propionyl]-pyrrolidine-2-carboxylic acid (2-benzyloxy-5-oxo-tetrahydro-furan-3-yl)-amide (98j)

Prepared from syn-{2-[2-(2-benzyloxy-5-oxo-tetrahydro-furan-3-ylcarbamoyl)-pyrrolidin-1-yl]-1-methyl-2-oxo-ethyl}-carbamic acid tert-butyl ester and 97c following the procedure used for 98a to afford the title compound (222 mg, 82% yield). $^1$H-NMR (500 MHz, CD$_3$OD) δ 1.23 (d, 0.6H), 1.42 (d, 2.4H), 1.72-2.27 (m, 4H), 2.23 (s, 3H), 2.63 (dd, 1H), 2.77-2.88 (m, 1H), 3.43-3.52 (m, 0.5H), 3.56-3.71 (m, 1.5H), 3.74-3.85 (m, 1H), 3.98 (s, 3H), 4.38-4.50 (m, 1.5H), 4.51-4.92 (m, 4.5H), 5.63-5.76 (m, 1H), 7.23-7.40 (m, 5H), 7.97 (s, 1H), 8.45 (d, 1H), 8.69-8.80 (m, 1H) Analytical HPLC 11.63 min LC-MS (ES$^+$) m/e=601.2 (MH$^+$).

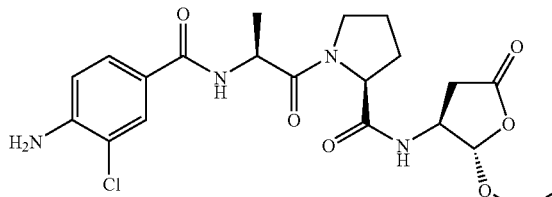

98k

Synthesis of 1-[2-(4-amino-3-chloro-benzoylamino)-propionyl]-pyrrolidine-2-carboxylic acid (2-ethoxy-5-oxo-tetrahydro-furan-3-yl)-amide (98k)

Prepared from anti-(2-ethoxy-5-oxo-tetrahydro-furan-3-yl)-carbamic acid allyl ester and 97a following the method used for 98a to afford 175 mg of title compound (59%). $^1$H-NMR (500 MHz, 1:1 CDCl$_3$:CD$_3$OD) δ 1.10-1.28 (m, 3H), 1.42 (d, 0.6H), 1.46 (d, 2.4H), 1.75-2.45 (m, 4H), 2.45-2.70 (m, 1H), 2.80-3.05 (m, 1H), 3.50-3.95 (m, 4H), 4.20-4.75 (m, 3H), 4.75-4.90 (m, 1H), 5.32 (s, 0.8H), 5.38

(s, 0.2H), 6.80 (d, 1H), 7.55-7.84 (m, 2H). Analytical HPLC: 10.47 min. LC-MS (ES+): m/e=467.3 (M+H+).

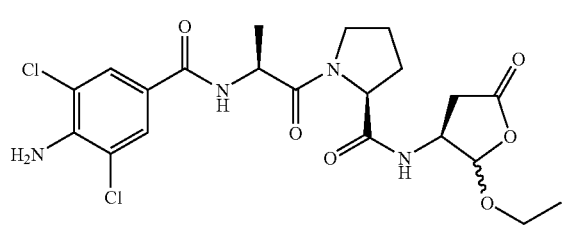

Synthesis of 1-[2-(4-amino-3,5-dichloro-benzoylamino)-propionyl]-pyrrolidine-2-carboxylic acid (2-ethoxy-5-oxo-tetrahydro-furan-3-yl)-amide (98l)

Prepared from (2-ethoxy-5-oxo-tetrahydro-furan-3-yl)-carbamic acid allyl ester and 1-[2-(4-amino-3,5-dichloro-benzoylamino)-propionyl]-pyrrolidine-2-carboxylic acid tert-butyl ester according to the method used for 98a to afford 158 mg of title compound (54% yield). $^1$H-NMR (500 MHz, 1:1 CDCl$_3$:CD$_3$OD) δ 1.08-1.30 (m, 3H), 1.32-1.52 (m, 3H), 1.72-2.44 (m, 4H), 2.40-3.05 (m, 2H), 3.50-3.97 (m, 4H), 4.25-4.70 (m, 3H), 4.70-4.86 (m, 1H), 5.33 (s, 0.4H), 5.47 (s, 0.1H), 5.56 (d, 0.4H), 5.62 (d, 0.1H), 7.50 (s, 1H), 7.80 (s, 1H). Analytical HPLC: 10.84 min. LC-MS (ES+): m/e=501.2 (M+H+).

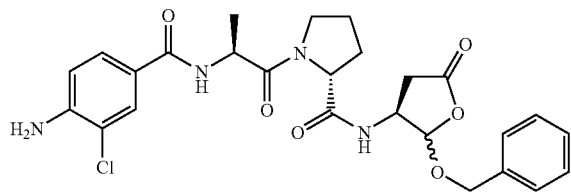

1-[2-(4-amino-3-chloro-benzoylamino)-propionyl]-pyrrolidine-2-carboxylic acid (2-benzyloxy-5-oxo-tetrahydro-furan-3-yl)-amide (98m)

Prepared according to the procedure used to prepare 98a using Cbz-Ala-D-pro-OH to afford 230 mg of title compound (69% yield). $^1$H-NMR (500 MHz, 1:1 CDCl$_3$:CD$_3$OD) δ 1.30 (d, 1.2H), 1.45 (d, 1.8H), 1.62-2.40 (m, 4H), 2.40-3.10 (m, 2H), 3.30-3.97 (m, 2H), 4.33-4.95 (m, 5H), 5.30 (s, 0.5H), 5.68 (d, 0.5H), 6.80 (d, 1H), 7.25-7.95 (m, 7H). Analytical HPLC: 11.56, 11.91 min. LC-MS (ES+): m/e=529.2 (M+H+).

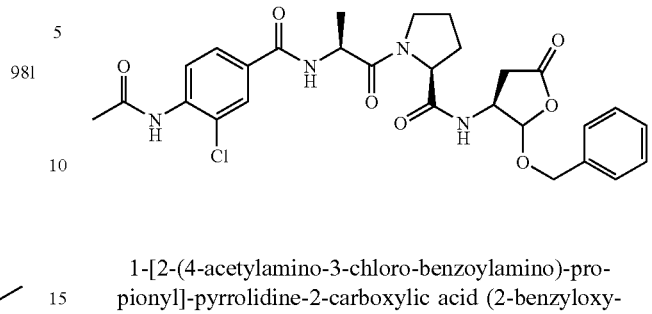

1-[2-(4-acetylamino-3-chloro-benzoylamino)-propionyl]-pyrrolidine-2-carboxylic acid (2-benzyloxy-5-oxo-tetrahydro-furan-3-yl)-amide (98n)

Prepared from 97b and syn-(2-benzyloxy-5-oxo-tetrahydro-furan-3-yl)-carbamic acid allyl according to the procedure used to prepare 98a to afford 210 mg of title compound (64% yield). $^1$H-NMR (500 MHz, 1:1 CDCl$_3$:CD$_3$OD) δ 1.33 (d, 0.6H), 1.44 (d, 2.4H), 1.68-2.40 (m, 4H), 2.26 (s, 3H), 2.55-3.05 (m, 2H), 3.40-3.90 (m, 2H), 4.20-4.95 (m, 5H), 5.68 (d, 0.8H), 5.84 (d, 0.2H), 7.15-8.30 (m, 8H). Analytical HPLC: 15.67 min. LC-MS (ES+): m/e=571.1 (M+H+).

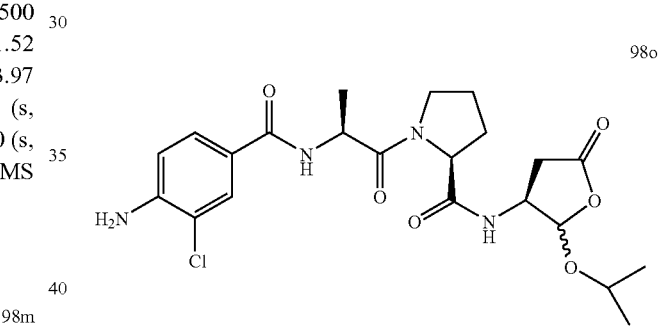

(2-Isopropoxy-5-oxo-tetrahydro-furan-3-yl)-carbamic acid allyl ester

Prepared as described for compound 40 using isopropanol to afford 3.80 grams (81% yield) of the title compound as a colorless oil. $^1$H-NMR (500 MHz, CDCl$_3$) δ 1.10-1.35 (m, 6H), 2.32-2.60 (m, 1H), 2.82 (dd, 0.5H), 3.02 (dd, 0.5H), 3.82-4.11 (m, 1H), 4.48-4.66 (m, 3H), 5.20-5.36 (m, 2H), 5.54 (dd, 1H), 5.82-6.05 (m, 1H). LC-MS (ES+): m/e=244.2 (M+H+).

1-[2-(4-amino-3-chloro-benzoylamino)-propionyl]-pyrrolidine-2-carboxylic acid (2-isopropoxy-5-oxo-tetrahydro-furan-3-yl)-amide (98o)

Prepared from 97a and (2-isopropoxy-5-oxo-tetrahydro-furan-3-yl)-carbamic acid allyl ester according to the procedure used to prepare 98a to afford 200 mg of title compound (66% yield). $^1$H-NMR (500 MHz, 1:1 CDCl$_3$:CD$_3$OD) δ 1.05-1.35 (m, 6H), 1.35-1.50 (m, 3H), 1.70-2.45

(m, 4H), 2.45-3.05 (m, 2H), 3.55-4.10 (m, 3H), 4.15-4.88 (m, 4H), 5.48 (s, 0.4H), 5.58 (s, 0.1H), 5.64 (d, 0.4H), 5.70 (d, 0.1H), 6.78 (d, 1H), 7.58 (d, 1H), 7.80 (s, 1H). Analytical HPLC: 12.19, 12.40 min. LC-MS (ES⁺): m/e=581.2 (M+H⁺).

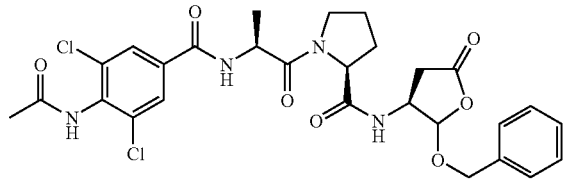

98p

1-[2-(4-acetylamino-3,5-dichloro-benzoylamino)-propionyl]-pyrrolidine-2-carboxylic acid (2-benzyloxy-5-oxo-tetrahydro-furan-3-yl)-amide (98p)

Prepared from 1-[2-(4-acetylamino-3,5-dichloro-benzoylamino)-propionyl]-pyrrolidine-2-carboxylic acid tert-butyl ester and syn-(2-benzyloxy-5-oxo-tetrahydro-furan-3-yl)-carbamic acid allyl ester according to the procedure used to prepare 98a to afford 230 mg of title compound (72% yield). ¹H-NMR (500 MHz, 1:1 CDCl₃:CD₃OD) δ 1.36 (d, 0.6H), 1.47 (d, 2.4H), 1.68-2.47 (m, 4H), 2.23 (s, 3H), 2.60-3.15 (m, 2H), 3.40-3.90 (m, 2H), 4.15-4.95 (m, 5H), 5.68 (d, 0.8H), 5.84 (d, 0.2H), 7.20-7.98 (m, 7H). Analytical HPLC: 13.07 min. LC-MS (ES⁺): m/e=605.1 (M+H⁺).

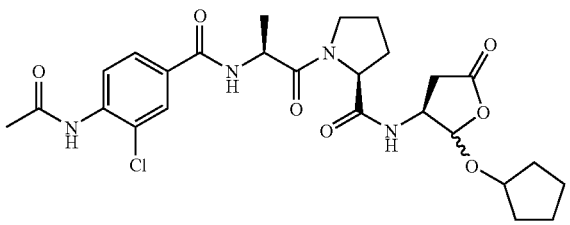

98q

1-[2-(4-acetylamino-3-chloro-benzoylamino)-propionyl]-pyrrolidine-2-carboxylic acid (2-cyclopentyloxy-5-oxo-tetrahydro-furan-3-yl)-amide (98q)

Prepared from 97b and (2-cyclopentyloxy-5-oxo-tetrahydro-furan-3-yl)-carbamic acid allyl ester according to the procedure used to prepare 98a to afford 215 mg of title compound (69% yield). ¹H-NMR (500 MHz, 1:1 CDCl₃:CD₃OD) δ 1.35-1.90 (m, 11H), 1.90-2.35 (m, 4H), 2.24 (s, 3H), 2.40-3.10 (m, 2H), 3.50-3.95 (m, 3H), 4.15-4.90 (m, 3H), 5.44 (s, 0.55H), 5.56 (s, 0.15H), 5.64 (d, 0.22H), 5.71 (d, 0.08H), 7.70-8.25 (m, 3H). Analytical HPLC: 12.13 min. LC-MS (ES⁺): m/e=549.2 (M+H⁺).

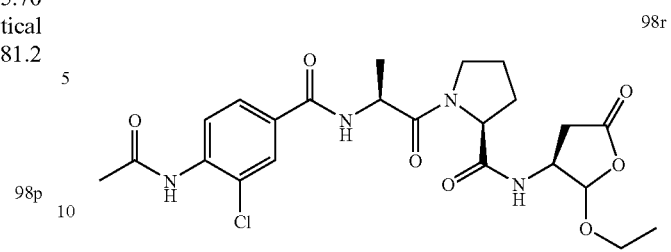

98r

Synthesis of 1-[2-(4-acetylamino-3-chloro-benzoylamino)-propionyl]-pyrrolidine-2-carboxylic acid (2-ethoxy-5-oxo-tetrahydro-furan-3-yl)-amide (98r)

Prepared from 97b and syn-(2-ethoxy-5-oxo-tetrahydro-furan-3-yl)-carbamic acid allyl ester according to the procedure used to prepare 98a to afford 68 mg of title compound (24%). ¹H-NMR (500 MHz, 1:1 CDCl₃:CD3OD) δ 1.13 (t, 0.6H), 1.28 (t, 2.4H), 1.38 (d, 0.6H), 1.48 (d, 2.4H), 1.75-2.40 (m, 4H), 2.22 (s, 3H), 2.55-2.88 (m, 2H), 3.50-3.92 (m, 4H), 4.40-4.90 (m, 3H), 5.57 (d, 0.8H), 5.61 (d, 0.2H), 7.60-8.20 (m, 3H). Analytical HPLC: 8.64 min. LC-MS (ES⁺): m/e=509.2 (M+H⁺).

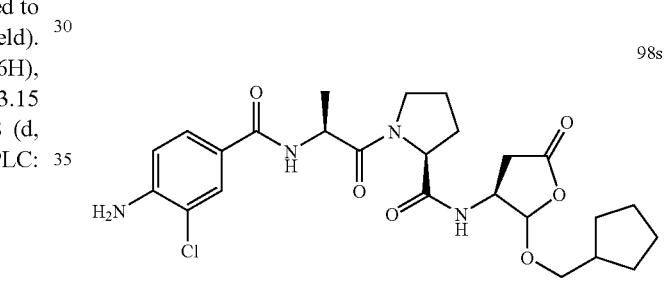

98s

Preparation of of (2-cyclopentylmethoxy-5-oxo-tetrahydro-furan-3-yl)-carbamic acid allyl ester Prepared from 3-allyloxycarbonylamino-4-hydroxy-butyric acid tert-butyl ester as described for compound 40 using cyclopentylmethanol (6.5 mL, 60 mmol) to afford 2.98 grams (52% total yield) of the title compound as a mixture of epimers. Purification provided 0.97 grams (17% yield) of the 4(S), 5(R) as a colorless oil. ¹H NMR (500 MHz, CDCl₃) δ 1.19 (m, 2H), 1.54 (m, 4H), 1.71 (m, 2H), 2.16 (m, 1H), 2.44 (dd, J=17.2, 10.4 Hz, 1H), 2.82 (dd, J=17.2, 8.4 Hz, 1H), 3.44 (dd, J=9.3, 7.2 Hz, 1H), 3.71 (dd, J=9.3, 7.2 Hz, 1H), 4.57 (m, 3H), 5.32 (m, 3H), 5.41 (d, J=5.2 Hz, 1H), 5.91 (ddt, J=17.1, 10.4, 5 Hz, 1H) ppm. LC-MS. (ES+): m/e=284.

Also isolated was epimer mixture (0.66 gram, 11% yield) and the 4(S), 5(S) epimer (1.35 gram, 24% yield) as a waxy solid. ¹H-NMR (500 MHz, CDCl₃) δ 1.20 (m, 2H), 1.54 (m, 4H), 1.69 (m, 2H), 2.10 (m, 1H), 2.37 (d, J=8.1 Hz, 1H), 2.97 (dd, J=18.0, 7.6 Hz, 1H), 3.42 (dd, J=7.3, 1.7 Hz, 1H), 3.49 (m, 2H), 3.64 (dd, J=9.0, 7.3 Hz, 1H), 4.19 (br, 1H), 4.55 (m, 2H), 5.25 (m, 2H), 5.36 (s, 1H), 5.87 (m, 1H) ppm. LC-MS (ES+): m/e=284 (M+H).

1-[2-(4-amino-3-chloro-benzoylamino)-propionyl]-pyrrolidine-2-carboxylic acid (2-cyclopentyl-methoxy-5-oxo-tetrahydro-furan-3-yl)-amide (98s)

Prepared from 97a and syn-(2-cyclopentyl methoxy-5-oxo-tetrahydro-furan-3-yl)-carbamic acid allyl ester according to the procedure used to prepare 98a to afford 195 mg of title compound (51% yield). $^1$H-NMR (500 MHz, 1:1 CDCl$_3$:CD$_3$OD) δ 1.15-1.90 (m, 11H), 1.90-2.40 (m, 5H), 2.55-2.78 (m, 2H), 3.50-3.90 (m, 4H), 4.38-4.92 (m, 3H), 5.53 (d, 0.8H), 5.57 (d, 0.2H), 6.78 (d, 1H), 7.50-8.15 (m, 2H). Analytical HPLC: 10.48 min. LC-MS (ES$^+$): m/e=521.2 (M+H$^+$).

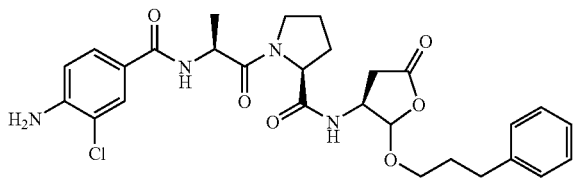

98t (5-oxo-2-(3-phenyl-propoxy)-tetrahydro-furan-3-yl)-carbamic acid allyl ester Prepared from 3-allyloxycarbonylamino-4-hydroxy-butyric acid tert-butyl ester as described for compound 40 using 3-phenylpropanol to afford 1.15 grams (32% yield) of the title compound as a colorless oil. $^1$H-NMR (500 MHz, CDCl$_3$) δ 1.82-2.05 (m, 2H), 2.38 (dd, 1H), 2.68 (m, 2H), 2.82 (dd, 1H), 3.55-3.65 (m, 1H), 3.82-3.92 (m, 1H), 4.48-4.72 (m, 3H), 5.12-5.59 (m, 3H), 5.82-6.03 (m, 1H), 7.11-7.45 (m, 5H). Analytical HPLC: 9.08 min. LC-MS (ES$^+$): m/e=320.2 (M+H$^+$).

1-[2-(4-amino-3-chloro-benzoylamino)-propionyl]-pyrrolidine-2-carboxylic acid (5-oxo-2-(3-phenyl-propoxyl)-tetrahydro-furan-3-yl)-amide (98t)

Prepared from 97b and syn-(5-oxo-2-(3-phenyl-propoxyl)-tetrahydro-furan-3-yl)-carbamic acid allyl ester according to the procedure used to prepare 98a to afford 200 mg of title compound (57% yield). $^1$H-NMR (500 MHz, 1:1 CDCl$_3$:CD$_3$OD) δ 1.34 (d, 0.6H), 1.44 (d, 2.4H), 1.75-2.40 (m, 6H), 2.50-2.95 (m, 4H), 3.47-3.95 (m, 4H), 4.38-4.82 (m, 3H), 5.52 (d, 0.8H), 5.56 (d, 0.2H), 6.75-8.25 (m, 8H). Analytical HPLC: 10.79 min. LC-MS (ES$^+$): m/e=557.2 (M+H$^+$).

98u

Synthesis of 1-[2-(4-acetylamino-3-chloro-benzoylamino)-propionyl]-pyrrolidine-2-carboxylic acid (2-cyclopentylmethoxy-5-oxo-tetrahydro-furan-3-yl)-amide (98u)

Prepared from 97b and syn-(2-cyclopentylmethoxy-5-oxo-tetrahydro-furan-3-yl)-carbamic acid allyl ester according to the procedure used to prepare 98a to afford 215 mg of title compound (67% yield). $^1$H-NMR (500 MHz, 1:1 CDCl$_3$:CD3OD) δ 1.38 (d, 0.6H), 1.47 (d, 2.4H), 1.11-1.88 (m, 8H), 1.92-2.40 (m, 5H), 2.24 (s, 3H), 2.53-2.86 (m, 2H), 3.30-3.90 (m, 4H), 4.38-4.89 (m, 3H), 5.53 (d, 0.8H), 5.60 (d, 0.2H), 7.68-8.22 (m, 3H). Analytical HPLC: 9.90 min. LC-MS (ES$^+$): m/e=563.3 (M+H$^+$).

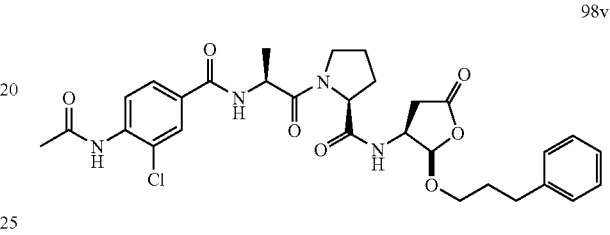

98v

1-[2-(4-acetylamino-3-chloro-benzoylamino)-propionyl]-pyrrolidine-2-carboxylic acid (5-oxo-2-(3-phenyl-propoxyl)-tetrahydro-furan-3-yl)-amide (98v)

Prepared from 1-[2-(4-acetylamino-3-chloro-benzoylamino)-propionyl]-pyrrolidine-2-carboxylic acid tert-butyl ester and syn-(5-oxo-2-(3-phenyl-propoxyl)-furan-3-yl)-carbamic acid allyl ester according to the procedure used to prepare 98a to afford 238 mg of title compound (75% yield). $^1$H-NMR (500 MHz, 1:1 CDCl$_3$:CD$_3$OD) δ 1.33 (d, 0.6H), 1.56 (d, 2.4H), 1.78-2.45 (m, 6H), 2.27 (s, 3H), 2.53-2.97 (m, 4H), 3.53-3.94 (m, 4H), 4.47-4.86 (m, 3H), 5.53 (d, 0.8H), 5.62 (d, 0.2H), 7.11-8.26 (m, 8H). Analytical HPLC: 10.27 min. LC-MS (ES$^+$): m/e=599.2 (M+H$^+$).

98w

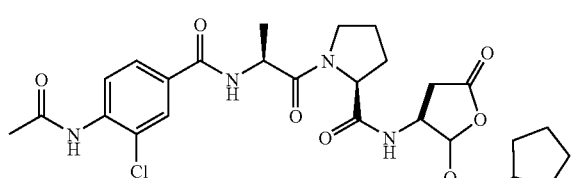

1-[2-(4-amino-3-trifluoromethyl-benzoylamino)-propionyl]-pyrrolidine-2-carboxylic acid (2-benzyloxy-5-oxo-tetrahydro-furan-3-yl)-amide (98w)

Prepared from {2-[2-(2-benzyloxy-5-oxo-tetrahydro-furan-3-ylcarbamoyl)-pyrrolidin-1-yl]-1-methyl-2-oxo-ethyl}-carbamic acid tert-butyl ester and 4-amino-3-trifluoromethyl-benzoic acid according to the procedure used to prepare 98a to afford 56 mg of title compound (48% yield). $^1$H-NMR (500 MHz, 1:1 CDCl$_3$:CD$_3$OD) δ 1.20-1.55 (m, 3H), 1.75-2.50 (m, 4H), 2.50-3.10 (m, 2H), 3.50-4.00 (m, 2H), 4.30-5.00 (m, 5H), 5.42 (s, 0.4H), 5.51 (s, 0.2H), 5.62 (d, 0.3H), 5.78 (d, 0.1H), 6.84 (d, 1H), 7.20-8.15 (m, 7H). Analytical HPLC: 14.90, 15.20 min. LC-MS (ES+): m/e=563.2 (M+H+).

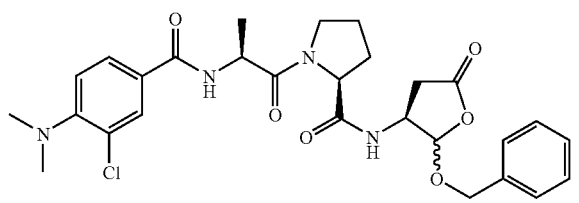

1-[2-(3-chloro-4-dimethylamino-benzoylamino)-propionyl]-pyrrolidine-2-carboxylic acid (2-benzyloxy-5-oxo-tetrahydro-furan-3-yl)-amide (98x)

Prepared from {2-[2-(2-benzyloxy-5-oxo-tetrahydro-furan-3-ylcarbamoyl)-pyrrolidin-1-yl]-1-methyl-2-oxo-ethyl}-carbamic acid tert-butyl ester and 3-chloro-4-dimethylamino-benzoic acid according to the procedure used to prepare 98a to afford 82 mg of title compound (44% yield). 1H-NMR (500 MHz, 1:1 CDCl3:CD3OD) δ 1.18-1.53 (m, 3H), 1.70-2.40 (m, 4H), 2.55-3.10 (m, 2H), 2.84 (s, 6H), 3.45-3.94 (m, 2H), 4.25-4.95 (m, 5H), 5.46 (s, 0.3H), 5.51 (s, 0.2H), 5.63 (d, 0.4H), 5.73 (d, 0.1H), 7.05 (d, 1H), 7.15-7.95 (m, 7H). Analytical HPLC: 11.85, 12.19 min. LC-MS (ES+): m/e=557.3 (M+H+).

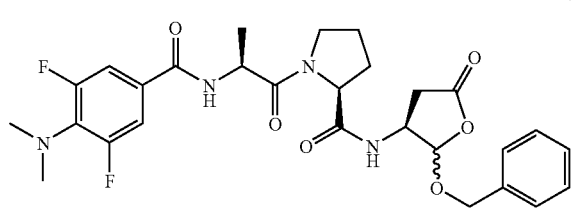

1-[2-(4-dimethylamino-3,5-difluoro-benzoylamino)-propionyl]-pyrrolidine-2-carboxylic acid (2-benzyloxy-5-oxo-tetrahydro-furan-3-yl)-amide (98y)

Prepared from {2-[2-(2-benzyloxy-5-oxo-tetrahydro-furan-3-ylcarbamoyl)-pyrrolidin-1-yl]-1-methyl-2-oxo-ethyl}-carbamic acid tert-butyl ester and 4-dimethylamino-3,5-dichloro-benzoic acid according to the procedure used to prepare 98a to afford 106 mg of title compound (65% yield). 1H-NMR (500 MHz, 1:1 CDCl3:CD3OD) δ 1.10-1.55 (m, 3H), 1.75-2.30 (m, 4H), 2.45-3.15 (m, 2H), 2.84 (s, 6H), 3.40-3.95 (m, 2H), 4.15-4.95 (m, 5H), 5.47 (s, 0.35H), 5.54 (s, 0.15H), 5.67 (d, 0.4H), 5.77 (d, 0.1H), 7.20-7.70 (m, 7H). Analytical HPLC: 12.21, 12.51 min. LC-MS (ES+): m/e=559.2 (M+H+).

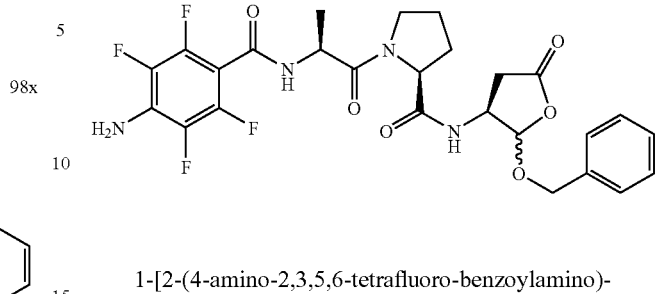

1-[2-(4-amino-2,3,5,6-tetrafluoro-benzoylamino)-propionyl]-pyrrolidine-2-carboxylic acid (2-benzyloxy-5-oxo-tetrahydro-furan-3-yl)-amide (98z)

Prepared from {2-[2-(2-benzyloxy-5-oxo-tetrahydro-furan-3-ylcarbamoyl)-pyrrolidin-1-yl]-1-methyl-2-oxo-ethyl}-carbamic acid tert-butyl ester and 4-amino-2,3,5,6-tetrafluoro-benzoic acid according to the procedure used to prepare 98a to afford 58 mg of title compound (73% yield). 1H-NMR (500 MHz, 1:1 CDCl3:CD3OD) δ 1.30-1.50 (m, 3H), 1.62-2.35 (m, 4H), 2.45-3.12 (m, 2H), 3.50-3.90 (m, 2H), 4.20-4.95 (m, 5H), 5.42 (s, 0.4H), 5.52 (s, 0.1H), 5.64 (d, 0.4H), 5.82 (d, 0.1H), 7.25-7.65 (m, 5H). Analytical HPLC: 16.56, 16.90 min. LC-MS (ES+): m/e=567.2 (M+H+).

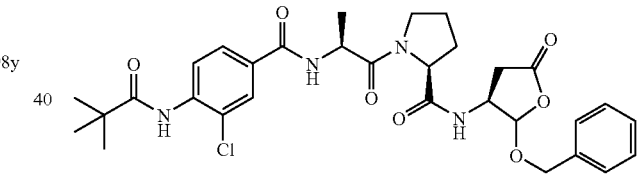

1-{2-[3-chloro-4-(2,2-dimethylpropionylamino)-benzoylamino]-propionyl}-pyrrolidine-2-carboxylic acid (2-benzyloxy-5-oxo-tetrahydro-furan-3-yl)-amide (98aa)

To a suspension of 98b (100 mg, 0.19 mmol) and poly (4-vinylpyridine) (200 mg) was added pivaloyl chloride (70 μL, 0.57 mmol). The resulting suspension was stirred overnight at room temperature the filtered and diluted with EtOAc (25 mL). The organic layer was washed with 10% NaHCO3 (2×25 mL), saturated NaCl (1×25 mL), dried (MgSO4), and evaporated to dryness to afford 98 mg of title compound (85% yield) after chromatography. 1H-NMR (500 MHz, 1:1 CDCl3:CD3OD) δ 1.10-1.55 (m, 3H), 1.38 (s, 9H), 1.65-2.40 (m, 4H), 2.60-3.10 (m, 2H), 3.46-3.88 (m, 2H), 4.20-4.95 (m, 5H), 5.62 (d, 0.8H), 5.78 (d, 0.2H), 7.15-8.30 (m, 8H). Analytical HPLC: 11.82 min. LC-MS (ES+): m/e=613.2 (M+H+).

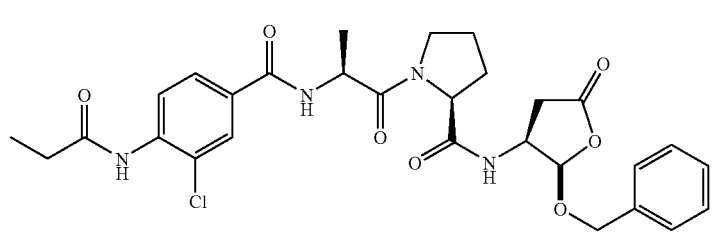

98ab

1-[2-(3-chloro-4-propionylamino)-benzoylamino)-propionyl]-pyrrolidine-2-carboxylic acid (2-benzyloxy-5-oxo-tetrahydro-furan-3-yl)-amide (98ab)

Prepared from 98b and propionyl chloride according to the procedure used to prepare 98aa to afford 104 mg of title compound (95% yield). $^1$H-NMR (500 MHz, 1:1 CDCl$_3$: CD$_3$OD) δ 1.16 (t, 0.6H), 1.18 (d, 0.6H), 1.27 (t, 2.4H), 1.38 (d, 2.4H), 1.72-2.35 (m, 4H), 2.45-2.58 (m, 2H), 2.58-3.05 (m, 2H), 3.45-3.85 (m, 2H), 4.20-4.88 (m, 5H), 5.64 (d, 0.8H), 5.76 (d, 0.2H), 7.20-8.35 (m, 8H). Analytical HPLC: 9.89 min. LC-MS (ES$^+$): m/e=585.2 (M+H$^+$).

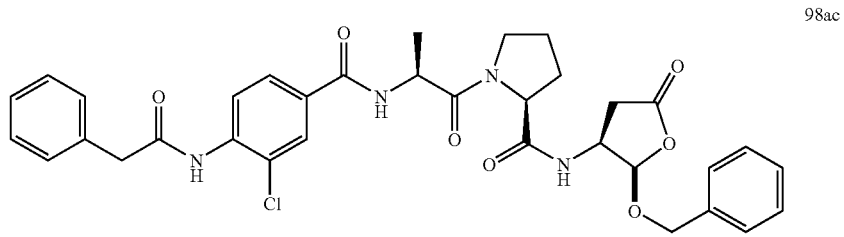

98ac

1-[2-(3-chloro-4-phenylacetylamino)-benzoylamino)-propionyl]-pyrrolidine-2-carboxylic acid (2-benzyloxy-5-oxo-tetrahydro-furan-3-yl)-amide (98ac)

Prepared from 98b and phenylacetyl chloride according to the procedure used to prepare 98aa to afford 85 mg of title compound (77% yield). $^1$H-NMR (500 MHz, 1:1 CDCl$_3$: CD$_3$OD) δ 1.18 (d, 0.6H), 1.40 (d, 2.4H), 1.72-2.38 (m, 4H), 2.58-3.05 (m, 2H), 3.46-3.78 (m, 2H), 3.85 (s, 2H), 4.18-4.92 (m, 5H), 5.63 (d, 0.8H), 5.75 (d, 0.2H), 7.15-8.34 (m, 13H). Analytical HPLC: 11.63 min. LC-MS (ES$^+$): m/e=647.2 (M+H$^+$).

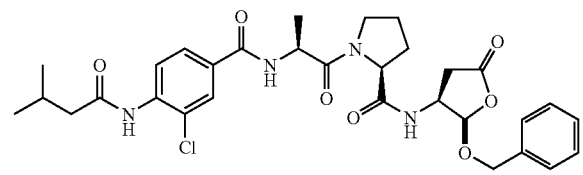

98ad

1-[2-(3-chloro-4-methyl-butyrylamino)-benzoylamino)-propionyl]-pyrrolidine-2-carboxylic acid (2-benzyloxy-5-oxo-tetrahydro-furan-3-yl)-amide (98ad)

Prepared from 98b and isovaleryl chloride according to the procedure used to prepare 98aa to afford 60 mg of title compound (58% yield). $^1$H-NMR (500 MHz, 1:1 CDCl$_3$: CD$_3$OD) δ 1.07 (d, 5H), 1.15 (d, 0.8H), 1.27 (d, 1H), 1.45 (d, 2.2H), 1.67-2.30 (m, 5H), 2.34 (d, 2H), 2.58-3.05 (m, 2H), 3.48-3.88 (m, 2H), 4.10-4.98 (m, 5H), 5.68 (d, 0.7H), 5.78 (m, 0.3H), 7.18-8.33 (m, 8H). Analytical HPLC: 10.74 min. LC-MS (ES$^+$): m/e=613.2 (M+H$^+$).

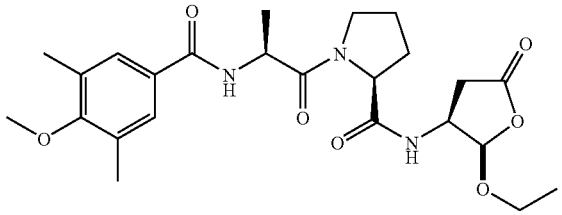

98ae

1-[2-(4-Methoxy-3,5-dimethyl-benzoylamino)-propionyl]-pyrrolidine-2-carboxylic acid (2-ethoxy-5-oxo-tetrahydro-furan-3-yl)-amide (98ae)

Prepared from 1-[2-(4-methoxy-3,5-dimethyl-benzoylamino)-propionyl]-pyrrolidine-2-carboxylic acid tert-butyl ester and syn-(2-ethoxy-5-oxo-tetrahydro-furan-3-yl)-carbamic acid allyl ester according to the procedure used to prepare 98a to afford 174 mg (81% yield) of the title compound. $^1$H-NMR (500 MHz, CDCl$_3$): δ 1.04 (t, 0.45H), 1.27 (t, 2.55H), 1.34-1.45 (m, 3H), 1.95-2.45 (m, 10H), 2.78-2.84 (m, H), 3.60-3.90 (m, 8H), 4.50-4.70 (m, 2H), 4.90-4.94 (m, H), 5.45 (d, 0.85H), 5.61 (d, 0.15H), 6.99 (d, H), 7.15 (d, H), 7.45 (s, 2H); retention time on analytical HPLC: 10.09 min; LC-MS: m/z=476 (M+H⁺).

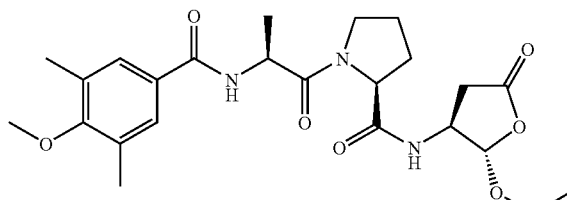

1-[2-(4-Methoxy-3,5-dimethyl-benzoylamino)-propionyl]-pyrrolidine-2-carboxylic acid (2-ethoxy-5-oxo-tetrahydro-furan-3-yl)-amide (98af)

Prepared from 1-[2-(4-methoxy-3,5-dimethyl-benzoylamino)-propionyl]-pyrrolidine-2-carboxylic acid tert-butyl ester and anti-(2-ethoxy-5-oxo-tetrahydro-furan-3-yl)-carbamic acid allyl ester according to the procedure used to prepare 98a to afford 168 mg (77% yield) of the title compound. ¹H-NMR (500 MHz, CDCl₃): δ 1.10-1.35 (m, 3H), 1.35-1.60 (m, 3H), 1.90-2.45 (m, 10H), 2.60-3.00 (m, H), 3.55-3.95 (m, 8H), 4.15-4.60 (m, 2H), 4.83-5.00 (m, H), 5.29 (s, H), 6.95-7.06 (m, H), 7.50 (s, 2H), 7.92 (d, H); retention time on analytical HPLC: 10.14 min; LC-MS: m/z=476 (M+H⁺).

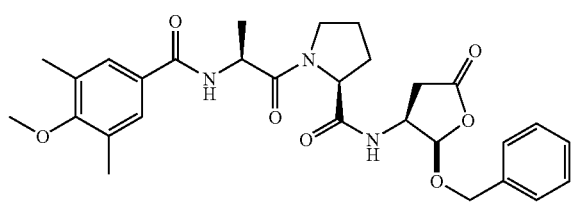

1-[2-(4-Methoxy-3,5-dimethyl-benzoylamino)-propionyl]-pyrrolidine-2-carboxylic acid (2-benzyloxy-5-oxo-tetrahydro-furan-3-yl)-amide (98ag)

Prepared from 1-[2-(4-methoxy-3,5-dimethyl-benzoylamino)-propionyl]-pyrrolidine-2-carboxylic acid tert-butyl ester and syn-(2-benzyloxy-5-oxo-tetrahydro-furan-3-yl)-carbamic acid allyl ester (40) according to the procedure used to prepare 98a to afford 406 mg (yield 71%) of the title compound. ¹H-NMR (500 MHz, CDCl₃): δ 1.09 (d, 0.6H), 1.35 (m, 2.4H), 1.90-2.20 (m, 3H), 2.22-2.50 (m, 10H), 2.84-2.90 (m, H), 3.52-3.62 (m, 1.6H), 3.65-3.80 (m, 3.4H), 4.10-4.40 (m, H), 4.50-4.75 (m, 3H), 4.82-4.95 (m, 2H), 5.54 (d, 0.8H), 5.80 (d, 0.2H), 6.87 (d, H), 7.10-7.40 (m, 6H), 7.45 (s, 2H); retention time on analytical HPLC: 16.71 min¹; LC-MS: m/z=538 (M+H⁺).

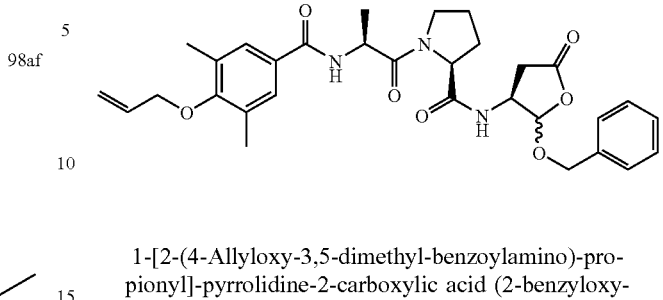

1-[2-(4-Allyloxy-3,5-dimethyl-benzoylamino)-propionyl]-pyrrolidine-2-carboxylic acid (2-benzyloxy-5-oxo-tetrahydro-furan-3-yl)-amide (98ah)

Prepared from 1-[2-(4-allyloxy-3,5-dimethyl-benzoylamino)-propionyl]-pyrrolidine-2-carboxylic acid tert-butyl ester and 40 according to the procedure used to prepare 98a to afford 264 mg (yield 46%) of the title compound. ¹H-NMR (500 MHz, CDCl₃): δ 1.09-1.43 (m, 3H), 1.90-2.20 (m, 3H), 2.20-2.38 (m, 7H), 2.38-2.52 (m, H), 2.80-2.95 (m, H), 3.52-3.67 (m, H), 3.70-3.80 (m, H), 4.10-4.40 (m, 2H), 4.40-4.95 (m, 5H), 5.26-5.55 (m, 3H), 6.00-6.14 (m, H), 6.87 (d, H), 7.10-7.70 (m, 8H); retention time on analytical HPLC: 18.56 and 18.92 min¹; LC-MS: m/z=564 (M+H⁺)

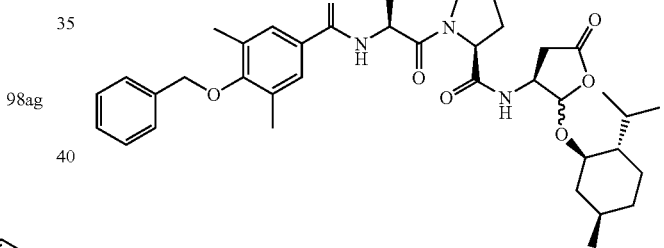

{2-[1R-(2S-Isopropyl-5R-methyl-cyclohexyloxy)]-5-oxo-tetrahydro-furan-3-yl}-carbamic acid allyl ester Prepared from 3-allyloxycarbonylamino-4-hydroxy-butyric acid tert-butyl ester as described for 40 using (1R,2S,5R)-(−)-menthol to afford 0.32 g of syn diastereomer (lower Rf) of the title compound and 4.25 g of the mixture of anti/syn diastereomers (overall yield 67%). ¹H-NMR (500 MHz, CDCl₃) mixture: δ 0.70-1.05 (m, 13H), 1.20-1.47 (m, 2H), 1.60-1.80 (m, 2H), 1.94-2.20 (m, 2H), 2.35-2.50 (m, H), 2.82-3.04 (m, H), 3.40-3.61 (m, H), 4.43-4.70 (m, 3H), 5.15-5.35 (m, 2H), 5.48-5.61 (m, H), 5.90-5.94 (m, H); for syn diastereomer 0.70-1.05 (m, 13H), 1.20-1.47 (m, 2H), 1.60-1.80 (m, 2H), 1.94-2.18 (m, 2H), 2.40-2.50 (m, H), 2.82-2.92 (m, H), 3.54-3.61 (m, H), 4.45-4.70 (m, 3H), 5.18-5.35 (m, 2H), 5.58-5.61 (m, H), 5.90-5.93 (m, H); LC-MS: m/z=340 (M+H⁺) for the mixture of anti/syn diastereomers.

4-Benzyloxy-3,5-dimethyl-benzoic acid

Prepared by the method used to synthesize 4-allyloxy-3,5-dimethyl-benzoic acid to afford 2.43 g (yield 56%) of the title compound. $^1$H-NMR (500 MHz, CDCl$_3$): δ 4.87 (s, 2H), 7.36-7.48 (m, 5H), 7.92 (s, 2H); LC-MS: m/z=255 (M–H$^+$).

1-[2-(4-Benzyloxy-3,5-dimethyl-benzoylamino)-propionyl]-pyrrolidine-2-carboxylic acid {2-[1R-(2S-isopropyl-5R-methyl-cyclohexyloxy)]-5-oxo-tetrahydro-furan-3-yl}-amide (98ai)

Prepared from 1-[2-(4-benzyloxy-3,5-dimethyl-benzoylamino)-propionyl]-pyrrolidine-2-carboxylic acid tert-butyl ester {2-[1R-(2S-Isopropyl-5R-methyl-cyclohexyloxy)]-5-oxo-tetrahydro-furan-3-yl}-carbamic acid allyl ester according to the procedure used to prepare 98a to afford 130 mg (yield 39%) of the title compound. $^1$H-NMR (500 MHz, CDCl$_3$): δ 0.45-1.10 (m, 12H), 1.15-1.90 (m, 8H), 1.90-2.45 (m, 12H), 2.80-2.84 (m, H), 3.50-3.85 (m, 3H), 4.45-4.70 (m, 2H), 4.80-4.95 (m, 3H), 5.62 (d, H), 7.05 (d, H), 7.17 (d, H), 7.30-7.60 (m, 7H), 7.62-7.75 (m, H); retention time on analytical HPLC: 15.90 and 16.08 min; LC-MS: m/z=662 (M+H$^+$).

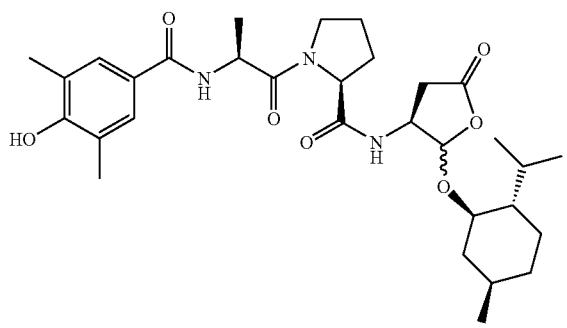

1-[2-(4-Hydroxy-3,5-dimethyl-benzoylamino)-propionyl]-pyrrolidine-2-carboxylic acid {2-[1R-(2S-isopropyl-5R-methyl-cyclohexyloxy)]-5-oxo-tetrahydro-furan-3-yl}-amide (98aj)

A solution of 1-[2-(4-benzyloxy-3,5-dimethyl-benzoylamino)-propionyl]-pyrrolidine-2-carboxylic acid {2-[1R-(2S-isopropyl-5R-methyl-cyclohexyloxy)]-5-oxo-tetrahydro-furan-3-yl}-amide (110 mg, 0.17 mmol) in ethyl acetate (2 mL) was stirred with 10% palladium on carbon (20 mg) under hydrogen atmosphere for 24 hours then filtered through Celite and evaporated in vacuo. The resulting residue was purified by chromatography using CH$_2$Cl$_2$/methanol (99/1 to 96/4) to afford 58 mg of the title compound. $^1$H-NMR (500 MHz, CDCl$_3$): δ 0.70-1.00 (m, 10H), 1.20-1.80 (m, 10H), 1.90-2.40 (m, 11H), 2.82-2.86 (m, H), 3.57-3.78 (m, 3H), 4.55-4.67 (m, 2H), 4.90-4.94 (m, H), 5.29 (s, H), 5.62 (d, H), 6.90 (d, H), 7.14 (d, H), 7.42 (s, 2H); retention time on analytical HPLC: 12.84 and 13.05 min; LC-MS: m/z=572 (M+H$^+$).

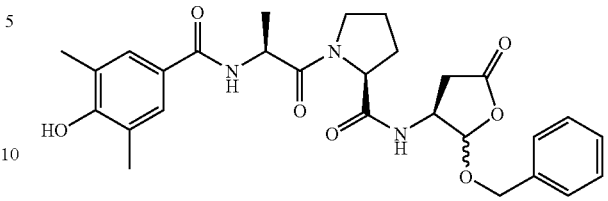

1-[2-(4-Hydroxy-3,5-dimethyl-benzoylamino)-propionyl]-pyrrolidine-2-carboxylic acid (2-benzyloxy-5-oxo-tetrahydro-furan-3-yl)-amide (98ak)

A solution of 98ah (230 mg, 0.41 mmol) in CH$_2$Cl$_2$ (10 mL) was treated with DMBA (65 mg, 0.42 mmol) and Pd(PPh$_3$)$_4$ (50 mg) at room temperature for 20 hours. The mixture was concentrated to dryness in vacuo and purified by flash chromatography using CH$_2$Cl$_2$/methanol (99.5/0.5 to 97/3) to afford 181 mg of the title compound. $^1$H-NMR (500 MHz, CDCl$_3$): δ 1.08 (d, 0.75H), 1.20-1.35 (m, 2.25H), 1.70-2.50 (m, 12H), 2.80-2.90 (m, H), 3.50-3.65 (m, H), 3.70-3.80 (m, H), 4.10-4.25 (m, H), 4.35-4.98 (m, 3H), 5.53 (d, 0.75H), 5.85 (d, 0.25H), 6.81 (d, H), 7.13-7.60 (m, 8H); retention time on analytical HPLC: 10.38 and 10.56 min; LC-MS: m/z=524 (M+H$^+$).

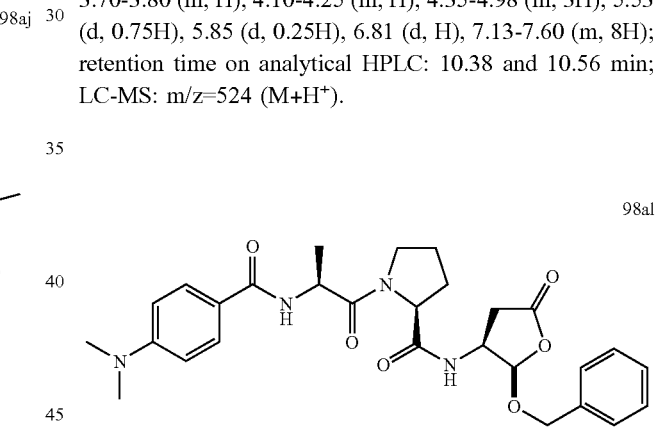

1-[2-(4-Dimethylamino-benzoylamino)-propionyl]-pyrrolidine-2-carboxylic acid (2-benzyloxy-5-oxo-tetrahydro-furan-3-yl)-amide (98al)

Prepared from 1-[2-(4-dimethylamino-benzoylamino)-propionyl]-pyrrolidine-2-carboxylic acid tert-butyl ester and syn-(2-benzyloxy-5-oxo-tetrahydro-furan-3-yl)-carbamic acid allyl ester according to the procedure used to prepare 98a to afford 60 mg (45% yield). $^1$H-NMR (500 MHz, CDCl$_3$): δ 1.04 (d, 0.75H), 1.35 (d, 2.25H), 1.80-2.50 (m, 5H), 2.75-3.20 (m, 8H), 3.45-3.75 (m, 2H), 4.05-4.20 (m, 0.5H), 4.30-4.80 (m, 3.5H), 4.80-4.95 (m, 1.5H), 5.52 (d, H), 5.75-6.00 (m, 0.5H), 6.60-6.90 (m, 3H), 7.10-7.50 (m, 4H), 7.50-7.80 (m, 2H); retention time on analytical HPLC: 10.46 min; LC-MS: m/z=523 (M+H$^+$).

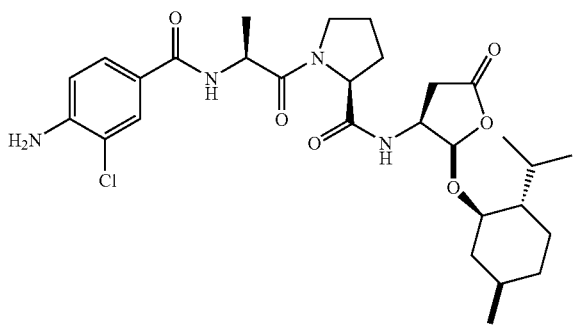

1-[2-(4-Amino-3-chloro-benzoylamino)-propionyl]-pyrrolidine-2-carboxylic acid {2R-[1R-(2S-isopropyl-5R-methyl-cyclohexyloxy)]-5-oxo-tetrahydro-furan-3-yl}-amide (98am)

Prepared from 1-[2-(4-amino-3-chloro-benzoylamino)-propionyl]-pyrrolidine-2-carboxylic acid tert-butyl ester (97a) and syn-{2-[1R-(2S-isopropyl-5R-methyl-cyclohexyloxy)]-5-oxo-tetrahydro-furan-3-yl}-carbamic acid allyl ester according to the procedure used to prepare 98a to afford 103 mg (yield 67%) of the title compound. $^1$H-NMR (500 MHz, CDCl$_3$): δ 0.70-1.10 (m, 12H), 1.20-1.50 (m, 5H), 1.50-1.85 (m, 2H), 1.90-2.30 (m, 5H), 2.75-2.85 (m, H), 3.50-3.70 (m, 2H), 3.70-3.82 (m, H), 4.20-4.65 (m, 4H), 4.80-4.95 (m, H), 5.61 (d, H), 6.70-6.73 (m, H), 6.95 (d, H), 7.15 (d, H), 7.49-7.51 (m, H), 7.73 (s, H); retention time on analytical HPLC: 12.88 min; LC-MS: m/z=577 (M+H$^+$).

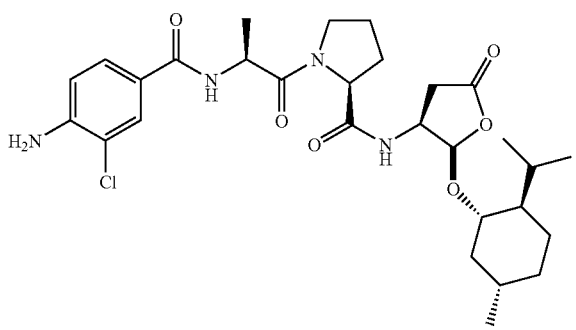

{2-[1S-(2R-Isopropyl-5S-methyl-cyclohexyloxy)]-5-oxo-tetrahydro-furan-3-yl}-carbamic acid allyl ester Prepared from 3-allyloxycarbonylamino-4-hydroxy-butyric acid tert-butyl ester as described for 40 using (1S,2R,5S)-(+)-menthol to afford 855 mg of anti diastereomer (higher Rf) of the title compound, 503 mg of syn diastereomer (lower Rf) and 459 mg of the mixture of anti/syn diastereomers (overall yield 66%). $^1$H-NMR (500 MHz, CDCl$_3$) anti diastereomer: δ 0.74-1.00 (m, 12H), 1.20-1.45 (m, 2H), 1.58-1.72 (m, 2H), 1.98-2.12 (m, 2H), 2.18-2.40 (m, H), 2.98-3.03 (m, H), 3.49-3.54 (m, H), 4.17 (br, H), 4.59 (br, 2H), 4.97 (br, H), 5.22-5.33 (m, 2H), 5.58 (s, H), 5.87-5.93 (m, H); for syn diastereomer 0.75-1.02 (m, 12H), 1.25-1.45 (m, 2H), 1.57-1.70 (m, 2H), 2.00-2.16 (m, 2H), 2.40-2.52 (m, H), 2.78-2.90 (m, H), 3.40-3.50 (m, H), 4.58 (br, 2H), 5.24-5.35 (m, 2H), 5.51-5.52 (d, H), 5.85-5.98 (m, H); LC-MS: m/z=340 (M+H$^+$) for both of diastereomers.

1-[2-(4-Amino-3-chloro-benzoylamino)-propionyl]-pyrrolidine-2-carboxylic acid {2R-[1S-(2R-isopropyl-5S-methyl-cyclohexyloxy)]-5-oxo-tetrahydro-furan-3-yl}-amide (98an)

Prepared from 97a and syn-{2-[1S-(2R-isopropyl-5S-methyl-cyclohexyloxy)]-5-oxo-tetrahydro-furan-3-yl}-carbamic acid allyl ester according to the procedure used to prepare 98a to afford 88 mg (50% yield) of the title compound. $^1$H-NMR (500 MHz, CDCl$_3$): δ 0.70-1.10 (m, 12H), 1.20-1.50 (m, 14H), 1.50-1.70 (br, 2H), 1.90-2.25 (m, 4H), 2.27-2.37 (m, H), 2.40-2.50 (m, H), 2.75-2.79 (m, H), 3.35-3.80 (m, 3H), 4.20-4.57 (m, 3H), 4.60-4.70 (m, H), 4.88-4.92 (m, H), 5.53 (d, H), 6.71-6.75 (m, H), 6.90 (d, H), 7.20 (d, H), 7.50-7.53 (m, H), 7.75 (d, H); retention time on analytical HPLC: 13.20 min; LC-MS: m/z=577 (M+H$^+$).

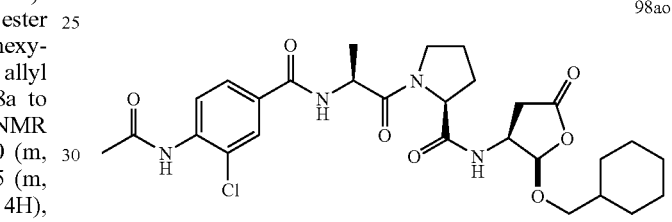

(2-Cyclohexylmethoxy-5-oxo-tetrahydro-furan-3-yl)-carbamic acid allyl ester

Prepared from 3-allyloxycarbonylamino-4-hydroxy-butyric acid tert-butyl ester as described for 40 using cyclohexylmethanol to afford 1.04 g (higher RF) (35% yield) of anti diastereomer of the title compound and 1.295 g (lower Rf) (44% yield) of syn diastereomer. $^1$H-NMR (500 MHz, CDCl$_3$) for anti diastereomer: δ 0.90-0.96 (m, 2H), 1.10-1.30 (m, 3H), 1.55-1.85 (m, 6H), 2.37-2.41 (d, H), 2.97-3.03 (m, H), 3.34-3.38 (m, H), 3.58-3.62 (m, H), 4.55-4.70 (m, 2H), 4.70-4.73 (m, H), 5.03 (bs, H), 5.22-5.37 (m, 3H), 5.87-5.93 (m, H); for syn diastereomer 0.91-0.97 (m, 2H), 1.10-1.31 (m, 3H), 1.56-1.90 (m, 7H), 2.44-2.48 (m, H), 2.81-2.87 (m, H), 3.35-3.39 (m, H), 3.63-3.67 (m, H), 4.53-4.70 (m, 3H), 5.20-5.50 (m, 3H), 5.89-5.95 (m, H); LC-MS: m/z=298 (M+H$^+$) for both of diastereomers.

1-[2-(4-Acetylamino-3-chloro-benzoylamino)-propionyl]-pyrrolidine-2-carboxylic acid (2-cyclohexylmethoxy-5-oxo-tetrahydro-furan-3-yl)-amide (98ao)

Prepared from 97b and syn-(2-cyclohexylmethoxy-5-oxo-tetrahydro-furan-3-yl)-carbamic acid allyl ester according to the procedure used to prepare 98a to afford 212 mg (64% yield) of the title compound. $^1$H-NMR (500 MHz, CDCl$_3$): δ 0.70-1.30 (m, 5H), 1.30-1.85 (m, 9H), 1.85-2.60 (m, 8H), 2.75-3.00 (m, H), 3.10-3.80 (m, 4H), 4.30-4.95 (m, 3H), 5.42 (d, 0.85H), 5.62 (d, 0.15H), 6.87 (d, 0.15H), 7.08 (d, 0.85H), 7.25 (d, H), 7.60-7.90 (m, 3H), 8.08 (d, 0.15H), 8.50 (d, 0.85H); retention time on analytical HPLC: 11.81 min; LC-MS: m/z=577 (M+H$^+$).

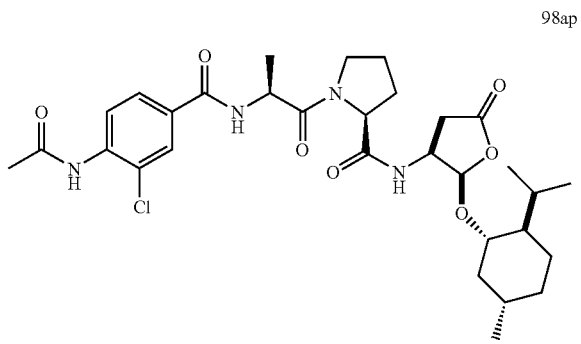

98ap

1-[2-(4-Acetylamino-3-chloro-benzoylamino)-propionyl]-pyrrolidine-2-carboxylic acid {2R-[1S-(2R-isopropyl-5S-methyl-cyclohexyloxy)]-5-oxo-tetrahydro-furan-3-yl}-amide (98ap)

Prepared from 97b and syn-{2-[1S-(2R-isopropyl-5S-methyl-cyclohexyloxy)]-5-oxo-tetrahydro-furan-3-yl}-carbamic acid allyl ester according to the procedure used to prepare 98a to afford 223 mg (63% yield) of the title compound. $^1$H-NMR (500 MHz, CDCl$_3$): δ 0.70-1.15 (m, 12H), 1.20-1.85 (m, 8H), 1.85-2.60 (m, 9H), 2.74-2.88 (m, H), 3.35-3.85 (m, 3H), 4.40-4.55 (m, H), 4.65-4.78 (m, H), 4.88-4.91 (m, H), 5.53 (d, H), 7.00-7.25 (m, 2H), 7.60-7.90 (m, 3H), 8.50 (d, H); retention time on analytical HPLC: 13.31 min; LC-MS: m/z=619 (M+H$^+$).

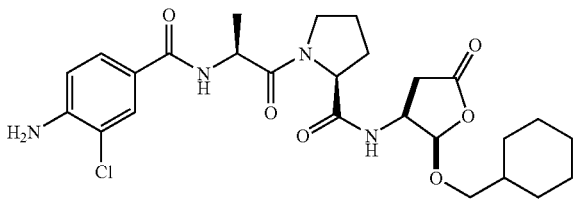

98aq

1-[2-(4-Amino-3-chloro-benzoylamino)-propionyl]-pyrrolidine-2-carboxylic acid (2-cyclohexylmethoxy-5-oxo-tetrahydro-furan-3-yl)-amide (98aq)

Prepared from 97a and syn-(2-cyclohexylmethoxy-5-oxo-tetrahydro-furan-3-yl)-carbamic acid allyl ester according to the procedure used to prepare 98a to afford 113 mg (56% yield) of the title compound. $^1$H-NMR (500 MHz, CDCl$_3$): δ 0.70-1.35 (m, 5H), 1.35-1.90 (m, 8H), 1.90-2.20 (m, 3H), 2.30-2.60 (m, H), 2.80-3.00 (m, H), 3.15-3.80 (m, 4H), 4.28-4.75 (m, 4H), 4.89-4.93 (m, H), 5.42 (d, H), 6.74 (d, H), 6.87 (d, H), 7.30 (d, H), 7.51-7.53 (m, H), 7.74 (d, H); retention time on analytical HPLC: 12.02 min; LC-MS: m/z=535 (M+H$^+$).

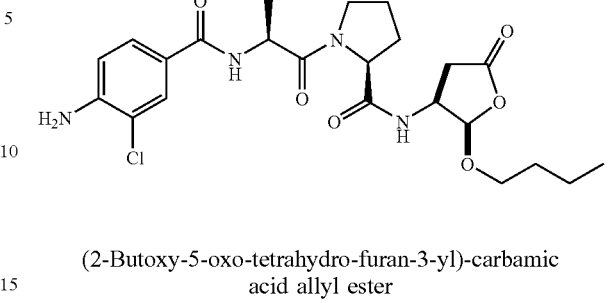

98ar (2-Butoxy-5-oxo-tetrahydro-furan-3-yl)-carbamic acid allyl ester

Prepared from 3-allyloxycarbonylamino-4-hydroxy-butyric acid tert-butyl ester as described for 40 using n-butanol to afford 878 mg (29% yield) of the title compound (313 mg of anti diastereomer, 260 mg of syn diastereomer and 305 mg of the mixture). $^1$H-NMR (500 MHz, CDCl$_3$) for anti diastereomer: δ (higher Rf) 0.89-0.96 (t, 3H), 1.32-1.40 (m, 2H), 1.54-1.63 (m, 2H), 2.37-2.41 (d, H), 2.98-3.04 (q, H), 3.55-3.60 (m, H), 3.77-3.82 (m, H), 4.19-4.22 (m, H), 4.58 (br, 2H), 5.03 (br, H), 5.23-5.40 (m, 3H), 5.87-5.93 (M, H), for syn diastereomer (lower Rf) 0.91-0.95 (t, 3H), 1.34-1.39 (m, 2H), 1.56-1.63 (m, 2H), 2.42-2.50 (m, H), 2.83-2.87 (m, H), 4.07-4.11 (t, H), 4.45-4.50 (m, 0.5H), 4.51-4.70 (m, 2.5H), 5.23-5.35 (m, 2H), 5.42-5.43 (d, H), 5.80-5.95 (m, H); LC-MS: m/z=258 (M+H$^+$) for both of diastereomers.

1-[2-(4-Amino-3-chloro-benzoylamino)-propionyl]-pyrrolidine-2-carboxylic acid (2-butoxy-5-oxo-tetrahydro-furan-3-yl)-amide (98ar)

Prepared from 97a and syn-(2-butoxy-5-oxo-tetrahydrofuran-3-yl)-carbamic acid allyl ester according to the procedure used to prepare 98a to afford 118 mg (48% yield) of the title compound as a syn diastereomer. $^1$H-NMR (500 MHz, CDCl$_3$): δ 0.80-1.02 (m, 2H), 1.35-1.51 (m, 5H), 1.51-1.70 (m, 2H), 1.90-2.27 (m, 3H), 2.30-2.46 (m, H), 2.80-2.90 (m, H), 3.55-3.94 (m, 4H), 4.30-4.75 (m, 4H), 4.90-5.00 (m, H), 5.44-5.46 (m, H), 6.73-6.80 (m, H), 6.80-6.93 (m, H), 7.16-7.25 (m, H), 7.49-7.60 (m, H), 7.70-7.84 (m, H); retention time on analytical HPLC: 9.71 min; LC-MS: m/z=495 (M+H$^+$).

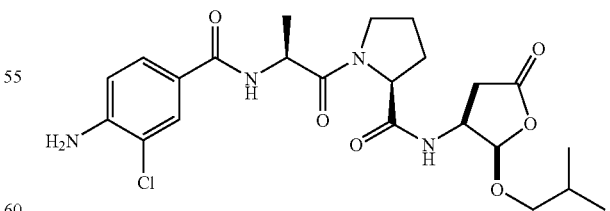

98as (2-Isobutoxy-5-oxo-tetrahydro-furan-3-yl)-carbamic acid allyl ester

Prepared from 3-allyloxycarbonylamino-4-hydroxy-butyric acid tert-butyl ester as described for 40 using isobutanol to afford 190 mg (yield 7.3%) of the title compound as an anti diastereomer and 290 mg (yield 11%) of the syn diastereomer. ¹H-NMR (500 MHz, CDCl₃) for anti diastereomer: δ (higher Rf) 0.85-1.05 (m, 6H), 1.82-1.98 (m, H), 2.37-2.42 (d, H), 2.98-3.04 (m, H), 3.31-3.35 (m, H), 3.55-3.58 (m, H), 4.20-4.30 (t, H), 4.58 (br, 2H), 5.07 (br, H), 5.22-5.43 (m, 3H), 5.84-5.96 (m, H), for syn diastereomer (lower Rf) 0.85-1.05 (m, 6H), 1.88-1.95 (m, H), 2.40-2.51 (m, H), 2.83-2.90 (m, H), 3.33-3.36 (m, H), 3.61-3.65 (m, H), 3.87-3.88 (d, H), 4.40-4.68 (m, 3H), 5.20-5.40 (m, 2H), 5.42-5.43 (d, H), 5.80-5.97 (m, H); LC-MS: m/z=258 (M+H⁺) for both of diastereomers.

1-[2-(4-Amino-3-chloro-benzoylamino)-propionyl]-pyrrolidine-2-carboxylic acid (2-isobutoxy-5-oxo-tetrahydro-furan-3-yl)-amide (98as)

Prepared from 97a and syn-(2-isobutoxy-5-oxo-tetrahydro-furan-3-yl)-carbamic acid allyl ester according to the procedure used to prepare 98a to afford 93 mg (38% yield) of the title compound. ¹H-NMR (500 MHz, CDCl₃): δ 0.74-0.76 (t, 0.6H), 0.80-1.00 (m, 5.4H), 1.40-1.50 (m, 3H), 1.90-2.22 (m, 3H), 2.33-2.45 (m, H), 2.80-2.90 (m, H), 3.32-3.38 (m, H), 3.55-3.80 (m, 3H), 4.38 (br, H), 4.50-4.60 (m, H), 4.70-4.80 (m, H), 4.90-5.00 (m, H), 5.42-5.45 (m, H), 6.74-6.76 (d, H), 6.86-6.88 (d, H), 7.31-7.33 (d, H), 7.51-7.53 (m, H), 7.74-7.75 (d, H); retention time on analytical HPLC: 9.63 & 9.80 min; LC-MS: m/z=495 (M+H⁺).

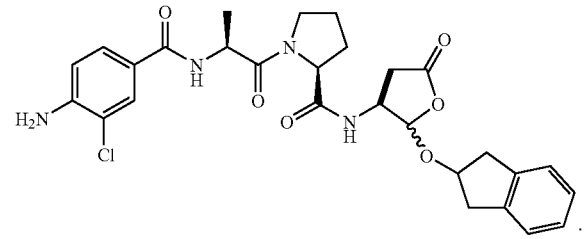

98at

[2-(indan-2-yl)oxy-5-oxo-tetrahydro-furan-3-yl]-carbamic acid allyl ester

Prepared from 3-allyloxycarbonylamino-4-hydroxy-butyric acid tert-butyl ester (5.2 gram, 20 mmol) as described for 40 using 2-indanol (8.05 gram, 60 mmol) to afford 4.10 grams (65% yield) of the title compound as a mixture of epimers. Purification provided 1.76 gram (28% yield) of the 4(S), 5(R) epimer as a yellow oil. ¹H NMR (500 MHz, CDCl₃) δ 2.42 (dd, J=17.2, 10.5 Hz, 1H), 2.79 (dd, J=17.2, 8.4 Hz, 1H), 2.99 (dd, J=16.7, 4.1 Hz, 1H), 3.04 (dd, J=16.7, 4.1 Hz, 1H), 3.22 (dd, J=17.2, 6.6 Hz, 1H), 3.26 (dd, J=17.2, 6.6 Hz, 1H), 4.53 (m, 3H), 4.70 (m, 1H), 5.20 (m, 2H), 5.60 (d, J=5.3 Hz, 1H), 5.87 (m, 1H), 7.17 (m, 4H) ppm. LC-MS (ES⁺): m/e=318 (M+H). Analytical HPLC (C18 column): 17.094 min.

Also isolated was epimer mixture (0.75 gram, 12% yield), and the 4(S), 5(S) epimer (1.59 gram, 25%) as a white solid. ¹H-NMR (500 MHz, CDCl₃) δ 2.38 (d, J=17.9 Hz, 1H), 3.0 (m, 3H), 3.22 (m, 2H), 4.13 (m, 1H), 4.58 (m, 2H), 4.68 (m, 2H), 4.98 (br s, 1H), 5.26 (m, 1H), 5.57 (s, 1H), 5.88 (ddt, J=18.0, 11.1, 5.4 Hz, 1H), 7.20 (m, 4H) ppm. LC-MS (ES⁺): m/e=318 (M+H). Analytical HPLC (C18 column):17.025 (5.5%), 17.325 (94.5%) min.

1-[2-(4-amino-3-chloro-benzoylamino)-propionyl]-pyrrolidine-2-carboxylic acid [2-(indan-2-yloxy)-5-oxo-tetrahydro-furan-3-yl]-amide (98at)

Prepared from 97a and [2-(indanol-2-yl]oxy-5-oxo-tetrahydro-furan-3-yl)-carbamic acid allyl ester according to the procedure used to prepare 98a to afford the title compound as a 71:29 mixture of epimers as an off-white solid (0.20 g, 58% yield). ¹H-NMR (500 MHz, CDCl₃) δ 1.0-1.5 (m, 3H), 1.6-2.3 (m, 4H), 2.42 (m, 1H), 2.6-3.4 (m, 6H), 3.5-4.1 (m, 3H), 4.2-4.9 (m, 4H), 5.65 (d, J=5.0 Hz, 0.80H), 5.8 (m, 0.07H), 5.85 (d, J=5.0 Hz, 0.13H), 6.8-7.3 (m, 6H), 7.4-7.9 (m, 3H) ppm. Analytical HPLC (C18 column) 16.035 (71.4%), 16.476 (28.6%) min. LC-MS (ES+): m/e=555 (M+H).

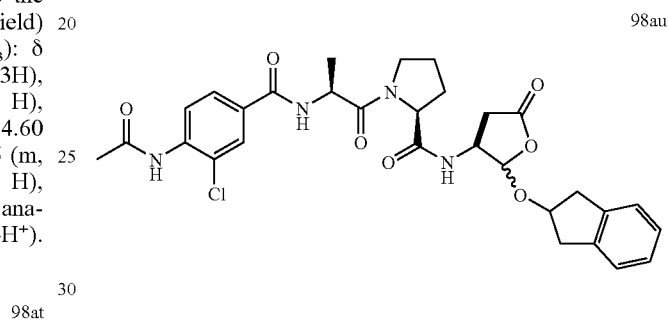

98au

1-[2-(4-Acetylamino-3-chloro-benzoylamino)-propionyl]-pyrrolidine-2-carboxylic acid [2-(indan-2-yloxy)-5-oxo-tetrahydro-furan-3-yl]-amide (98au)

Prepared from 97b and [2-(indanol-2-yl]oxy-5-oxo-tetrahydro-furan-3-yl)-carbamic acid allyl ester according to the procedure used to prepare 98a to afford the title compound as a 76:24 mixture of epimers as an off-white solid (0.22 g, 57% yield). ¹H-NMR (500 MHz, CDCl₃) δ 1.08 (d, J=6.9 Hz, 0.4H), 1.26 (d, J=6.9 Hz, 0.6H), 1.35 (d, J=6.9 Hz, 2H), 1.8-2.3 (m, 3H), 2.28 (s, 2H), 2.29 (s, 1H), 2.4 (m, 1H), 2.8 (m, 1H), 3.10 (m, 2H), 3.27 (m, 2H), 3.58 (m, 2H), 3.69 (m, 1H), 4.5-4.9 (m, 4H), 5.65 (d, J=5.3 Hz, 0.68H), 5.84 (d, J=5.3 Hz, 0.18H), 6.38 (br, 0.14H), 6.9-7.7 (m, 6H), 7.6-7.9 (m, 3H), 8.33 (br d, J=6.8 Hz, 0.18H), 8.51 (br d, J=8.0 Hz, 0.82H) ppm. Analytical HPLC (C18 column) 15.596 (76.2%), 15.932 (23.8%) min. LC-MS (ES+): m/e=597 (M+H).

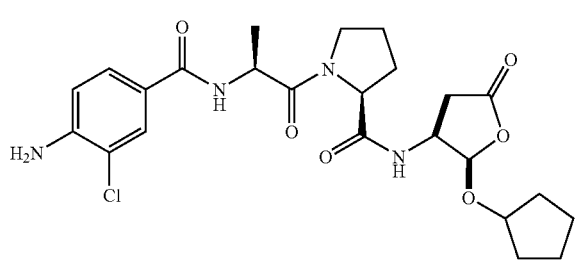

98av

1-[2-(4-amino-3-chloro-benzoylamino)-propionyl]-pyrrolidine-2-carboxylic acid (2-cyclopentyloxy-5-oxo-tetrahydro-furan-3-yl)-amide (98av)

Prepared from 97a and syn-(2-cyclopentyloxy-5-oxo-tetrahydro-furan-3-yl)-carbamic acid allyl ester according to the procedure used to prepare 98a to afford the title compound as an off-white solid (0.19 g, 59% yield). $^1$H-NMR (500 MHz, CDCl$_3$) δ 1.2-2.4 (m, 15H), 2.4-3.1 (m, 2H), 3.6-3.9 (m, 2H), 4.2-4.4 (m, 2H), 4.5-5.0 (m, 4H), 5.40 (d, J=5.0 Hz, 0.35H), 5.55 (d, J=5.0 Hz, 0.65H), 6.8-8.2 (m, 5H) ppm. Analytical HPLC (C18column) 14.065 min. LC-MS (ES+): m/e=507 (M+H).

1-[2-(4-Amino-3-chloro-benzoylamino)-propionyl]-pyrrolidine-2-carboxylic acid (2-cyclopentyloxy-5-oxo-tetrahydro-furan-3-yl)-amide (98ax)

Prepared according to the procedure used to prepare (98av) using anti-(2-cyclopentyloxy-5-oxo-tetrahydro-furan-3-yl)-amide to afford the title compound as an off-white solid (0.24 g, 74% yield). $^1$H-NMR (500 MHz, CDCl$_3$) δ 1.41 (d, J=6.5 Hz, 3H), 1.7 (m, 7H), 1.98 (br, 2H), 2.13 (br, 2H), 2.27 (m, 1H), 2.69 (m, 1H), 2.86 (dd, J=18.0, 6.8 Hz, 0.7H), 2.98 (dd, J=18.3, 8.2 Hz, 0.3H), 3.60 (br, 1.4H), 3.77 (br, 0.6H), 4.1-4.6 (m, 5H), 4.82 (m, 1H), 5.27 (m, 0.65H), 5,51 (d, J=5.3 Hz, 0.05H), 5.59 (br s, 0.3H), 6.76 (br, 1H), 7.00 (br, 1H), 7.49 (br, 1H), 7.74 (br, 1H), 7.89 (br, 1H) ppm. Analytical HPLC (C18 column) 9.756 min. LC-MS (ES+): m/e=507 (M+H).

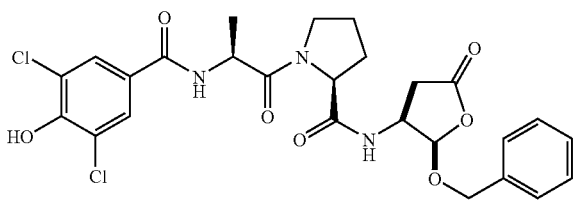

98aw

1-[2-(3,5-Dichloro-4-hydroxy-benzoylamino)-propionyl]-pyrrolidine-2-carboxylic acid (2-benzyloxy-5-oxo-tetrahydro-furan-3-yl)-amide (98aw)

Prepared from 1-[2-(4-allyloxy-3,5-dimethyl-benzoylamino)-propionyl]-pyrrolidine-2-carboxylic acid tert-butyl ester and syn-40 according to the procedure used to prepare 98a to afford the title compound as a pale yellow solid (1.087 g, 64% yield). $^1$H-NMR (500 MHz, CDCl$_3$) δ 1.09 (d, J=6.9 Hz, 0.6H), 1.33 (d, J=6.9 Hz, 2.4H), 1.96 (m, 1H), 2.03 (m, 1H), 2.10 (m, 1H), 2.28 (m, 0.8H), 2.40 (dd, J=17.3, 10.2 Hz, 0.8H), 2.56 (m, 0.2H), 2.85 (dd, J=17.3, 8.5 Hz, 0.8H), 3.09 (dd, J=17.7, 10.2 Hz, 0.2H), 3.57 (m, 1H), 3.73 (dt, J=9.2, 7.9 Hz, 0.8H), 4.09 (m, 0.2H), 4.21 (d, J=7.9 Hz, 0.2H), 4.44 (d, J=9.8 Hz, 0.2H), 4.55 (dd, J=8.0, 3.0 Hz, 0.8H), 4.62 (d, J=11.6 Hz, 1H), 4.70 (m, 1H), 4.80 (m, 1H), 4.89 (d, J=11.6 Hz, 0.8H), 5.52 (d, J=5.2 Hz, 0.8H), 5.82 (d, J=5.2 Hz, 0.2H), 6.51 (br, 0.2H), 6.62 (br, 0.8H), 7.0-7.4 (m, 7H), 7.43 (s, 0.4H), 7.66 (d, J=1.0 Hz, 1.6H) ppm. Analytical HPLC (C18 column) 10.135 min. LC-MS (ES+): m/e=564, 566 (6:4) (M+H).

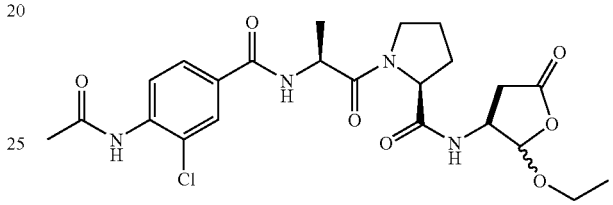

98ay

1-[2-(4-Acetylamino-3-chloro-benzoylamino)-propionyl]-pyrrolidine-2-carboxylic acid (2-ethoxy-5-oxo-tetrahydro-furan-3-yl)-amide (98ay)

Prepared from (2-ethoxy-5-oxo-tetrahydro-furan-3-yl)-carbamic acid allyl ester and 97b following the method used for 98a. The title compound was isolated as a white solid (51 mg, 18% yield). $^1$H-NMR (500 MHz, 1:1 CDCl$_3$:CD3OD) δ 1.08-1.35 (m, 3H), 1.35-1.55 (m, 3H), 1.75-2.44 (m, 4H), 2.26 (s, 3H), 2.44-3.07 (m, 2H), 3.48-3.97 (m, 2H), 4.18-4.92 (m, 5H), 5.32 (d, 0.4H), 5.47 (d, 0.1H), 5.58 (d, 0.4H), 5.64 (d, 0.1H), 7.70-8.35 (m, 3H). Analytical HPLC 10.37, 10.54 min. LC-MS (ES$^+$) m/e=509.2 (M+H$^+$).

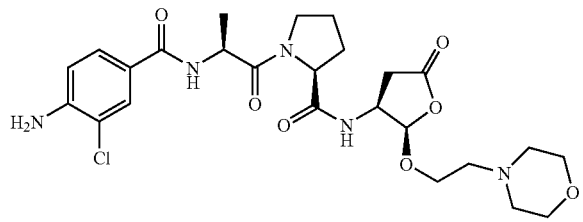

98az

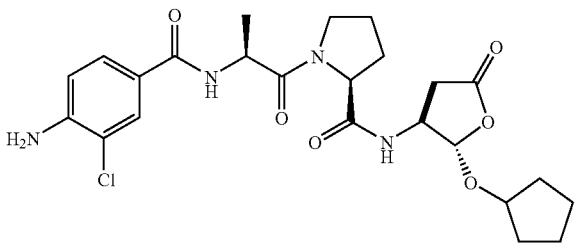

98ax

[2-(2-Chloro-ethoxy)-5-oxo-tetrahydro-furan-3-yl]-carbamic acid allyl ester

Prepared from 3-allyloxycarbonylamino-4-hydroxy-butyric acid tert-butyl ester (5.2 g, 20 mmol) as described for 40 using chloroethanol (4.05 mL, 60 mmol) to afford 1.84 g (35% yield) of the title compound as a mixture of epimers. For the anti-diastereomer: $^1$H-NMR (500 MHz, CDCl$_3$) δ 2.42 (dd, J=18.1 Hz, 1H), 3.00 (dd, J=18.1, 7.8 Hz, 1H), 3.63 (m, 2H), 3.85 (m, 1H), 4.02 (m, 1H), 4.23 (m, 1H), 4.57 (br s, 2H), 5.17 (br s, 1H), 5.22 (d, H=11.5 Hz, 1H), 5.29 (d, J=16.8 Hz, 1H), 5.44 (s, 1H), 5.89 (m, 1H) ppm; LC-MS (ES+) m/e=264 (M+H). For the syn-diastereomer: $^1$H-NMR (500 MHz, CDCl3) δ 2.47 (dd, J=17.3, 10.7 Hz, 1H), 2.83 (dd, J=17.3, 8.4 Hz, 1H), 3.65 (m, 2H), 3.83 (m, 1H), 4.11 (m, 1H), 4.57 (m, 3H), 5.22 (d, H=10.4 Hz, 1H), 5.30 (d, J=17.2 Hz, 1H), 5.33 (m, 1H), 5.47 (d, J=5.2 Hz, 1H), 5.89 (ddt, J=17.1, 11.0, 5.4 Hz, 1H) ppm; LC-MS (ES+) m/e=264 (M+H).

[2-(2-Morpholin-4-yl-ethoxy)-5-oxo-tetrahydro-furan-3-yl]-carbamic acid allyl ester Is prepared from [2-(2-chloro-ethoxy)-5-oxo-tetrahydro-furan-3-yl]-carbamic acid allyl ester by reaction with morpholine (2 eq) and KI (1 eq) in DMF.

1-[2-(4-Amino-3-chloro-benzoylamino)-propionyl]-pyrrolidine-2-carboxylic acid [2-(2-morpholin-4-yl-ethoxy)-5-oxo-tetrahydro-furan-3-yl]-amide (98az)

Is prepared from 97a and syn-[2-(2-morpholin-4-yl-ethoxy)-5-oxo-tetrahydro-furan-3-yl]-carbamic acid allyl ester following the method used for 98a.

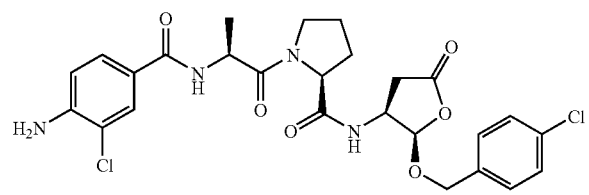

98ba

[2-(4-Chloro-benzyloxy)-5-oxo-tetrahydro-furan-3-yl]-carbamic acid allyl ester

Prepared from 3-allyloxycarbonylamino-4-hydroxy-butyric acid tert-butyl ester as described for 40 using 4-chlorobenzylalcohol to afford the title compound as a white solid. Anti-diastereomer: HPLC (C18 column) 10.924 min; $^1$H-NMR (500 MHz, CDCl$_3$) δ 2.41 (d, J=8.0 Hz, 1H), 3.02 (dd, J=18.1, 7.8 Hz, 1H), 4.25 (br, 1H), 4.56 (m, 2H), 4.58 (d, J=11.7 Hz, 1H), 4.79 (d, J=11.7 Hz, 1H), 4.99 (br, 1H), 5.22 (dd, J=10.4, 1.1 Hz, 1H), 5.28 (dd, J=17.2, 1.3 Hz, 1H), 5.44 (s, 1H), 5.86 (m, 1H), 7.25 (d, J=8.4 Hz, 2H), 7.32 (d, J=8.4 Hz, 2H) ppm; LC-MS (ES+) m/e=326 (M+H); Syn-diastereomer: HPLC (C18 column) 10.780 min; $^1$H-NMR (500 MHz, CDCl$_3$) δ 2.47 (dd, J=17.3, 10.5 Hz, 1H), 2.85 (dd, J=17.3, 8.4 Hz, 1H), 4.55 (m, 3H), 4.58 (d, J=11.7 Hz, 1H), 4.84 (d, J=11.7 Hz, 1H), 5.23 (dd, H=10.4, 1.1 Hz, 1H), 5.30 (d, J=16.6 Hz, 1H), 5.49 (d, J=5.0 Hz, 1H), 5.89 (ddt, J=17.1, 11.0, 5.4 Hz, 1H), 7.23 (d, J=8.3 Hz, 2H), 7.31 (d, J=8.3 Hz, 2H) ppm; LC-MS (ES+) m/e=326 (M+H).

1-[2-(4-Amino-3-chloro-benzoylamino)-propionyl]-pyrrolidine-2-carboxylic acid [2-(4-chloro-benzyloxy)-5-oxo-tetrahydro-furan-3-yl]-amide (98ba)

Prepared from 97a and syn-[2-(4-chloro-benzyloxy)-5-oxo-tetrahydro-furan-3-yl]-carbamic acid allyl ester following the method used for 98a to afford 154 mg (65% yield) of the title compound as a pale pink solid. HPLC (C18 column) 10.597 min; $^1$H-NMR (500 MHz, CDCl$_3$) δ 1.14 (d, J=6.8 Hz, 0.75H), 1.34 (d, J=6.8 Hz, 2.25H), 1.6 (br, 0.25H), 1.91 (m, 1H), 2.03 (m, 1H), 2.10 (m, 1H), 2.29 (m, 0.75H), 2.40 (dd, J=17.3, 10.3 Hz, 0.75H), 2.51 (m, 0.25H), 2.82 (dd, J=17.3, 8.5 Hz, 0.75H), 3.08 (dd, J=17.9, 10.9 Hz, 0.25H), 3.58 (m, 1H), 3.72 (dd, J=16.5, 8.7 Hz, 0.75H), 4.10 (m, 0.25H), 4.22 (d, J=8.0 Hz, 0.25H), 4.39 (d, J=10.8 Hz, 0.25H), 4.54 (dd, J=9.1, 2.9 Hz, 0.75H), 4.60 (d, J=11.9 Hz, 0.75H), 4.68 (m, 1H), 4.85 (d, J=11.7 Hz, 0.75H), 4.86 (m, 1H), 5.49 (d, J=5.2 Hz, 0.75H), 5.81 (d, J=5.2 Hz, 0.25H), 6.2 (br, 0.25H), 6.74 (m, 2H), 7.05 (d, J=8.5 Hz, 0.5H), 7.17 (d, J=8.4 Hz, 0.5H), 7.30 (m, 3.25H), 7.48 (dd, J=8.4, 2.0 Hz, 0.75H), 7.56 (d, J=1.9 Hz, 0.25H), 7.73 (d, J=1.9 Hz, 0.75H), 8.42 (d, J=5.7 Hz, 0.25H) ppm; LC-MS (ES+) m/e=563, 565 (M+H).

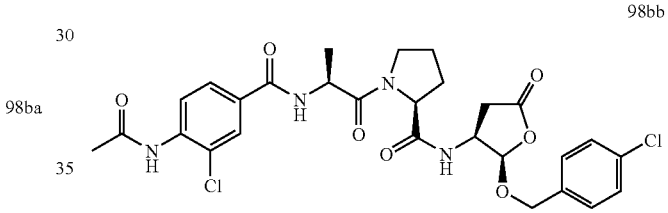

98bb

1-[2-(4-Acetylamino-3-chloro-benzoylamino)-propionyl]-pyrrolidine-2-carboxylic acid [2-(4-chloro-benzyloxy)-5-oxo-tetrahydro-furan-3-yl]-amide (98bb)

Prepared from 97b and syn-[2-(4-chloro-benzyloxy)-5-oxo-tetrahydro-furan-3-yl]-carbamic acid allyl ester according to the procedure used to prepare 98a to afford 165 mg (64% yield) of the title compound as pale yellow solid. HPLC (C18 column) 10.491 min; $^1$H-NMR (500 MHz, CDCl$_3$) δ 1.16 (d, J=6.8 Hz, 0.6H), 1.35 (d, J=6.8 Hz, 2.4H), 1.94 (m, 1H), 2.04 (m, 1H), 2.10 (m, 1H), 2.25 (s, 3H), 2.28 (m, 1H), 2.40 (dd, J=17.3, 10.4 Hz, 0.8H), 2.53 (m, 0.2H), 2.84 (dd, J=17.3, 8.5 Hz, 0.8H), 3.02 (dd, J=17.5, 10.5 Hz, 0.2H), 3.58 (m, 1H), 3.72 (ddd, J=17.2, 8.3, 8.3 Hz, 0.8H), 4.13 (m, 0.2H), 4.22 (d, J=8.2 Hz, 0.2H), 4.40 (d, J=10.9 Hz, 0.2H), 4.54 (dd, J=8.1, 3.0 Hz, 0.8H), 4.60 (d, J=11.8 Hz, 0.8H), 4.69 (m, 1H), 4.85 (d, J=11.8 Hz, 0.8H), 4.87 (m, 1H), 5.49 (d, J=5.2 Hz, 0.8H), 5.80 (d, J=5.2 Hz, 0.2H), 6.47 (br, 0.2H), 6.95 (d, J=8.3 Hz, 0.8H), 7.05 (d, J=8.3 Hz, 0.4H), 7.18 (d, J=8.3 Hz, 0.4H), 7.29 (m, 3.2H), 7.49 (dd, J=8.6, 1.9 Hz, 0.2H), 7.63 (dd, J=8.6, 1.9 Hz, 0.8H), 7.74 (d, J=1.9 Hz, 1H), 7.85 (d, J=1.9 Hz, 0.8H), 8.25 (d, J=6.4 Hz, 0.2H), 8.51 (m, 0.8H) ppm; LC-MS (ES+) m/e=605, 607 (M+H).

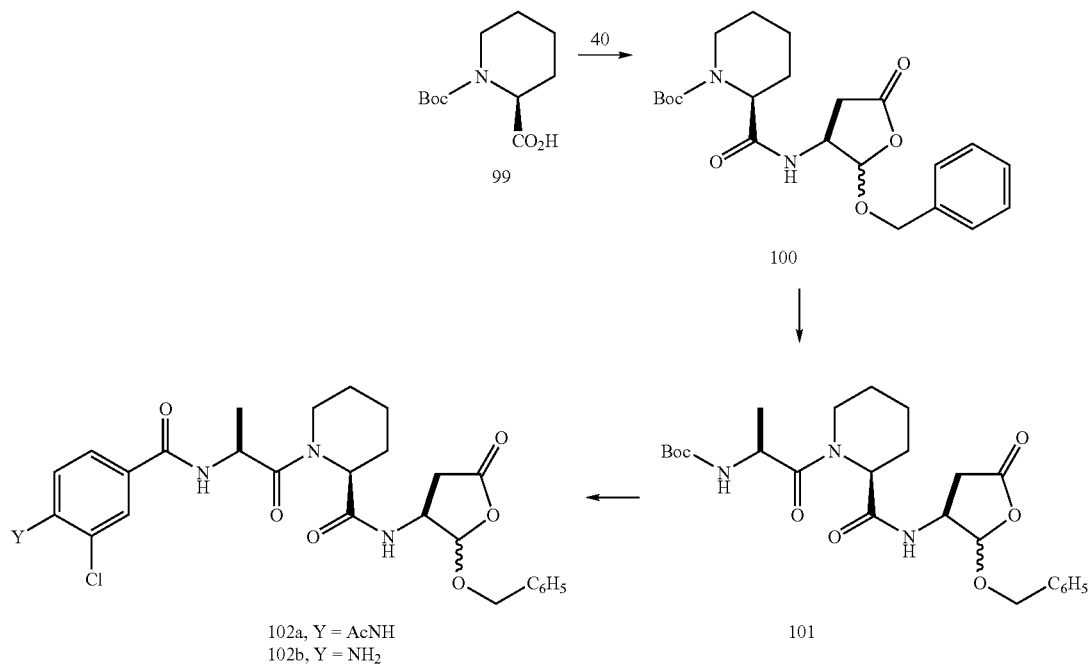

2-(2-Benzyloxy-5-oxo-tetrahydro-furan-3-ylcarbamoyl)-piperidine-1-carboxylic acid-tert butyl ester (100)

Prepared from piperidine-1,2-dicarboxylic acid 1-tert-butyl ester 99 and 40 following the method used in the preparation of 75 to give the title compound as a yellow solid (2.63 g, 57% yield). $^1$H-NMR (500 MHz, CDCl$_3$) δ 1.15-1.79 (m, 15H), 2.12-2.50 (m, 2H), 2.56-2.83 (m, 1H), 2.89 (dd, 0.5H), 3.05 (dd, 0.5H), 3.81-4.15 (br s, 1H), 4.36-4.97 (m, 3H), 5.37-5.61 (m, 1H), 6.42-6.89 (br s, 1H), 7.17-7.51 (m, 5H). LC-MS (ES$^+$) m/e=419.4 (MH$^+$).

{2-[2-(2-Benzyloxy-5-oxo-tetrahydro-furan-3-ylcarbamoyl)-piperidin-1-yl]-1-methyl-2-oxo-ethyl}-carbamic acid tert-butyl ester (101)

2-(2-Benzyloxy-5-oxo-tetrahydro-furan-3-ylcarbamoyl)-piperidine-1-carboxylic acid tert-butyl ester (100) was dissolved in 20% TFA in CH$_2$Cl$_2$ (25 mL) and stirred at room temperature for 50 min. The solvent was evaporated and the residual acid azeotroped with CH$_2$Cl (4×). The resulting oil was dissolved in CH$_2$Cl$_2$ (20 mL) and DMF (5 mL), cooled to 0° C. and treated with DIEA (4.7 mL, 27.0 mmol), Boc-alanine (970 mg, 5.1 mmol), HOBT (924 mg, 6.8 mmol) and EDC (1.31 g, 6.8 mmol) and the solution stirred under N$_2$ for 18 hours. The solvent was concentrated in vacuo then dissolved in EtOAc and washed with 0.5N NaHSO$_4$ (2×), saturated NaHCO$_3$ (2×) and brine. The organic layer was dried over anhydrous Na$_2$SO$_4$ and evaporated to give an orange solid that was dissolved in CH$_2$Cl$_2$ and added dropwise to diethyl ether to afford a white precipitate. The title compound as a white solid (1.21 g, 73% yield). $^1$H-NMR (500 MHz, CDCl$_3$) δ 1.10-1.79 (m, 18H), 1.98-2.19 (m, 0.5H), 2.28-2.88 (m, 3H), 2.89-3.13 (m, 0.5H), 3.78-3.95 (m, 0.5H), 4.21-5.16 (m, 5.5H), 5.38-5.59 (m, 0.3H), 5.66 (d, 0.4H), 5.80 (d, 0.3H), 7.24-7.40 (m, 5H). LC-MS (ES$^+$) m/e=490.3 (MH$^+$).

1-[2-(4-Acetylamino-3-chloro-benzoylamino)-propionyl]-piperidine-2-carboxylic acid (2-benzyloxy-5-oxo-tetrahydro-furan-3-yl)amide (102a)

Prepared from {2-[2-(2-benzyloxy-5-oxo-tetrahydro-furan-3-ylcarbamoyl)-piperidin-1-yl]-1-methyl-2-oxo-ethyl}-carbamic acid tert butyl ester and 4-acetylamino-3-chlorobenzoic acid by the procedure used in the preparation of 98a to give the title compound (71 mg, 47% yield). $^1$H-NMR (500 MHz, CDCl$_3$) δ 1.10-1.97 (m, 10H), 2.10-2.68 (m, 5H), 2.73-3.24 (m, 2H), 3.62-3.92 (m, 1H), 4.24-5.27 (m, 5H), 5.48-5.59 (m, 0.5H), 5.75-5.85 (m, 0.5H), 6.51-6.61 (d, 1H), 7.05-7.45 (m, 4H), 7.52-8.12 (m, 4H). Analytical HPLC 8.30 min. LC-MS (ES$^+$) m/e=585.3 (MH$^+$).

1-[2-(4-Amino-3-chloro-benzoylamino)-propionyl]-piperidine-2-carboxylic acid (2-benzyloxy-5-oxo-tetrahydro-furan-3-yl)-amide (102b)

Prepared as above for 102a to give the title compound (0.06 g, 27% yield) as a yellow solid. $^1$H-NMR (500 MHz, CDCl$_3$) δ 1.2-1.8 (m, 7H), 2.1-2.6 (m, 2H), 2.7-3.2 (m, 4H), 3.6-4.0 (m, 1H), 4.3-4.9 (m, 7H), 5.0-5.8 (m, 2H), 6.5-7.0 (m, 2H), 7.2-7.8 (m, 8H) ppm. Analytical HPLC (cyano column) 14.559 (39.6%), 15.198 (60.4%). LC-MS (ES+): m/e=543 (M+H).

Scheme XIX

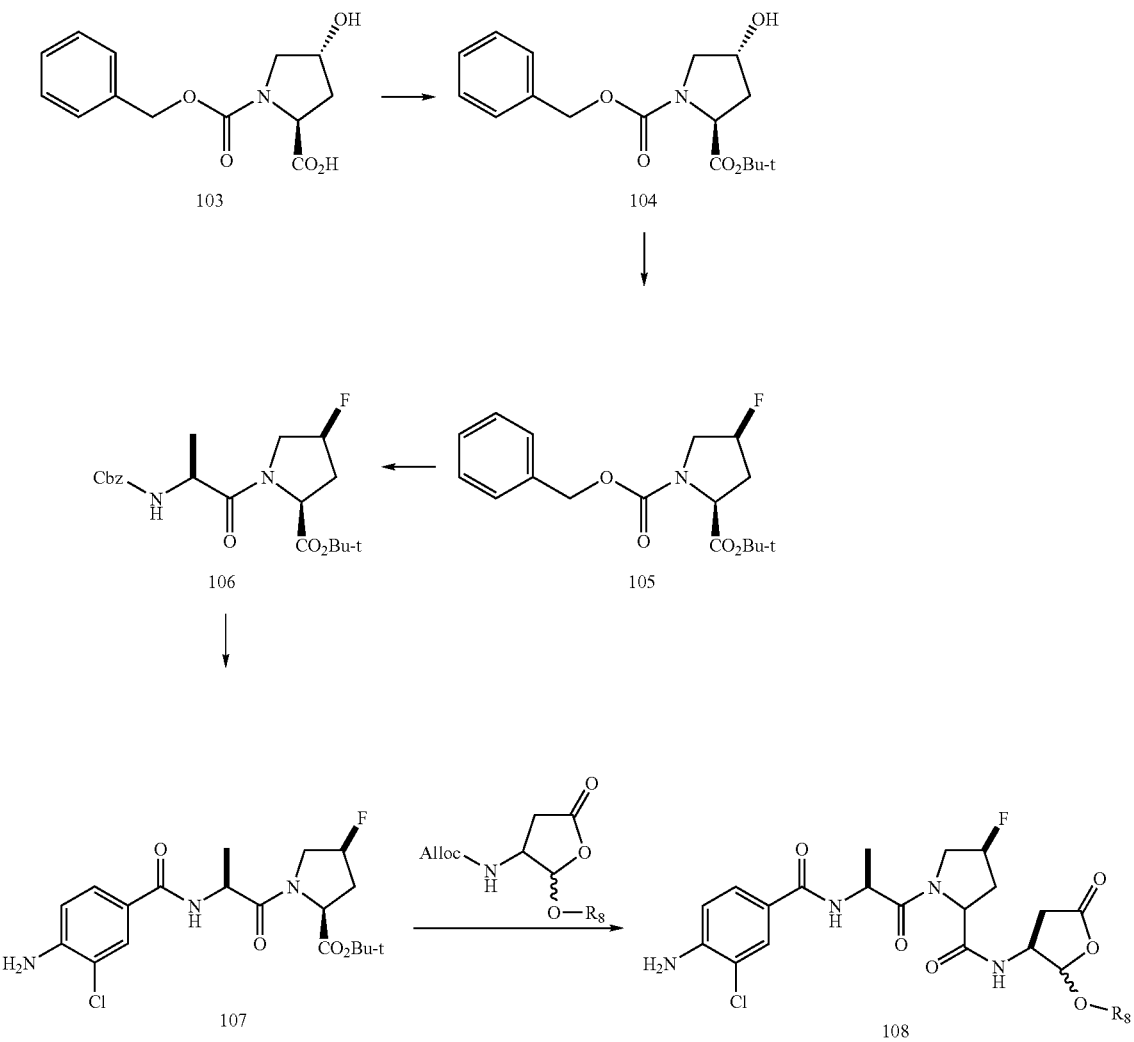

4-Hydroxy-pyrrolidine-1,2-dicarboxylic acid
1-benzyl ester 2-tert-butyl ester (104)

Compound 104 was prepared according to the procedure used to prepare compound 95.

A suspension of Cbz-Hyp-OH (4.854 g, 18 mmol) in DMA (135 ml), benzyltriethylammonium chloride (4.105 g, 18 mmol), $K_2CO_3$ (64 g, 46 mmol) and 2-bromo-2-methyl-propane (99 ml, 859 mmol) was stirred at 55° C. for 18 hours. The mixture was diluted with iced water and extracted with EtOAc (3×). The organic phase washed with water, 0.5N $NaHSO_4$ solution and brine dried and the solvent in vacuo to yield the title compound as a yellow oil (5.368 g, 98% yield). $^1$H-NMR (500 MHz, $CDCl_3$) δ 1.33 (s, 5H), 1.47 (s, 4H), 2.01-2.14 (m, 1H), 2.22-2.38 (m, 1H), 3.50-3.72 (m, 2H), 4.34-4.45 (m, 1H), 4.45-4.53 (m, 1H), 5.04-5.20 (m, 2H), 7.22-7.42 (m, 5H). Analytical HPLC 10.14 min. LC-MS (ES$^+$) m/e=322.2 (MH$^+$).

4-Fluoro-pyrrolidine-1,2-dicarboxylic acid 1-benzyl
ester 2-tert-butyl ester (105)

A solution of 104 (4.262, 13.96 mmol) in $CH_2Cl_2$ (100 ml) at −78° C. was treated with DAST (1.80 ml, 13.6 mmol), stirred for 10 min then warmed to room temperature and stirred for 60 h under $N_2$. The mixture was poured into iced $NaHCO_3$ (10% solution, 350 ml) and extracted with $CH_2Cl_2$ (2×). The organic phase was washed with water, brine, dried over anhydrous $Na_2SO_4$ and concentrated to give a brown oil (4.299 g) which was purified by flash column chromatography on silica gel using hexanes/EtOAc (90/10 to 80/20%). The title compound was obtained as a yellow oil (2.805 g, 64% yield). $^1$H-NMR (500 MHz, $CDCl_3$) δ 1.37 (s, 4.5H), 1.45 (s, 4.5H), 2.20-2.55 (m, 2H), 3.61-3.93 (m, 2H), 4.41 (d, 0.5H), 4.49 (d, 0.5H), 5.03-5.21 (m, 3H), 7.23-7.44 (m, 5H). Analytical HPLC 12.15 min. LC-MS (ES$^+$) m/e=324.2 (MH$^+$).

1-(2-Benzyloxycarbonylamino-propionyl)-4-fluoro-pyrrolidine-1,2-dicarboxylic acid 1-benzyl ester 2-tert-butyl ester (106)

A solution of 105 (2.72 g, 8.42 mmol) in MeOH (50 ml) and 10% Pd/C (1.27 g) was stirred under $H_2$ for 2 hours then filtered through celite and the solvent evaporated to give a yellow oil (1.526 g). This oil was dissolved in $CH_2Cl_2$ (30 ml) and treated with DIEA (1.5 ml, 8.6 mmol), Cbz-ala-OH (2.34 g, 10.5 mmol) and EDC (2.32 g, 12 mmol) at 0° C. The mixture was stirred an additional 10 min at 0° C. then allowed to warm to room temperature and stir for 18 hours. The solvent was concentrated in vacuo and the residue dissolved in EtOAc then washed with 0.5N $NaHSO_4$ (2×), saturated $NaHCO_3$ (2×) and brine. The organic layer was dried over anhydrous $Na_2SO_4$ and evaporated to give a white solid which was purified by flash column chromatography, eluting using hexanes/EtOAc (80/20 to 60/40%). The title compound was isolated as a white solid (286 g, 86% from 4-fluoro-pyrrolidine-1,2-dicarboxylic acid 1-benzyl ester 2-tert-butyl ester). $^1$H-NMR (500 MHz, $CD_3OD$) δ 1.26-1.59 (m, 12H), 2.20-2.67 (m, 2H), 3.45-4.13 (m, 2H), 4.25-4.47 (m, 1H), 4.58-4.71 (m, 1H), 4.96-5.17 (m, 2H), 5.19-5.45 (m, 1H), 7.23-7.48 (m, 5H). Analytical HPLC 16.36 min. LC-MS (ES$^+$) m/e=395.3 (MH$^+$).

1-[2-(4-Amino-3-chloro-benzoylamino)-propionyl]-4-fluoro-pyrrolidine-2-carboxylic acid-tert-butyl ester (107)

A suspension of 106 (2.65 g, 6.72 mmol) in MeOH (40 ml) and 10% Pd/C (1.32 g) was stirred under an atmosphere of $H_2$ for 1.5 hours, filtered through celite and the concentrated to give a waxy solid (1.694 g). The solid was dissolved in $CH_2Cl_2$ (25 ml) and treated with DIEA (3.4 ml, 19.5 mmol), 4-amino-3-chlorobenzoic acid (1.362 g, 7.9 mmol), HOBT (1.164 g, 8.62 mmol) and EDC (1.645 g, 8.57 mmol) at 0° C. under $N_2$. The mixture was allowed to warm to room temperature and stirred for 18 hours. The solvent was concentrated in vacuo. The residue was dissolved in EtOAc, washed with water (4×), 0.5N $NaHSO_4$ (2×), saturated $NaHCO_3$ (2×) and brine. The organic layer was dried over anhydrous $Na_2SO_4$ and evaporated to give a white solid which was purified by flash column chromatography, using $CH_2Cl_2$/MeOH (99/1 to 98/2%). The product obtained as a white solid (2.705 g, 97%). $^1$H-NMR (500 MHz, $CD_3OD$) δ 1.33 (s, 9H), 1.48 (d, 3H), 2.31-2.55 (m, 2H), 3.93 (d,d, 1H), 4.02-4.21 (m, 1H), 4.59-4.76 (m, 1H), 5.31 (br s, 0.5H), 5.41 (br s, 0.5H), 6.78 (d, 1H), 7.57 (d,d, 1H), 7.78 (s, 1H), 8.31 (d, 1H). Analytical HPLC 14.14 min. LC-MS (ES$^+$) m/e=414.2 (MH$^+$)

1-[2-(4-Amino-3-chloro-benzoylamino)-propionyl]-4-fluoro-pyrrolidine-2-carboxylic acid (2-benzyloxy-5-oxo-tetrahydro-furan-3-yl)-amide (108a)

Prepared from syn-(2-benzyloxy-5-oxo-tetrahydro-furan-3-yl)-carbamic acid allyl ester and 107a following the method used for the synthesis of 98a. The title compound was isolated as a white solid (41 mg, 15% yield). $^1$H-NMR (500 MHz, $CD_3OD$) δ 0.94 (d, 0.3H), 1.07 (d, 1H), 1.40 (m, 1.7H), 2.21-2.65 (m, 2.2H), 2.70-2.85 (m, 1.4H), 2.96-3.08 (m, 1.4H), 2.96-3.08 (dd, 0.4H), 3.57-4.24 (m, 3H), 4.41-4.93 (m, 4H), 5.14-5.45 (M, 1H), 5.60-5.67 (m, 0.6H), 5.77 (d, 0.4H), 6.77 (dd, 1H), 7.15-7.41 (m, 5H), 7.51-7.62 (m, 1H), 7.77 (dd, 1H) Analytical HPLC 12.83 min. LC-MS (ES$^+$) m/e=547.1 (MH$^+$)

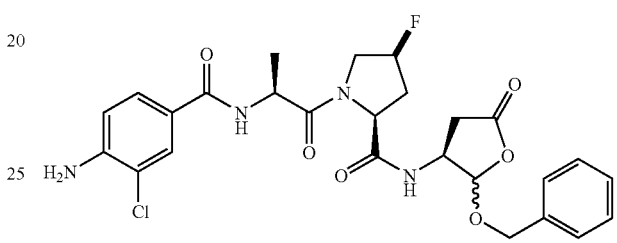

108b

1-[2-(4-Amino-3-chloro-benzoylamino)-propionyl]-4-fluoro-pyrrolidine-2-carboxylic acid (2-benzyloxy-5-oxo-tetrahydro-furan-3-yl)-amide (108b)

Prepared from (2-benzyloxy-5-oxo-tetrahydro-furan-3-yl)-carbamic acid allyl ester 107a following the method used for the synthesis of 98a. The title compound was isolated as a white solid (654 mg, 54% yield). $^1$H-NMR (500 MHz, $CD_3OD$) δ 1.07 (d, 0.5H), 1.25-1.56 (m, 2.5H), 2.21-2.65 (m, 2.3H), 2.68-2.89 (m, 1H), 2.91-3.10 (m, 0.7H), 3.57-4.23 (m, 2H), 4.32-4.95 (m, 5H), 5.16-5.52 (m, 1H), 5.45-5.50 (m, 0.3H), 5.54-5.58 (m, 0.2H), 5.61-5.67 (m, 0.3H), 5.77 (d, 0.2H), 6.72-6.84 (m, 1H), 7.16-7.41 (m, 5H), 7.50-7.65 (m, 1H), 7.71-7.87 (m, 1H). Analytical HPLC 12.83 min. LC-MS (ES$^+$) m/e=547.1 (MH$^+$).

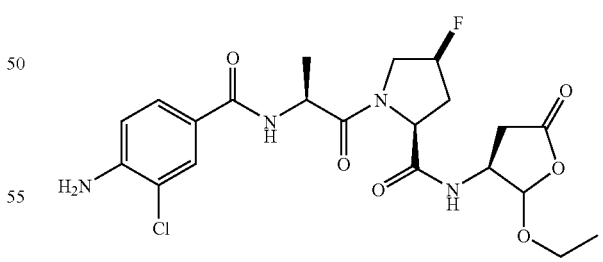

108c

108a

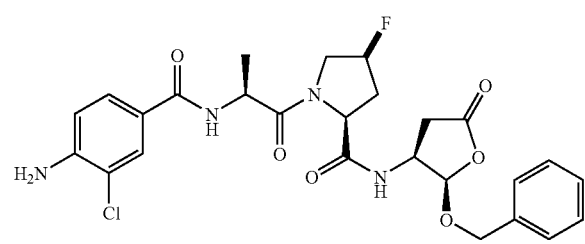

1-[2-(4-Amino-3-chloro-benzoylamino)-propionyl]-4-fluoro-pyrrolidine-2-carboxylic acid (2-ethoxy-5-oxo-tetrahydro-furan-3-yl)-amide (108c)

Prepared from syn-(2-ethoxy-5-oxo-tetrahydro-furan-3-yl)-carbamic acid allyl ester and 107a following the method used for the synthesis of 98a to give the title compound (100.3 mg, 38% yield). $^1$H-NMR (500 MHz, CD3OD) δ

1.09 (t, 1.2H), 1.25 (t, 1.8H), 1.40 (d, 1H), 1.49 (d, 2H), 2.33-2.61 (m, 2H), 2.65-2.95 (m, 2H), 3.44-4.30 (m, 4H), 4.47-4.79 (m, 3H), 5.18-5.25 (m, 0.2H), 5.27-5.36 (m, 0.5H), 5.39-5.46 (m, 0.3H), 5.56 (m, 1H), 6.72-6.94 (m, 0.8H), 7.54-7.69 (m, 0.8H), 7.79 (d, 0.55H), 8.06 (d, 0.55H), 9.00 (d, 0.3H). Analytical HPLC 8.46 min. LC-MS (ES+) m/e=485.2 (MH+).

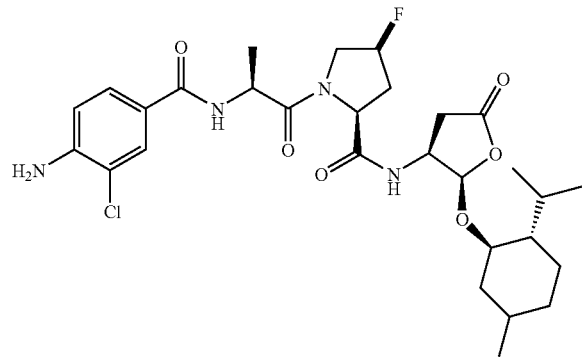

108d

1-[2-(4-Amino-3-chloro-benzoylamino)-propionyl]-4-fluoro-pyrrolidine-2-carboxylic acid [2-(2-isopropyl-5-methyl-cyclohexyl)-5-oxo-tetrahydro-furan-3-yl]-amide (108d)

Prepared from {2-[1R-(2S-Isopropyl-5R-methyl-cyclohexyloxy)]-5-oxo-tetrahydro-furan-3-yl}-carbamic acid allyl ester and 107a following the method used for the synthesis of 98a to give the title compound (95 mg, 31% yield). 1H-NMR (500 MHz, CD3OD) δ 0.42 (d, 2H), 0.57 (d, 2H), 0.60-1.10 (m, 10H), 1.22-1.76 (m, 6H) 1.96-2.17 (m, 1H), 2.29-2.60 (m, 2H), 2.61-2.88 (m, 1.5H), 3.02-3.23 (dd, 0.5H), 3.37-3.47 (m, 0.5H), 3.50-3.61 (m, 0.5H), 3.63-4.24 (m, 2H), 4.48-4.62 (m, 3H), 5.18-5.48 (m, 1H), 5.72 (d, 0.4H), 5.82 (d, 0.6H), 6.77-6.84 (m, 1H), 7.53-7.67 (m, 1H), 7.78 (d, 0.4H), 7.84 (d, 1H) Analytical HPLC 8.34 min. LC-MS (ES+) m/e=595 (MH+).

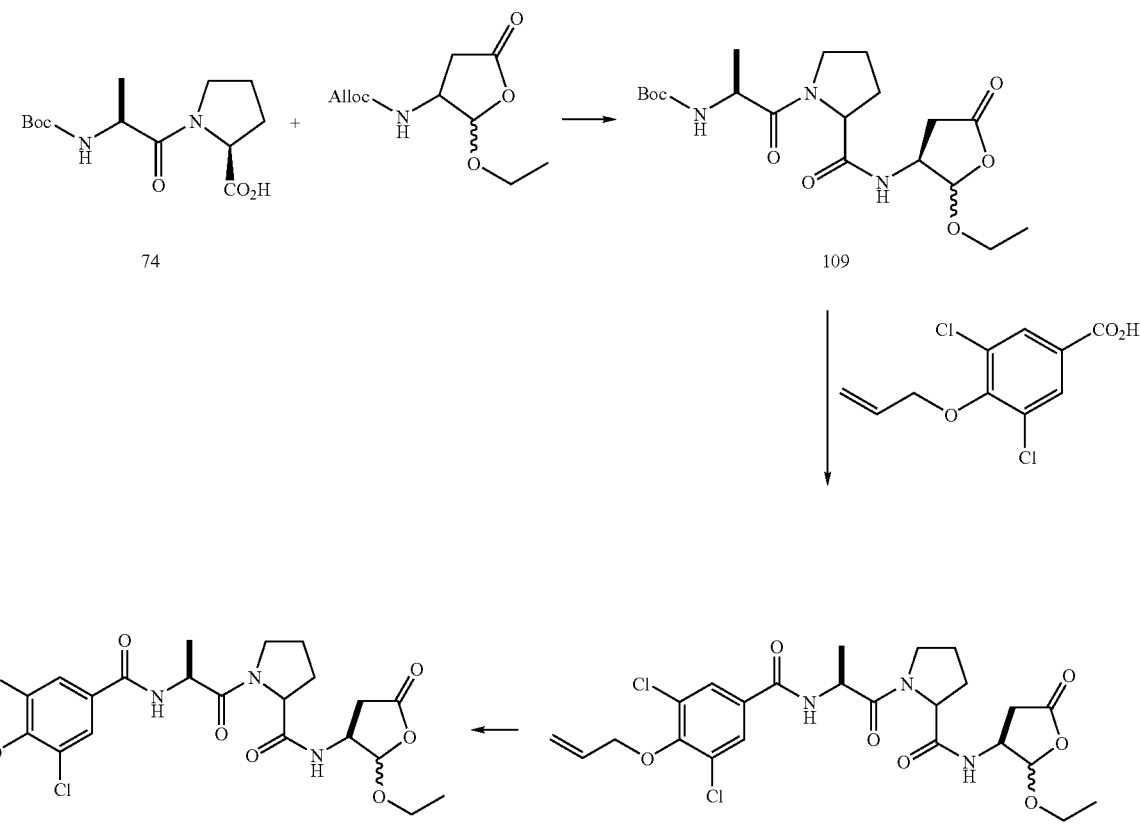

{2-[2-(2-Ethoxy-5-oxo-tetrahydro-furan-3-ylcarbamoyl)-pyrrolidin-1-yl]-1-methyl-2-oxo-ethyl}carbamic acid tert-butyl ester (109)

Prepared from (2-ethoxy-5-oxo-tetrahydro-furan-3-yl) carbamic acid allyl ester 74 following the method used in the synthesis of 75 to give the title compound as a pale yellow solid (660 mg, 73% yield). 1H-NMR (500 MHz, CD3OD) δ 1.14-1.36 (m, 6H), 1.42 (s, 9H), 1.75-2.29 (m, 4H), 2.48 (dd, 0.5H), 2.58 (dd, 0.5H), 2.72-2.85 (m, 0.5H), 2.99 (dd, 0.5H), 3.43-3.91 (m, 4H), 4.07-4.52 (m, 2.5H), 4.53-4.72 (m, 0.5H), 5.37 (s, 0.5H), 5.57 (d, 0.5H). Analytical HPLC (mixture of 2 diastereomers) 7.92, 8.14 min. LC-MS (ES+) m/e=414.3 (MH+).

1-[2-(4-Allyloxy-3,5-dichloro-benzoylamino)-propionyl]-pyrrolidine-2-carboxylic acid (2-ethoxy-5-oxo-tetrahydro-furan-3-yl)-amide (110)

Prepared from 109 and 4-allyloxy-3,5-dichloro-benzoic acid following the method used in the synthesis of 82 to give the title compound as a white solid (228 mg, 65%). 1H-NMR (500 MHz, CD3OD) δ 1.10-1.30 (m, 4H), 1.32-1.52 (m, 3H), 1.63-2.31 (m, 4H), 2.41-2.50 (d, 0.5H), 2.52-2.61 (dd, 0.5H), 2.67-2.81 (m, 0.5H), 2.94-3.05 (dd, 0.5H), 3.47-3.96 (m, 4H), 4.21-4.81 (m, 5H), 5.22-5.32 (m, 1H), 5.35-5.49 (m, 1.5H), 5.55-5.63 (m, 0.5H), 6.06-6.21 (m, 1H), 7.90 (s, 2H). Analytical HPLC (mixture of 2 diastereomers) 12.56 min. LC-MS (ES+) m/e=542.3(MH+)

1-[2-(3,5-Dichloro-4-hydroxy-benzoylamino)-propionyl]-pyrrolidine-2-carboxylic acid (2-ethoxy-5-oxo-tetrahydro-furan-3-yl)-amide (111)

To a solution of 110 (194 mg, 0.36 mmol) in CH2Cl2 (5 ml) was added DMBA (70.7 mg, 0.45 mmol) and Pd(PPh3)4 (50.3 mg, 0.044 mmol) at 0° C. The solution was warmed to room temperature after 15 mins, stirred for 2 hours, diluted with CH2Cl2 then washed with water (2×) and brine. The organic layer was dried over anhydrous Na2SO4 and evaporated to give the crude product. Flash chromatography using CH2Cl2/MeOH (99/1 to 95/5%) afforded the title compound (138.6 mg, 77% yield). $^1$H-NMR (500 MHz, CD$_3$OD) δ 1.13-1.31 (m, 3H), 1.35-1.49 (m, 3H), 1.84-2.35 (m, 4H), 2.43-3.05 (m, 2H), 3.48-3.93 (m, 4H), 4.22-4.80 (m, 3H), 5.38 (d, 0.4H), 5.46 (s, 0.1H), 5.55-5.61 (m, 0.5H), 7.76-7.94 (m, 2H). Analytical HPLC 8.70 min. LC-MS (ES$^+$) m/e=502.2 (MH$^+$).

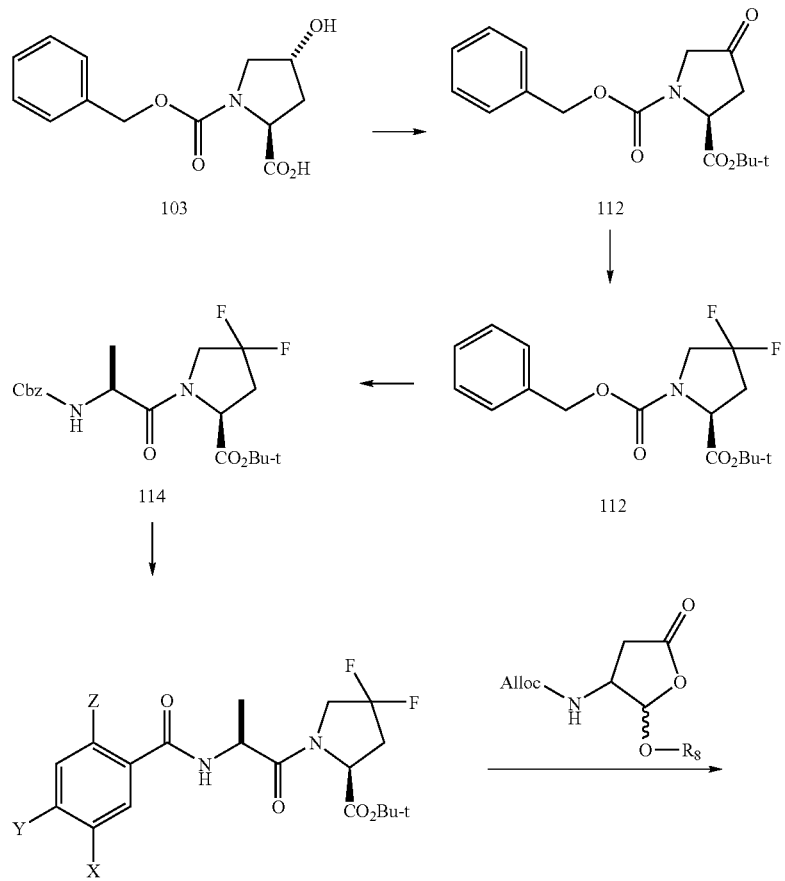

Scheme XXI

-continued

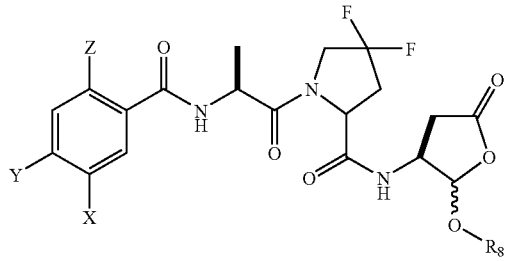

116a-116h

Compounds 116a-116h were prepared as described above for compounds 98 only substituting 1-(2-benzyloxycarbonylamino-propionyl)-4,4-difluoro-pyrrolidine-2-carboxylic acid tert-butyl ester (114) for 1-(2-benzyloxycarbonylamino-propionyl)-pyrrolidine-2-carboxylic acid tert-butyl ester (95).

Preparation of 1-(2-benzyloxycarbonylamino-propionyl)-4,4-difluoro-pyrrolidine-2-carboxylic acid tert-butyl ester (114)

A solution of 4,4-difluoro-pyrrolidine-1,2-dicarboxylic acid-1-benzyl ester-2-tert-butyl ester (113) (Karanewsky, et. al., *J. Med. Chem.* 33, pp. 1459-1469 (1990)) (0.42 g, 1.23 mmol) and 10% palladium on carbon (0.22 g) in methanol (6 mL) was stirred at 1 atm hydrogen pressure for 3 h. The mixture was filtered through Celite and evaporated. The residue was dissolved in $CH_2Cl_2$ (4 mL) and DMF (2 mL) and cooled to 0° C. 2-Benzyloxycarbonylamino-propionic acid (0.30 g, 1.35 mmol), EDC (0.30 g, 1.54 mmol), DIEA (0.65 mL) and HOBt (0.17 g, 1.23 mmol) was added and the reaction was stirred 0.5 h at 0° C., then 16 h at room temperature under nitrogen. The solvent was removed in vacuo and the residue was dissolved in ethyl acetate, then was washed with 10% sodium bisulfate, saturated sodium bicarbonate, water and brine, was dried over sodium sulfate and was evaporated. Purification by flash chromatography on silica, eluted with 25:75 ethyl acetate: hexanes provided 1-(2-benzyloxycarbonylamino-propionyl)-4,4-difluoro-pyrrolidine-2-carboxylic acid tert-butyl ester (0.39 g, 77% yield) as a colorless oil.

$^1$H-NMR (500 MHz, $CDCl_3$) δ 1.3-1.6 (m, 12H), 2.5 (m, 0.8H), 2.7 (m, 1.2H), 3.9 (m, 1H), 4.1 (m, 1H), 4.4 (m, 1H), 4.7 (m, 1H), 5.1 (m, 2H), 5.59 (br d, J=7.7 Hz, 0.8H), 5.7 (br d, J=7.7 Hz, 0.2H), 7.35 (m, 5H) ppm. Analytical HPLC (cyano column) 17.069 min. LC-MS (ES+): m/e=413 (M+H), 357 (M+H-tert-butyl), 313 [M+H-($CO_2$tert-butyl)].

116a

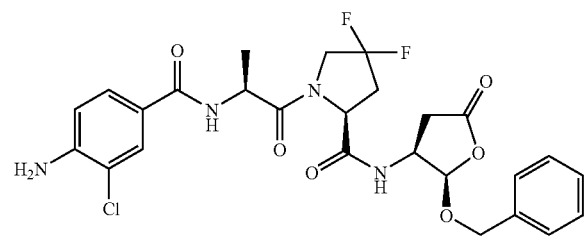

1-[2-(4-Amino-3-chloro-benzoylamino)-propionyl]-4,4-difluoro-pyrrolidine-2-carboxylic acid (2-benzyloxy-5-oxo-tetrahydro-furan-3-yl)-amide (116a)

Prepared from 115a and syn-40 to afford the title compound as an off-white solid (0.14 g, 73% yield). $^1$H-NMR (500 MHz, $CD_3OD$) δ 1.0-1.5 (m, 3H), 2.0-3.5 (m, 4H+$CH_3OH$), 3.5-5.5 (M, 6H+$H_2O$), 5.6-5.8 (m, 1H), 6.7-6.8 (m, 1H), 7.1-7.8 (m, 8H), 8.2-8.6 (m, 1H) ppm. Analytical HPLC (cyano column) 13.744 min. LC-MS (ES+) m/e=565 (M+H).

116b

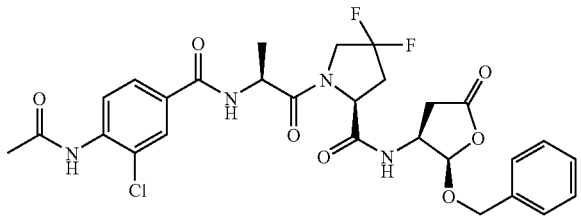

1-[2-(4-Acetylamino-3-chloro-benzoylamino)-propionyl]-4,4-difluoro-pyrrolidine-2-carboxylic acid (2-benzyloxy-5-oxo-tetrahydro-furan-3-yl)-amide (116b)

Prepared from 115b and syn-40 to afford the title compound as an off-white solid (0.08 g, 38% yield) $^1$H-NMR (500 MHz, $CDCl_3$) δ 1.03 (d, J=6.9 Hz, 0.4H), 1.30 (d, J=6.9 Hz, 0.6H), 2.25 (d, J=2.9 Hz, 3H), 2.4-3.2 (m, 4H), 3.6-4.4 (m, 4H), 4.6-4.9 (m 3H), 5.52 (d, J=5.2 Hz, 0.6H), 5.78 (d, J=5.2 Hz, 0.4H), 6.6 (br s, 1H), 6.9-7.9 (m, 8H), 8.39 (d, J=8.1 Hz, 0.4H), 8.44 (d, J=8.3 Hz, 0.6H), 8.74 (d, J=6.8 Hz, 1H) ppm. Analytical HPLC (cyano column) 11.830 min. LC-MS (ES+): m/e=607 (M+H).

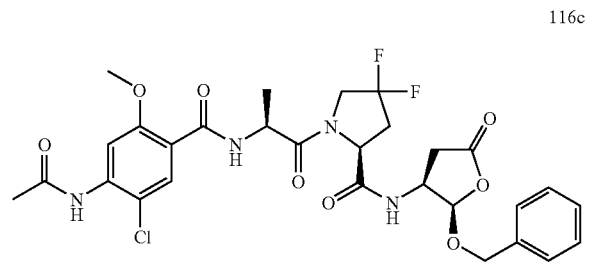

1-[2-(4-Acetylamino-5-chloro-2-methoxy-benzoylamino)-propionyl]-4,4-difluoro-pyrrolidine-2-carboxylic acid (2-benzyloxy-5-oxo-tetrahydro-furan-3-yl)-amide (116c)

Prepared from 115c and syn-40 to afford the title compound as an off-white (0.07 g, 29% yield). $^1$H-NMR (500 MHz, CDCl$_3$) δ 0.99 (d, J=6.9 Hz, 1.35H), 1.32 (d, J=6.9 Hz, 1.65H), 2.25 (s, 1.5H), 2.26 (s, 1.5H), 2.3-3.2 (m, 4H), 3.95 (s, 0.55H), 3.98 (s, 0.45H), 3.7-4.1 (m, 2.5H), 4.2-4.5 (m, 1.5H), 4.6-4.9 (m, 3H), 5.52 (d, J=5.3 Hz, 0.55H), 5.80 (d, J=5.3 Hz, 0.45H), 7.0-7.4 (m, 4H), 7.7-7.9 (m, 2H), 8.0-8.4 (m, 2H), 8.49 (d, J=6.5 Hz, 1H), 8.93 (d, J=6.7 Hz, 1H) ppm. Analytical HPLC (cyano column) 12.959 min. LC-MS (ES+): m/e=637 (M+H).

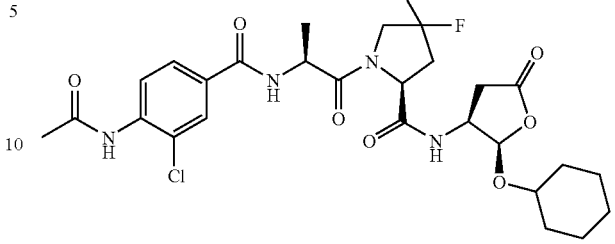

1-[2-(4-Acetylamino-3-chloro-benzoylamino)-propionyl]-4,4-difluoro-pyrrolidine-2-carboxylic acid (2-cyclohexyloxy-5-oxo-tetrahydro-furan-3-yl)-amide (116e)

Prepared from 115b and syn-(2-cyclohexyloxy-5-oxo-tetrahydro-furan-3-yl)-carbamic acid allyl ester to afford the title compound as a 93:7 mixture of epimers. $^1$H-NMR (500 MHz, CDCl$_3$) δ 1.0-2.0 (m, 13H), 2.25 (s, 2H), 2.26 (s, 1H), 2.40 (dd, J=17.3, 10.1 Hz, 1H), 2.84 (dd, J=17.3, 8.5 Hz, 1H), 2.5-3.0 (m, 2H), 3.5-4.3 (m, 3.5H), 4.5-4.9 (m, 2.5H), 5.59 (d, J=5.3 Hz, 0.75H), 5.76 (d, J=5.2 Hz, 0.25 H), 6.74 (br d, J=5.7 Hz, 0.25H), 6.93 (br d, J=7.1 Hz, 1H), 7.06 (br d, J=7.8 Hz, 0.75H), 7.62 (dd, J=8.6, 2.0 Hz, 1H), 7.78 (m, 1H), 7.85 (d, J=2.0 Hz, 1H), 8.35 (br d, J=6.6 Hz, 0.25H), 8.50 (br d, J=8.2 Hz, 0.75H) ppm. Analytical HPLC (C18 column) 17.112 (93%), 17.433 (7%) min. LC-MS (ES+): m/e=599 (M+H).

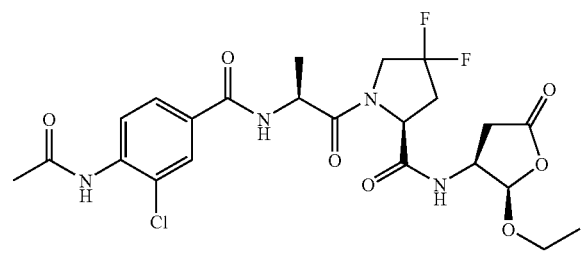

1-[2-(4-Acetylamino-3-chloro-benzoylamino)-propionyl]-4,4-difluoro-pyrrolidine-2-carboxylic acid (2-ethoxy-5-oxo-tetrahydro-furan-3-yl)-amide (116d)

Prepared from 115b and syn-(2-ethoxy-5-oxo-tetrahydro-furan-3-yl)-carbamic acid allyl ester to afford the title compound as a 92:8 mixture of epimers. Off-white solid (0.27 g, 66% yield). $^1$H-NMR (500 MHz, CDCl$_3$) δ 1.0-1.5 (m, 6H), 2.25 (s, 1.8H), 2.26 (s, 1.2H), 2.3-3.1 (m, 4H), 3.3-4.3 (m, 4H), 4.5-4.9 (m, 3H), 5.45 (d, J=5.3 Hz, 0.75H), 5.59 (d, J=5.2 Hz, 0.25H), 6.7-7.1 (m, 2H), 7.62 (dd, J=8.7, 2.0 Hz, 1H), 7.76 (m, 1H), 7.85 (d, J=2.0 Hz, 1H), 8.48 (m, 1H) ppm. Analytical HPLC (C18 column) 13.300 (91.8%), 14.046 (8.2%) min. LC-MS (ES+): m/e 545 (M+H).

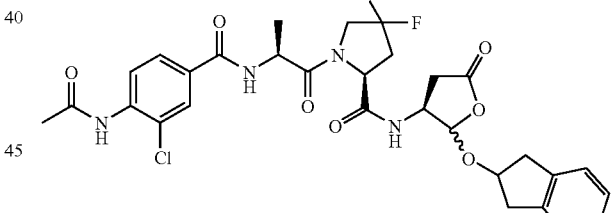

1-[2-(4-Acetylamino-3-chloro-benzoylamino)-propionyl]-4,4-difluoro-pyrrolidine-2-carboxylic acid [2-(indanol-2-yl)oxy-5-oxo-tetrahydro-furan-3-yl]-amide (116f)

Prepared from 115b and [2-(indanol-2-yl)oxy-5-oxo-tetrahydro-furan-3-yl)-carbamic acid allyl ester to afford the title compound as a 62:38 mixture of epimers. Off-white solid (0.34 g, 71% yield). $^1$H-NMR (500 MHz, CDCl$_3$) δ 1.09 (d, J=6.9 Hz, 0.6H), 1.21 (d, J=6.9 Hz, 0.9H), 1.33 (d, J=6.9 Hz, 0.9H), 1.42 (d, J=6.9 Hz, 0.6H), 2.28 (s, 2H), 2.29 (s, 1H), 2.40 (dd, J=17.4, 10.3 Hz, 1H), 2.4-3.3 (m, 7H), 3.6-4.2 (m, 2H), 4.5-4.8 (m, 4H), 5.66 (m, 0.6H), 5.84 (d, J=4.3 Hz, 0.2H), 6.22 (m, 0.2H), 6.7-7.0 (m, 2H), 7.2-7.3 (m, 4H), 7.5-7.7 (m, 1H), 7.8-8.0 (m, 2H), 8.52 (m, 0.6H), 8.62 (br d, J=6.5Hz, 0.4H) ppm. Analytical HPLC (C18 column) 16.556 (62.0%), 16.824 (38.0%) min. LC-MS (ES+): m/e=633 (M+H).

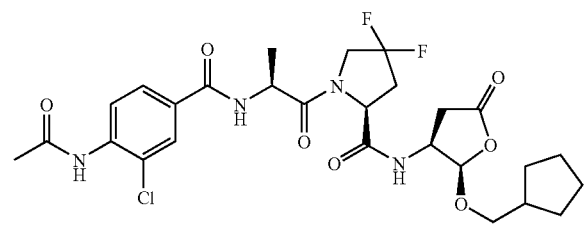

1-[2-(4-Acetylamino-3-chloro-benzoylamino)-propionyl]-4,4-difluoro-pyrrolidine-2-carboxylic acid (2-cyclopentylmethoxy-5-oxo-tetrahydro-furan-3-yl)-amide (116g)

Prepared from 115b and syn-(2-cyclopentylmethoxy-5-oxo-tetrahydro-furan-3-yl)-carbamic acid allyl ester to afford the title compound as an off-white solid (0.20 g, 44% yield). $^1$H-NMR (500 MHz, CDCl$_3$) δ 1.0-1.8 (m, 11H), 1.9-3.0 (m, 5H), 2.26 (s, 3H), 3.29 (m, 0.25H), 3.47 (m, 0.75H), 3.58 (m, 0.25H), 3.74 (m, 0.75H), 3.8 (m, 0.75H), 4.1 (m, 0.25H), 4.25 (m, 1H), 4.4-4.8 (m, 3H), 5.44 (d, J=5.2 Hz, 0.75H), 5.62 (d, J=5.2 Hz, 0.25H), 6.7 (br 0.25H), 6.91 (d, J=7.1 Hz, 1H), 7.1 (m, 0.75H), 7.59 (d, J=8.5 Hz, 0.25H), 7.63 (dd, J=8.5, 2.5 Hz, 0.75H), 7.75 (m, 1H), 7.86 (d, J=1.8 Hz, 1H), 8.33 (br d, J=6.5 Hz, 0.25H), 8.49 (br d, J=8.4 Hz, 0.75H) ppm. Analytical HPLC (C18 column) 17.705 min. LC-MS (ES+): m/e=599 (M+H).

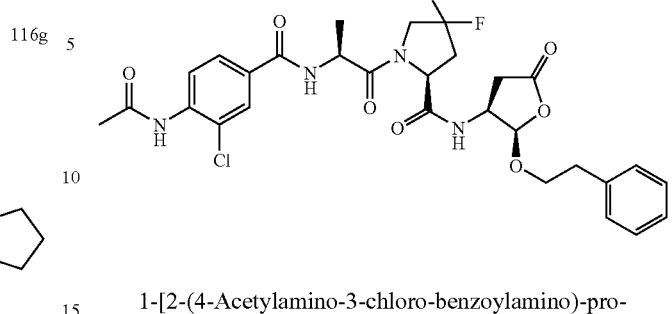

1-[2-(4-Acetylamino-3-chloro-benzoylamino)-propionyl]-4,4-difluoro-pyrrolidine-2-carboxylic acid (2-phenylethoxy-5-oxo-tetrahydro-furan-3-yl)-amide (116h)

Was prepared from 115b and syn-(5-oxo-2-phenethyloxy-tetrahydro-furan-3-yl)-carbamic acid allyl ester to afford the title compound as an off-white solid (0.15 g, 24% yield). $^1$H-NMR (500 MHz, CDCl$_3$) δ 1.29 (d, J=6.9 Hz, 0.75H), 1.40 (d, J=6.9 Hz, 2.25H), 2.25 (s, 2.25H), 2.26 (s, 0.75H), 2.3-3.0 (m, 6H), 3.7-4.8 (m, 7H), 5.38 (d, J=5.3 Hz, 0.75H), 5.67 (d, J=5.1 Hz, 0.25H), 6.65 (m, 1H), 6.90 (d, J=7.0 Hz, 0.75H), 7.06 (d, J=7.6 Hz, 0.25H), 7.1-7.3 (m, 5H), 7.57 (d, J=8.6 Hz, 0.25H), 7.63 (d, J=8.6 Hz, 0.75H), 7.75 (m, 1H), 7.86 (d, J=1.8 Hz, 1H), 8.35 (d, J=6.2 Hz, 0.25H), 8.49 (d, J=8.3 Hz, 0.75H) ppm. Analytical HPLC (C18 column) 17.265 min. LC-MS (ES+): m/e=621 (M+H).

Scheme XXII

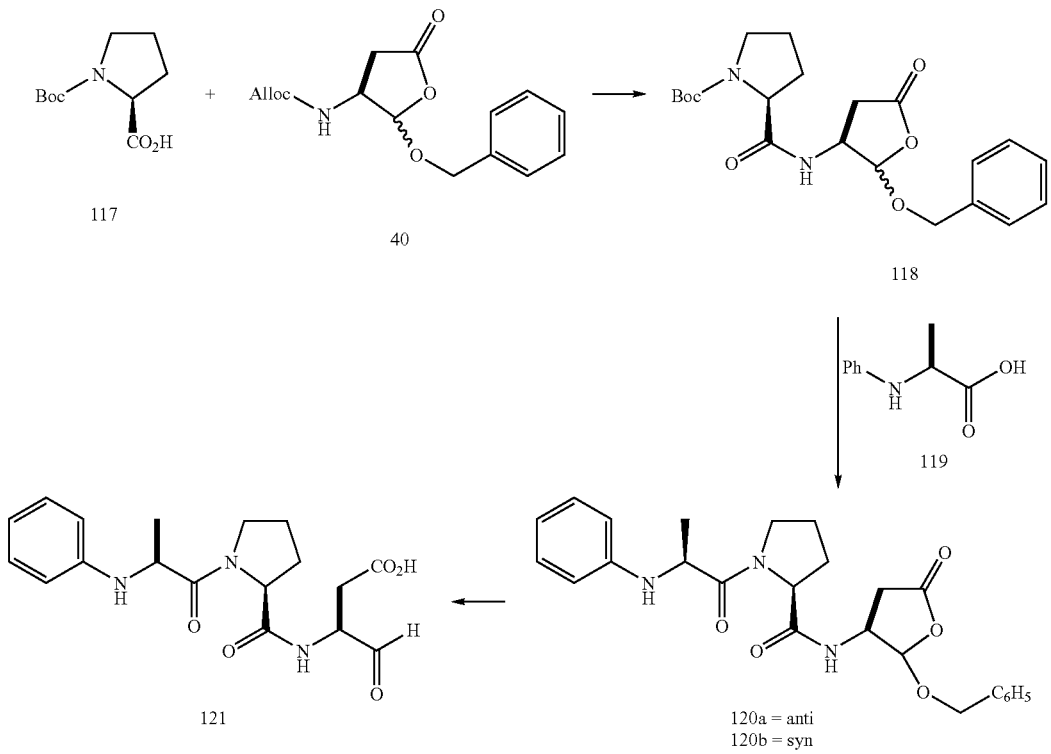

2-(2-Benzyloxy-5-oxo-tetrahydro-furan-3-ylcarbamoyl)-pyrrolidine-1-carboxylic acid tert-butyl ester (118)

Prepared from 40 (1.16 g, 4.0 mmol) and Boc-Pro-OH according to the procedure used to prepare 100 (Scheme XVIII) to afford 1.53 g (94% yield) of the title compound as a white solid. $^1$H-NMR (500 MHz, CDCl$_3$): δ 1.61 (br, 9H), 1.88 (br, 2H), 2.00-2.50 (m, 3H), 2.80-3.10 (m, H), 3.20-3.60 (m, 2H), 4.05-4.45 (m, 1.5H), 4.58-4.80 (m, 1.5H), 4.83-4.98 (m, H), 5.43-5.53 (m, H), 7.26-7.45 (m, 5H), 7.60-7.80 (d, H); Analytical HPLC: 11.32 min; LC-MS: m/e=405 (M+H$^+$).

2-Phenylaminopropionic acid (119)

A mixture of alanine (356 mg, 4.0 mmol), iodobenzene (816 mg, 4.0 mmol), trans-dichlorobis(tri-o-tolylphosphine)palladium(II) {Pd[P(o-Tol)$_3$]$_2$Cl$_2$} (160 mg, 0.2 mmol), copper(I) iodide (40 mg, 0.2 mmol), K$_2$CO$_3$ (552 mg, 4.0 mmol), benzyltriethylammonium chloride (160 mg, 0.8 mmol), triethylamine (1.6 mL) and water (0.8 mL) in DMF (8 mL) was stirred under nitrogen atmosphere at 100° C. for 20 hours. The mixture was cooled to room temperature, diluted with ethyl acetate (50 mL) and water (50 mL), acidified with 6N HCl to the pH=2 to 3. The aqueous layer was extracted with ethyl acetate (50 mL×4). The combined organic layers were washed with water, brine, dried over anhydrous Na$_2$SO$_4$, filtered and evaporated in vacuo to give a red oil. Flash chromatography using hexane/ethyl acetate/acetic acid (95/5/0.5 to 80/20/0.5) to afford 300 mg (45% yield) of the title compound as a pink solid. $^1$H-NMR (500 MHz, CDCl$_3$/CD$_3$OD=0.5 ml/3 drops) δ 1.45 (d, 3H), 4.02-4.15 (m, H), 6.57-6.70 (m, 3H), 7.11-7.25 (m, 2H); Analytical HPLC: 6.10 min. LC-MS: m/e=166 (M+H$^+$).

1-(2-Phenylamino-propionyl)-pyrrolidine-2-carboxylic acid (2-benzyloxy-5-oxo-tetrahydro-furan-3-yl)-amide (120a and 120b)

A solution of 118 (405 mg, 1.0 mmol) was treated with TFA (2 mL) in CH$_2$Cl$_2$ (2 mL) for one hour. The reaction solution was evaporated in vacuo and azeotrapped with CH$_2$Cl$_2$ four times to give pyrrolidine-2-carboxylic acid (2-benzyloxy-5-oxo-tetrahydro-furan-3-yl)-amide as a pale yellow solid. $^1$H-NMR (500 MHz, CDCl$_3$): δ 1.87-2.15 (m, 4H), 2.30-2.70 (m, 2H), 2.80-3.08 (m, H), 3.45 (br, 2H), 4.35-4.98 (m, 3H), 5.30-5.56 (m, H), 7.10-7.60 (m, 5H); Analytical HPLC: 7.78/8.20 min.; LC-MS: m/e=305 (M+H$^+$).

2-Phenylaminopropionic acid (119) (300 mg, 1.8 mmol) in CH$_2$Cl$_2$ (10 mL) was treated with HOBT (270 mg, 2.0 mmol) and EDC (2.1 g, 11 mmol) at 0° C. for 10 min. Diisopropylethylamine (2 mL) was added followed by a solution of pyrrolidine-2-carboxylic acid (2-benzyloxy-5-oxo-tetrahydro-furan-3-yl)-amide in CH$_2$Cl$_2$ (10 mL). The mixture was stirred at room temperature for 4 hours, diluted with CH$_2$Cl$_2$ (40 mL), washed with water then brine. The organic layer was dried over anhydrous Na$_2$SO$_4$, filtered and evaporated in vacuo to give a pale yellow solid. Flash chromatography using CH$_2$Cl$_2$/methanol (99/1 to 98/2) afforded 151 mg (33% yield) of anti diastereomer of the title compound (120a) and 129 mg (29% yield) of syn diastereomer (120b) as a white solid. $^1$H-NMR (500 MHz, CDCl$_3$) for the anti diastereomer: δ 1.37-1.41 (m, 3H), 1.50-2.45 (m, 4H) 2.60-2.70 (m, 0.3H), 2.89-2.94 (m, 0.7H), 3.40-3.80 (m, 2H), 4.10-4.50 (m, 3H), 4.50-4.90 (m, 3H), 5.26 (s, 0.3H), 5.38 (s, 0.7H), 6.45-6.60 (m, 2.3H), 6.65-6.80 (m, H), 7.10-7.20 (m, 2.5H), 7.25-7.50 (m, 4.5H), 7.53-7.70 (m, 0.7H), 7.82 (d, H). For the syn diastereomer: δ 0.86-0.89 (m, H), 1.20-1.40 (m, 4H), 1.80-2.45 (m, 4H), 2.80-2.86 (m, H), 3.58-3.65 (m, 2H), 4.20-4.40 (m, H), 4.50-4.75 (m, 2H), 4.90 (d, H), 5.52 (d, H), 6.45-6.70 (m, 3H), 6.75-6.85 (m, H), 7.10-7.20 (m, 2.3H), 7.30-7.50 (m, 5.7H); Analytical HPLC: 10.55 min for anti diastereomer and 10.62 min for syn diastereomer; LC/MS: m/e=452 (M+H$^+$) for both diastereomers.

4-Oxo-3-{[1-(2-phenylamino-propionyl)-pyrrolidine-2-carbonyl]-amino}-butyric acid (121)

Prepared from 120 (151 mg, 0.33 mmol) using hydrolysis method A to afford 101 mg (83% yield) of the title compound as a white solid. $^1$H-NMR (500 MHz, CDCl$_3$/CD$_3$OD=1/1): δ 1.20-1.65 (m, 2H), 1.65-2.35 (m, 3H), 2.40-3.00 (m, H), 3.20-3.80 (m, 2H), 3.90-4.90 (m, 7H), 7.25-7.80 (m, 5H); Analytical HPLC: 6.38 min.; LC-MS: m/e=362 (M+H$^+$).

General Procedures for the Preparation of Compounds of Embodiment C Formula I (Schemes XXIII-XXV)

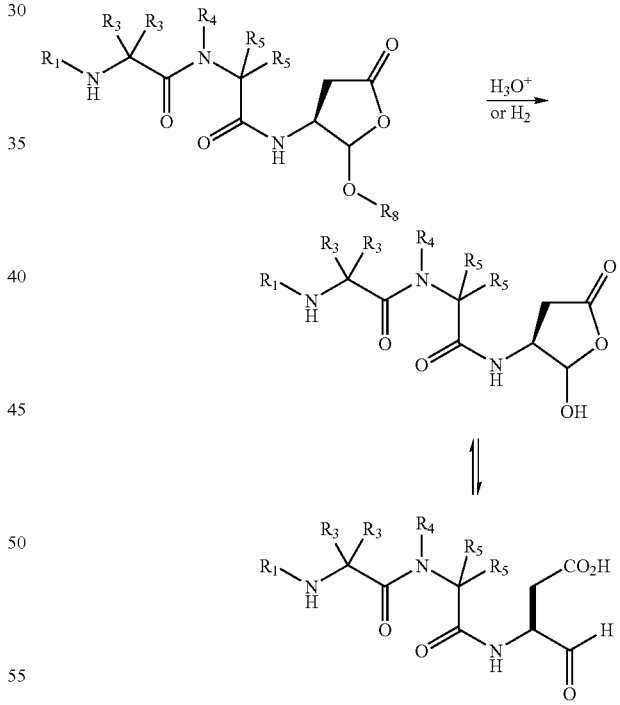

Scheme XXIII

Hydrolysis Method A:

A 0.005-50 mmole sample of the alkylhemiacetal was dissolved in 2.5 N HCl/CH$_3$CN (10/1) and stirred at room temperature until the reaction was complete. The resulting aqueous layer was washed with diethyl ether (2×20 mL) and lyophilized to afford the product.

Hydrolysis Method B:

A 0.005-50 mmole sample of alkylhemiacetal was taken into neat formic acid and stirred overnight at room temperature. The mixture was triturated with a 3:1 mixture of hexane/diethyl ether to give a precipitate. The solvent was decanted and the precipitate washed with diethyl ether to afford the product.

Hydrolysis Method C:

A 0.005-50 mmole sample of the alkylhemiacetal was dissolved in CH$_3$OH and 20% Pd(OH)$_2$/C and stirred under H$_2$ until the reaction was complete. The resulting suspension was filtered and the solution concentrated in vacuo, then triturated with a 3:1 mixture of hexane/diethyl ether to give a precipitate. The is solvent was decanted and the precipitate washed with diethyl ether to afford the product.

Hydrolysis Method D:

A 0.005-50 mmole sample of the alkylhemiacetal in CH$_3$CN/water (1/2) was shaken with acidic resin (Dowex 50w×2, H$^+$ type) until the reaction was complete. The solution was filtered and the resin washed with CH$_3$CN/water (1/4). The resulting water layer was washed with diethyl ether, concentrated to a smaller volume in vacuo then lyophilized to afford the product.

Scheme XXIV

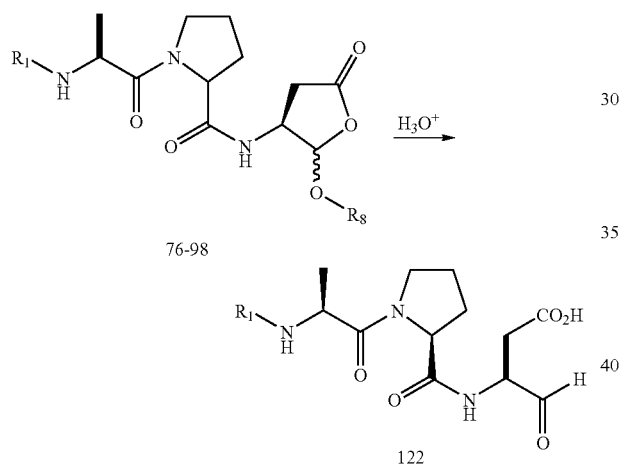

76-98

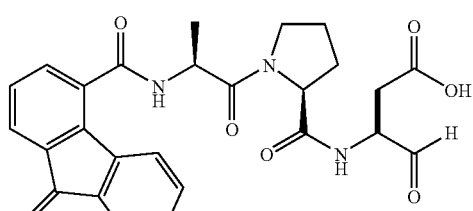

122

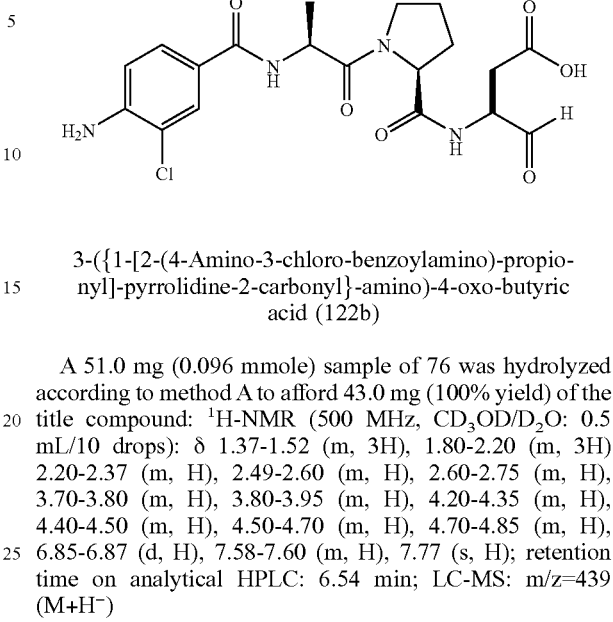

122a

4-Oxo-3-[(1-{2-[9-oxo-9H-fluorene-4-carbonyl)-amino]-propionyl}-pyrrolidine-2-carbonyl)-amino]-butyric acid (122a)

A 109.0 mg (0.19 mmol) sample of 91 was hydrolyzed according to method A to afford 88 mg (96% yield) of the title compound: Analytical HPLC 7.15 min. LC-MS (ES$^+$) m/e=492.2 (M+H).

122b 3-({1-[2-(4-Amino-3-chloro-benzoylamino)-propionyl]-pyrrolidine-2-carbonyl}-amino)-4-oxo-butyric acid (122b)

A 51.0 mg (0.096 mmole) sample of 76 was hydrolyzed according to method A to afford 43.0 mg (100% yield) of the title compound: $^1$H-NMR (500 MHz, CD$_3$OD/D$_2$O: 0.5 mL/10 drops): δ 1.37-1.52 (m, 3H), 1.80-2.20 (m, 3H) 2.20-2.37 (m, H), 2.49-2.60 (m, H), 2.60-2.75 (m, H), 3.70-3.80 (m, H), 3.80-3.95 (m, H), 4.20-4.35 (m, H), 4.40-4.50 (m, H), 4.50-4.70 (m, H), 4.70-4.85 (m, H), 6.85-6.87 (d, H), 7.58-7.60 (m, H), 7.77 (s, H); retention time on analytical HPLC: 6.54 min; LC-MS: m/z=439 (M+H$^-$)

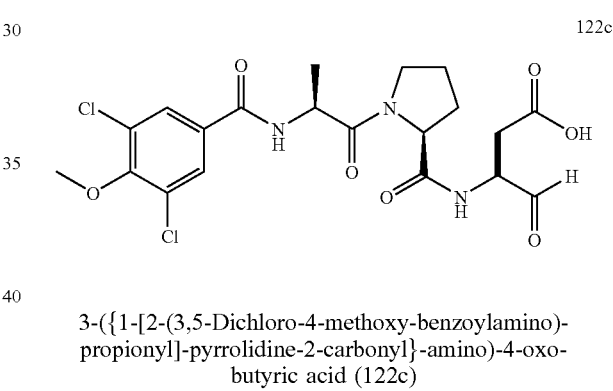

122c 3-({1-[2-(3,5-Dichloro-4-methoxy-benzoylamino)-propionyl]-pyrrolidine-2-carbonyl}-amino)-4-oxo-butyric acid (122c)

A 51.0 mg (0.088 mmole) sample of 92 was hydrolyzed according to method A to afford 24.0 mg (56% yield) of the title compound: Analytical HPLC 6.41 min. LC-MS (ES$^+$) m/e=488.3 (M+H).

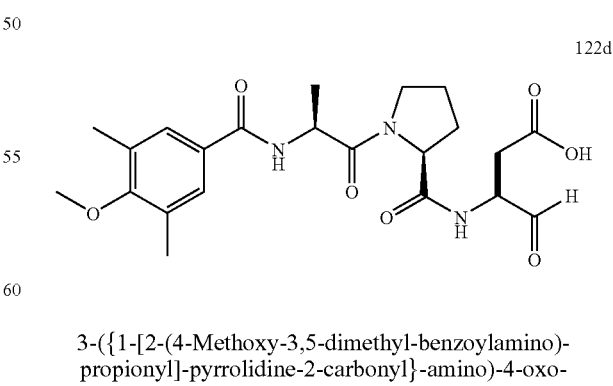

122d 3-({1-[2-(4-Methoxy-3,5-dimethyl-benzoylamino)-propionyl]-pyrrolidine-2-carbonyl}-amino)-4-oxo-butyric acid (122d)

A 55.0 mg (0.102 mmole) sample of 77 was hydrolyzed according to method A to afford 44.0 mg (96% yield) of the title compound: Analytical HPLC (C18) 8.70 min, ¹H-NMR (CDCl₃, 500 MHz): δ 1.23-1.70 (m, 3H), 1.80-2.70 (m, 10H), 2.70-3.15 (m, 2H), 3.58-4.20 (m, 5H), 4.32-5.50 (m, 3H), 5.60-6.00 (m, H), 6.80-7.90 (m, 4H); LC-MS (ES⁺) m/e=448.2 (M+H).

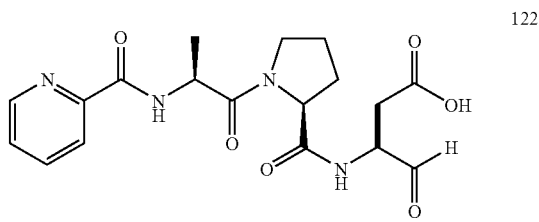

4-Oxo-3-[(1-{2-[pyridine-2-carbonyl)-amino]-propionyl}-pyrrolidine-2-carbonyl)-amino]-butyric acid (122e)

A 55.0 mg (0.114 mmole) sample of 88 was hydrolyzed according to method A to afford 30.0 mg (67% yield) of the title compound Analytical HPLC 4.60 min. LC-MS (ES⁺) m/e=391.3 (M+H).

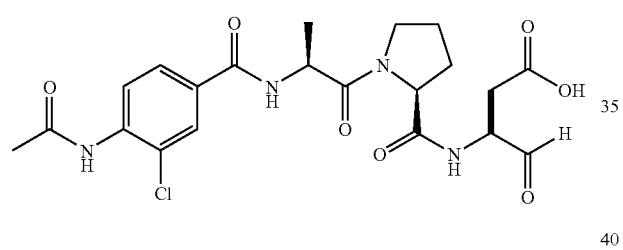

3-({1-[2-(4-Acetylamino-3-chloro-benzoylamino)-propionyl]-pyrrolidine-2-carbonyl}-amino)-4-oxo-butyric acid (122f)

A 52 mg (0.091 mmole) sample of 78 was hydrolyzed according to method A to afford 40 mg (91% yield) of the title compound: ¹H NMR (500 MHz, CD₃OD) δ 1.08-1.61 (m, 3H), 1.77-2.41 (m, 3H), 2.21 (s, 3H), 2.41-2.77 (m, 2H), 3.43-3.63 (m, 0.3H), 3.65-3.76 (m, 1H), 3.81-3.94 (m, 1H), 4.18-4.34 (m, 1H), 4.42-4.64 (m, 1.7H), 4.77 (q, 1H), 7.79 (dd, 1H); Analytical HPLC 4.97 min. LC-MS (ES⁺) m/e=481.3 (M+H).

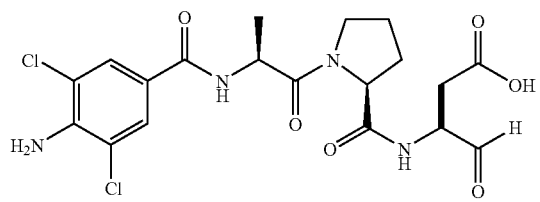

3-({1-[2-(4-Amino-3,5-dichloro-benzoylamino)-propionyl]-pyrrolidine-2-carbonyl}-amino)-4-oxo-butyric acid (122g)

A 44.3 mg (0.079 mmole) sample of 89 was hydrolyzed according to method A to afford 30 mg (81% yield) of the title compound: Analytical HPLC 5.40 min. LC-MS (ES⁺) m/e=473.2 (M+H).

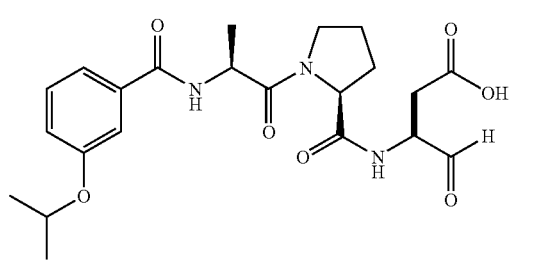

3-({1-[2-(3-Isopropoxy-benzoylamino)-propionyl]-pyrrolidine-2-carbonyl}-amino)-4-oxo-butyric acid (122h)

A 52.0 mg (0.097 mmole) sample of 79 was hydrolyzed according to method A to afford 30.0 mg (69% yield) of the title compound: Analytical HPLC 8.92 min. LC-MS (ES⁺) m/e=448.3 (M+H).

3-({1-[2-(3-benzyloxy-4-methoxy-benzoylamino)-propionyl]-pyrrolidine-2-carbonyl}-amino)-4-oxo-butyric acid (122i)

A 50.8 mg (0.082 mmole) sample of 81 was hydrolyzed according to method A to afford 22.4 mg (52% yield) of the title compound: Analytical HPLC 6.72 min. LC-MS (ES⁺) m/e=526.3 (M+H).

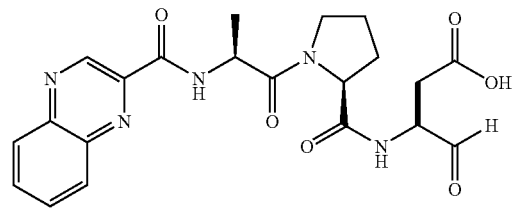

4-Oxo-3-[(1-{2-[(quinoxaline-2-carbonyl)-amino]-propionyl}-pyrrolidine-2-carbonyl)-amino]-butyric acid (122j)

A 38.0 mg (0.072 mmole) sample of 80 was hydrolyzed according to method A to afford 32.0 mg (100% yield) of the title compound: Analytical HPLC 5.95 min. LC-MS (ES+) m/e=442.3 (M+H).

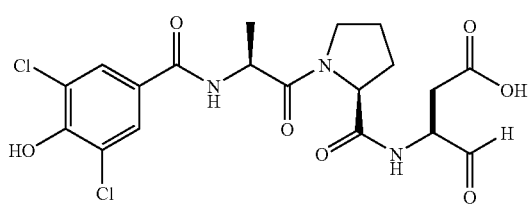

3-({1-[2-(3,5-Dichloro-4-hydroxy-benzoylamino)-propionyl]-pyrrolidine-2-carbonyl}-amino)-4-oxo-butyric acid (122k)

A 35 mg (0.060 mmole) sample of 83 was hydrolyzed according to method A to afford 29.4 mg (75% yield) of the title compound: Analytical HPLC 7.91 min. $^1$H-NMR (500 MHz, CD$_3$OD) δ 1.47 (m, 3H), 1.8-2.3 (m, 4H), 2.49 (m, 1H), 2.61 (m, 1H), 3.5 (br m, 0.2H), 3.69 (br m, 0.9H), 3.84 (br m, 0.9H), 4.27 (m, 1H), 4.46 (m, 1H), 4.57 (m, 1H), 4.73 (m, 1H), 7.83 (m 2H) ppm, LC-MS (ES+) m/e=474.1 (M+H).

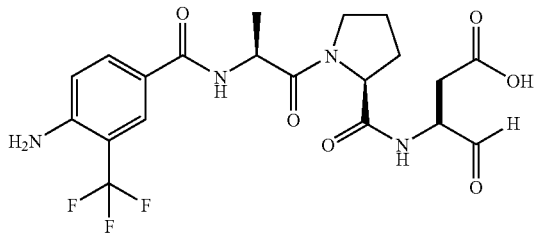

3-({1-[2-(4-Amino-3-trifluoromethyl-benzoylamino)-propionyl]-pyrrolidine-2-carbonyl}-amino)-4-oxo-butyric acid (122l)

A 10 mg (0.021 mmole) sample of 98w was hydrolyzed according to method A to afford 7.9 mg (94% yield) of the title compound: Analytical HPLC 6.64 min. LC-MS (ES+) m/e=473.3 (M+H).

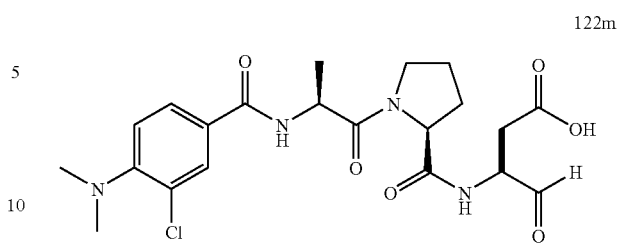

3-({1-[2-(3-Chloro-4-dimethylamino-benzoylamino)-propionyl]-pyrrolidine-2-carbonyl}-amino)-4-oxo-butyric acid (122m)

A 10.0 mg (0.021 mmole) sample of 98x was hydrolyzed according to method A to afford 7.0 mg (84% yield) of the title compound: Analytical HPLC 5.15 min. LC-MS (ES+) m/e=467.3 (M+H).

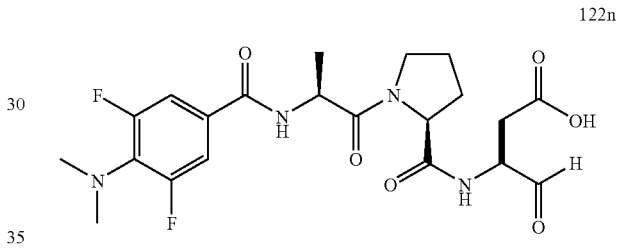

3-({1-[2-(4-Dimethylamino-3,5-difluoro-benzoylamino)-propionyl]-pyrrolidine-2-carbonyl}-amino)-4-oxo-butyric acid (122n)

A 20.0 mg (0.043 mmole) sample of 98y was hydrolyzed according to method A to afford 16.8 mg (100% yield) of the title compound: Analytical HPLC 5.86 min. LC-MS (ES+) m/e=469.3 (M+H).

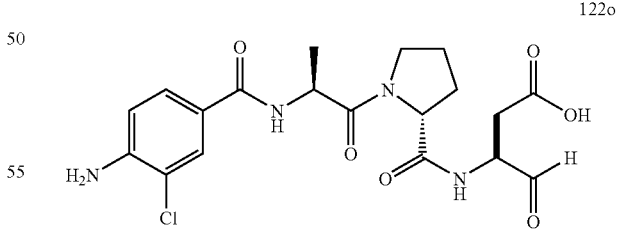

3-({1-[2-(4-Amino-3-chloro-benzoylamino)-propionyl]-pyrrolidine-2-carbonyl}-amino)-4-oxo-butyric acid (122o)

A 20.0 mg (0.046 mmole) sample of 98m was hydrolyzed according to method A to afford 16.7 mg (100% yield) of the title compound: Analytical HPLC 8.47 min. LC-MS (ES+) m/e=439.2 (M+H).

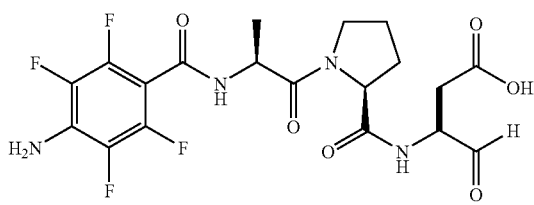

3-({1-[2-(4-Amino-2,3,5,6-tetrafluoro-benzoy-lamino)-propionyl]-pyrrolidine-2-carbonyl}-amino)-4-oxo-butyric acid (122p)

A 20.0 mg (0.042 mmole) sample of 98z was hydrolyzed according to method A to afford 15.3 mg (91% yield) of the title compound: Analytical HPLC 7.90 min. LC-MS (ES+) m/e=477.2 (M+H).

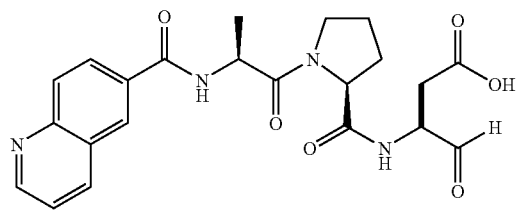

4-Oxo-3-[(1-{2-[(quinoline-6-carbonyl)-amino]-propionyl}-pyrrolidine-2-carbonyl)-amino]-butyric acid (122q)

A 44 mg (0.080 mmole) sample of 93 was hydrolyzed according to method A to afford 41 mg (100% yield) of the title compound: $^1$H NMR (500 MHz, CD$_3$OD) δ 1.24-1.69 (m, 3H), 1.75-2.37 (m, 4H), 2.39-2.87 (m, 2H), 3.46-4.04 (m, 2H), 4.11-4.77 (m, 3H), 8.19 (dd, 1H), 8.33 (d, 1H), 8.56-8.58 (m, 1H), 8.85 (s, 1H), 9.27-9.39 (m, 2H); Analytical HPLC 4.91 min. LC-MS (ES+) m/e=441.2 (M+H).

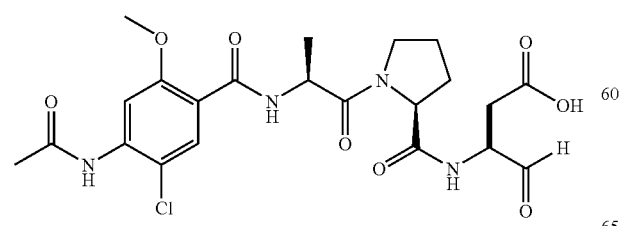

3-({1-[2-(4-Acetylamino-5-chloro-2-methoxy-benzoylamino)-propionyl]-pyrrolidine-2-carbonyl}-amino-4-oxo-butyric acid (122r)

A 44.5 mg (0.074 mmole) sample of 87 was hydrolyzed according to method A to afford 34.5 mg (91% yield) of the title compound: Analytical HPLC 6.88 min. LC-MS (ES+) m/e=511.2 (M+H).

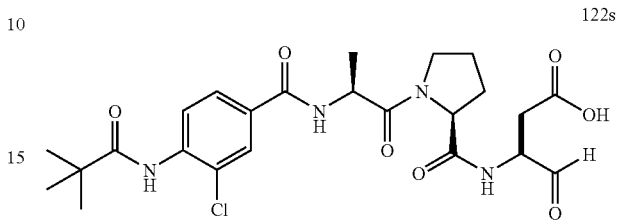

3-[(1-{2-[3-Chloro-4-(2,2-dimethyl-propionylamino)-benzoylamino]-propionyl}-pyrrolidine-2-carbonyl)-amino]-4-oxo-butyric acid (122s)

A 19.0 mg (0.036 mmole) sample of 98aa was hydrolyzed according to method A to afford 14.5 mg (90% yield) of the title compound: Analytical HPLC 7.28 min. LC-MS (ES+) m/e=523.3 (M+H).

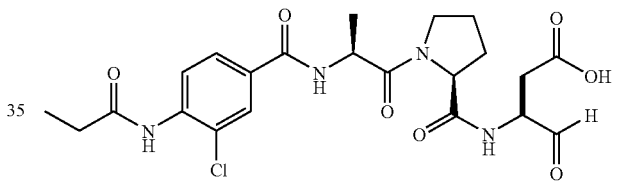

3-({1-[2-(3-Chloro-4-propionylamino-benzoylamino)-propionyl]-pyrrolidine-2-carbonyl}-amino)-4-oxo-butyric acid (122t)

A 21.0 mg (0.042 mmole) sample of 98ab was hydrolyzed according to method A to afford 17.5 mg (97% yield) of the title compound: Analytical HPLC 5.72 min. LC-MS (ES+) m/e=495.2 (M+H).

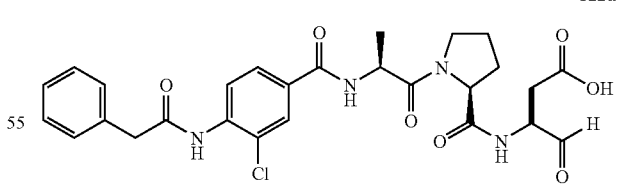

3-({1-[2-(3-Chloro-4-phenylacetylamino-benzoylamino)-propionyl]-pyrrolidine-2-carbonyl}-amino)-4-oxo-butyric acid (122u)

A 10.0 mg (0.017 mmole) sample of 98ac was hydrolyzed according to method A to afford 7.9 mg (85% yield) of the title compound: Analytical HPLC 7.52 min. LC-MS (ES+) m/e=557.2 (M+H).

122v

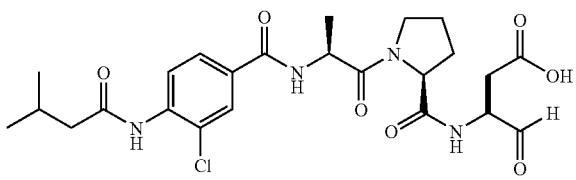

3-[(1-{2-[3-Chloro-4-(3-methyl-butyrylamino)-benzoylamino]-propionyl}-pyrrolidine-2-carbonyl}-amino]-4-oxo-butyric acid (122v)

An 8.0 mg (0.015 mmole) sample of 98ad was hydrolyzed according to method A to afford 6.5 mg (96% yield) of the title compound: Analytical HPLC 6.92 min. LC-MS (ES$^+$) m/e=523.2 (M+H).

Scheme XXV

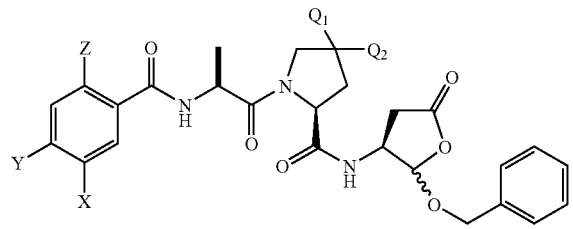

108a, X = Cl, Y = NH$_2$, Z = H, Q$_1$ = F, Q$_2$ = H
116b, X = Cl, Y = AcNH, Z = H, Q$_1$ = Q$_2$ = F
116c, X = Cl, Y = AcNH, Z = CH$_3$O, Q$_1$ = Q$_2$ = F

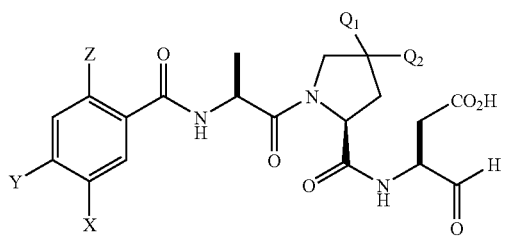

123a, X = Cl, Y = NH$_2$, Z = H, Q$_1$ = F, Q$_2$ = H
123b, X = Cl, Y = AcNH, Z = H, Q$_1$ = Q$_2$ = F
123c, X = Cl, Y = AcNH, Z = CH$_3$O, Q$_1$ = Q$_2$ = F 3-({1-[2-(4-Amino-3-chloro-benzoylamino)-propionyl]-4-fluoro-pyrrolidine-2-carbonyl}-amino)-4-oxo-butyric acid (123a)

A 12.4 mg (0.022 mmole) sample of 108b was hydrolyzed according to method A to afford 9.6 mg (93% yield) of the title compound: Analytical HPLC 6.99 min. LC-MS (ES$^+$) m/e=473.2 (M+H).

3-({1-[2-(4-Acetylamino-3-chloro-benzoylamino)-propionyl]-4,4-difluoro-pyrrolidine-2-carbonyl}-amino)-4-oxo-butyric acid (123b)

A 26.2 mg (0.043 mmole) sample of 116b was hydrolyzed according to method A to afford 10.8 mg (49% yield) of the title compound: Analytical HPLC 9.89 min. LC-MS (ES$^+$) m/e=517.2

3-({1-[2-(4-Acetylamino-3-chloro-2-methoxy-benzoylamino)-propionyl]-4,4-difluoro-pyrrolidine-2-carbonyl)-amino)-4-oxo-butyric acid (123c)

A 23.1 mg (0.036 mmole) sample of 116c was hydrolyzed according to method A to afford 1.8 mg (9% yield) of the title compound: Analytical HPLC 11.87 min. LC-MS (ES$^+$) m/e=547.1 (M+H).

Biological Methods

We obtained in vitro, ex vivo, and in vivo data for selected compounds of this invention using the methods described below. The results are shown in the Tables 2-8. The designation "ND" indicates that the compound was not tested in the described assay.

In the ICE Caspase assays, category "A" indicates <10 nM inhibition. Category "B" indicates 10-1000 nM inhibition. Category "C" indicates >1000 nM inhibition. See Tables 2 and 3.

In the PBMC assay, category "A" indicates <500 nM inhibition. Category "B" indicates 500-1000 nM inhibition. Category "C" indicates 1001-2000 nM inhibition. Category "D" indicates >2000 nM inhibition. See Table Table 4.

In the whole blood assay, category "A" indicates <2500 nM inhibition. Category "B" indicates 2500-7500 nM inhibition. Category "C" indicates >7500 nM. See Table 5

In the in situ metabolism assay, values of [f(g)×f(h)] are disclosed as follows: category "A" indicates <0.25. Category "B" indicates 0.25-0.49. Category "C" indicates 0.5-0.75. Category "D" indicates >0.75. In the biliary excretion measurement, category "A" indicates <5%. Category "B" indicates 5-10%. Category "C" indicates >10%. See Table 6.

In the i.v. clearance assay, values are reported as follows: category "A" indicates <50. Category "B" indicates 50-80. Category "C" indicates >80. See Table 7.

In the bioavailability assay, the Cmax values (µg/ml) are disclosed as follows: category "A" indicates <2.5. Category "B" indicates 2.5-5.0. Category "C" indicates >5.0. The AUC values (µg×hr/ml) are disclosed as follows category "A" indicates <2.5. Category "B" indicates 2.5-5.0. Category "C" indicates >5.0. Half-life (hrs) ranges are disclosed as follows: category "A" indicates <1.5. Category "B" indicates 1.5-2.0. Category "C" indicates >2.0. The F values (%) are disclosed as follows: category "A" indicates <33. Category "B" indicates 33-67. Category "C" indicates >67. See Table 8.

In Vitro Assays

Enzyme Inhibition

Ki values for test compounds with the various caspases were obtained by the method of Margolin et al. (*J. Biol. Chem.*, 272 pp. 7223-7228 (1997)). Assays were performed in 10 mM Tris (Sigma Corp, St Louis Mo.) pH 7.5, 1 mM Dithiothreitol (DTT, Research Organic INC, Cleveland, Ohio) and 0.1% CHAPS (Pierce, Rockford Ill.) at 37° C. For caspase-3, a solution of 8% glycerol was added to the assay buffer to improve enzyme stability. A 65 µL aliquot of the assay buffer and 5 µL aliquot of the appropriate dilutions of inhibitor in DMSO where pipetted into a 96 well plate, treated with 10 µL of caspase, then diluted in assay buffer (0.5-40 nM active protein by active site titration). A control containing DMSO but no compound was included for each determination. The plates were then incubated for 15 minutes at 37° C., before addition of the appropriate substrate (20 µL, final concentration 1-4×$K_M$, final assay volume 100 µL) to initiate the reaction. Reaction rates were measured at 37° C. either by following the time dependant increase in absorbance at 405 nM (for the pNA substrates) or in fluorescence (Ex 390, Em 460) (for the AMC substrates). The rates obtained were plotted against inhibitor concentration and the data fit to the Morrison tight-binding equation for competitive inhibitors (Morrison, J. F., *Biochem. Biophys. Acta,* 185 pp. 269-286 (1969)). The substrates used for the individual assays were as follows:

Caspase-1 Suc-YVAD-pNA (Bachem, King of Prussia, Pa.) (final concentration in the assay 80 µM), Caspase-3 Ac-DEVD-pNA (Bachem, King of Prussia, Pa.) (final concentration in assay, 60 µM)

Caspase-4 Ac-WEHD-AMC (Synpep, Dublin, Calif.) (final concentration in Assay 20 µM), Caspase-7 Ac-DEVD-AMC (Bachem, King of Prussia, Pa.) (final concentration in assay 50 µM), Caspase-8 Ac-DEVD-pNA (Bachem, King of Prussia, Pa.) (final concentration in assay 80 µM).

TABLE 2

Caspase-1 Inhibition Data

| Example | Caspase-1 Ki (nM) |
|---|---|
| 5a | A |
| 5b | A |
| 5c | A |
| 5d | A |
| 5e | B |
| 5f | B |
| 5g | B |
| 5h | A |
| 5i | A |
| 5j | A |
| 5k | A |
| 5l | B |
| 5m | A |
| 5n | A |
| 5o | B |
| 5p | B |
| 5q | B |
| 5r | B |
| 5s | B |
| 5t | C |
| 5u | B |
| 5v | B |
| 5w | B |
| 5x | A |
| 5y | A |
| 5z | A |
| 5aa | A |
| 5ab | B |
| 5ac | A |
| 5ad | A |
| 5ae | B |
| 5af | B |
| 5ag | A |
| 5ah | B |
| 5ai | A |
| 5aj | B |
| 5ak | B |
| 5al | A |
| 5am | A |
| 5an | B |
| 5ao | B |
| 5ap | B |
| 5aq | B |
| 5ar | A |
| 5as | A |
| 5at | B |
| 5au | B |
| 5av | B |
| 5aw | A |
| 5ax | A |
| 5ay | A |
| 5az | A |
| 5ba | A |
| 5bb | A |
| 5bc | B |
| 5bd | A |
| 7a | A |
| 7b | B |
| 7c | A |
| 7d | A |
| 7e | B |
| 7f | B |
| 7g | A |
| 7h | B |
| 7i | B |
| 7j | C |
| 7k | B |
| 7l | B |
| 7m | B |
| 7n | B |
| 7o | A |
| 7p | A |
| 7q | B |
| 7r | B |
| 7s | B |
| 7t | B |
| 7u | B |
| 7v | B |
| 7w | A |
| 7x | B |
| 7y | B |
| 7z | B |
| 7aa | A |
| 7ab | B |
| 7ac | B |
| 7ad | B |
| 7ae | B |
| 7af | B |
| 7ag | B |
| 7ah | A |
| 7ai | A |
| 7aj | A |
| 7ak | A |
| 7al | B |
| 7am | A |
| 7an | A |
| 7ao | B |
| 7ap | B |
| 7aq | B |
| 7ar | A |
| 7as | A |
| 7at | A |
| 9a | B |
| 9b | A |
| 9c | A |
| 9d | A |
| 9e | A |
| 9f | A |
| 9g | A |
| 15a | A |
| 15b | A |
| 15c | A |
| 15d | B |

TABLE 2-continued

Caspase-1 Inhibition Data

| Example | Caspase-1 Ki (nM) |
|---|---|
| 15e | B |
| 15f | B |
| 16a | B |
| 16b | A |
| 17a | B |
| 17b | B |
| 17c | A |
| 17d | B |
| 17e | B |
| 18a | B |
| 18b | A |
| 18c | B |
| 18d | B |
| 18e | A |
| 18f | B |
| 20a | A |
| 20b | A |
| 20c | A |
| 20d | B |
| 20e | A |
| 20f | A |
| 20g | A |
| 20h | A |
| 20i | B |
| 20j | B |
| 20k | A |
| 20l | A |
| 20m | A |
| 20n | A |
| 20o | A |
| 20p | A |
| 20q | B |
| 20r | B |
| 20s | A |
| 20t | B |
| 23a | A |
| 23b | B |
| 23c | A |
| 23d | A |
| 23e | A |
| 23f | B |
| 23g | A |
| 23h | A |
| 23i | B |
| 24a | A |
| 24b | C |
| 24c | A |
| 24d | B |
| 24e | B |
| 25a | A |
| 25b | A |
| 25c | A |
| 25d | A |
| 25e | A |
| 26a | A |
| 26b | A |
| 26c | A |
| 26d | A |
| 26e | A |
| 26f | A |
| 26g | A |
| 26h | A |
| 27a | B |
| 27b | B |
| 27c | B |
| 27d | A |
| 27e | B |
| 27f | B |
| 27g | A |
| 27h | B |
| 27i | B |
| 27j | B |
| 27k | B |
| 27l | B |
| 27m | B |
| 27n | B |
| 28a | A |
| 28b | A |
| 28c | A |
| 29a | A |
| 29b | A |
| 29c | A |
| 29d | A |
| 29e | A |
| 29f | A |
| 29g | A |
| 29h | A |
| 29i | A |
| 29j | A |
| 29k | A |
| 29l | B |
| 29m | A |
| 29n | B |
| 29o | B |
| 29p | A |
| 29q | A |
| 29r | A |
| 29s | B |
| 32a | C |
| 32b | C |
| 32c | C |
| 32d | C |
| 32e | B |
| 34 | C |
| G1 | C |
| G2 | B |
| 42 | B |
| 46b | A |
| 46a | C |
| 57 | A |
| 65 | A |
| 61 | A |
| 69 | A |
| 73 | A |
| 121 | C |
| 122a | A |
| 122b | A |
| 122c | A |
| 122d | A |
| 122e | B |
| 122f | A |
| 122g | A |
| 122h | B |
| 122i | A |
| 122j | B |
| 122k | A |
| 122l | B |
| 122m | B |
| 122n | B |
| 122o | C |
| 122p | A |
| 122q | B |
| 122r | B |
| 122s | B |
| 122t | B |
| 122u | A |
| 122v | B |
| 123a | B |
| 123b | B |
| 123c | B |

TABLE 3

Caspase-3, Caspase-4, and Caspase-8 Inhibition Data

| Example | Caspase-3 Ki (nM) | Caspase-4 Ki (nM) | Caspase-8 Ki (nM) |
|---|---|---|---|
| 7c | C | ND | C |
| 7d | C | ND | B |
| 7f | C | ND | C |
| 24a | C | ND | ND |
| 29a | C | ND | ND |
| 29b | C | ND | ND |
| 32d | B | ND | ND |
| 46b | B | ND | ND |
| 69 | C | ND | B |
| 122b | C | A | B |
| 122d | C | A | C |
| 122f | C | ND | B |
| 122k | C | ND | B |

PBMC Cell Assay

IL-1β Assay with a Mixed Population of Human Peripheral Blood Mononuclear Cells (PBMC) or Enriched Adherent Mononuclear Cells Processing of pre-IL-1β by ICE can be measured in cell culture using a variety of cell sources. Human PBMC obtained from healthy donors provides a mixed population of lymphocyte subtypes and mononuclear cells that produce a spectrum of interleukins and cytokines in response to many classes of physiological stimulators. Adherent mononuclear cells from PBMC provides an enriched source of normal monocytes for selective studies of cytokine production by activated cells.

Experimental Procedure:

An initial dilution series of test compound in DMSO or ethanol is prepared, with a subsequent dilution into RPMI-10% FBS media (containing 2 mM L-glutamine, 10 mM HEPES, 50 U and 50 ug/ml pen/strep) respectively to yield drugs at 4× the final test concentration containing 0.4% DMSO or 0.4% ethanol. The final concentration of DMSO is 0.1% for all drug dilutions. A concentration titration which brackets the apparent $K_i$ for a test compound determined in an ICE inhibition assay is generally used for the primary compound screen.

Generally 5-6 compound dilutions are tested and the cellular component of the assay is performed in duplicate, with duplicate ELISA determinations on each cell culture supernatant.

PBMC Isolation and IL-1 Assay:

Buffy coat cells isolated from one pint human blood (yielding 40-45 ml final volume plasma plus cells) are diluted with media to 80 ml and LeukoPREP separation tubes (Becton Dickinson) are each overlaid with 10 ml of cell suspension. After 15 min centrifugation at 1500-1800×g, the plasma/media layer is aspirated and then the mononuclear cell layer is collected with a Pasteur pipette and transferred to a 15 ml conical centrifuge tube (Corning). Media is added to bring the volume to 15 ml, gently mix the cells by inversion and centrifuge at 300×g for 15 min. The PBMC pellet is resuspended in a small volume of media, the cells are counted and adjusted to $6 \times 10^6$ cells/ml.

For the cellular assay, 1.0 ml of the cell suspension is added to each well of a 24-well flat bottom tissue culture plate (Corning), 0.5 ml test compound dilution and 0.5 ml LPS solution (Sigma #L-3012; 20 ng/ml solution prepared in complete RPMI media; final LPS concentration 5 ng/ml).

The 0.5 ml additions of test compound and LPS are usually sufficient to mix the contents of the wells. Three control mixtures are run per experiment, with either LPS alone, solvent vehicle control, and/or additional media to adjust the final culture volume to 2.0 ml. The cell cultures are incubated for 16-18 hr at 37° C. in the presence of 5% $CO_2$.

At the end of the incubation period, cells are harvested and transferred to 15 ml conical centrifuge tubes. After centrifugation for 10 min at 200×g, supernatants are harvested and transferred to 1.5 ml Eppendorf tubes. It may be noted that the cell pellet may be utilized for a biochemical evaluation of pre-IL-1β and/or mature IL-1β content in cytosol extracts by Western blotting or ELISA with pre-IL-1β specific antisera.

Isolation of Adherent Mononuclear Cells:

PBMC are isolated and prepared as described above. Media (1.0 ml) is first added to wells followed by 0.5 ml of the PBMC suspension. After a one hour incubation, plates are gently shaken and nonadherent cells aspirated from each well. Wells are then gently washed three times with 1.0 ml of media and final resuspended in 1.0 ml media. The enrichment for adherent cells generally yields $2.5$-$3.0 \times 10^5$ cells per well. The addition of test compounds, LPS, cell incubation conditions and processing of supernatants proceeds as described above.

ELISA:

Quantikine kits (R&D Systems) may be used for the measurement of mature IL-1β. Assays are performed according to the manufacturer's directions. Mature IL-1β levels of about 1-3 ng/ml in both PBMC and adherent mononuclear cell positive controls are observed. ELISA assays are performed on 1:5, 1:10 and 1:20 dilutions of supernatants from LPS positive controls to select the optimal dilution for supernatants in the test panel.

The inhibitory potency of the compounds can be represented by an $IC_{50}$ value, which is the concentration of inhibitor at which 50% of mature IL-1β is detected in the supernatant as compared to the positive controls.

The skilled practitioner realizes that values obtained in cell assays may depend on multiple factors. The values may not necessarily represent fine quantitative results.

TABLE 4

PBMC Cell Assay Data

| Example | PBMC IC50 (nM) |
|---|---|
| 5a | D |
| 5b | B |
| 5c | B |
| 5d | B |
| 5e | B |
| 5f | C |
| 5g | C |
| 5h | A |
| 5i | C |
| 5j | D |
| 5k | D |
| 5l | A |
| 5m | A |
| 5n | B |
| 5r | D |
| 5s | B |
| 5u | C |
| 5v | D |
| 5w | B |
| 5x | B |
| 5y | B |
| 5z | B |

TABLE 4-continued

PBMC Cell Assay Data

| Example | PBMC IC50 (nM) |
|---|---|
| 5aa | B |
| 5ab | B |
| 5ac | A |
| 5ad | A |
| 5ag | B |
| 5ai | A |
| 5aj | B |
| 5ak | B |
| 5al | D |
| 5am | D |
| 5ao | D |
| 5aq | D |
| 5ar | D |
| 5as | D |
| 5at | D |
| 5au | D |
| 5av | D |
| 5aw | C |
| 5ax | B |
| 5ay | B |
| 5az | B |
| 5ba | C |
| 5bb | B |
| 5bd | C |
| 7a | D |
| 7b | B |
| 7c | A |
| 7d | A |
| 7e | D |
| 7f | D |
| 7g | A |
| 7h | B |
| 7k | B |
| 7l | B |
| 7m | B |
| 7n | B |
| 7o | A |
| 7p | D |
| 7q | D |
| 7s | B |
| 7t | D |
| 7u | D |
| 7v | D |
| 7w | C |
| 7x | D |
| 7y | D |
| 7z | C |
| 9a | B |
| 9b | B |
| 9c | A |
| 9d | B |
| 9e | C |
| 9f | B |
| 9g | C |
| 15a | D |
| 15b | C |
| 15c | B |
| 15d | C |
| 15e | D |
| 15f | D |
| 16a | A |
| 16b | C |
| 17b | C |
| 17c | D |
| 17d | D |
| 17e | B |
| 18a | B |
| 18b | B |
| 18c | B |
| 18d | B |
| 18e | C |
| 18f | D |
| 20a | B |
| 20b | B |
| 20c | C |
| 20d | D |
| 20e | C |
| 20f | B |
| 20g | A |
| 20h | A |
| 20i | B |
| 20j | D |
| 20k | A |
| 20l | B |
| 20m | B |
| 20n | B |
| 20o | A |
| 20p | A |
| 20q | B |
| 20r | B |
| 20s | C |
| 20t | B |
| 23a | C |
| 23b | B |
| 23c | C |
| 23d | B |
| 23e | B |
| 23f | C |
| 23g | C |
| 23h | C |
| 23i | A |
| 24a | B |
| 24b | D |
| 24c | A |
| 24d | B |
| 24e | C |
| 25a | A |
| 25b | B |
| 25c | B |
| 26a | C |
| 26b | B |
| 26c | B |
| 26d | B |
| 26e | A |
| 26f | A |
| 26g | A |
| 26h | A |
| 27a | A |
| 28a | B |
| 28b | B |
| 28c | B |
| 29a | A |
| 29b | C |
| 29c | B |
| 29d | B |
| 29e | A |
| 29g | B |
| 29h | A |
| 29i | A |
| 29j | B |
| 29k | A |
| 29l | B |
| 29m | B |
| 42 | D |
| 46b | D |
| 57 | B |
| 65 | B |
| 61 | B |
| 69 | A |
| 73 | B |
| 122a | D |
| 122b | B |
| 122c | D |
| 122d | B |
| 122e | C |
| 122f | B |
| 122g | B |
| 122h | C |
| 122i | C |
| 122j | D |

TABLE 4-continued

PBMC Cell Assay Data

| Example | PBMC IC50 (nM) |
|---------|----------------|
| 122k | A |
| 122l | B |

Whole Blood Assay for IL-1β Production

Whole blood assay $IC_{50}$ values for compounds of this invention were obtained using the method described below:

Purpose:

The whole blood assay is a simple method for measuring the production of IL-1β (or other cytokines) and the activity of potential inhibitors. The complexity of this assay system, with its full complement of lymphoid and inflammatory cell types, spectrum of plasma proteins and red blood cells is an ideal in vitro representation of human in vivo physiologic conditions.

Materials:
Pyrogen-free syringes ([1]30 cc)
Pyrogen-free sterile vacuum tubes containing lyophilized $Na_2EDTA$ (4.5 mg/10 ml tube)
Human whole blood sample (~30-50 cc)
1.5 ml Eppendorf tubes
Test compound stock solutions (~25 mM in DMSO or other solvent)
Endotoxin—free sodium chloride solution (0.9%) and HBSS
Lipopolysaccharide (Sigma; Cat.# L-3012) stock solution at 1 mg/ml in HBSS
IL-1β ELISA Kit (R & D Systems; Cat # DLB50)
TNFα ELISA Kit (R & D Systems; Cat # DTA50)
Water bath or incubator Whole Blood Assay Experimental Procedure:

Set incubator or water bath at 30° C. Aliquot 0.25 ml of blood into 1.5 ml eppendorf tubes. Note: be sure to invert the whole blood sample tubes after every two aliquots. Differences in replicates may result if the cells sediment and are not uniformly suspended. Use of a positive displacement pipette will also minimize differences between replicate aliquots.

Prepare drug dilutions in sterile pyrogen-free saline by serial dilution. A dilution series which brackets the apparent $K_i$ for a test compound determined in an ICE inhibition assay is generally used for the primary compound screen. For extremely hydrophobic compounds, prepare compound dilutions in fresh plasma obtained from the same blood donor or in PBS-containing 5% DMSO to enhance solubility.

Add 25 µl test compound dilution or vehicle control and gently mix the sample. Then add 5.0 µl LPS solution (250 ng/ml stocked prepared fresh: 5.0 ng/ml final concentration LPS), and mix again. Incubate the tubes at 30° C. in a water bath for 16-18 hr with occasional mixing. Alternatively, the tubes can be placed in a rotator set at 4 rpm for the same incubation period. This assay should be set up in duplicate or triplicate with the following controls: negative control—no LPS; positive control—no test inhibitor; vehicle control—the highest concentration of DMSO or compound solvent used in the experiment. Additional saline is added to all control tubes to normalize volumes for both control and experimental whole blood test samples.

After the incubation period, whole blood samples are centrifuged for 10 minutes at ~2000 rpm in the microfuge, plasma is transferred to a fresh microfuge tube and centrifuged at 1000×g to pellet residual platelets if necessary. Plasma samples may be stored frozen at −70° C. prior to assay for cytokine levels by ELISA.

ELISA:

R & D Systems (614 McKinley Place N.E. Minneapolis, Minn. 55413) Quantikine kits may be used for measurement of IL-1β and TNF-α. The assays are performed according to the manufacture's directions. IL-1β levels of ~1-5 ng/ml in positive controls among a range of individuals may be observed. A 1:200 dilution of plasma for all samples is usually sufficient for experiments for ELISA results to fall on the linear range of the ELISA standard curves. It may be necessary to optimize standard dilutions if you observe differences in the whole blood assay. Nerad, J. L. et al., *J. Leukocyte Biol.*, 52, pp. 687-692 (1992).

Table 5

Whole Blood Assay Data

| Example | Whole Blood IC50 (nM) |
|---------|------------------------|
| 5a | A |
| 5b | A |
| 5c | A |
| 5d | B |
| 5e | A |
| 5f | B |
| 5h | A |
| 5i | C |
| 5j | C |
| 5k | B |
| 5l | C |
| 5m | A |
| 5n | B |
| 5r | C |
| 5s | C |
| 5u | A |
| 5w | A |
| 5x | A |
| 5y | B |
| 5z | C |
| 5aa | A |
| 5ab | B |
| 5ac | A |
| 5ad | A |
| 5ag | B |
| 5ai | C |
| 5aj | C |
| 5ak | C |
| 5ax | B |
| 5ay | B |
| 5az | A |
| 5bb | B |
| 7a | B |
| 7b | A |
| 7c | A |
| 7d | B |
| 7e | C |
| 7f | B |
| 7g | B |
| 7h | A |
| 7k | A |
| 7l | A |
| 7m | B |
| 7n | A |
| 7o | A |
| 7p | B |
| 7q | A |
| 7s | B |
| 7t | B |
| 7u | B |
| 7v | A |

Table 5-continued

Whole Blood Assay Data

| Example | Whole Blood IC50 (nM) |
|---|---|
| 7w | A |
| 7x | C |
| 7y | C |
| 7z | A |
| 7aa | B |
| 7ab | A |
| 7ac | B |
| 7ad | B |
| 7ah | B |
| 7ai | B |
| 7aj | C |
| 7ak | B |
| 7am | B |
| 7an | B |
| 7ao | B |
| 7ap | C |
| 9a | B |
| 9b | B |
| 9c | A |
| 9d | A |
| 9e | B |
| 9f | A |
| 9g | B |
| 15a | B |
| 15b | B |
| 15c | A |
| 16b | A |
| 18a | A |
| 18b | A |
| 18c | A |
| 18d | A |
| 18e | A |
| 18f | B |
| 20a | A |
| 20b | C |
| 20c | B |
| 20d | B |
| 20e | B |
| 20f | A |
| 20g | A |
| 20h | A |
| 20i | A |
| 20k | A |
| 20l | A |
| 20m | A |
| 20n | A |
| 20o | A |
| 20p | A |
| 20q | C |
| 20r | B |
| 20s | A |
| 20t | A |
| 23a | B |
| 23b | B |
| 23c | B |
| 23d | A |
| 23e | B |
| 23f | A |
| 23g | A |
| 23h | A |
| 23i | B |
| 24a | B |
| 24c | B |
| 24d | B |
| 24e | B |
| 25a | B |
| 25b | B |
| 25c | B |
| 25d | A |
| 25e | C |
| 26c | B |
| 26d | A |
| 26e | A |
| 26f | B |
| 26g | B |
| 26h | A |
| 27a | A |
| 27b | A |
| 27d | A |
| 27e | A |
| 27f | B |
| 27g | B |
| 27h | B |
| 27i | B |
| 27l | B |
| 27m | B |
| 27n | A |
| 28a | B |
| 28b | B |
| 28c | C |
| 29a | A |
| 29c | A |
| 29d | A |
| 29e | A |
| 29g | A |
| 29h | A |
| 29i | A |
| 29j | A |
| 29k | A |
| 29l | A |
| 29n | B |
| 29o | A |
| 29p | A |
| 29q | A |
| 29r | A |
| 29s | A |
| G2 | B |
| 42 | B |
| 46b | B |
| 57 | C |
| 65 | A |
| 61 | A |
| 69 | A |
| 73 | A |
| 122a | A |
| 122b | A |
| 122c | B |
| 122d | A |
| 122e | B |
| 122f | A |
| 122g | A |
| 122h | A |
| 122i | A |
| 122j | B |
| 122k | A |
| 122l | A |
| 122m | B |
| 122p | B |
| 122q | B |
| 122r | B |
| 122s | B |
| 123a | A |
| 123b | B |

Ex Vivo Assays

Metabolism and Excretion

Single pass perfusion studies in rat were performed to assess gastrointestinal (GI) wall metabolism (f(g)), liver metabolism (f(h)), and biliary excretion. The method used has been described in Pang, C. S., *J. Pharmacol. Exp. Therapeutics,* 333, pp. 788-798 (1984).

TABLE 6

Metabolism and Excretion Data

| Example | f (g) Xf (h) | Biliary Excretion |
|---|---|---|
| 5c | A | C |
| 5k | B | A |
| 5m | B | C |
| 7d | D | A |
| 7f | C | A |
| 7ac | C | C |
| 18f | D | A |
| 20f | B | C |
| 20g | B | A |
| 23b | B | B |
| 24a | C | A |
| 24c | A | C |
| 24e | A | C |
| 25d | C | C |
| 25e | C | B |
| 26c | A | C |
| 26e | B | B |
| 26f | A | C |
| 27a | C | A |
| 27b | B | A |
| 29b | A | B |
| 29g | B | B |
| 29n | C | A |
| 29o | C | A |
| 29p | B | C |
| 29q | C | A |
| 29r | C | B |
| 46b | B | C |
| 57 | B | B |
| 65 | B | C |
| 69 | C | A |
| 122a | B | A |
| 122b | C | A |
| 122c | C | B |
| 122d | C | A |
| 122r | B | A |

In Vivo Assays

In Vivo Rat Clearance Assay—Clearance Rates

The rate of clearance in the rat (ml/min/kg) for compounds of this invention may be obtained using the method described below:

Representative Procedure

Cannulations of the jugular and carotid vessels of rats under anesthesia are performed one day prior to the pharmacokinetic study. M. J. Free, R. A. Jaffee; 'Cannulation techniques for the collection blood and other bodily fluids'; in: *Animal Models*; p. 480-495; N. J. Alexander, Ed.; Academic Press; (1978). Drug (10 mg/mL) is administered via the jugular vein in a vehicle usually consisting of: propylene glycol/saline, containing 100 mM sodium bicarbonate in a 1:1 ratio. Animals are dosed with 10-20 mg drug/kg and blood samples are drawn at 0, 2, 5, 7, 10, 15, 20, 30, 60, and 90 minutes from an indwelling carotid catheter. The blood is centrifuged to plasma and stored at −20° C. until analysis. Pharmacokinetic analysis of data is performed by non-linear regression using standard software such as RStrip (MicroMath Software, UT) and/or Pononlin (SCI Software, NC) to obtain clearance values.

Representative Analytical:

Rat plasma is extracted with an equal volume of acetonitrile (containing 0.1% TFA). Samples are then centrifuged at approximately 1,000×g and the supernatant analyzed by gradient HPLC. A typical assay procedure is described below.

200 μL of plasma is precipitated with 200 μL of 0.1% trifluoroacetic acid (TFA) in acetonitrile and 10 μL of a 50% aqueous zinc chloride solution, vortexed then centrifuged at ~1000×g and the supernatant collected and analyzed by HPLC.

| HPLC procedure: | |
|---|---|
| Column: | Zorbax SB-CN (4.6 × 150 mm) (5μ particle size) |
| Column temperature: | 50° C. |
| Flow rate: | 1.0 mL/min |
| Injection volume: | 75 μL. |
| Mobile phase: | A = 0.1% TFA in water and B = 100% acetonitrile |
| Gradient employed: | 100% A to 30% A in 15.5 min |
| | 0% A at 16 min |
| | 100% A at 19.2 min |
| Wavelength: | 214 nm |

A standard curve is run at 20, 10, 5, 2 and 1 μg/mL concentrations.

TABLE 7

Clearance Data

| Example | Rat I.V. Clearance (ml/min/kg) |
|---|---|
| 7d | A |
| 7f | B |
| 20h | B |
| 20m | A |
| 65 | C |
| 122b | B |
| 122c | C |
| 122d | B |
| 122f | A |

Bioavailability

Oral Pharmacokinetic Studies

Male Sprague-Dawley rats (Harlan, Indianapolis, Ind., 300-350 g) were anesthetized by an intramuscular injection of ketamine/rompun mixture. A PE-50 cannula was inserted in the right carotid artery for arterial blood sampling. The rats were allowed to recover from surgery overnight (≧16 hours) prior to being used in the study. Test compounds were administered orally in 25% Cremophor EL/water (w/w) or 100% propylene glycol (PG) in a dose volume of 10 mL/kg. Blood samples (~0.30 mL) were removed at 0.25, 0.50, 1.0, 1.5, 2, 3, 4, 6, and 8 hours post-dose, plasma separated by centrifugation and stored at −20° C. pending analysis. Quantitation of the plasma samples was conducted using a gradient HPLC/MS/MS or enzymatic method detailed below:

HPLC/MS/MS Method for the Quantitation of ICE Inhibitors in Rat Plasma

Sample Preparation

50 μl of plasma are aliquotted into Ependorf centrifuge vials.

An equal volume of Acetonitrile is added to the plasma to precipitate plasma proteins.

Samples are Votexed for 5 minutes, and centrifuged at 14,000 rpms for 5 minutes.

75 μl of the supernatant is loaded into 12 mm HPLC liquid sampler vials.

50 μl of sample is injected for analysis via the mass spectrometer.

HPLC Instrumental Parameters

HPLC: Hewlett Packard HP1100 Binary Solvent Delivery System.

HPLC Gradient Conditions

A=$H_2O$ 0.2% Formic Acid
B=Acetonitrile 0.2% Formic Acid

| | Mobile Phase | |
|---|---|---|
| Time | % A | % B |
| 0 | 100 | 0 |
| 2 | 100 | 0 |
| 5 | 0 | 100 |
| 11 | 0 | 100 |
| 11.5 | 100 | 0 |
| 17 | 100 | 0 |

HPLC Analytical Column: Keystone Phenyl –2 Hypersil 2.0×100 mm, 5μ 120 Å pore pore size, P/N#105-39-2

| | |
|---|---|
| Injection Volume: | 50 μl |
| Flow Rate: | 0.20 mL/min. |

Mass Spectrometry Instrumental Parameters

| | |
|---|---|
| Instrument: | P E Sciex API-365 Tandem Mass Spectrometer |
| Ionization Technique: | Turbo-Ionspray (ESI) |
| Polarity: | Positive |
| Dwell Time: | 300 msec |
| Pause Time: | 5 msec |
| Scan time: | 0.9 sec |
| Scan Mode: | MRM (Multiple Reaction Monitoring) |

Ice Enzymatic Assay for the Quantitation of Ice Inhibitors in Rat Plasma

50 μL of plasma was extracted with 150 μL acetonitrile, sonicated, vortexed, centrifuged at 10,000×g and 180 μL of the supernatant dried in a Sorvall vortex evaporator at room temperature. Samples were reconstituted in 100 μL buffer (10 mM tris-HCl, pH 7.5 with 0.1% CHAPS, 1 mM DTT) with sonication. 10 μL of each sample was mixed with 10 μL ICE (1.1 mg/mL) in a microtitre plate with 60 μL buffer. Samples were incubated for 15 min. at room temperature then 20 μL Succ YVAD-pNA(400 μM, prewarmed to 37° C.) added, and the plate monitored at 405 nm for 20 min. at 37° C. used a SpectraMax reader. The data were fitted using a 4 parameter fit with the the SpectraMax software using an extracted standard curve. The assay was linear from 0.15 to 2.0-3.0 μg/mL aldehyde.

Pharmacokinetic Parameters

Pharmacokinetic analysis of these plasma concentration data was conducted using noncompartmental methods. The area under the curve ($AUC_{(0-t)}$) was estimated from time zero to the last measured time point using the linear trapezoidal rule. The rate of elimination (ke) was estimated by log-linear regression from the terminal phase of the plasma concentration to ke. The area under the curve from time zero to infinity (AUC(0-∞)) was obtained by addition of the area under the tail to AUC(0-t). Elimination half-life was estimated as 0.693/ke. The observed values for the peak plasma concentration (Cmax) were recorded. For prodrug studies: aldehyde availability (bioavailability) was calculated as: ($AUC_{ald}$/prodrug p.o.)/($AUC_{ald}$/ald i.v.)×(dose ald, ald i.v./dose prodrug, prodrug p.o.)×(MW prodrug/MW aldehyde).

TABLE 8

| | Bioavailability Data | | | |
|---|---|---|---|---|
| Example | Cmax (μg/mL) | AUC (μgXh/mL) | t ½ (hrs) | F (%) |
| 56 | A | B | | A |
| 45 | A | B | | |
| 90 | C | C | A | C |
| 85 | A | B | B | A |
| 68 | A | C | B | |
| 76 | C | C | C | |
| 77 | B | B | A | A |
| 78 | A | A | B | A |
| 89 | B | C | C | |
| 83 | A | C | C | |
| 98d | A | A | B | |
| 98h | A | C | B | |
| 98e | C | C | B | |
| 98c | B | C | C | |
| 98k | B | C | B | |
| 98ae | A | A | B | |
| 98af | A | A | B | |
| 98b | C | C | B | |
| 111 | A | A | C | |
| 98o | A | A | B | |
| 108a | A | A | B | |
| 98ag | C | C | B | C |
| 98a | B | B | C | |
| 98am | A | A | B | |
| 116a | C | C | B | |
| 98an | A | A | B | |
| 116g | A | A | C | |
| 116h | A | A | B | |
| 116e | A | A | B | |
| 108b | A | A | B | |

Antiviral Assays

The efficacy of the compounds of this invention at treating or preventing antiviral related diseases, disorders, or conditions may be evaluated in various in vitro and in vivo assays. For example, assays may be preformed to determine the ability of these compounds to inhibit inflammatory responses associated with viral infections. In vitro assays may employ whole cells or isolated cellular components. In vivo assays include animal models for viral diseases. Examples of such animal models include, but are not limited to, rodent models for HBV or HCV infection, the Woodchuck model for HBV infection, and chimpanzee model for HCV infection.

Compounds of this invention may also be evaluated in animal models for dietary alcohol-induced disease.

Other assays that may be used to evaluate the compounds of this invention-are disclosed in PCT application PCT/US96/20843, published Jun. 26, 1997, under publication no. WO 97/22619. Such assays include in vivo pharmacokinetic studies in the mouse, inhibition of ICE homologs, inhibition of apoptosis, in vivo acute assay for anti-inflammatory efficacy, measurement of blood levels of drugs, IGIF assays, mouse carrageenan peritoneal inflammation assay, and type II collagen-induced arthritis.

Insofar as the compounds of this invention are able to inhibit caspases, particularly ICE, in vitro and furthermore, may be delivered orally to mammals, they are of evident clinical utility for the treatment of IL-1-, apoptosis-, IGIF-, and IFN-γ-mediated diseases.

While we have described a number of embodiments of this invention, it is apparent that our basic constructions may be altered to provide other embodiments which utilize the products and processes of this invention.

What is claimed is:

1. A compound represented by formula I:

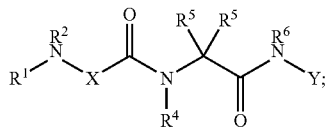

wherein: Y is:

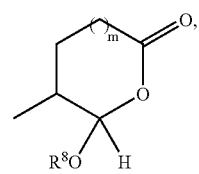
(c)

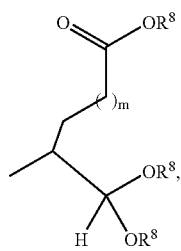
(d)

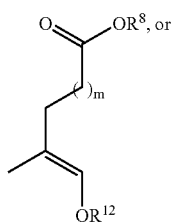
(e)

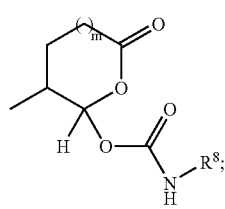
(f)

$R^6$ is —H or $R^6$ and Y, together with the nitrogen to which they are bound, form a ring (g):

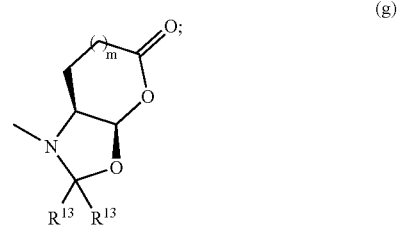
(g)

x is —C(R$^3$)$_2$— or —N(R$^3$)—;
m is 0 or 1;
$R^1$ is H, —C(O)R$^8$, —C(O)C(O)R$^8$, —S(O)$_2$R$^8$, —S(O)R$^8$, —C(O)OR$^8$, —C(O)N(H)R$^8$, —S(O)$_2$N(H)—R$^8$, —S(O)N(H)—R$^8$, —C(O)C(O)N(H)R$^8$, —C(O)CH=CHR$^8$, —C(O)CH$_2$OR$^8$, —C(O)CH$_2$N(H)R$^8$, —C(O)N(R$^8$)$_2$, —S(O)$_2$N(R$^8$)$_2$, S(O)N(R$^8$)$_2$, —C(O)C(O)N(R$^8$)$_2$, —C(O)CH$_2$N(R$^8$)$_2$, —CH$_2$R$^8$, —CH$_2$-alkenyl-R$^8$, or —CH$_2$-alkynyl-R$^8$;
$R^2$ is —H and each $R^3$ is independently —H, an amino acid side chain, —R$^8$, alkenyl-R$^9$, or alkynyl-R$^9$, or $R^2$ and one $R^3$ together with the atoms to which they are bound, form a 3 to 7 membered heterocyclic ring system, wherein a hydrogen atom bound to any -alkyl or -cycloalkyl carbon atom is optionally replaced by —R$^{10}$, a hydrogen atom bound to any -aryl or -heteroaryl carbon atom is optionally replaced by —R$^{11}$, a hydrogen atom bound to any nitrogen atom of the ring system is optionally replaced by —R$^1$;
$R^4$ is —H and each $R^5$ is independently —H, an amino acid side chain, —R$^8$, -alkenyl-R$^9$, or -alkynyl-R$^9$, or $R^4$ and one $R^5$ together with the atoms to which they are bound form a ring system:

and the other $R^5$ is H;
each $R^8$ is independently -alkyl, -cycloalkyl, -aryl, -heteroaryl, -heterocyclyl, -alkylcycloalkyl -alkylaryl, -alkylheteroaryl, or -alkylheterocyclyl, wherein a hydrogen atom bound to any -alkyl or -cycloalkyl carbon atom is optionally replaced by R$^{10}$, a hydrogen atom bound to any -aryl or -heteroaryl carbon atom is optionally replaced by R$^{11}$, and a hydrogen atom bound to any nitrogen atom is optionally replaced by R$^1$;
each $R^9$ is independently -aryl, -heteroaryl, cycloalkyl, or -heterocyclyl, wherein a hydrogen atom bound to any -alkyl or -cycloalkyl carbon atom is optionally replaced by R$^{10}$, a hydrogen atom bound to any -aryl or -heteroaryl carbon atom is optionally replaced by R$^{11}$, and a hydrogen atom bound to any nitrogen atom is optionally replaced by R$^1$;
each R$^{10}$ is independently —OH, —SH, —F, —Cl, —Br, —I, —NO$_2$, —CN, —NH$_2$, —CO$_2$H, —C(O)NH$_2$, —N(H)C(O)H, —N(H)C(O)NH$_2$, -perfluoroalkyl, —O-alkyl, —O-aryl, —O-alkylaryl, —N(H)alkyl, —N(H)aryl, —N(H)-alkylaryl, —N(alkyl)$_2$, —C(O)N(H)alkyl, —C(O)N(alkyl)$_2$, —N(H)C(O)alkyl, —N(H)

C(O)N(H)alkyl, —N(H)C(O)N(alkyl)$_2$, —S-alkyl, —S-aryl, —S-alkylaryl, —S(O)$_2$alkyl, —S(O)alkyl, —C(O)alkyl, —CH$_2$NH$_2$, —CH$_2$N(H)alkyl, or —CH$_2$N(alkyl)$_2$, -alkyl, -cycloalkyl, -aryl, -heteroaryl, -heterocyclyl, -alkylcycloalkyl -alkylaryl, -alkylheteroaryl, or -alkylheterocyclyl, wherein a hydrogen atom bound to any -aryl or -heteroaryl carbon atom is optionally replaced by R$^{11}$ and a hydrogen atom bound to any nitrogen atom is optionally replaced by R$^1$; and each R$^{11}$ is independently —OH, —SH, —F, —Cl, —Br, —I, —NO$_2$, —CN, —NH$_2$, —CO$_2$H, —C(O)NH$_2$, —N(H)C(O)H, —N(H)C(O)NH$_2$, -alkyl, -cycloalkyl, -perfluoroalkyl, —O-alkyl, —O-aryl, —O-alkylaryl, —N(H)alkyl, —N(H)aryl, —N(H)-alkylaryl, —N(alkyl)$_2$, —C(O)N(H)alkyl, —C(O)N(alkyl)$_2$, —N(H)C(O)alkyl, —N(H)C(O)N(H)alkyl, —N(H)C(O)N(alkyl)$_2$, —S-alkyl, —S-aryl, —S-alkylaryl, —S(O)$_2$alkyl, —S(O)alkyl, —C(O)alkyl, —CH$_2$NH$_2$, —CH$_2$N(H)alkyl, or —CH$_2$N(alkyl)$_2$;

R$^{12}$ is —C(O)alkyl, —C(O)cycloalkyl, —C(O)alkylaryl, —C(O)alkylheteroaryl, —C(O)heterocyclyl, or —C(O)alkylheterocyclyl; and R$^{13}$ is —H, -alkyl, -aryl, -alkylaryl or -alkylheteroaryl.

2. A compound represented by formula I:

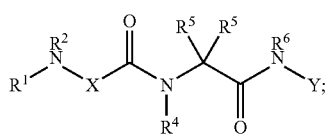

wherein: Y is:

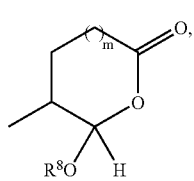  (c)

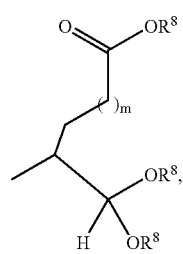  (d)

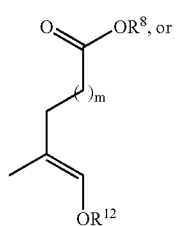  (e)

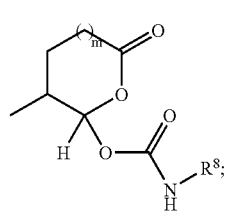  (f)

m is 0 or 1;

X is —C(R$^3$)$_2$—;

R$^1$ is H, —C(O)R$^8$, —C(O)C(O)R$^8$, —S(O)$_2$R$^8$, —S(O)R$^8$, —C(O)OR$^8$, —C(O)N(H)R$^8$, —S(O)$_2$N(H)—R$^8$, —S(O)N(H)—R$^8$, —C(O)C(O)N(H)R$^8$, —C(O)CH=CHR$^8$, —C(O)CH$_2$OR$^8$, —C(O)CH$_2$N(H)R$^8$, —C(O)N(R$^8$)$_2$, —S(O)$_2$N(R$^8$)$_2$, —S(O)N(R$^8$)$_2$, —C(O)C(O)N(R$^8$)$_2$, —C(O)CH$_2$N(R$^8$)$_2$, —CH$_2$R$^8$, —CH$_2$-alkenyl-R$^8$, or —CH$_2$-alkynyl-R$^8$;

R$^2$ is —H and each R$^3$ is independently —H, an amino acid side chain, —R$^8$, alkenyl-R$^9$, or alkynyl-R$^9$, or R$^2$ and one R$^3$ together with the atoms to which they are bound, form a 3 to 7 membered heterocyclic ring system, wherein a hydrogen atom bound to any -alkyl or -cycloalkyl carbon atom is optionally replaced by —R$^{10}$, a hydrogen atom bound to any -aryl or -heteroaryl carbon atom is optionally replaced by —R$^{11}$, a hydrogen atom bound to any nitrogen atom of the ring system is optionally replaced by —R$^1$;

R$^4$ is —H and each R$^5$ is independently —H, an amino acid side chain, —R$^8$, -alkenyl-R$^9$, or -alkynyl-R$^9$, or and one R$^5$ together with the atoms to which they are bound form a ring system:

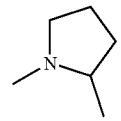

and the other R$^5$ is H;

R$^6$ is —H;

each R$^8$ is independently -alkyl, -cycloalkyl, -aryl, -heteroaryl, -heterocyclyl, -alkylcycloalkyl -alkylaryl, -alkylheteroaryl, or -alkylheterocyclyl, wherein a hydrogen atom bound to any -alkyl or -cycloalkyl carbon atom is optionally replaced by R$^{10}$, a hydrogen atom bound to any -aryl or -heteroaryl carbon atom is optionally replaced by R$^{11}$, and a hydrogen atom bound to any nitrogen atom is optionally replaced by R$^1$;

each R$^9$ is independently -aryl, -heteroaryl, cycloalkyl, or -heterocyclyl, wherein a hydrogen atom bound to any -alkyl or -cycloalkyl carbon atom is optionally replaced by R$^{10}$, a hydrogen atom bound to any -aryl or -heteroaryl carbon atom is optionally replaced by R$^{11}$, and a hydrogen atom bound to any nitrogen atom is optionally replaced by R$^1$;

each R$^{10}$ is independently —OH, —SH, —F, —Cl, —Br, —I, —NO$_2$, —CN, —NH$_2$, —CO$_2$H, —C(O)NH$_2$, —N(H)C(O)H, —N(H)C(O)NH$_2$, -perfluoroalkyl, —O-alkyl, —O-aryl, —O-alkylaryl, —N(H)alkyl, —N(H)aryl, —N(H)-alkylaryl, —N(H)C(O)N(H)alkyl, —N(H)C(O)N(alkyl)₂, —S-alkyl, —S-aryl, —S-alkylaryl, —S(O)₂alkyl, —S(O)alkyl, —C(O)alkyl, —CH₂NH₂, —CH₂N(H)alkyl, or —CH₂N(alkyl)₂, -alkyl, -cycloalkyl, -aryl, -heteroaryl, -heterocyclyl, -alkylcycloalkyl -alkylaryl, -alkylheteroaryl, or -alkyl-heterocyclyl, wherein a hydrogen atom bound to any -aryl or -heteroaryl carbon atom is optionally replaced by R¹¹ and a hydrogen atom bound to any nitrogen atom is optionally replaced by R¹; and each R¹¹ is independently —OH, —SH, —F, —Cl, —Br, —I, —NO₂, —CN, —NH₂, —CO₂H, —C(O)NH₂, —N(H)C(O)H, —N(H)C(O)NH₂, -alkyl, -cycloalkyl, -perfluoroalkyl, —O-alkyl, —O-aryl, —O-alkylaryl, —N(H)alkyl, —N(H)aryl, —N(H)-alkylaryl, —N(alkyl)₂, —C(O)N(H)alkyl, —C(O)N(alkyl)₂, —N(H)C(O)alkyl, —N(H)C(O)N(H)alkyl, —N(H)C(O)N(alkyl)₂, —S-alkyl, —S-aryl, —S-alkylaryl, —S(O)₂alkyl, —S(O)alkyl, —C(O)alkyl, —CH₂NH₂, —CH₂N(H)alkyl, or —CH₂N(alkyl)₂; and R¹² is —C(O)alkyl, —C(O)cycloalkyl, —C(O)alkylaryl, —C(O)alkylheteroaryl, —C(O)heterocyclyl, or —C(O)alkylheterocyclyl.

3. The compound according to claim 1 wherein Y is:

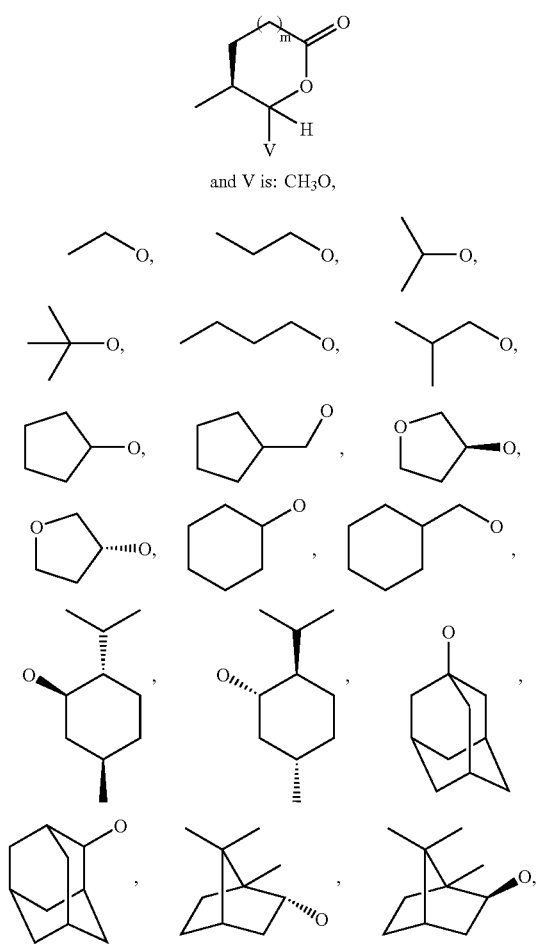

4. The compound according to any one of claims 1, 2 and 3 wherein one R³ is —H and the other R³ is methyl, isopropyl, tert-butyl, —CH₂SR⁸, —CH₂SO₂R⁸, —CH₂CH₂SR⁸, or —CH₂CH₂SO₂R⁸.

5. The compound according to claim 4 wherein one R³ is —H and the other R³ is methyl.

6. The compound according to claim 5 wherein R¹ is —C(O)R⁸ or —C(O)C(O)R⁸.

7. A compound represented by formula I:

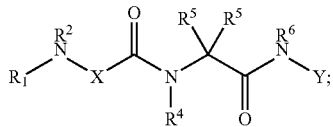

wherein: Y is:

(c) 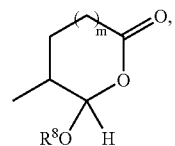

(d) 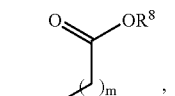

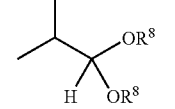

(e) 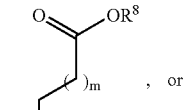, or

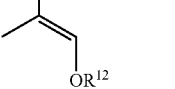

(f) 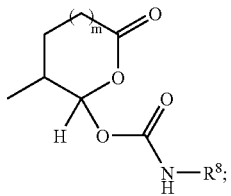

$R^6$ is —H or $R^6$ and Y, together with the nitrogen to which they are bound, form a ring (g):

(g) 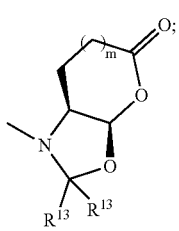

X is —C($R^3$)$_2$— or —N($R^3$)—;

m is 0 or 1;

$R^1$ is H, —$R^8$, —C(O)$R^8$, —C(O)C(O)$R^8$, —S(O)$_2R^8$, —S(O)$R^8$, —C(O)N(H)$R^8$, —S(O)$_2$N(H)—$R^8$, —S(O)N(H)—$R^8$, —C(O)C(O)N(H)$R^8$, —C(O)CH=CH$R^8$, —C(O)CH$_2$O$R^8$, —C(O)CH$_2$N(H)$R^8$, —C(O)N($R^8$)$_2$, —S(O)$_2$N($R^8$)$_2$, —S(O)N($R^8$)$_2$, —C(O)C(O)N($R^8$)$_2$, —C(O)CH$_2$N($R^8$)$_2$, —CH$_2R^8$, —CH$_2$-alkenyl-$R^8$, or —CH$_2$-alkynyl-$R^8$;

$R^2$ is —H and each $R^3$ is independently —H, an amino acid side chain, —$R^8$, alkenyl-$R^9$, or alkynyl-$R^9$, or $R^2$ and one $R^3$ together with the atoms to which they are bound, form a 3 to 7 membered heterocyclic ring system, wherein a hydrogen atom bound to any -alkyl or -cycloalkyl carbon atom is optionally replaced by —$R^{10}$, a hydrogen atom bound to any -aryl or -heteroaryl carbon atom is optionally replaced by —$R^{11}$, a hydrogen atom bound to any nitrogen atom of the ring system is optionally replaced by —$R^1$;

$R^4$ is —H and each $R^5$ is independently —H, an amino acid side chain, —$R^8$, -alkenyl-$R^9$, or -alkynyl-$R^9$, or $R^4$ and one $R^5$ together with the atoms to which they are bound form a ring system:

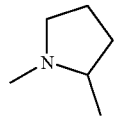

and the other $R^5$ is H;

each $R^8$ is independently -alkyl, -cycloalkyl, -aryl, -heteroaryl -heterocyclyl, -alkylcycloalkyl -alkylaryl, -alkylheteroaryl, or -alkylheterocyclyl, wherein a hydrogen atom bound to any -alkyl or -cycloalkyl carbon atom is optionally replaced by $R^{10}$, a hydrogen atom bound to any -aryl or -heteroaryl carbon atom is optionally replaced by $R^{11}$, and a hydrogen atom bound to any nitrogen atom is optionally replaced by $R^1$;

each $R^9$ is independently -aryl, -heteroaryl, cycloalkyl, or -heterocyclyl, wherein a hydrogen atom bound to any -alkyl or -cycloalkyl carbon atom is optionally replaced by $R^{10}$, a hydrogen atom bound to any -aryl or -heteroaryl carbon atom is optionally replaced by $R^{11}$, and a hydrogen atom bound to any nitrogen atom is optionally replaced by $R^1$;

each $R^{10}$ is independently —OH, —SH, F, —Cl, —Br, —I, —NO$_2$, —CN, —NH$_2$, —CO$_2$H, —C(O)NH$_2$, —N(H)C(O)H, —N(H)C(O)NH$_2$, -perfluoroalkyl, —O-alkyl, —O-aryl, —O-alkylaryl, —N(H)alkyl, —N(H)aryl, —N(H)-alkylaryl, —N(alkyl)$_2$, —C(O)N(H)alkyl, —C(O)N(alkyl)$_2$, —N(H)C(O)alkyl, —N(H)C(O)N(H)alkyl, —N(H)C(O)N(alkyl)$_2$, —S-alkyl, —S-aryl, —S-alkylaryl, —S(O)$_2$alkyl, —S(O)alkyl, —C(O)alkyl, —CH$_2$NH$_2$, —CH$_2$N(H)alkyl, or —CH$_2$N(alkyl)$_2$, -alkyl, -cycloalkyl, -aryl, -heteroaryl, -heterocyclyl, -alkylcycloalkyl -alkylaryl, -alkylheteroaryl, or -alkylheterocyclyl, wherein a hydrogen atom bound to any -aryl or -heteroaryl carbon atom is optionally replaced by $R^{11}$ and a hydrogen atom bound to any nitrogen atom is optionally replaced by $R^1$; and each $R^{11}$ is independently —OH, —SH, —F, —Cl, —Br, —I, —NO$_2$, —CN, —NH$_2$, —CO$_2$H, —C(O)NH$_2$, —N(H)C(O)H, —N(H)C(O)NH$_2$, -alkyl, -cycloalkyl, -perfluoroalkyl, —O-alkyl, —O-aryl, —O-alkylaryl, —N(H)alkyl, —N(H)aryl, —N(H)-alkylaryl, —N(alkyl)$_2$, —C(O)N(H)alkyl, —C(O)N(alkyl)$_2$, —N(H)C(O)alkyl, —N(H)C(O)N(H)alkyl, —N(H)C(O)N(alkyl)$_2$, —S-alkyl, —S-aryl, —S-alkylaryl, —S(O)$_2$alkyl, —S(O)alkyl, —C(O)alkyl, —CH$_2$NH$_2$, —CH$_2$N(H)alkyl, or —CH$_2$N(alkyl)$_2$;

$R^{12}$ is —C(O)alkyl, —C(O)cycloalkyl, —C(O)alkylaryl, —C(O)alkylheteroaryl, —C(O)heterocyclyl, or —C(O)alkylheterocyclyl; and $R^{13}$ is —H, -alkyl, -aryl, -alkylaryl or -alkylheteroaryl.

8. A compound selected from the group consisting of: 51, 56, 60, 64, 68, 72, 76-93, 98a-z, 98aa-az, 98ba-bb, 110, 111, 120a and 120b:
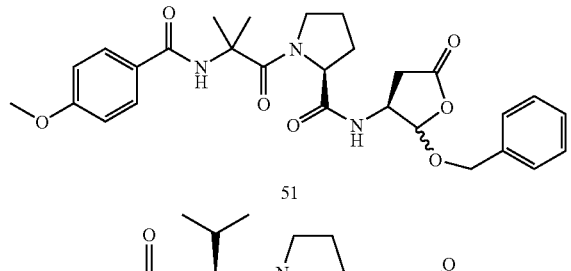
51
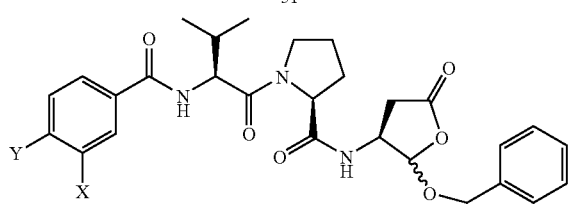
56, X = H, Y = MeO
60, X = Cl, Y = NH₂
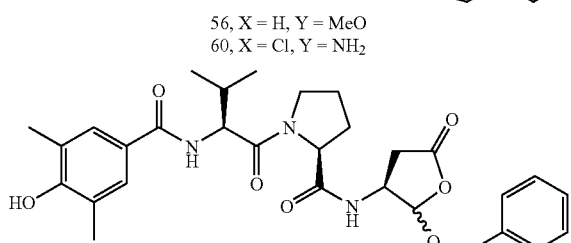
64
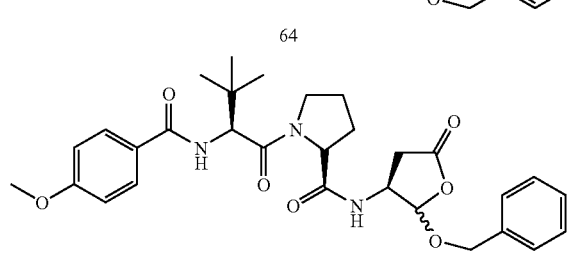
68
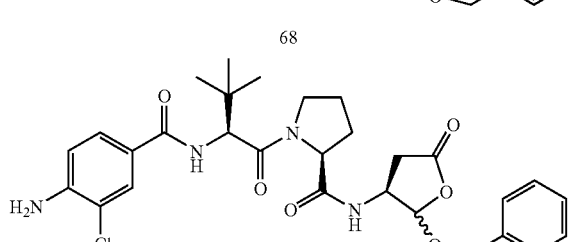
72
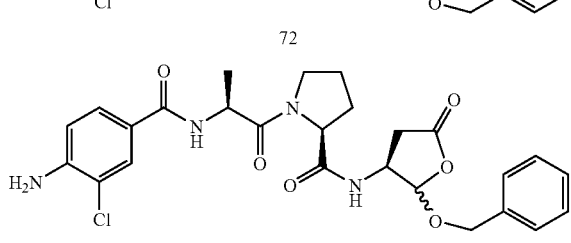
76
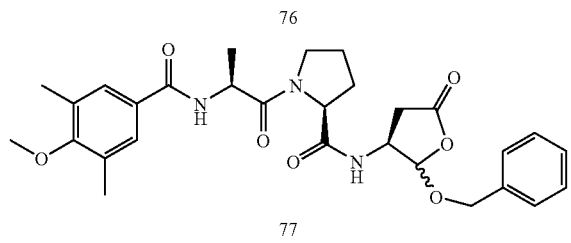
77
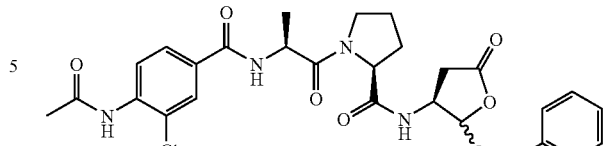
78
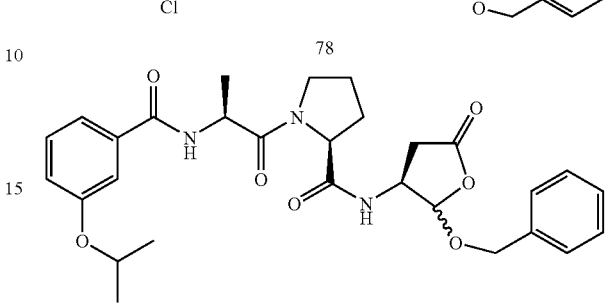
79
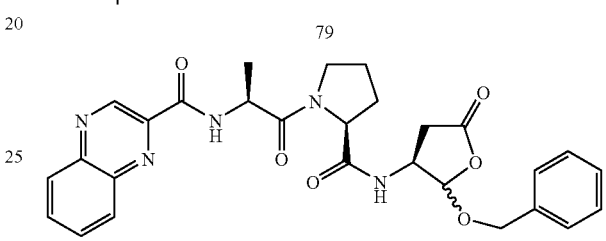
80
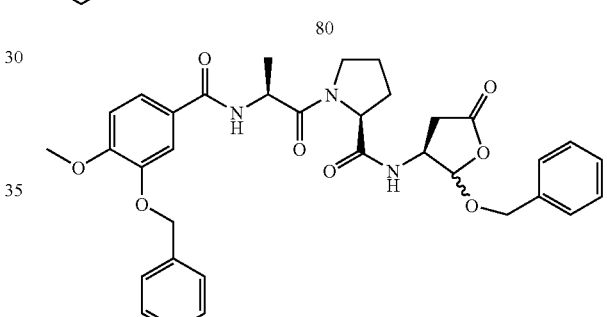
81
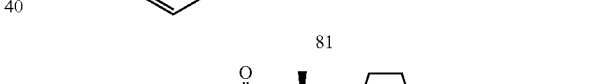
82
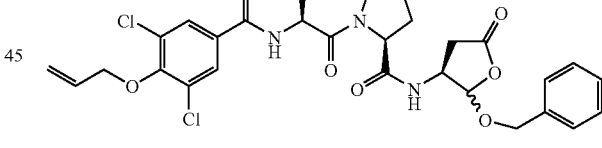
83
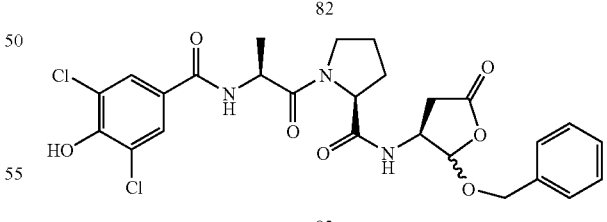
84
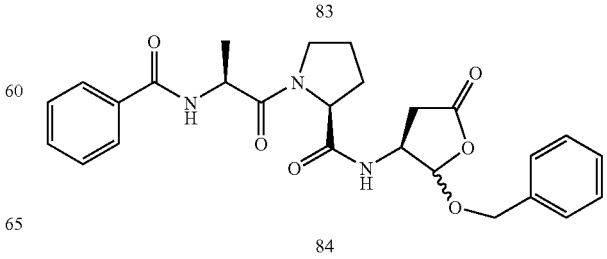

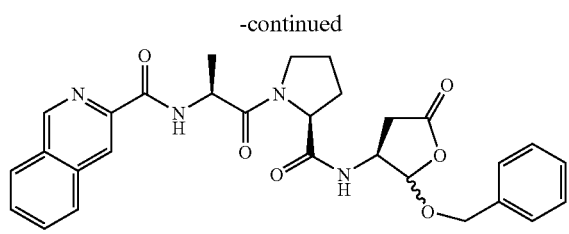
85
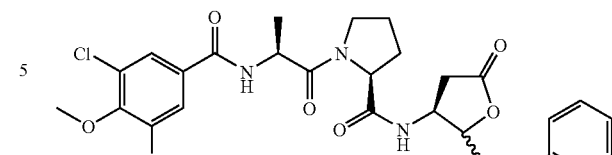
92
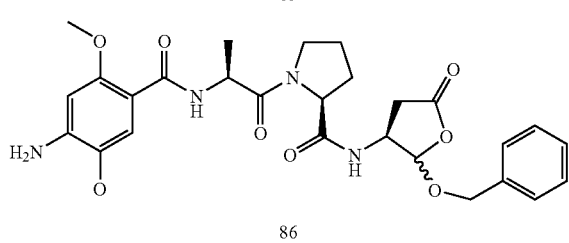
86
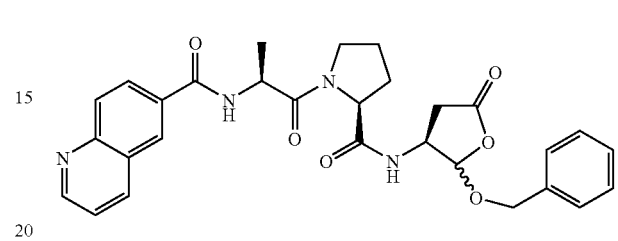
93
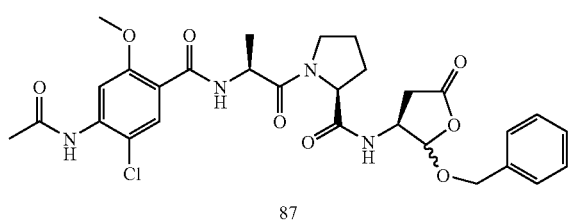
87
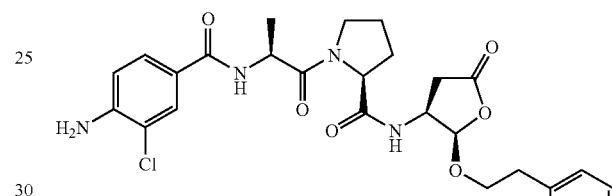
98a
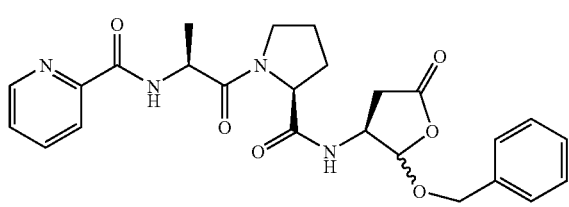
88
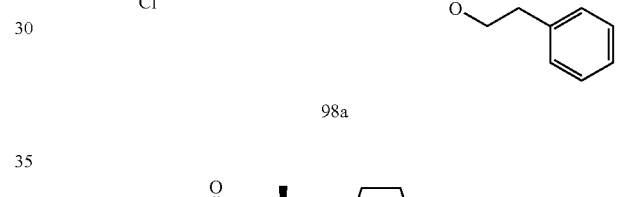
98b
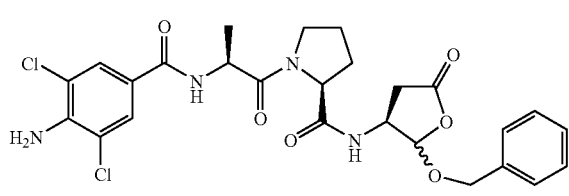
89
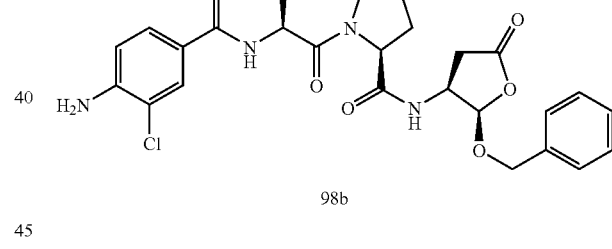
98c
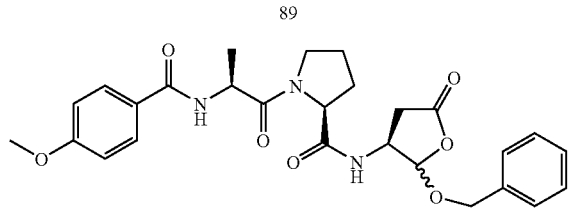
90
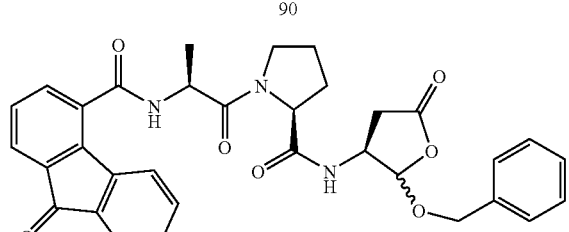
91
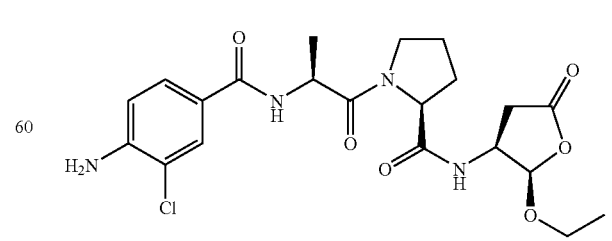
98d -continued
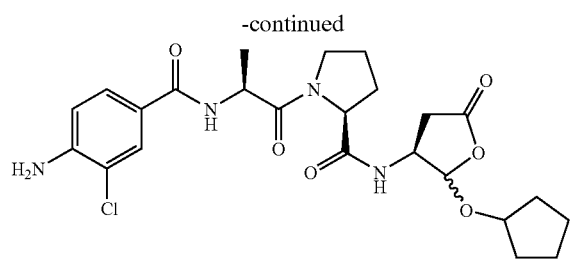
98e
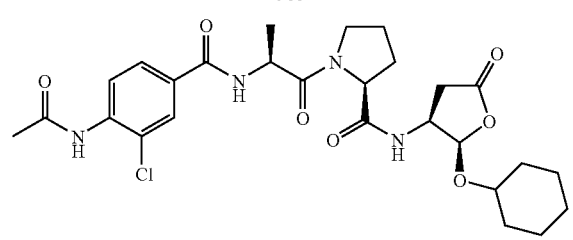
98f
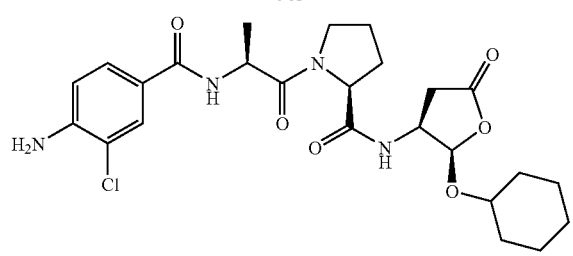
98g
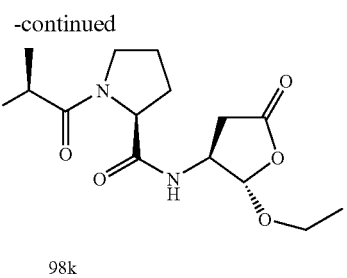
98h
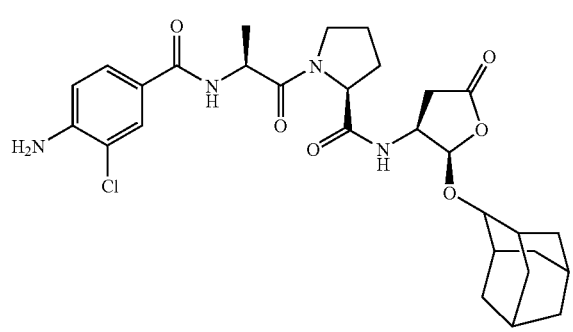
98i
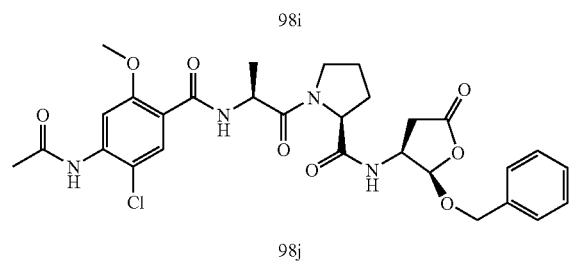
98j
-continued
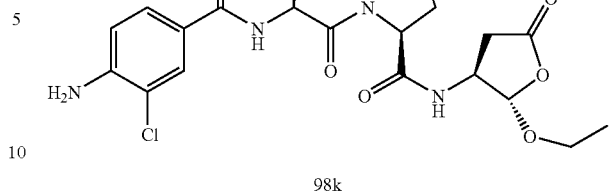
98k
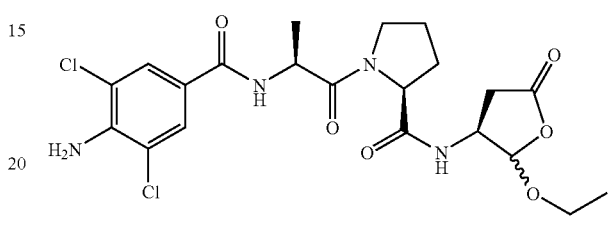
98l
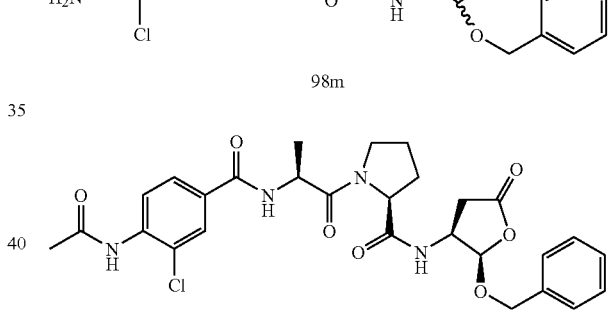
98m
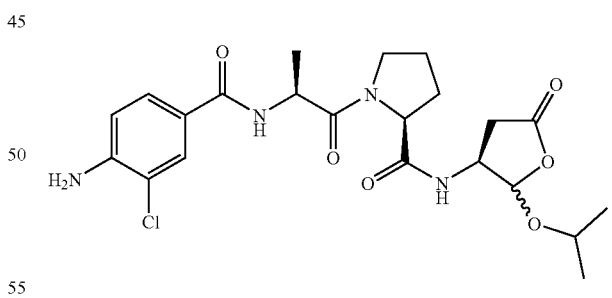
98n
98o
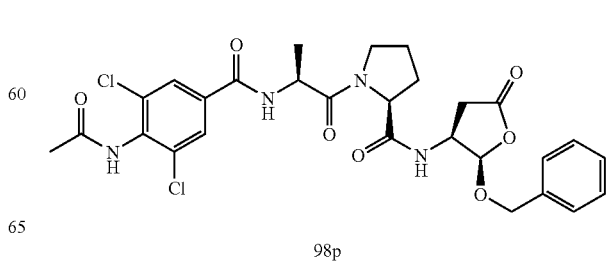
98p -continued
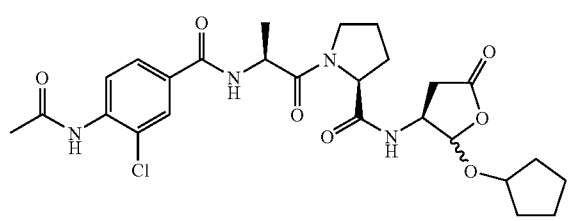
98q
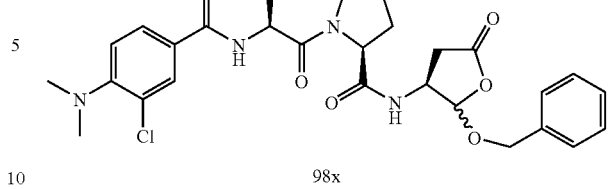
98x
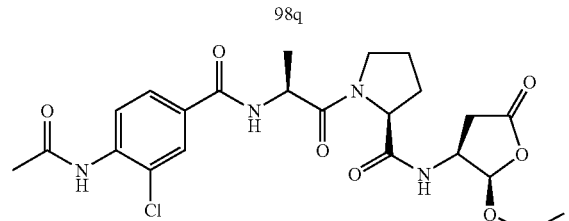
98r
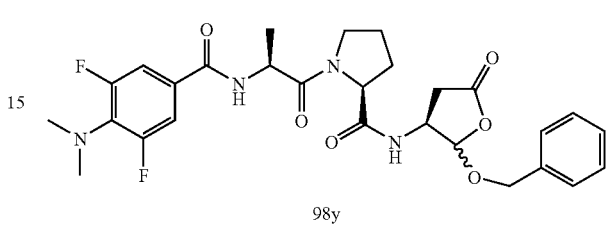
98y
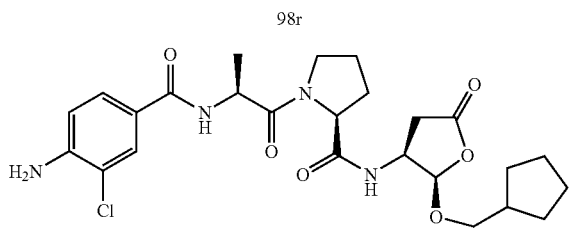
98s
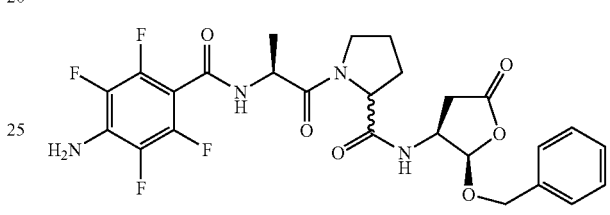
98z
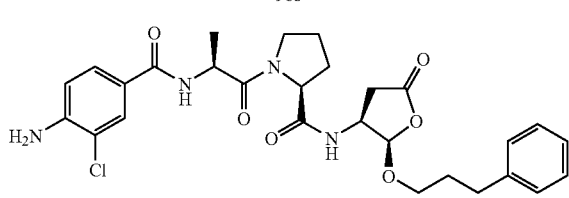
98t
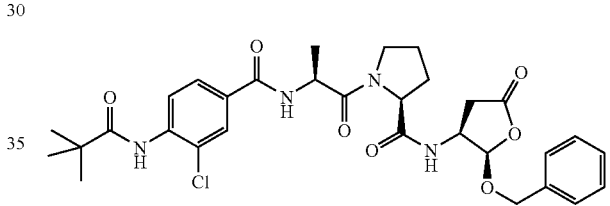
98aa
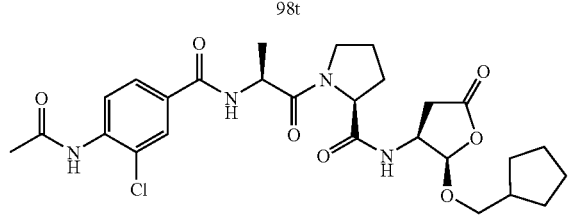
98u
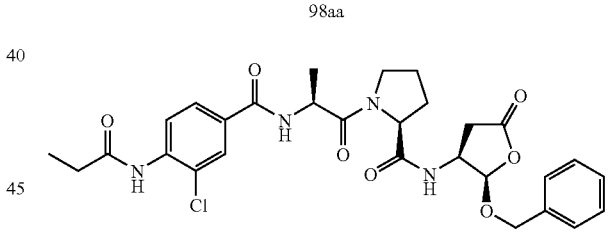
98ab
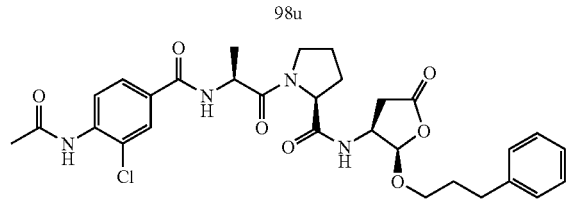
98v
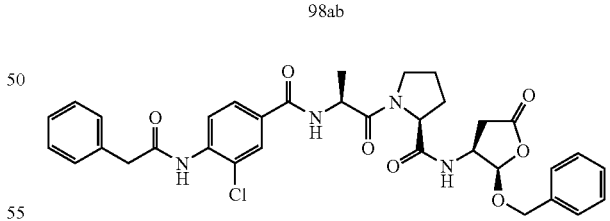
98ac
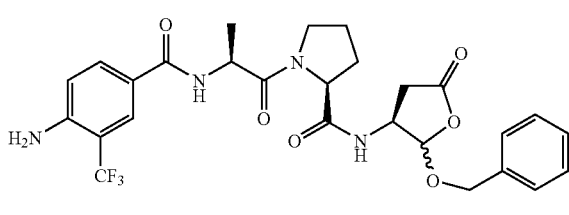
98w
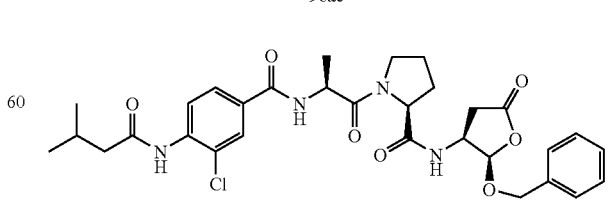
98ad -continued
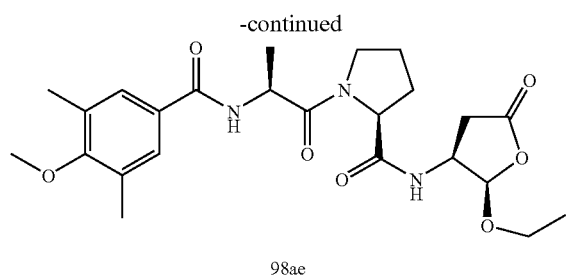
98ae
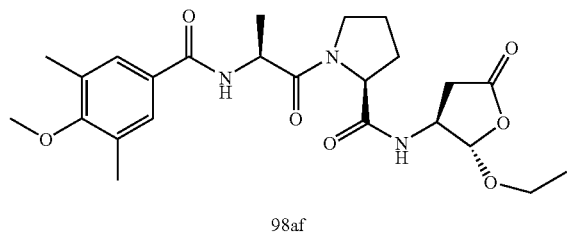
98af
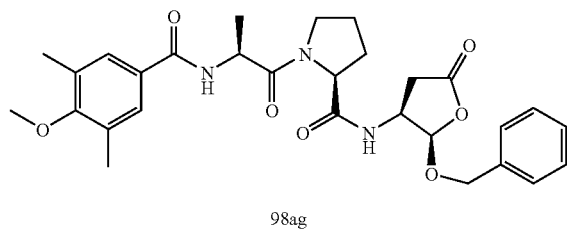
98ag
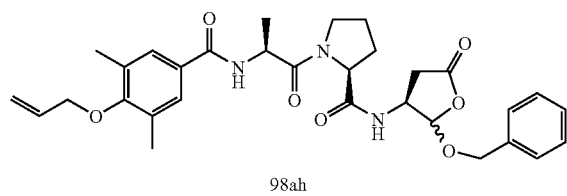
98ah
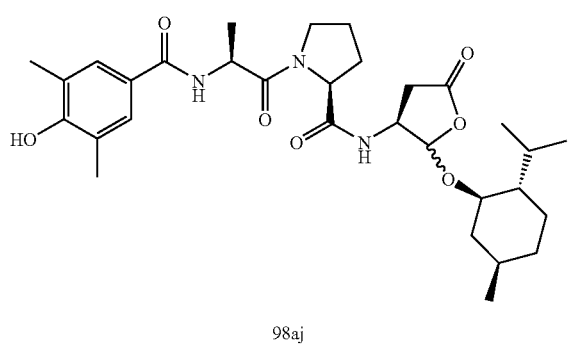
98ai
98aj
-continued
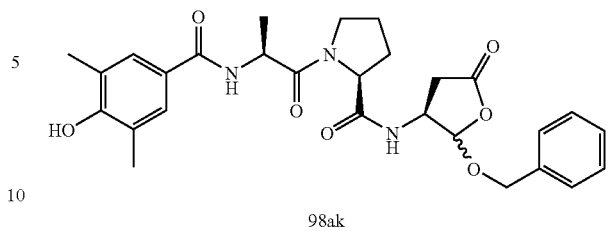
98ak
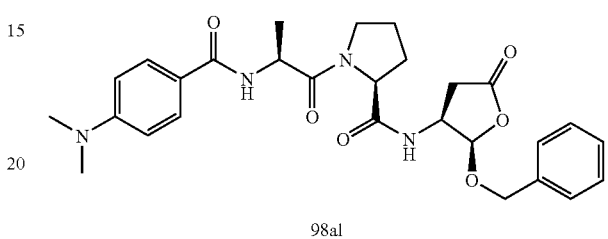
98al
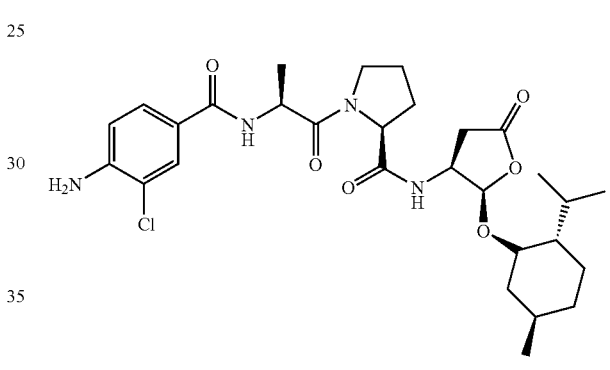
98am
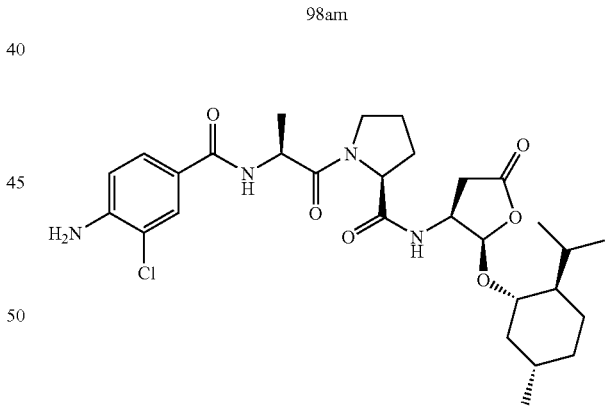
98an
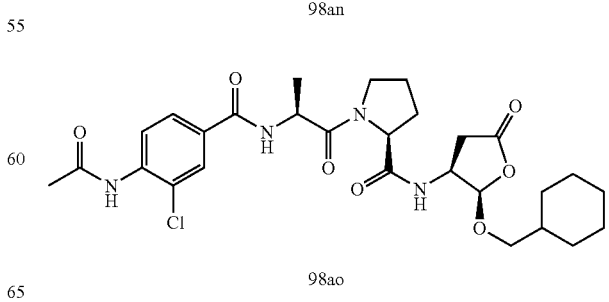
98ao

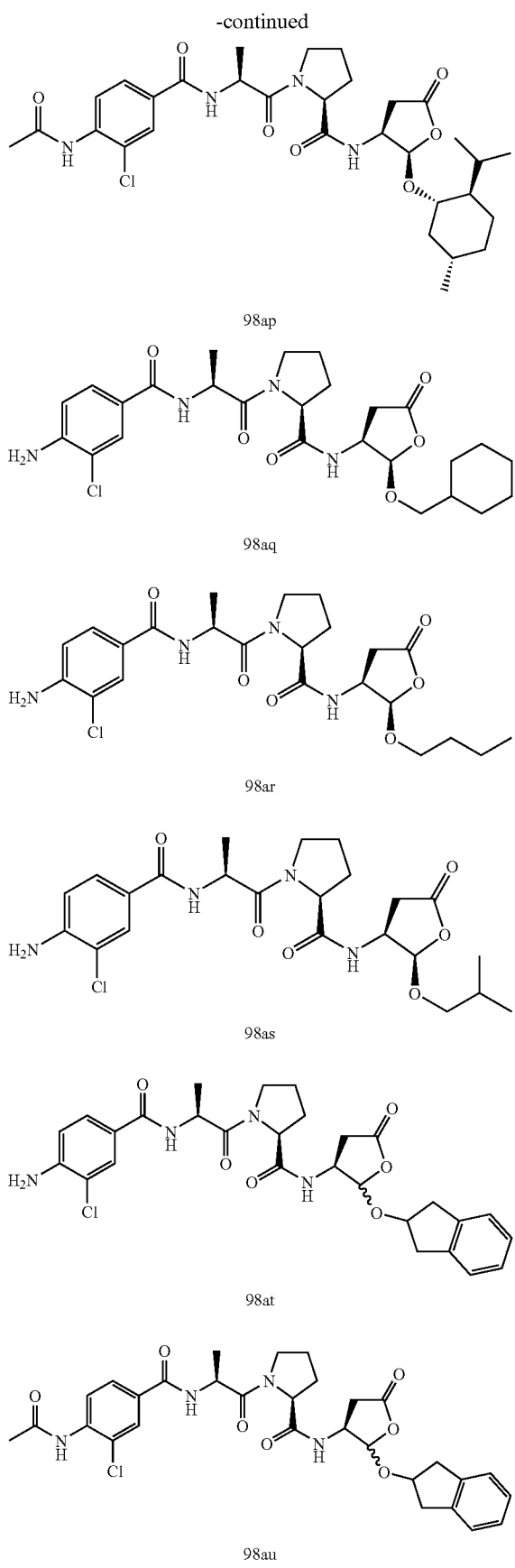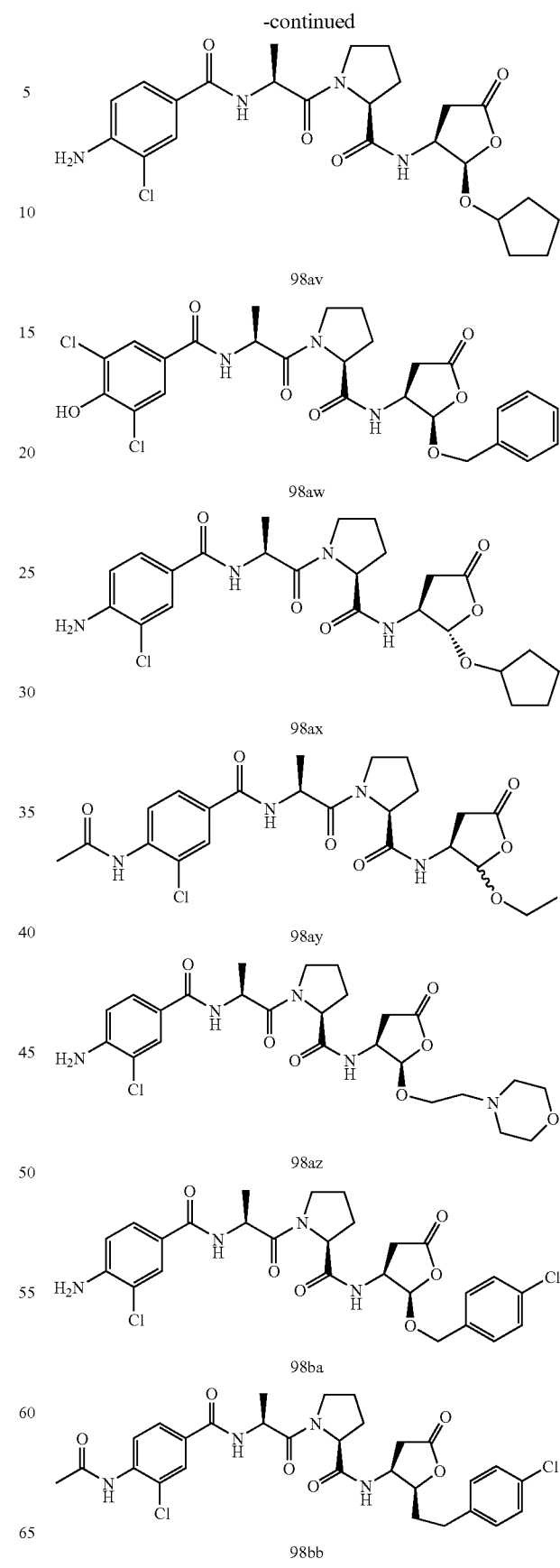

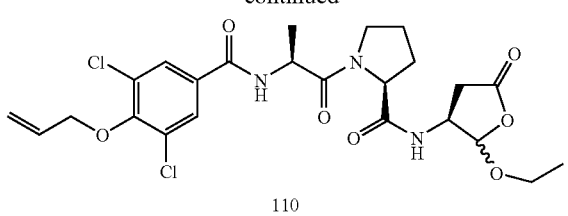

110

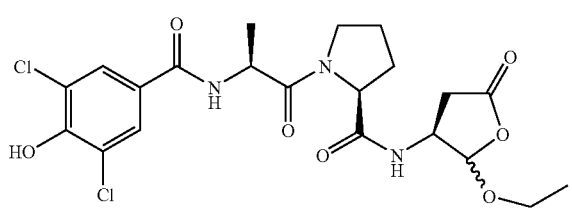

111 and

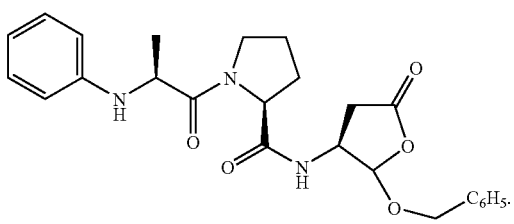

120a = anti
120b = syn

9. A pharmaceutical composition comprising: a) a compound according to any one of claims 1, 2, 3 and 8; and b) a pharmaceutically acceptable carrier, adjuvant or vehicle.

10. A method for treating a disease selected from osteoarthritis, glomerulonephritis, rheumatoid arthritis, psoriasis, atopic dermatitis, eczema, graft vs. host disease, sepsis, or septic shock, in a patient comprising the step of administering to said patient a compound according to any one of claims 1, 2, 3 and 8.

11. The method according to claim 10, wherein the disease is rheumatoid arthritis, septic shock, osteoarthritis, psoriasis, atopic dermatitis, or eczema.

12. A method for treating a disease selected from osteoarthritis, glomerulonephritis, rheumatoid arthritis, psoriasis, atopic dermatitis, eczema, graft vs. host disease, sepsis, or septic shock, in a patient comprising the step of administering to said patient a pharmaceutical composition according to claim 9.

13. The method according to claim 12, wherein the disease is rheumatoid arthritis, septic shock, osteoarthritis, psoriasis, atopic dermatitis, or eczema.

14. A method for treating an inflammatory disease in a patient comprising the step of administering to said patient a compound according to any one of claims 1, 2, 3 and 8, wherein said inflammatory disease is selected from the group consisting of osteoarthritis, acute pancreatitis, chronic pancreatitis, adult respiratory distress, syndrome, inflammatory liver diseases, inflammatory bowel disease, Crohn's disease, ulcerative colitis, cerebral ischemia, myocardial ischeinia, and inflammatory peritonitis.

15. A method for treating an inflammatory disease in a patient comprising the step of administering to said patient a pharmaceutical composition according to claim 9, wherein said inflammatory disease is selected from the group consisting of osteoarthritis, acute pancreatitis, chronic pancreatitis, adult respiratory distress syndrome, inflammatory liver diseases, inflammatory bowel disease, Crohn's disease, ulcerative colitis, cerebral ischemia, myocardial ischemia, and inflammatory peritonitis.

* * * * *

UNITED STATES PATENT AND TRADEMARK OFFICE
CERTIFICATE OF CORRECTION

| | | |
|---|---|---|
| PATENT NO. | : 7,358,273 B2 | Page 1 of 1 |
| APPLICATION NO. | : 10/314103 | |
| DATED | : April 15, 2008 | |
| INVENTOR(S) | : Wannamaker et al. | |

It is certified that error appears in the above-identified patent and that said Letters Patent is hereby corrected as shown below:

In claim 1, column 200, line 21, please replace "$S(ON(R^8)_2,$" with -- $-S(O)N(R^8)_2,$ --;

In claim 2, column 202, lines 35-36, please replace "or and one $R^5$" with -- or $R^4$ and one $R^5$ --;

In claim 2, column 203, line 1, after "-N(H)-alkylaryl," please insert -- -N(alkyl)$_2$, -C(O)N(H)alkyl, -C(O)N(alkyl)$_2$, -N(H)C(O)alkyl, --;

In claim 4, column 204, line 62, please replace "tert-butyl," with -- *tert*-butyl, --;

In claim 14, column 220, line 25, please replace "distress," with -- distress --;

In claim 14, column 220, line 28, please replace "ischeinia," with -- ischemia, --.

Signed and Sealed this

Nineteenth Day of August, 2008

JON W. DUDAS
*Director of the United States Patent and Trademark Office*